United States Patent
Pedersen et al.

(10) Patent No.: US 8,663,640 B2
(45) Date of Patent: Mar. 4, 2014

(54) METHODS USING RECOMBINANT ANTI-EPIDERMAL GROWTH FACTOR RECEPTOR ANTIBODY COMPOSITIONS

(75) Inventors: Mikkel Wandahl Pedersen, Alleroed (DK); Michael Kragh, Copenhagen (DK); Adam S. Hey, Vanloese (DK); Helle Jacobsen, Virum (DK)

(73) Assignee: Symphogen A/S, Lyngby (DK)

( * ) Notice: Subject to any disclaimer, the term of this patent is extended or adjusted under 35 U.S.C. 154(b) by 0 days.

(21) Appl. No.: 13/061,417

(22) PCT Filed: Aug. 27, 2009

(86) PCT No.: PCT/DK2009/050217
§ 371 (c)(1),
(2), (4) Date: May 23, 2011

(87) PCT Pub. No.: WO2010/022736
PCT Pub. Date: Mar. 4, 2010

(65) Prior Publication Data
US 2011/0229463 A1    Sep. 22, 2011

Related U.S. Application Data
(60) Provisional application No. 61/136,391, filed on Sep. 2, 2008.

(30) Foreign Application Priority Data
Aug. 29, 2008 (DK) .................................. 2008 01202

(51) Int. Cl.
*A61K 39/395* (2006.01)
*C07K 16/30* (2006.01)
(52) U.S. Cl.
USPC .................. 424/143.1; 424/155.1; 424/133.1; 424/136.1; 424/174.1

(58) Field of Classification Search
None
See application file for complete search history.

(56) References Cited

U.S. PATENT DOCUMENTS
4,943,533 A    7/1990    Mendelsohn et al.
5,459,061 A    10/1995   Sato et al.
(Continued)

FOREIGN PATENT DOCUMENTS
WO    WO 92/15683 A1    9/1992
WO    WO 94/00136 A1    1/1994
(Continued)

OTHER PUBLICATIONS
Lamminmaki et al., Chrystal structure of a recombinant anti-estradiol Fab fragment in complex with the 17beta-estradiol, J. Blol. Chem. 276:36687-94, 2001.*

(Continued)

*Primary Examiner* — Claire Kaufman
(74) *Attorney, Agent, or Firm* — Ropes & Gray LLP

(57) ABSTRACT

The invention relates to the field of recombinant antibodies for use in human cancer therapy. More specifically the invention provides the use of an antibody composition with two distinct non-overlapping binding specificities to human EGFR. The antibody composition is effecting in treating cancer following treatment with other anti-EGFR antibodies, whether the cancer shows progression during or following the prior treatment or not. The antibody composition can also be used for repeated treatment of recurrent tumors following first-line therapy with the antibody composition of the invention, as the composition does not lead to selection of resistant tumors. A further therapeutic use is the use of an antibody composition of the invention for treatment of cancer that is resistant to known anti-EGFR antibodies.

59 Claims, 49 Drawing Sheets

(56) References Cited

U.S. PATENT DOCUMENTS

| | | |
|---|---|---|
| 5,558,864 A | 9/1996 | Bendig et al. |
| 5,891,996 A | 4/1999 | Mateo de Acosta del Rio et al. |
| 6,217,866 B1 | 4/2001 | Schlessinger et al. |
| 6,235,883 B1 | 5/2001 | Jakobovits et al. |
| 6,506,883 B2 | 1/2003 | Meteo de Acosta del Rio et al. |
| 6,806,055 B2 * | 10/2004 | Berman et al. |
| 6,849,259 B2 | 2/2005 | Haurum et al. |
| 7,060,808 B1 | 6/2006 | Goldstein et al. |
| 7,132,511 B2 | 11/2006 | Carr et al. |
| 7,655,751 B2 | 2/2010 | Itoh et al. |
| 7,749,697 B2 | 7/2010 | Oleksiewicz et al. |
| 7,887,805 B2 | 2/2011 | Pedersen et al. |
| 8,414,896 B2 | 4/2013 | Pedersen et al. |
| 2005/0019833 A1 | 1/2005 | Ohkawa et al. |
| 2006/0073140 A1 | 4/2006 | Greene et al. |
| 2006/0275766 A1 | 12/2006 | Haurum et al. |
| 2007/0009972 A1 | 1/2007 | Chao et al. |
| 2007/0141048 A1 | 6/2007 | Oleksiewicz et al. |
| 2007/0178102 A1 | 8/2007 | Yarden et al. |
| 2008/0069822 A1 | 3/2008 | Jensen et al. |
| 2008/0131882 A1 | 6/2008 | Rasmussen et al. |
| 2008/0227660 A1 | 9/2008 | Kastrup et al. |
| 2008/0299581 A1 | 12/2008 | Nielsen et al. |
| 2009/0004192 A1 | 1/2009 | Pedersen et al. |
| 2009/0017017 A1 | 1/2009 | Rasmussen et al. |
| 2009/0137784 A1 | 5/2009 | Chao et al. |
| 2010/0310558 A1 | 12/2010 | Oleksiewicz et al. |
| 2011/0129855 A1 | 6/2011 | Pedersen et al. |
| 2011/0135636 A1 | 6/2011 | Pedersen et al. |
| 2012/0107234 A1 | 5/2012 | Pederson et al. |

FOREIGN PATENT DOCUMENTS

| | | |
|---|---|---|
| WO | WO 95/20045 A1 | 7/1995 |
| WO | WO 96/40210 A1 | 12/1996 |
| WO | WO 01/70965 A1 | 9/2001 |
| WO | WO 01/70985 A2 | 9/2001 |
| WO | WO 02/066058 A1 | 8/2002 |
| WO | WO 02/092771 A2 | 11/2002 |
| WO | WO 02/100348 A2 | 12/2002 |
| WO | WO 03/074705 A1 | 9/2003 |
| WO | WO 03/097086 A2 | 11/2003 |
| WO | WO 03/099205 A2 | 12/2003 |
| WO | WO 2004/008099 A2 | 1/2004 |
| WO | WO 2004/009618 A2 | 1/2004 |
| WO | WO 2004/032961 A1 | 4/2004 |
| WO | WO 2004032960 A1 * | 4/2004 |
| WO | WO 2004/056847 A2 | 7/2004 |
| WO | WO 2004/061104 A2 | 7/2004 |
| WO | WO 2004/085474 A2 | 10/2004 |
| WO | WO 2004/106379 A1 | 12/2004 |
| WO | WO 2005/042774 A2 | 5/2005 |
| WO | WO 2005/071075 A1 | 8/2005 |
| WO | WO 2006/007850 A1 | 1/2006 |
| WO | WO 2006/007853 A2 | 1/2006 |
| WO | WO 2006/009694 A2 | 1/2006 |
| WO | WO 2006/078307 A1 | 7/2006 |
| WO | WO 2006/091693 A2 | 8/2006 |
| WO | WO 2006/091899 A2 | 8/2006 |
| WO | WO 2006/102504 A2 | 9/2006 |
| WO | WO 2006/108627 A1 | 10/2006 |
| WO | WO 2006/110478 A2 | 10/2006 |
| WO | WO 2006/116001 A2 | 11/2006 |
| WO | WO 2007/065433 A2 | 6/2007 |
| WO | WO 2007/101441 A1 | 9/2007 |
| WO | WO 2008/104183 A2 | 9/2008 |
| WO | WO 2008/104184 A2 | 9/2008 |
| WO | WO 2010/022736 | 3/2010 |

OTHER PUBLICATIONS

Hussein et al., Construction and characterization of single-chain variable fragment antibodies directed against *Bordetella pertussis* surface adhesins filamentous hemagglutinin and pertactin, Infect. Immunol. 75(11):5476, 2007.*

Schmiedel et al., Matuzumab binding to EGFR prevents the conformational rearragnement required for dimerization, NIH Public Access Author Mauscript, published in final edited form as Cancer Cell. Apr. 2008; 13(4):365-373, 2008.*

Arteaga, C.L., "The Epidermal Growth Factor Receptor: From Mutant Oncogene in Nonhuman Cancers to Therapeutic Target in Human Neoplasia," *J. Clin. Oncol.* 19(18s):32s-40s, American Society of Clinical Oncology, United States (2001).

Bregenholt, S., et al., "Recombinant Human Polyclonal Antibodies: A New Class of Therapeutic Antibodies Against Viral Infections," *Curr. Pharm. Des.* 12:2007-2015, Bentham Science Publishers Ltd., Netherlands (2006).

Bui, N.B., et al., "Liposarcoma: Patterns of Tumor Differentiation Following Induction Chemotherapy," *Oncology* 41:170-173, S. Karger AG, United States (1984).

Chao, G., et al., "Engineering anti-Epidermal Growth Factor Receptor (EGFR) Antibodies to Block Receptor Dimerization," Department of Chemical Engineering and Division of Biological Engineering, Massachusetts Institute of Technology, Cambridge, MA 02139, Poster 108 and Poster Abstract presented Feb. 18, 2005, at Keystone Symposium entitled "Antibody-Based Therapeutics for Cancer," held Feb. 17-22, 2005, in Santa Fe, New Mexico.

Chao, G., et al., "Engineering Antibodies against the Epidermal Growth Factor Receptor to Block Dimerization," Abstract 457c presented Nov. 3, 2005, at the AIChE 2005 Annual Meeting, Cincinnati, Ohio, United States.

Cochran, J.R., et al., "Domain-level antibody epitope mapping through yeast surface display of epidermal growth factor receptor fragments," *J. Immunol. Meth.* 287:147-158, Elsevier B.V., Netherlands (2004).

Drug information sheet for Erbitux® (Cetuximab), 27 pages, ImClone Systems Incorporated and Bristol-Myers Squibb Company (2006).

Drug information sheet for Vectibix™ (panitumumab), 14 pages, Amgen Inc. (2006).

Friedman, L.M., et al., "Synergistic down-regulation of receptor tyrosine kinases by combinations of mAbs: Implications for cancer immunotherapy," *Proc. Natl. Acad. Sci.* 102(6):1915-1920, National Academy of Sciences, United States (2005).

Guidicelli, V., et al., "IMGT/LIGM-DB, the IMGT® comprehensive database of immunoglobulin and T cell receptor nucleotide sequences," *Nucleic Acid Res.* 34: D781-D784, Oxford University Press, England (2006).

Harwerth, I.-M., et al., "Monoclonal antibodies directed to the *erb*B-2 receptor inhibit in vivo tumour cell growth," *Br. J. Cancer* 68:1140-1145, Macmillan Press Ltd., England (1993).

Haurum, J.S., "Recombinant polyclonal antibodies: the next generation of antibody therapeutics?" *Drug Discov. Today* 11(13/14):655-660, Elsevier Ltd., England (2006).

Ivascu, A. and M. Kubbies, "Rapid Generation of Single-Tumor Spheroid for High-Throughput Cell Function and Toxicity Analysis," *J. Biomol. Screen* 11(8):922-932, Society for Biomolecular Sciences, United States (2006).

Kawamata, H., et al., "Differentiation-Inducing Therapy for Solid Tumors," *Curr. Pharm. Des.* 12:379-385, Bentham Science Publishers Ltd., Netherlands (2006).

Larbouret, C., et al., "In vivo Therapeutic Synergism of Anti-Epidermal Growth Factor Receptor and Anti-HER2 Monoclonal Antibodies against Pancreatic Carcinomas," *Clin. Cancer Res.* 13(11):3356-3362, American Association for Cancer Research, United States (2007).

Lefranc, M-P., "IMGT-ONTOLOGY and IMGT databases, tools and Web resources for immunogenetics and immunoinformatics," *Mol. Immunol.* 40:647-660, Elsevier Ltd., England (2004).

Li, D., et al., "Therapeutic anti-EGFR antibody 806 generates responses in murine de novo EGFR mutant-dependent lung carcinomas," *J. Clin. Invest.* 117(2):346-352, American Society for Clinical Investigation, United States (2007).

Logtenberg, T., "Antibody cocktails: next-generation biopharmaceuticals with improved potency," *Trends Biotechnol.* 25(9):390-394, Elsevier Ltd., England (Aug. 2007).

(56) References Cited

OTHER PUBLICATIONS

MacCallum, R.M., et al., "Antibody-antigen Interactions: Contact Analysis and Binding Site Topography," *J. Mol. Biol. 262*:732-745, Academic Press Limited, England (1996).

Masui, H., et al., "Mechanism of Antitumor Activity in Mice for Anti-Epidermal Growth Factor Receptor Monoclonal Antibodies with Different Isotypes," *Cancer Res. 46*:5592-5598, American Association for Cancer Research, United States (1986).

Meijer, P-J., et al., "Isolation of Human Antibody Repertoires with Preservation of the Natural Heavy and Light Chain Pairing," *J. Mol. Biol. 358*:764-772, Elsevier Ltd., England (2006).

Modjtahedi, H., et al., "Antitumor Activity of Combinations of Antibodies Directed Against Different Epitopes on the Extracellular Domain of the Human EGF Receptor," *Cell Biophys. 22*:129-146, Humana Press Inc., United States (1993).

Modjtahedi, H., et al., "Immunotherapy of human tumour xenografts overexpressing the EGF receptor with rat antibodies that block growth factor-receptor interaction," *Br. J. Cancer 67*:254-261, Macmillan Press Ltd., England (1993).

Modjtahedi, H., et al, "Differentiation or Immune Destruction: Two Pathways for Therapy of Squamous Cell Carcinomas with Antibodies to the Epidermal Growth Factor Receptor," *Cancer Res. 54*:1695-1701, American Association for Cancer Research, United States (1994).

Nahta, R., et al., "The HER-2-Targeting Antibodies Trastuzumab and Pertuzumab Synergistically Inhibit the Survival of Breast Cancer Cells," *Cancer Res. 64*:2343-2346, American Association for Cancer Research, United States (2004).

Normanno, N., et al., "Cooperative inhibitory effect of ZD1839 (Iressa) in combination with trastuzumab (Herceptin) on human breast cancer cell growth," *Ann. Oncol. 13*:65-72, European Society for Medical Oncology, England (2002).

Patel, D., et al., "Activity and binding mechanism of cetuximab (Erbitux®) to the type III EGF deletion-mutant receptor," *Proc. Amer. Assoc. Cancer Res. 47*, Abstract No. 1238, American Association for Cancer Research, 2006, United States.

Pedersen, M.W., et al., "Sym004: A Novel Synergistic Anti-Epidermal Growth Factor Receptor Antibody Mix with Superior Anticancer Efficacy," *Cancer Res. 70*(2):588-597, American Association for Cancer Research, United States (2010).

Perera, R.M., et al., "Treatment of Human Tumor Xenografts with Monoclonal Antibody 806 in Combination with a Prototypical Epidermal Growth Factor Receptor-Specific Antibody Generates Enhanced Antitumor Activity," *Clin. Cancer Res. 11*(17):6390-6399, American Association for Cancer Research, United States (2005).

Poulsen, T., et al., "Kinetic, Affinity, and Diversity Limits of Human Polyclonal Antibody Responses against Tetanus Toxoid," *J. Immunol. 179*:3841-3850, The American Association of Immunologists, United States (Sep. 2007).

Rudikoff, S., et al., "Single amino acid substitution altering antigen-binding specificity," *Proc. Natl. Acad. Sci. USA 79*:1979-1983, National Academy of Sciences, United States (1982).

Sharon, J., et al., "Recombinant Polyclonal Antibodies for Cancer Therapy," *J. Cell. Biochem. 96*:305-313, Wiley-Liss, Inc., United States (2005).

Spiridon, C.I., et al., "A Comparison of the in Vitro and in Vivo Activities of IgG and F(ab ')$_2$ Fragments of a Mixture of Three Monoclonal Anti-Her-2 Antibodies," *Clin. Cancer Res. 10*:3542-3551, American Association for Cancer Research, United States (2004).

Spiridon, C.I., et al., "Targeting Multiple Her-2 Epitopes with Monoclonal Antibodies Results in Improved Antigrowth Activity of a Human Breast Cancer Cell Line in Vitro and in Vivo," *Clin. Cancer Res. 8*:1720-1730, American Association for Cancer Research, United States (2002).

Tolstrup, A.B., et al., "Development for recombinant human polyclonal antibodies for the treatment of complex human diseases," *Expert Opin. Biol. Ther. 6*:905-912, Informa UK Ltd., England (2006).

Ullrich, A., et al., "Human epidermal growth factor receptor cDNA sequence and aberrant expression of the amplified gene in A431 epidermoid carcinoma cells," *Nature 309*:418-425, Nature Publishing Group, England (1984).

Verheul, H.M.W., et al., "Sequence-dependent antitumor effects of differentiation agents in combination with cell cycle-dependent cytotoxic drugs," *Cancer Chemother. Pharmacol. 60*:329-339, Springer-Verlag, Germany (2006).

Welsh, J.B., et al., "A Negative Feedback Loop Attenuates EGF-induced Morphological Changes," *J. Cell. Biol. 114*(3):533-543, Rockefeller University Press, United States (1991).

Whitson, K., et al., "Functional Effects of Glycosylation at Asn-579 of the Epidermal Growth Factor Receptor," *Biochemistry 44*:14920-14931, American Chemical Society, United States (2005).

Wiberg, F.C., et al., "Production of Target-Specific Recombinant Human Polyclonal Antibodies in Mammalian Cells," *Biotechnol. Bioeng. 94*:396-405, Wiley Periodicals, Inc., United States (2006).

Zhen, Y., et al., "Characterization of Glycosylation Sites of the Epidermal Growth Factor Receptor," *Biochemistry 42*:5478-5492, American Chemical Association, United States (2003).

NCBI Entrez, GenBank Report, Accession No. X00588, "Human mRNA for precursor of epidermal growth factor receptor," (Oct. 2008).

Database UniProt Accession No. Q68GS6, "Cloning of the cDNA for the extracellular domain of EGF receptor from human placenta," Xu et al. (2004).

English language Abstract of WO Patent Publication No. WO 01/70965 A1, European Patent Office, espacenet database—Worldwide (listed as document FP11 on the accompanying form PTO/SB/08A).

Baselga, J., and Mendelsohn, J., "Receptor Blockade with Monoclonal Antibodies as Anti-Cancer Therapy," *Pharmacology & Therapeutics 64*:127-154, Elsevier Science Ltd., England (1994).

Ferguson, K., et al., "EGF Activates Its Receptor by Removing Interactions that Autoinhibit Ectodomain Dimerization," *Molecular Cell 11*:507-517, Cell Press, United States (2003).

Garrett, T., et al., "Crystal Structure of a Truncated Epidermal Growth Factor Receptor Extracellular Domain Bound to Transforming Growth Factor α," *Cell 110*:763-773, Cell Press, United States (Sep. 2002).

Karnes, W., et al., "Inhibition of Epidermal Growth Factor Receptor Kinase Induces Protease-Dependent Apoptosis in Human Color Cancer Cells," *Gastroenterology 114*:930-939, The American Gastroenterological Association, United States (1998).

Modjtahedi, H. and Dean, C., "The Receptor for EGF and its Ligands—Expression, Prognostic Value and Target Therapy in Cancer (Review)," *International Journal of Oncology 4*(2):277-96, Spandidos Publications Ltd., Greece (1994).

Ogiso, H., et al., "Crystal Structure of the Complex of Human Epidermal Growth Factor and Receptor Extracellular Domains," *Cell 110*:775-787, Cell Press, United States (Sep. 2002).

Price, J.T., et al., "Epidermal Growth Factor (EGF) Increases the In Vitro Invasion, Motility and Adhesion Interactions of the Primary Renal Carcinoma Cell Line, A704," *European Journal of Cancer 32A*(11):1977-1982, Elsevier Science Ltd., England (1996).

Salomon, D., et al., "Epidermal growth factor-related peptides and their receptors in human malignancies," *Critical Reviews in Oncology/Hematology 19*:183-232, Elsevier Science Ireland Ltd., Ireland (1995).

Wheeler, D.L., et al., "Mechanisms of Acquired Resistance to Cetuximab: Role of HER (ErbB) Family Members," *Oncogene 27*:3944-3956, Nature Publishing Group, England (2008).

Woodburn, J.R., "The Epidermal Growth Factor Receptor and Its Inhibition in Cancer Therapy," *Pharmacology & Therapeutics 82*(2-3):241-250, Elsevier Science Inc., England (1999).

Wu, X., et al., "Apoptosis Induced by an Anti-Epidermal Growth Factor Receptor Monoclonal Antibody in a Human Colorectal Carcinoma Cell Line and Its Delay by Insulin," *The Journal of Clinical Investigation 95*:1897-1905, The American Society for Clinical Investigation, Inc., United States (Apr. 1995).

International Search Report for International Application No. PCT/DK2009/050217, European Patent Office, Rijswijk, Netherlands, mailed Mar. 3, 2010.

(56) References Cited

OTHER PUBLICATIONS

International Preliminary Report on Patentability with the Written Opinion of the International Searching Authority for International Application No. PCT/DK2009/050217, European Patent Office, Munich, Germany, issued Mar. 1, 2011.
International Search Report for International Application No. PCT/DK2008/050047, mailed on Sep. 26, 2008, European Patent Office, NL.
NCBI GenBank Accession No. AY698023.1, (2004).
NCBI Entrez, GenBank Report, Accession No. X00588, Ullrich, A. et al. (1995).
Schildbach, et al., "Modulation of antibody affinity by a non-contact residue," Protein Science, 2(2):206-214 (1993).
Niederfellner et al., "Epitope characterization and crystal structure of GA101 provide insights into the molecular basis for type I/II distinction of CD20 antibodies," Blood 118(2):358-367 (2011).

* cited by examiner

|  | I | | II | III | | | |
|---|---|---|---|---|---|---|---|
| Clone | ICR10 | Ab-11 | Ab-3 | Ab-5 | Ab-10 | Ab-1 | Ab-2 |
| 992 | -20 | -2 | -21 | -3 | -14 | 78 | 77 |
| 1024 | 11 | 18 | 11 | 12 | 27 | 3 | 75 |
| 1030 | 12 | -20 | -35 | 92 | 92 | 91 | -1 |
| 1042 | -7 | 7 | -29 | -7 | 15 | 24 | 81 |
| 1208 | -21 | -3 | -10 | 84 | 89 | 82 | 20 |
| 1229 |  |  |  |  |  |  |  |
| 1257 | 78 | 92 | 77 | 25 | 33 | 6 | 37 |
| 1260 | 90 | 92 | 12 | 17 | 24 | 12 | 8 |
| 1261 | 57 | 88 | 30 | 6 | 13 | 3 | 6 |
| 1277 | 32 | 28 | 8 | 77 | 85 | 61 | 20 |
| 1284 | 88 | 52 | 9 | 31 | 30 | 12 | 26 |
| 1308 | 71 | 91 | 19 | 0 | 12 | 4 | 11 |
| 1320 | 2 | 8 | 0 | 6 | 7 | 9 | -9 |
| 1344 | 82 | 82 | 40 | 28 | 36 | 19 | 14 |
| 1428 | 91 | 94 | 34 | 11 | 17 | 18 | 14 |
| Erbitux | -17 | 4 | -4 | 21 | -73 | 78 | 69 |
| Erbitux | -22 | 2 | -5 | 22 | -81 | 78 | 66 |
| Vectibix | -30 | -12 | -24 | 6 | 57 | 60 | 42 |
| Vectibix | -13 | -1 | -6 | 16 | 64 | 68 | 46 |

Fig. 6A

|  | I | | II | III | | | | Epitope |
|---|---|---|---|---|---|---|---|---|
| Clone | ICR10 | Ab-11 | Ab-3 | Ab-5 | Ab-10 | Ab-1 | Ab-2 | specificity |
| 992 |  |  |  |  |  | +++ | +++ | Domain III |
| 1024 |  |  |  |  | + | +++ |  | Domain III |
| 1030 |  |  |  | +++ | +++ | +++ |  | Domain III |
| 1042 |  |  |  |  |  |  | +++ | Domain III |
| 1208 |  |  |  | +++ | +++ | +++ |  | Domain III |
| 1229 |  |  |  |  |  |  |  | Unknown |
| 1257 | +++ | +++ | +++ | + | + |  | + | Domain I / II |
| 1260 | +++ | +++ |  |  |  |  |  | Domain I |
| 1261 | ++ | +++ | + |  |  |  |  | Domain I |
| 1277 | + | + |  | +++ | +++ | +++ |  | Domain III |
| 1284 | +++ | ++ |  | + | + |  | + | Domain I |
| 1308 | ++ | +++ |  |  |  |  |  | Domain I |
| 1320 |  |  |  |  |  |  |  | Unknown |
| 1344 | +++ | +++ | + | + | + |  |  | Domain I |
| 1428 | +++ | +++ | + |  |  |  |  | Domain I |
| Erbitux |  |  |  |  |  | +++ | ++ | Domain III |
| Erbitux |  |  |  |  |  | +++ | ++ | Domain III |
| Vectibix |  |  |  |  | ++ | ++ | + | Domain III |
| Vectibix |  |  |  |  | ++ | ++ | + | Domain III |

Fig. 6B

|        | I     | II    |       | III   |       |       |         |          |
|--------|-------|-------|-------|-------|-------|-------|---------|----------|
| Clone  | ICR10 | Ab-11 | Ab-3  | Ab-5  | Ab-10 | Ab-1  | Erbitux | Vectibix |
| 992    | -4    | -3    | 7     | 1     | -4    | 99    | 90      | 106      |
| 1024   | -3    | -13   | 0     | 0     | -5    | 6     | 101     | 102      |
| 1030   | 54    | -5    | 6     | 104   | 84    | 98    | -1      | 16       |
| 1042   | -6    | -8    | 0     | 10    | -4    | 14    | 107     | 110      |
| 1208   | 5     | 4     | 5     | 66    | 32    | 37    | 18      | 29       |
| 1229*  |       |       |       |       |       |       |         |          |
| 1257   | 22    | 100   | 85    | -5    | 1     | -1    | 0       | -2       |
| 1260   | 91    | 99    | 64    | 1     | 12    | 7     | 8       | 10       |
| 1261   | 24    | 94    | 54    | -3    | -6    | -4    | -2      | -5       |
| 1277   | 5     | 3     | 10    | 85    | 62    | 81    | 60      | 86       |
| 1284   | 86    | -15   | 9     | -13   | -8    | -9    | -7      | -13      |
| 1308   | 15    | 65    | 11    | -4    | -3    | -5    | -6      | -8       |
| 1320   | -3    | -6    | 2     | -3    | -2    | 3     | 2       | 6        |
| 1344   | 87    | 86    | 25    | -3    | 0     | -2    | -4      | -5       |
| 1347   | 17    | 86    | 11    | -1    | -1    | -3    | -4      | -6       |
| 1428   | 77    | 88    | 42    | 0     | 1     | 0     | 2       | 0        |
| Erbitux| -3    | -3    | 0     | 29    | 0     | 101   | 94      | 104      |
| Vectibix| 0    | -4    | 5     | 0     | 0     | 88    | 79      | 102      |

Fig. 8A

|         | I     | II    |      | III   |       |       |         |          | Epitope       |
|---------|-------|-------|------|-------|-------|-------|---------|----------|---------------|
| Clone   | ICR10 | Ab-11 | Ab-3 | Ab-5  | Ab-10 | Ab-1  | Erbitux | Vectibix | Specificity   |
| 992     |       |       |      |       |       | +++   | +++     | +++      | Domain III    |
| 1024    |       |       |      |       |       | +++   | +++     | +++      | Domain III    |
| 1030    | ++    |       |      | +++   | +++   | +++   |         |          | Domain III    |
| 1042    |       |       |      |       |       |       | +++     | +++      | Domain III    |
| 1208    |       |       |      | ++    | +     | +     |         | +        | Domain III    |
| 1229*   |       |       |      |       |       |       |         |          | no binding    |
| 1257    |       | +++   | +++  |       |       |       |         |          | Domain I / II |
| 1260    | +++   | +++   | ++   |       |       |       |         |          | Domain I / II |
| 1261    |       | +++   | ++   |       |       |       |         |          | Domain I / II |
| 1277    |       |       |      | +++   | ++    | +++   | ++      | +++      | Domain III    |
| 1284    | +++   |       |      |       |       |       |         |          | Domain I      |
| 1308    |       | +++   |      |       |       |       |         |          | Domain I      |
| 1320    |       |       |      |       |       |       |         |          | Unknown       |
| 1344    | +++   | +++   |      |       |       |       |         |          | Domain I      |
| 1347    |       | +++   |      |       |       |       |         |          | Domain I      |
| 1428    | +++   | +++   | +    |       |       |       |         |          | Domain I / II |
| Erbitux |       |       |      | +     |       | +++   | +++     | +++      | Domain III    |
| Vectibix|       |       |      |       |       | +++   | +++     | +++      | Domain III    |

Fig. 8B

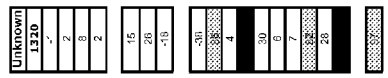
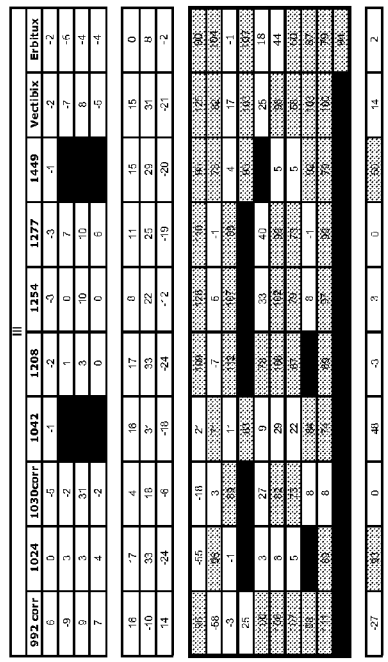
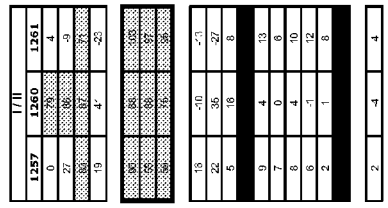
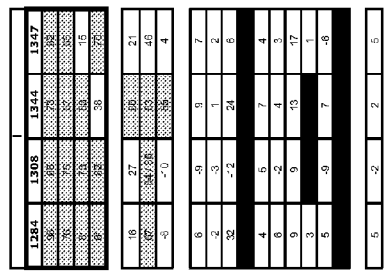
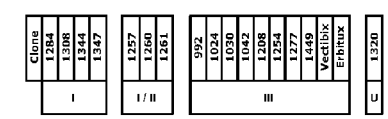
Fig. 9A
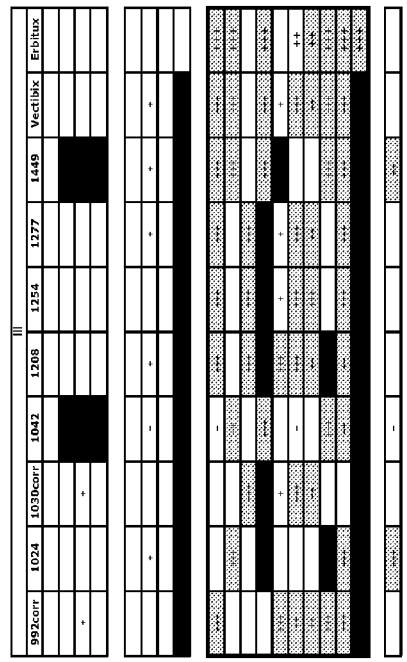
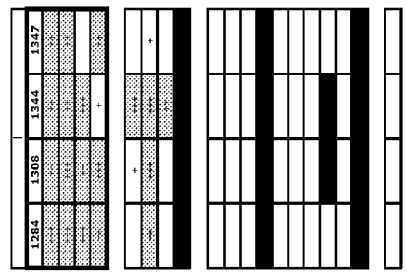
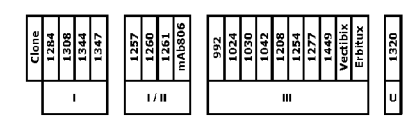
Fig. 9B

| Sample mAb | Inhibition Sample mAb | Rumax Reference cycle | Rumax Competition cycle |
|---|---|---|---|
| Domain III 992 | 1030 Vs. 992 -6 | 81 | 85^^ |
| Domain III 1024 | 992 + 1030 Vs. 1024 -26 | 100 | 126^^ |
| Domain I/II 1261 | 992 + 1030 + 1024 Vs. 1261 -13 | 157 | 177^^ |
| Domain I 1347 | 992 + 1030 + 1024 -5 | 75 | 79^^ |
| Unknown Domain 1361 | 992+1030+1024 Vs. 1361 -11 | 162 | 181^^ |

Fig. 11A

| Sample mAb | Antibody mix (N=6) 1261+1347+992+1024+1030+1361 | | | Antibody mix (N=6-1) Without tested sample mAb | | |
|---|---|---|---|---|---|---|
| | Inhibition Sample mAb | Rumax Reference Cycle | Rumax Competition Cycle | Inhibition Sample mAb | Rumax Reference Cycle | Rumax Competition Cycle |
| Domain I/II 1261 | 1261+1347+992+1024+1030+1361 Vs. 1261 95 | 135 | 7 | 1347+992+1024+1030+1361 Vs. 1261 -21 | 139 | 168^^ |
| Domain I 1347 | 1261+1347+992+1024+1030+1361 Vs. 1347 80 | 91 | 19 | 1261+992+1024+1030+1361 Vs. 1347 15 | 107 | 92 |
| Domain III 992 | 1261+1347+992+1024+1030+1361 Vs. 992 116 | 85 | -14* | 1261+1347+1024+1030+1361 Vs. 992 -56 | 71 | 111^^ |
| Domain III 1024 | 1261+1347+992+1024+1030+1361 113 | 110 | -14* | 1261+1347+992+1030+1361 Vs. 1024 -25 | 122 | 152^^ |
| Domain III 1030 | 1261+1347+992+1024+1030+1361 Vs. 1030 87 | 87 | 12 | 1261+1347+992+1024+1361 Vs. 1030 -10 | 74 | 82^^ |
| Unknown Domain 1361 | 1261+1347+992+1024+1030+1361 Vs. 1361 102 | 178 | -3* | 1261+1347+992+1024+1030 Vs. 1361 4 | 159 | 152 |

Fig. 11B

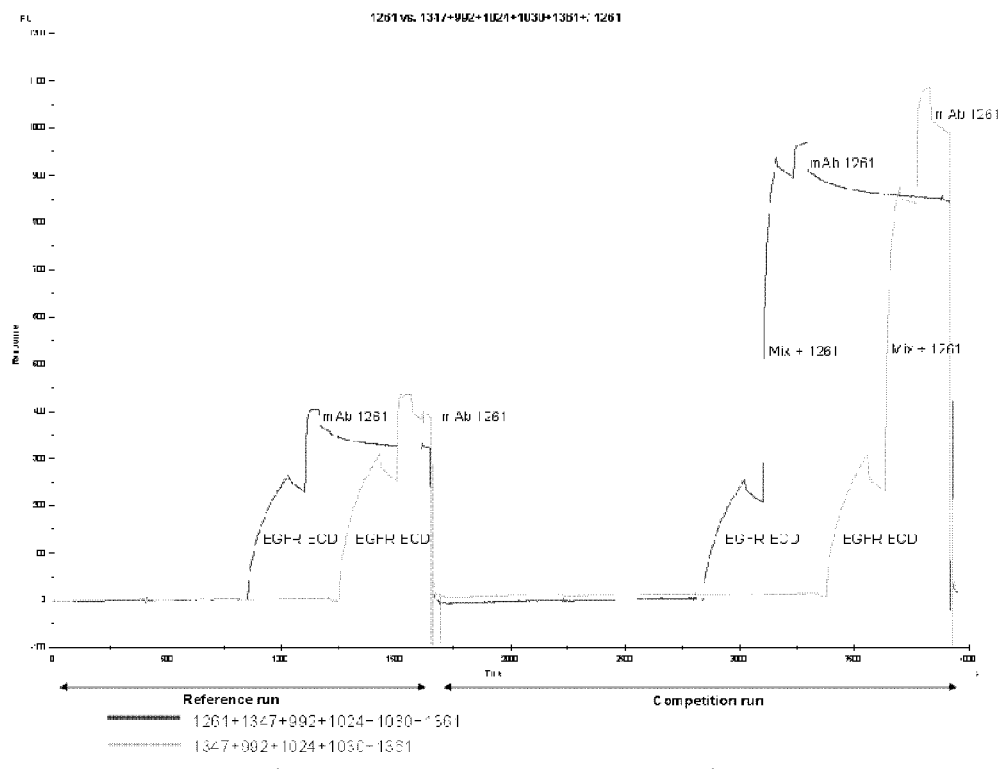
A) 1261 Vs. 1347+992+1024+1030+1361+/-1261
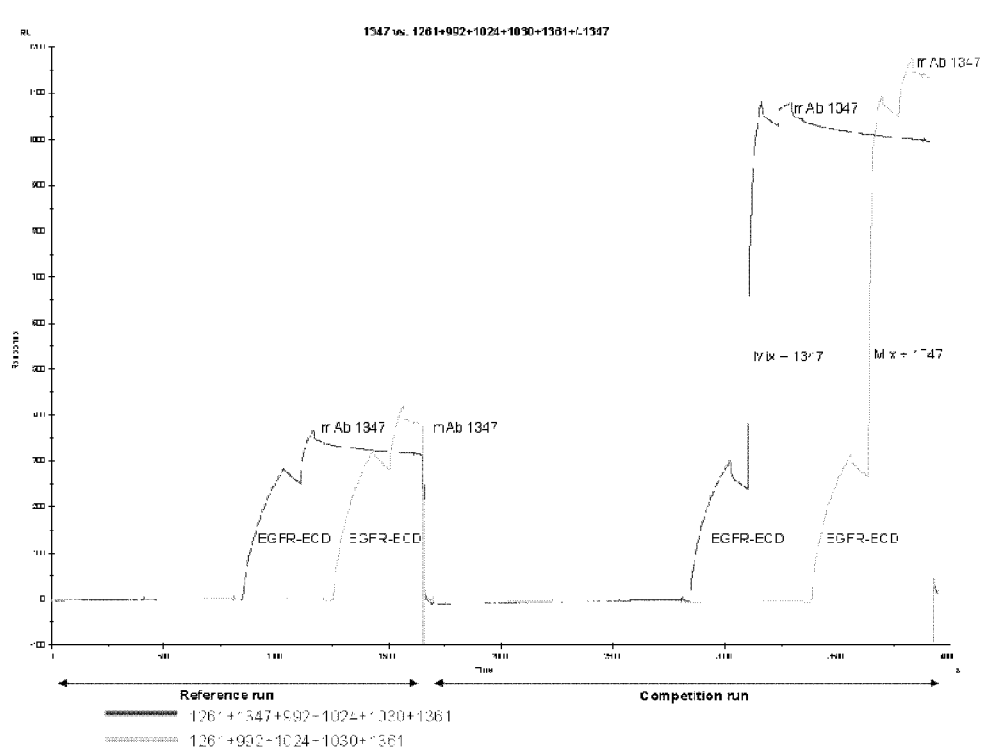
B) 1347 Vs. 1261+992+1024+1030+1361+/-1347
Fig. 11C

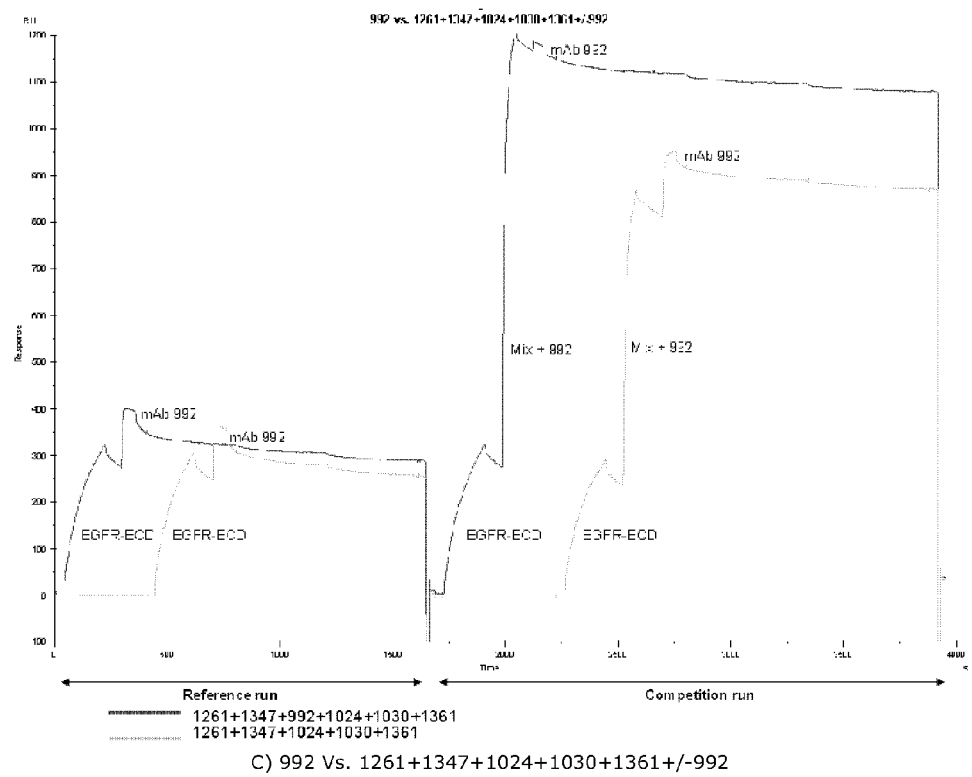
C) 992 Vs. 1261+1347+1024+1030+1361+/-992
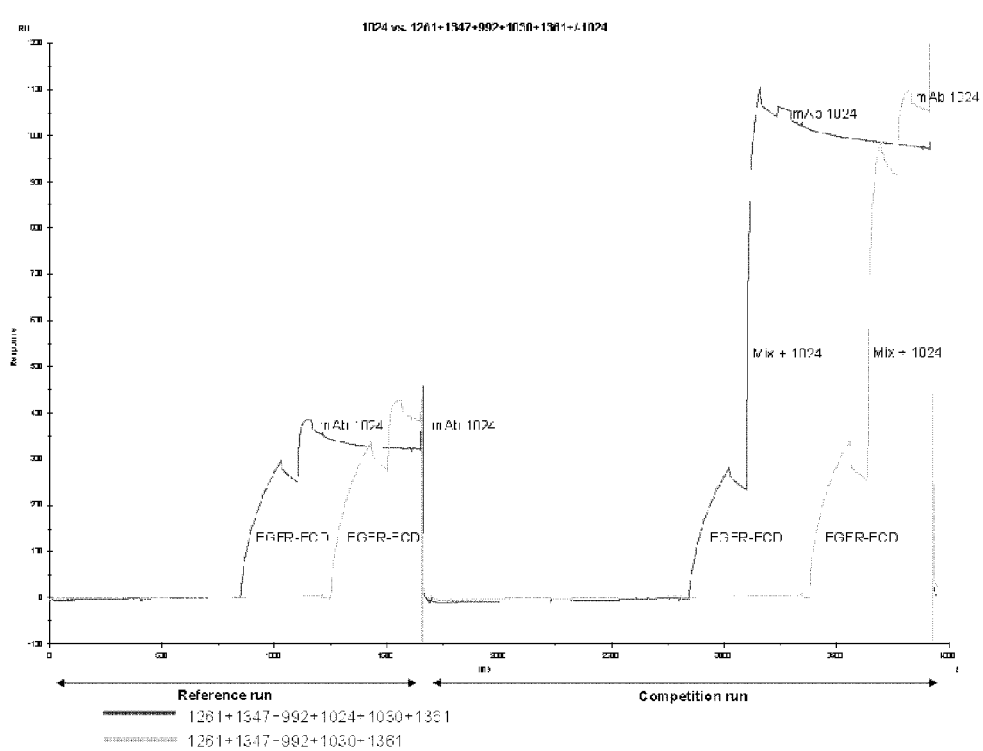
D) 1024 Vs. 1261+1347+992+1030+1361+/-1024
Fig. 11C (Cont.)

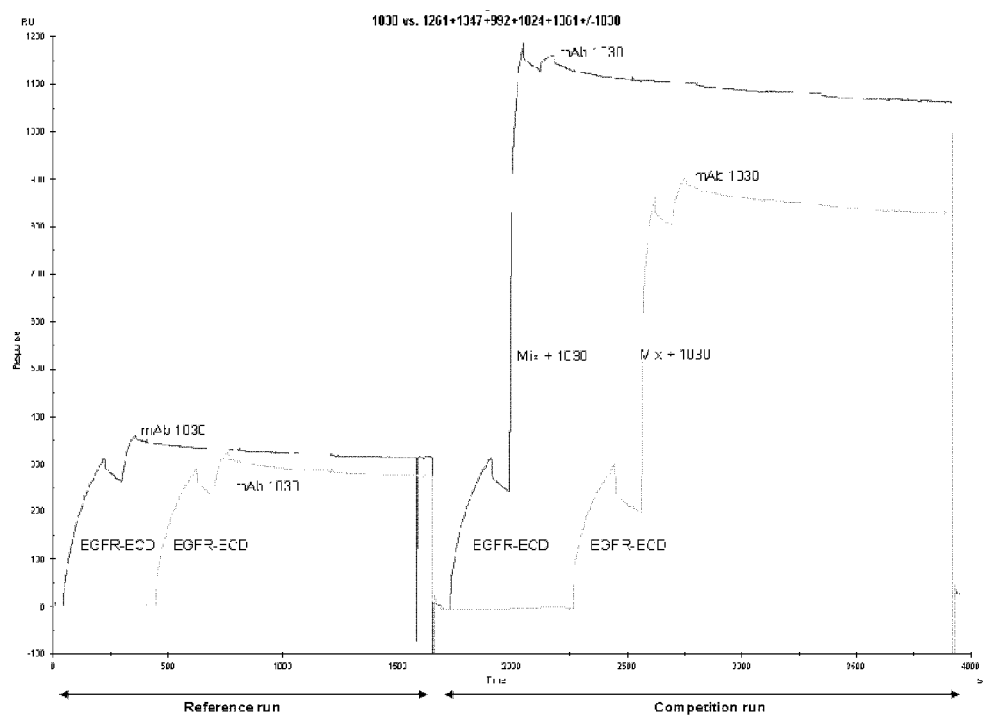
E) 1030 Vs. 1261+1347+992+1024+1361+/-1030
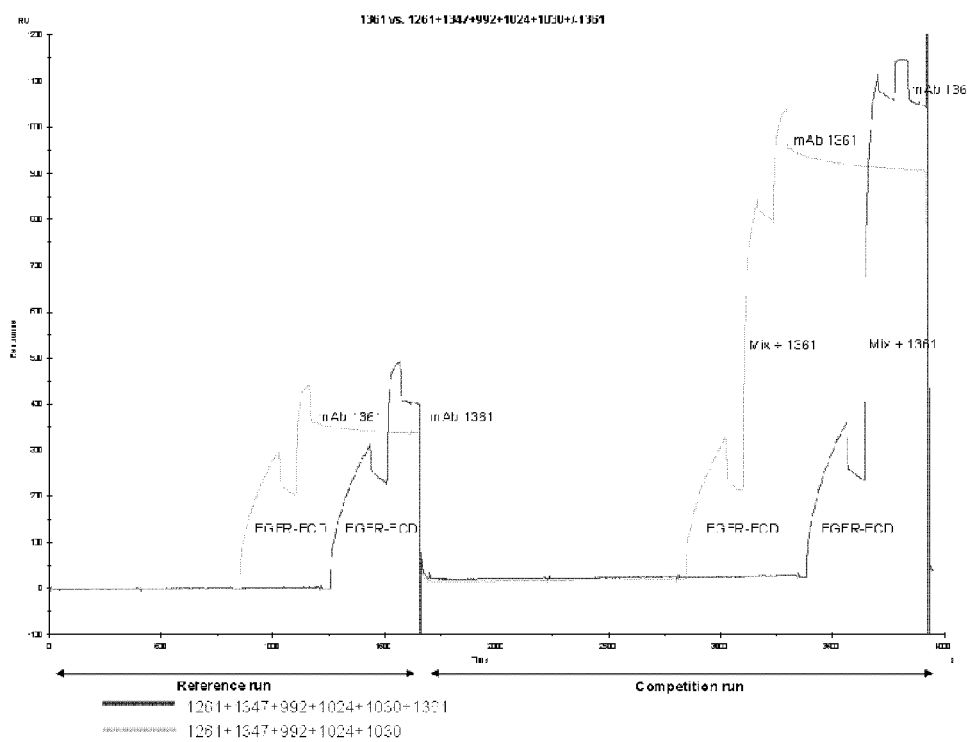
F) 1361 Vs. 1261+1347+992+1024+1030+/-1361
Fig. 11C (cont.)

| | | | |
|---|---|---|---|
| Domain I<br>1284 | 1261+1347+992+1024+1030+1361<br>Vs. 1284<br>75 | 68 | 17 |
| Domain I/II<br>1257 | 1261+1347+992+1024+1030+1361<br>Vs. 1257<br>106 | 107 | -7* |
| Unknown Domain<br>1183 | 1261+1347+992+1024+1030+1361<br>Vs. 1183<br>112 | 56 | -7* |
| Unknown Domain<br>1255 | 1261+1347+992+1024+1030+1361<br>Vs. 1255<br>107 | 79 | -5* |

Fig. 11D

```
ctggaggaaaagaaagtttgccaaggcacgagtaacaaactcacgcagttgggcacttttgaagatcatt
ttctcagcctccagaggatgttcaataactgtgaggtggtccttgggaatttggaaattacctacgtgca
gaggaattatgatcttccttcttaaagaccatccaggaggtggctggttatgtcctcatcgccctcaac
acagtggagcggattcctttggaaaacctgcagatcatcagaggaaacatgtactatgaaaattcctatg
ccttagcagtcttatctaactatgatgcaaataaaaccggactgaaggagctgcccatgagaaacttaca
ggaaatcctgcatggcgccgtgcggttcagcaacaaccctgccctgtgcaacgtggagagcatccagtgg
cgggacatagtcagcagcgagtttctcagcaacatgtcgatggacttccagaaccacctgggcagctgcc
aaaagtgtgatccaagctgtcccaatgggagctgctggggtgcaggagaggagaactgccagaaactgac
caaaatcatctgtgcccagcagtgctccgggcgctgccgcggcaagtccccagtgactgctgccacaac
cagtgtgccgcgggctgcacgggccccgggagagcgactgcctggtctgccgcaattccgagacgaag
ccacgtgcaaggacacctgccccccactgtctacaaccccaccacataccagatggatgtgaaccc
cgagggcaaatacagctttggtgccacctgcgtgaagaagtgtcccgtaattatgtgtgacagatcac
ggctcgtgcgtccgagcctgcggggccgacagctatgagatggaggaagacggcgtccgcaagtgtaaga
agtgcgaagggccttgccgcaaagtgtgtaatggaataggtattggtgaatttaaagacacactctccat
aaatgctacaaatattaaacacttcaaaaactgcacctccatcagtggcgatctccacatcctgccggtg
gcatttagggtgactccttcacacacactccgcctctggatccacaggaactggatattctgaaaaccg
taaggaaatcacagggttttttgctgattcaggcttggcctgaaaacaggacggacctccatgcttttga
gaacctagaaatcatacgtggcaggaccaagcaacacggtcagttttctcttgcggtcgtcagcctgaac
ataacatccttgggattacgctccctcaaggagataagcgatggagatgtgataaatttcaggaaacaaaa
atttgtgctatgcaaatacaataaactggaaaaaactgtttgggacctccagtcagaaaaccaaaattat
aagcaacagaggtgaaaacagctgcaaggccacgggccaggtctgccatgccttgtgctcccccgagggc
tgctggggccggagcccagggactgcgtctcctgccagaatgtcagccgaggcagagaatgcgtggaca
agtgcaacatcctggagggcgagccaagggagtttgtggagaactctgagtgcatacagtgccacccaga
atgcctgccccaggtcatgaacatcacctgcacaggacggggaccagacaactgtatccagtgtgcccac
tacattgacggccccactgcgtcaagacctgcccagcaggagtcatgggagaaaacaacacctggtct
ggaagtacgcagacgccggccacgtgtgccacctgtgccatccaaactgcacctacggatgcactgggcc
aggtcttgaaggctgtgcaaggaacgggcctaagatccatcc
```

Fig. 23A

```
LEEKKVCQGTSNKLTQLGTFEDHFLSLQRMFNNCEVVLGNLEITYVQRNYDLSFLKTIQEVAGYVLIALN
TVERIPLENLQIIRGNMYYENSYALAVLSNYDANKTGLKELPMRNLQEILHGAVRFSNNPALCNVESIQW
RDIVSSEFLSNMSMDFQNHLGSCQKCDPSCPNGSCWCAGEENCQKLTKIICAQQCSCRCRCKSPSDCCHN
QCAAGCTGPRESDCLVCRKFRDEATCKDTCPPLMLYNPTTYQMDVNPEGKYSFGATCVKKCPRNYVVTDH
GSCVRACGADSYEMEEDGVRKCKKCEGPCRKVCNGIGIGEFKDTLSINATNIKHFKNCTSISGDLHILPV
AFRGDSFTHTPPLDPQELDILKTVKEITGFLLIQAWPENRTDLHAFENLEIIRGRTKQHGQFSLAVVSLN
ITSLCLRSLKEISDGDVIISCNKNLCYANTINWKKLFCTSSQKTKIISNRCENSCKATCQVCHALCSPEC
CWGPEPRDCVSCQNVSRGRECVDKCNILEGEPREFVENSECIQCHPECLPQVMNITCTGRGPDNCIQCAH
YIDGPHCVKTCPAGVMGENNTLVWKYADAGHVCHLCHPNCTYGCTGPGLEGCARNGPKIPS
```

Fig. 23B

|  | (1) | 1 | 10 | 20 | 30 | 47 |
|---|---|---|---|---|---|---|
| Cynomolgus EGFR ECD | (1) | LEEKKVCQGTSNKLTQLGTFEDHFLSLQRMFNNCEVVLGNLEITYVQ | | | | |
| Human EGFR ECD | (1) | LEEKKVCQGTSNKLTQLGTFEDHFLSLQRMFNNCEVVLGNLEITYVQ | | | | |
| Consensus | (1) | LEEKKVCQGTSNKLTQLGTFEDHFLSLQRMFNNCEVVLGNLEITYVQ | | | | |

Section 2

|  | (48) | 48 | 60 | 70 | 80 | 94 |
|---|---|---|---|---|---|---|
| Cynomolgus EGFR ECD | (48) | RNYDLSFLKTIQEVAGYVLIALNTVERIPLENLQIIRGNMYYENSYA | | | | |
| Human EGFR ECD | (48) | RNYDLSFLKTIQEVAGYVLIALNTVERIPLENLQIIRGNMYYENSYA | | | | |
| Consensus | (48) | RNYDLSFLKTIQEVAGYVLIALNTVERIPLENLQIIRGNMYYENSYA | | | | |

Section 3

|  | (95) | 95 | 100 | 110 | 120 | 130 | 141 |
|---|---|---|---|---|---|---|---|
| Cynomolgus EGFR ECD | (95) | LAVLSNYDANKTGLKELPMRNLQEILHGAVRFSNNPALCNVESIQWR | | | | | |
| Human EGFR ECD | (95) | LAVLSNYDANKTGLKELPMRNLQEILHGAVRFSNNPALCNVESIQWR | | | | | |
| Consensus | (95) | LAVLSNYDANKTGLKELPMRNLQEILHGAVRFSNNPALCNVESIQWR | | | | | |

Section 4

|  | (142) | 142 | 150 | 160 | 170 | 188 |
|---|---|---|---|---|---|---|
| Cynomolgus EGFR ECD | (142) | DIVSSDFLSNMSMDFQNHLGSCQKCDPSCPNGSCWGAGEENCQKLTK | | | | |
| Human EGFR ECD | (142) | DIVSSDFLSNMSNDFQNHLGSCQKCDPSCPNGSCWGAGEENCQKLTK | | | | |
| Consensus | (142) | DIVSSDFLSNMSNDFQNHLGSCQKCDPSCPNGSCWGAGEENCQKLTK | | | | |

Section 5

|  | (189) | 189 | 200 | 210 | 220 | 235 |
|---|---|---|---|---|---|---|
| Cynomolgus EGFR ECD | (189) | IICAQQCSGRCRGKSPSDCCHNQCAAGCTGPRESDCLVCRKFRDEAT | | | | |
| Human EGFR ECD | (189) | IICAQQCSGRCRGKSPSDCCHNQCAAGCTGPRESDCLVCRKFRDEAT | | | | |
| Consensus | (189) | IICAQQCSGRCRGKSPSDCCHNQCAAGCTGPRESDCLVCRKFRDEAT | | | | |

Section 6

|  | (236) | 236 | 250 | 260 | 270 | 282 |
|---|---|---|---|---|---|---|
| Cynomolgus EGFR ECD | (236) | CKDTCPPLMLYNPTTYQMDVNPEGKYSFGATCVKKCPRNYVVTDHGS | | | | |
| Human EGFR ECD | (236) | CKDTCPPLMLYNPTTYQMDVNPEGKYSFGATCVKKCPRNYVVTDHGS | | | | |
| Consensus | (236) | CKDTCPPLMLYNPTTYQMDVNPEGKYSFGATCVKKCPRNYVVTDHGS | | | | |

Section 7

|  | (283) | 283 | 290 | 300 | 310 | 329 |
|---|---|---|---|---|---|---|
| Cynomolgus EGFR ECD | (283) | CVRACGADSYEMEEDGVRKCKKCEGPCRKVCNGIGIGEFKDSLSINA | | | | |
| Human EGFR ECD | (283) | CVRACGADSYEMEEDGVRKCKKCEGPCRKVCNGIGIGEFKDSLSINA | | | | |
| Consensus | (283) | CVRACGADSYEMEEDGVRKCKKCEGPCRKVCNGIGIGEFKDSLSINA | | | | |

Section 8

|  | (330) | 330 | 340 | 350 | 360 | 376 |
|---|---|---|---|---|---|---|
| Cynomolgus EGFR ECD | (330) | TNIKHFKNCTSISGDLHILPVAFRGDSFTHTPPLDPQELDILKTVKE | | | | |
| Human EGFR ECD | (330) | TNIKHFKNCTSISGDLHILPVAFRGDSFTHTPPLDPQELDILKTVKE | | | | |
| Consensus | (330) | TNIKHFKNCTSISGDLHILPVAFRGDSFTHTPPLDPQELDILKTVKE | | | | |

Section 9

|  | (377) | 377 | 390 | 400 | 410 | 423 |
|---|---|---|---|---|---|---|
| Cynomolgus EGFR ECD | (377) | ITGFLLIQAWPENRTDLHAFENLEIIRGRTKQHGQFSLAVVSLNITS | | | | |
| Human EGFR ECD | (377) | ITGFLLIQAWPENRTDLHAFENLEIIRGRTKQHGQFSLAVVSLNITS | | | | |
| Consensus | (377) | ITGFLLIQAWPENRTDLHAFENLEIIRGRTKQHGQFSLAVVSLNITS | | | | |

Fig.24

```
                         (424) 424       430       440       450       460       470
Cynomolgus EGFR ECD (424) LGLRSLKEISDGDVIISGNKNLCYANTINWKKLFGTSSQKTKIISNR
    Human EGFR ECD (424) LGLRSLKEISDGDVIISGNKNLCYANTINWKKLFGTSGQKTKIISNR
         Consensus (424) LGLRSLKEISDGDVIISGNKNLCYANTINWKKLFGTS QKTKIISNR
                                                                         Section 11
                         (471) 471       480       490       500            517
Cynomolgus EGFR ECD (471) GENSCKATGQVCHALCSPEGCWGPEPRDCVSCQNVSRGRECVDKCNL
    Human EGFR ECD (471) GENSCKATGQVCHALCSPEGCWGPEPRDCVSCRNVSRGRECVDKCNL
         Consensus (471) GENSCKATGQVCHALCSPEGCWGPEPKDCVSC NVSRGRECVDKCNL
                                                                         Section 12
                         (518) 518       530       540       550            564
Cynomolgus EGFR ECD (518) LEGEPREFVENSECIQCHPECLPQVMNITCTGPGPDNCIQCAHYIDG
    Human EGFR ECD (518) LEGEPREFVENSECIQCHPECLPQAMNITCTGRGPDNCIQCAHYIDG
         Consensus (518) LEGEPREFVENSECIQCHPECLPQ MNITCTGRGPDNCIQCAHYIDG
                                                                         Section 13
                         (565) 565    570       580       590       600       611
Cynomolgus EGFR ECD (565) PHCVKTCPAGVMGENNTLVWKYADAGHVCHLCHPNCTYGCTGPGLEG
    Human EGFR ECD (565) PHCVKTCPAGVMGENNTLVWKYADAGHVCHLCHPNCTYGCTGPGLEG
         Consensus (565) PHCVKTCPAGVMGENNTLVWKYADAGHVCHLCHPNCTYGCTGPGLEG
                                                                         Section 14
                         (612) 612       622
Cynomolgus EGFR ECD (612) CARNGPKIPS-
    Human EGFR ECD (612) CPTNGPKIPS-
         Consensus (612) C  NGPKIPS
```

Fig.24 (Cont.)

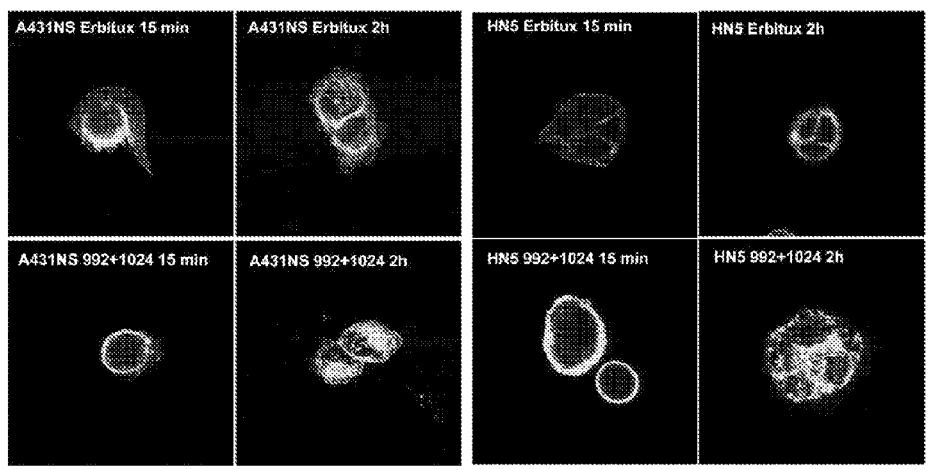
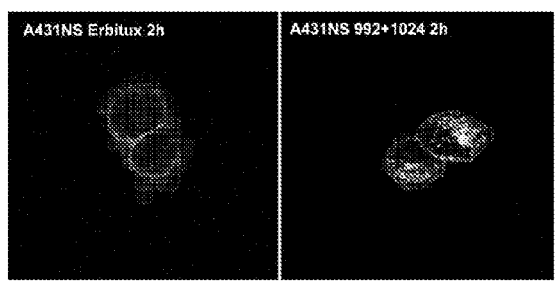
Fig. 29
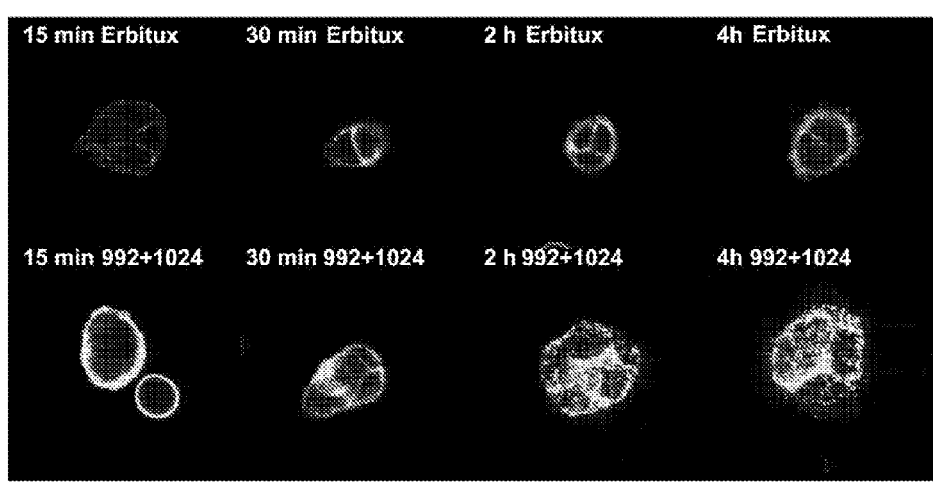
Fig. 30 atgcgaccctccgggacggccggggccgcgctcctggcgctgctggctgcgctttgccccgcgagtcgggctctggaggaaaa
gaaagtttgccaaggcacgagtaacaaactcacgcagttgggcacttttgaagatcatttctcagcctccagaggatgttca
ataactgtgaggtggtccttgggaatttggaaattacctacgtgcagaggaattatgatctttccttcttaaagaccatccag
gaggtggctggttatgtcctcatcgccctcaacacagtggagcggattcctttggaaaacctgcagatcatcagaggaaacat
gtactatgaaaattcctatgccttagcagtcttatctaactatgatgcaaataaaaccggactgaaggagctgcccatgagaa
acttacaggaaatcctgcatggcgcgtgcggttcagcaacaaccctgccctgtgcaacgtggagagcatccagtggcgggac
atagtcagcagcgagtttctcagcaacatgtcgatggacttccagaaccacctgggcagctgccaaaagtgtgatccaagctg
tcccaatgggagctgctgggtgcaggagaggagaactgccagaaactgaccaaaatcatctgtgcccagcagtgctccgggc
gctgccgcggcaagtccccagtgactgctgccacaaccagtgtgccgcgggctgcacgggccccggagagcgactgcctg
gtctgccgcaaattccgagacgaagccacgtgcaaggacacctgcccccactcatgctctacaaccccaccatacccagat
ggatgtgaaccccgagggcaaatacagctttggtgccacctgcgtgaagaagtgtcccccgtaattatgtggtgacagatcacg
gctcgtgctccgagcctgcggggccgacagctatgagatggaggaagacggcgtccgcaagtgtaagaagtgcgaagggct
tgccgcaaagtgtgtaatggaataggtattggtgaatttaaagacacactctccataaatgctacaaatattaaacacttcaa
aaactgcacctccatcagtggcgatctccacatcctgccggtggcatttaggggtgactccttcacacacactccgcctctgg
atccacaggaactggatattctgaaaaccgtaaggaaatcacagggttttgctgattcaggcttggcctgaaaacaggacg
gacctccatgctttgagaacctagaaatcatacgtggcaggaccaagcaacacggtcagtttttctcttgcggtcgtcagcct
gaacataacatccttgggattacgctccctcaaggagataagcgatggagatgtgataatttcaggaaacaaaaatttgtgct
atgcaaatacaataaactggaaaaaactgtttgggacctccagtcagaaaaccaaaattataagcaacagaggtgaaaacagc
tgcaaggccacgggccaggtctgccatgccttgtgctccccgagggctgctggggcccggagcccagggactgcgtctcctg
tcagaatgtcagccgaggcagagaatgcgtggacaagtgcaacatcctggagggcgagccaaggagtttgtggagaactctg
agtgcatacagtgtcaccagaatgcctgcccaggtcatgaacatcacctgcacaggacggggaccagacaactgtatccag
tgtgcccactacattgacggccccactgcgtcaagacctgcccagcaggagtcatgggagaaaacaacccctggtctggaa
gtacgcagacgccggccacgtgtgccacctgtgccatccaaactgcacctacggatgcactgggccaggtcttgaaggctgtg
caaggaacgggcctaagatcccatccatcgccactgggatggtgggggccctcctcttgctgctggtggtggccctggggatc
ggcctcttcatgcgaaggcgccacatcgttcggaagcgcacactgcggaggctgctgcaggagagggagcttgtggagcctct
tacgcccagtggagaagctcccaaccaagctctcttgaggatcttgaaggaaactgaattcaagaagatcaaagtgctgggct
ccggtgcgttcggaactgtgtataagggactctggatcccagaaggtgagaaagttaaaattcccgtcgctatcaaggaatta
agagaagcaacatctccgaaagccaacaaggaaatcctcgatgaagcctacgtgatggccagcgtggacaaccccatgtgtg
ccgcctgctgggcatctgcctcacctccaccgtgcagctcattacgcagctcatgcccttcggctgcctcctggactacgtcc
gggaacacaaggacaatatcggctcccagtacctgctcaactggtgtgtgcagattgcaaagggcatgaactacttggaggac
cggcgcttggtgcaccgcgacctggcagccaggaacgtactggtgaaaacgccacagcatgtcaagatcacagatttgggct
ggccaaactgctgggtgcagaagagaaagaataccatgcagaaggaggcaaagtgcctatcaagtggatgcgttggaatcaa
ttttacaccgaatttatacccaccagagtgatgtctggagctacggggtgaccgtttgggagttgatgacctttggatccaag
ccatatgacggaatccctgccagcgagatctcctccatcctggagaaaggagaacgcctccccagccacccatatgtaccat
cgatgtctacatgatcatggtcaagtgctggatgatagacgcagatagtcgcccaaagttccgtgagttgatcattgaattct
ccaaaatggcccgagaccccagcgctaccttgttattcaggggatgaaagaatgcattgccaagccctacagactccaac
ttctaccgtgccctgatggatgaagaagacatggacgacgtggtgatgccgacgagtacctcatcccacagcaaggcttctt
cagcagccctccacgtcacggactccctcctgagctctctgagtgcaactagcaacaattccactgtggcttgcattgata

```
gaaatgggctgcaaagctgttccatcaaggaagacagcttcttacagcgatacagctcagaccccacaggcgccttgactgag
gacagcatagacgacaccttcctcccagtgcctgaatacataaaccagtctgttcccaaaaggcccgctggctctgtgcagaa
tcctgtctatcacaatcagcctctgaaccctgcgcccagcagagacccacactaccaggaccccacagcaccgcagtgggca
accccgagtatctcaacactgtccagcccacctgtgtcaacagcacattcgacagccctgctcattgggcccagaaaggcagc
caccaaattagcctggacaaccctgactaccagcaggacttcttccccaaggaagccaagccaaatggcatcttcaagggctc
cacagctgaaaatgcagaatacctaagggtcgcaccacaaagcagtgaatttattggagcatga
```

Fig. 34A (Cont.)

```
MRPSGTAGAALLALLAALCPASRALEEKKVCQGTSNKLTQLGTFEDHFLSLQRMFNNCEV
VLGNLEITYVQRNYDLSFLKTIQEVAGYVLIALNTVERIPLENLQIIRGNMYYENSYALA
VLSNYDANKTGLKELPMRNLQEILHGAVRFSNNPALCNVESIQWRDIVSSEFLSNMSMDF
QNHLCSCQKCDPSCPNCSCWGACEENCQKLTKIICAQQCSCRCRCKSPSDCCHNQCAACC
TGPRESDCLVCRKFRDEATCKDTCPPLMLYNPTTYQMDVNPEGKYSFGATCVKKCPRNYV
VTDHGSCVRACGADSYEMEEDGVRKCKKCEGPCRKVCNGIGIGEFKDTLSINATNIKHFK
NCTSISGDLHILPVAFRGDSFTHTPPLDPQELDILKTVKEITGFLLIQAWPENRTDLHAF
ENLEIIRGRTKQHGQFSLAVVSLNITSLGLRSLKEISDGDVIISGNKNLCYANTINWKKL
FGTSSQKTKIISNRGENSCKATGQVCHALCSPEGCWGPEPRDCVSCQNVSRGRECVDKCN
ILECEPREFVENSECIQCHPECLPQVMNITCTCRCPDNCIQCAHYIDGPHCVKTCPACVM
GENNTLVWKYADAGHVCHLCHPNCTYGCTGPGLEGCARNGPKIPSIATGMVGALLLLLVV
ALGIGLFMRRRHIVRKRTLRRLLQERELVEPLTPSGEAPNQALLRILKETEFKKIKVLGS
GAFGTVYKGLWIPEGEKVKIPVAIKELREATSPKANKEILDEAYVMASVDNPHVCRLLGI
CLTSTVQLITQLMPFGCLLDYVREHKDNIGSQYLLNWCVQIAKGMNYLEDRRLVHRDLAA
RNVLVKTPQHVKITDFGLAKLLGAEEKEYHAEGGKVPIKWMALESILHRIYTHQSDVWSY
GVTVWELMTFGSKPYDGIPASEISSILEKGERLPQPPICTIDVYMIMVKCWMIDADSRPK
FRELIIEFSKMARDPQRYLVIQGDERMHLPSPTDSNFYRALMDEEDMDDVVDADEYLIPQ
QGFFSSPSTSRTPLLSSLSATSNNSTVACIDRNGLQSCSIKEDSFLQRYSSDPTGALTED
SIDDTFLPVPEYINQSVPKRPAGSVQNPVYHNQPLNPAPSRDPHYQDPHSTAVGNPEYLN
TVQPTCVNSTFDSPAHWAQKGSHQISLDNPDYQQDFFPKEAKPNCIFKCSTAENAEYLRV
APQSSEFIGA
```

Fig. 34B

```
hu992VH    QVQLVQSGA-EVKKPGASVKVSCKASGYTFTSYW----MHWVRQAPGQGLEWMGIIYPGS 60
chi992VH   EVQLQQPGS-ELVRPGASVKLSCKASGYTFTSYW----MHWVKQRPGQGLEWIGNIYPGS 60
           :*** *.*: *: :****:****** **:* *******:* ***** hu992VH    RST--SYAQKFQ-GRVTMTRDTSTSTVYMELSSLRSEDTAVYYCTRNGDYYVSSGDAMDY 117
chi992VH   RST--NYDEKFK-SKATLTVDTSSSTAYMQLSSLTSEDSAVYYCTRNGDYYVSSGDAMDY 117
           ***  .* :**: .:.*:* *:.:*: *:*********** hu992VH    WGQGTLVTVS 127
chi992VH   WGQGTSVTVS 127
           *** ** hu992VL    DIQMTQSPSSLSASVGDRVTITCRASQDIGNY------LAWYQQKPGKVPKLLIYYTS-- 60
chi992VL   DIQMTQTTSSLSASLGDRVTISCRTSQDIGNY------LNWYQQKPDGTVKLLIYYTS-- 60
           ** ***:.******:*****:**:******        * ******.  *********

Hu992VL    -----TLQSGVP-SRFSGSG-SGTDFTLTISSLQPEDVATYYCQHYNT----VPPTFGGG TKV 124
chi992VL   -----RLHSGVP-SRFSGSG-SGTDFSLTINNVEQEDVATYFCQHYNT----VPPTFGGG TKL 124
                :**** ******* ******:***. .::******:*****    *******:

hu992VL    EIK 127
chi992VL   EIK 127
           ***
```

Fig. 41A

```
hu1024VH   QVQLVQSGA-EVKKPGASVKVSCKASGYTFTSHW----MHWVRQAPGQGLEWMGWINPSS 60
chi1024VH  QVQLQQPGA-ELVEPGGSVKLSCKASGYTFTSHW----MHWVKQRPGQGLEWIGEINPSS 60
           **** *.* :. *:****** **:* ***** : *** hu1024VH   GRN--NYAQKFQ-GRVTMTRDTSISTAYMELSRLTSDDTAVYYCARYYGYDE-AMDYWGQG 121
chi1024VH  GRN--NYNEKFK-SKATLTVDKSSSTAYMQFSSLTSEDSAVYYCVRYYGYDE-AMDYWGQG 121
           *   :**: .:.*:* *.* ***** :* **:** ******* hu1024VH   TSVTVS 127
chi1024VH  TLVTVS 127
           * **** chi1024VL  DIVMTQAAFSNPVTLGTSASISCRSSKSLLHSNGITY-LYWYLQKPGQSPQLLIYQMS-- 65
hu1024VL   DIVMTQSPLSLPVTPGEPASISCRSSKSLLHSNGITY-LDWYLQKPGQSPQLLIYQMS-- 65
           ******:..:* *** * .************* * ******************* chi1024VL  -----NLASGVP-DRFSSSG--SGTDFTLRISRVEAEDVGVYYCAQNLE----LPYTFGGGTKL 124
hu1024VL   -----NRASGVP-DRFSGSG--SGTDFTLKISRVEAEDVGVYYCAQNLE----LPYTFGGGTKV 124
                * ***** ****.**  ********:*********************  **********:

chi1024VL  EIK 127
hu1024VL   EIK 127
           ***
```

METHODS USING RECOMBINANT ANTI-EPIDERMAL GROWTH FACTOR RECEPTOR ANTIBODY COMPOSITIONS

CROSS-REFERENCE TO RELATED APPLICATIONS

This application is the National Stage of International Application Number PCT/DK2009/050217, filed Aug. 27, 2009, which claims the benefit of U.S. Provisional Application No. 61/136,391, filed Sep. 2, 2008, and Danish Application No. PA 2008 01202, filed Aug. 29, 2008, which are incorporated by reference herein.

REFERENCE TO A SEQUENCE LISTING SUBMITTED ELECTRONICALLY VIA EFS-WEB

The content of the electronically submitted sequence listing (Name: amended_sequencelisting_ascii.txt; Size: 147,535 bytes; and Date of Creation: Feb. 25, 2011) is herein incorporated by reference in its entirety.

FIELD OF THE INVENTION

The invention relates to the field of recombinant antibodies for use in human cancer therapy.

BACKGROUND OF THE INVENTION

Epidermal Growth Factor Receptor (EGFR) plays an important role in cellular proliferation as well as apoptosis, angiogenesis and metastatic spread, processes that are crucial to tumour progression (Salomon et al, Crit. Rev. Oncology/Haematology, 19:183-232 (1995); Wu et al, J. Clin. Invest., 95:1897-1905 (1995); Karnes et al, Gastroenterology, 114: 930-939 (1998); Woodburn et al, Pharmacol. Therap. 82: 241-250 (1999); Price et al, Eur. J. Cancer, 32A:1977-1982 (1996)). Indeed, studies have shown that EGFR-mediated cell growth is increased in a variety of solid tumours including non-small cell lung cancer, prostate cancer, breast cancer, gastric cancer, and tumours of the head and neck (Salomon D S et al, Critical Reviews in Oncology/Haematology, 19:183-232 (1995)). Furthermore, excessive activation of EGFR on the cancer cell surface is now known to be associated with advanced disease, the development of a metastatic phenotype and a poor prognosis in cancer patients (Salomon D S et al., Critical Reviews in Oncology/Haematology 19:183-232 (1995)).

Furthermore, EGFR expression is frequently accompanied by the production of EGFR-ligands, TGF-alpha and EGF among others, by EGFR-expressing tumour cells which suggests that an autocrine loop participates in the progression of these cells (Baselga, et al. (1994) Pharmac. Therapeut. 64: 127-154; Modjtahedi, et al. (1994) Int. J. Oncology. 4: 277-296). Blocking the interaction between such EGFR ligands and EGFR therefore can inhibit tumor growth and survival (Baselga, et al. (1994) Pharmac. Therapeut. 64: 127-154).

The EGFR is a membrane bound glycoprotein with a molecular weight of approximately 170 kDa. EGFR consists of a glycosylated external ligand-binding domain (621 residues) and a cytoplasmic domain (542 residues) connected by a short 23 amino acid transmembrane linker. The extracellular part of EGFR contains 25 disulfide bonds and 12 N-linked glycosylation sites, and is generally considered to consist of four sub-domains. X-ray crystal structures of the EGFR suggest that the receptor adopts both an autoinhibited tethered— conformation that cannot bind EGF (Ferguson et al, Mol Cell, 2003, vol 11: 507-517) and an active conformation that may mediate EGF ligand binding and receptor dimerisation (Garret et al, Cell 2002, vol 110:763-773; Ogiso et al, Cell, 2002, vol 110:775-787). In particular, domain I and domain III have been suggested to provide additive contributions for formation of a high-affinity ligand binding site. Domains II and IV are cysteine-rich laminin-like regions that stabilise protein folding and contain a possible EGFR dimerisation interface.

EGFR is known to exist in a number of different conformations on the cell surface, where the tethered or locked confirmation is the most frequent. The tethered conformation cannot dimerise and hence is inactive. The therapeutic antibody Erbitux is known to stabilise the tethered conformation by binding to domain III and sterically hampering the receptor in reaching the untethered state. However, some receptors may still be able to adopt the untethered conformation, bind ligand and dimerise. A monoclonal antibody (mAb) will typically only be effective in binding against one of the conformations and therefore cannot effectively target cancer cells exhibiting other conformations or cancer cells exhibiting a variety of conformations.

Monoclonal antibodies (mAbs) directed to the ligand-binding domain of EGFR can block the interaction with EGFR ligands and, concomitantly, the resultant intracellular signaling pathway.

Erbitux™ (Cetuximab) is a recombinant, human/mouse chimeric monoclonal antibody that binds specifically to the extracellular domain of the human (EGFR). Erbitux is composed of the Fv regions of a murine anti-EGFR antibody with human IgG1 heavy and kappa light chain constant regions and has an approximate molecular weight of 152 kDa. Erbitux is produced in mammalian cell culture (murine myeloma). Erbitux is approved for the treatment of patients with metastatic colorectal cancer and whose tumor expresses EGFR. In addition, Erbitux is used in combination with radiation therapy to treat patients with squamous cell cancer of the head and neck that cannot be removed by surgery or as second line treatment of squamous cell cancer of the head and neck that have failed standard platinum-based therapy.

Vectibix™ (panitumumab) is a recombinant, human IgG2 kappa monoclonal antibody that binds specifically to the human EGFR. Vectibix has an approximate molecular weight of 147 kDa. Panitumumab is produced in genetically engineered mammalian cells (Chinese Hamster Ovary). Vectibix is approved for the treatment of patients with metastatic colorectal cancer and whose tumor expresses EGFR with disease progression on or following fluoropyrimidine-, oxaliplatin-, and irinotecan-containing chemotherapy regimens.

Cetuximab, marketed by Imclone under the trademane Erbitux, is described in U.S. Pat. No. 4,943,533 and WO 96/40210. Panitumumab, marketed by Abgenix under the tradename Vectibix, is described in U.S. Pat. No. 6,235,883. Zalutuzumab (Humax-EGFR) is another anti-EGFR antibody currently undergoing clinical development. The antibody has been developed by Genmab and is described in WO 02/100348 and WO 2004/056847. Cetuximab, Panitumumab, and Zalutumumab bind the same epitope on EGFR.

Nimotuzumab (TheraCIM hR3) described in U.S. Pat. No. 5,891,996 and U.S. Pat. No. 6,506,883 is approved for treatment of cancer in a number of countries around the world but not in Europe or the US.

Further monoclonal anti-EGFR antibodies that are or have been under clinical development include:
  ICR62 developed by The Institute of Cancer Research. The antibody is described in WO 95/20045.
  mAb806, which is a monoclonal antibody directed against a mutant form of EGFR, (EGFR vIII). The antibody is developed by Ludwig Institute of Cancer Research and is described in WO 02/092771.

Matuzumab (EMD72000) being developed by Merck-Serono is described in WO 02/66058. The murine precursor, mAb425 is described in WO 92/15683.

It is known in the art that prolonged exposure to a monoclonal antibody may cause selection of resistant tumours. Such a situation may arise in patients receiving prolonged treatment with a monoclonal antibody. With the widespread use of Erbitux (from Imclone) and Vectibix (from Abgenix), two monoclonal antibodies binding the same epitope, it is likely clinicians will experience tumours with resistance to these antibodies. Further monoclonal antibodies are in clinical testing and may enter the market in the coming years, Among these are Humax-Egfr (Zalutumumab from Genmab) that binds the same epitope as Erbitux and Vectibix. It can be assumed that a tumour being resistant to any of these three monoclonal antibodies is also resistant to the two others.

Likewise, there may be clinical examples of tumours being resistant to any of the other monoclonal anti-EGFR antibodies that are currently in clinical testing: Nimotuzumab (YM Biosciences, Cuba), Matuzumab (Merck KGaA), mAb806 (Ludwig Institute), and ICR62 (Institute of Cancer Research).

Complete or partial tumour resistance to any of these monoclonal antibodies may be assayed using a sample isolated from a patient, so that it can be known a priori whether the tumour is resistant or not.

Apart from resistance to monoclonal antibody therapy (or refractory tumours) another problem in treating the EGFR expressing cancers is tumour recurrence or progression following surgery, radiation therapy and/or medical treatment with chemotherapeutics, tyrosine Kinase inhibitors (TKIs) and/or monoclonal antibodies. There is a presumption that a recurrent or progressive tumour should be treated with a different medicament as the recurrence or progression may be the result of resistance or at least partial resistance. Thus, there is a need for a second or third line treatment of cancer that is non-responsive to an earlier anti-EGFR antibody treatment or progresses following said earlier anti-EGFR antibody treatment.

SUMMARY OF THE INVENTION

The present inventors have discovered that a cancer cell line being resistant to Erbitux (Cetixumab) can be treated effectively in vitro with an antibody composition of the present invention, whereas exposure of the resistant cell line to Vetibix (Panitumumab) is as ineffective as is treatment with Erbitux. It is expected that Zalutumumab will also be ineffective against this cell line. These results have led to the conclusion that an antibody composition of the present invention is effective against Erbitux, Vectibix and Zalutumumab resistant tumours. Thus an antibody composition of the present invention can be used to treat patients that do not respond to either of these products. Likewise, an antibody composition of the present invention can be used to treat tumours that are from the beginning resistant to either of these monoclonal antibodies. Resistance to a monoclonal antibody such as Erbitux can be assayed in vitro using methods described in Example 21. Thus when a cancer cell line proliferates in medium containing 10 µg/mL of Erbitux, it is considered partially resistant to Erbitux. Resistance to Panitumumab and Zalutumumab can be assayed in the same way.

Based on these observations the inventors also contemplate the use of an antibody composition of the present invention for the treatment of cancer that is resistant or partially resistant to any of the other anti-EGFR antibodies that are currently under development, including but not limited to Cetuximab, panitumumab, Zalutumumab, nimotuzumab, ICR62, mAb806, Matuzumab, and antibodies capable of binding the same epitope as any of these.

The results have been confirmed by an in vivo study (Example 23), where an aggressive cancer cell line has been implanted into mice. Following initial treatment with Erbitux, partial responders were selected and exposed either to prolonged treatment with Erbitux or to treatment with an antibody composition of the present invention. The latter resulted in rapid reduction in the size of tumours, whereas continued Erbitux treatment resulted in maintained tumour size. The preclinical efficacy is achieved even though there is a partial overlap in binding between Erbitux and antibodies 1024 and 992 of the present invention. Thus immediately after shifting from Erbitux to 1024/992 therapy, there will be residual Erbitux in the tumours, and there will be competition in binding between Erbitux and the two antibodies of the composition of the present invention potentially reducing the efficacy of the antibody composition of the invention. However this does not significantly affect the efficacy of the 1024/992 treatment.

An in vivo study has also confirmed (Example 25) that Erbitux resistant cells can be efficiently treated with the combination of antibodies of the present invention. Thus, the acquired resistance mechanism against Erbitux does not affect the efficacy of the antibody composition of the present invention.

In conclusion, an antibody composition of the invention can be used to treat cancer that is resistant or partially resistant to a monoclonal anti-EGFR antibody such as Erbitux, and to treat cancer in a subject that has received treatment with a monoclonal anti-EGFR antibody such as Erbitux in a previous treatment regimen.

Based on the identical binding of Erbitux, Vectibix and Zalutumumab, it is expected that similar results can be achieved for these three mAbs. Based on these observations, the inventors also contemplate the use of an antibody composition of the present invention in the treatment of cancer that has previously been treated with another monoclonal anti-EGFR antibody including but not limited to Cetuximab, panitumumab, Zalutumumab, nimotuzumab, ICR62, mAb806, Matuzumab, and antibodies capable of binding the same epitope as any of these. The efficacy of such treatment can be verified in a pre-clinical study similar to the study described in Example 23.

Furthermore, the present inventors have determined that recurring tumour growth following treatment with an antibody composition of the present invention can be successfully eliminated using an antibody composition of the present invention. This has been demonstrated in the preclinical study described in Example 22. Recurring tumours were eliminated as efficiently as the originally implanted tumours clearly indicating that these tumours were not resistant to treatment with an antibody composition of the invention.

Therefore, in a first aspect the invention relates to an antibody composition for use in a method of treatment of cancer in a subject that has been subjected to a prior treatment regimen involving an anti human EGFR antibody, said antibody composition comprising at least 2 distinct anti-human EGFR antibody molecules, a. wherein a first distinct anti-EGFR antibody molecule is selected from the group consisting of antibody 992, an antibody comprising the VL (amino acids 3-109 of SEQ ID NO 72) and VH (amino acids 3-124 of SEQ ID NO 40) sequences of antibody 992, an antibody having the CDR3s of antibody 992 (SEQ ID NO 116 and 111), an antibody binding to the same epitope as antibody 992, and an antibody capable of inhibiting the binding of antibody 992 to human EGFR; and b. wherein a second distinct anti-EGFR antibody molecule is selected from the group consisting of antibody 1024, an antibody comprising the VL (amino acids 3-114 of SEQ ID NO 73) and VH (amino acids 3-120 of SEQ ID NO 41) sequences of antibody 1024, an antibody having the CDR3s of antibody 1024 (SEQ ID NO 120 and 114), an antibody binding to the same epitope as antibody 1024, and an antibody capable of inhibiting the binding of antibody 1024 to human EGFR, In one embodiment said prior treatment regimen involved an antibody composition identical to said antibody composition.

In another embodiment said prior treatment regimen involved an anti-human-EGFR antibody selected from the group consisting of Cetuximab, panitumumab, Zalutumumab, nimotuzumab, ICR62, mAb806, Matuzumab, and antibodies capable of binding the same epitope as any of these. Preferably, said anti-human EGFR antibody is selected from the group consisting of Cetuximab, Panitumumab, and Zalutumumab and antibodies capable of binding the same epitope as any of these. More preferably, said anti-human EGFR antibody is selected from the group consisting of Cetuximab and Panitumumab and antibodies capable of binding the same epitope as any of these. More preferably, said anti-human EGFR antibody is Cetuximab or an antibody capable of biding the same epitope as Cetuximab.

The cancer may be selected from the group consisting of head-and-neck cancer, colon cancer, breast cancer, renal cancer, lung cancer, ovarian cancer, prostate cancer, glioma, pancreatic cancer, bladder cancer, non-small-cell-lung-carcinoma (NSCLC), gastric cancer, cervical cancer, hepatocellular cancer, gastrophageal cancer, colorectal cancer, rectal cancer, epithelioid carcinoma, RCC, squamous cell carcinoma of the head and neck (SCCHN), esophageal cancer, glioblastoma multiforme, squamous cell carcinoma, and kidney cancer, melanoma, carcinoma and sarcoma as described herein.

The antibody treatment may be adjuvant therapy, following surgery and/or radiation therapy.

The treatment may be a combination therapy involving treatment with chemotherapy and/or at least one tyrosine kinase inhibitors and/or at least one angiogenesis inhibitor and/or at least one hormone and/or at least one differentiation inducing agent.

The prior treatment regimen may be a first-line therapy, a second-line therapy, or a third-line therapy.

The first-line therapy may additionally involve a treatment regimen with chemotherapy and/or at least one tyrosine kinase inhibitors and/or at least one angiogenesis inhibitor and/or at least one hormone and/or at least one differentiation inducing agent.

Chemotherapy preferably includes administration of a chemotherapeutic compound selected from the group consisting of adriamycin, cisplatin, taxol, doxorubicin, topotecan, fluoropyrimidine, oxaliplatin, and irinotecan.

In some embodiments of the invention the subject has progressed on or following the prior treatment regimen. In other embodiments, the subject has progressed following said prior treatment regimen.

The cancer may be resistant or partially resistant to the prior treatment regimen.

In a further aspect the invention relates to an antibody composition for use in a method of treatment of cancer, wherein said cancer is resistant or partially resistant to treatment with at least one other anti-EGFR antibody selected from the group consisting of Cetuximab, panitumumab, Zalutumumab, nimotuzumab, ICR62, mAb806, Matuzumab, and antibodies capable of binding the same epitope as any of these; said antibody composition comprising at least 2 distinct anti-human EGFR antibody molecules, a. wherein a first distinct anti-EGFR antibody molecule is selected from the group consisting of antibody 992, an antibody comprising the VL (amino acids 3-109 of SEQ ID NO 72) and VH (amino acids 3-124 of SEQ ID NO 40) sequences of antibody 992, an antibody having the CDR3s of antibody 992 (SEQ ID NO 116 and 111), an antibody binding to the same epitope as antibody 992, and an antibody capable of inhibiting the binding of antibody 992 to human EGFR; and b. wherein a second distinct anti-EGFR antibody molecule is selected from the group consisting of antibody 1024, an antibody comprising the VL (amino acids 3-114 of SEQ ID NO 73) and VH (amino acids 3-120 of SEQ ID NO 41) sequences of antibody 1024, an antibody having the CDR3s of antibody 1024 (SEQ ID NO 120 and 114), an antibody binding to the same epitope as antibody 1024, and an antibody capable of inhibiting the binding of antibody 1024 to human EGFR, According to this aspect, the composition may be used for first-line therapy.

In other embodiments of this aspect, the composition is used for second-line therapy following a treatment regimen involving chemotherapy and/or at least one tyrosine kinase inhibitors and/or at least one angiogenesis inhibitor and/or at least one hormone and/or at least one differentiation inducing agent. The composition may also be used for third-line therapy.

The composition may be used for combination therapy together with chemotherapy and/or at least one tyrosine kinase inhibitors and/or at least one angiogenesis inhibitor and/or at least one hormone and/or at least one differentiation inducing agent.

In some embodiments, the composition is used for as adjuvant therapy following surgery and/or radiation therapy.

The complete or partial resistance is preferably determined by assaying a sample of cancer cells isolated from said subject. This assay may include measuring binding of Cetuximab, panitumumab, Zalutumumab, nimotuzumab, ICR62, mAb806, Matuzumab, and antibodies capable of binding the same epitope as any of these to cancer cells from said subject. The absence of binding indicates resistance to the antibody. Alternatively, partial or complete resistance can be determined in a proliferation assay similar to the assay in Example 21.

In further related aspects the invention relates to a method of reducing EGFR signalling, a method of killing cells expressing EGFR, a method of inducing apoptosis in cells expressing EGFR, a method of inhibiting proliferation of cells expressing EGFR, a method of inducing differentiation of tumour cells in vivo, and a method for inducing internalisation of EGFR, said methods comprising administering an antibody composition to a composition of EGFR expressing cells, said cells having previously been subjected to an anti-EGFR antibody selected from the group consisting of Cetuximab, panitumumab, Zalutumumab, nimotuzumab, ICR62, Matuzumab, Mab806, and antibodies capable of binding the same epitope as any of these, said antibody composition being as described in the present application.

In still further aspects the invention relates to a method of reducing EGFR signalling, a method of killing cells expressing EGFR, a method of inducing apoptosis in cells expressing EGFR, a method of inhibiting proliferation of cells expressing EGFR, a method of inducing differentiation of tumour cells in vivo, and a method for inducing internalisation of EGFR, said methods comprising administering an antibody composition to a composition of EGFR expressing cells, said cells being resistant or partially resistant to an anti-EGFR antibody selected from the group consisting of Cetuximab, panitumumab, Zalutumumab, nimotuzumab, ICR62, Matuzumab, Mab806, and antibodies capable of binding the same epitope as any of these, said antibody composition being as described in the present application.

For these aspects of the invention, the antibody composition of the invention can be any of the compositions described herein. Preferably the antibody composition of the invention is as described in section headed A preferred antibody composition, i.e. an antibody composition based on antibodies 1024 and 992 as described herein.

DEFINITIONS

The term "antibody" describes a functional component of serum and is often referred to either as a collection of molecules (antibodies or immunoglobulin) or as one molecule (the antibody molecule or immunoglobulin molecule). An antibody molecule is capable of binding to or reacting with a specific antigenic determinant (the antigen or the antigenic epitope), which in turn may lead to induction of immunological effector mechanisms. An individual antibody molecule is usually regarded as monospecific, and a composition of antibody molecules may be monoclonal (i.e., consisting of identical antibody molecules) or polyclonal (i.e., consisting of two or more different antibody molecules reacting with the same or different epitopes on the same antigen or even on distinct, different antigens). Each antibody molecule has a unique structure that enables it to bind specifically to its corresponding antigen, and all natural antibody molecules have the same overall basic structure of two identical light chains and two identical heavy chains. Antibodies are also known collectively as immunoglobulins. The terms antibody or antibodies as used herein are also intended to include chimeric and single chain antibodies, as well as binding fragments of antibodies, such as Fab, Fv fragments or scFv fragments, as well as multimeric forms such as dimeric IgA molecules or pentavalent IgM. An antibody may be human, murine, chimeric, humanised, or reshaped.

The term "cognate $V_H$ and $V_L$ coding pair" describes an original pair of $V_H$ and $V_L$ coding sequences contained within or derived from the same antibody producing cell. Thus, a cognate $V_H$ and $V_L$ pair represents the $V_H$ and $V_L$ pairing originally present in the donor from which such a cell is derived. The term "an antibody expressed from a $V_H$ and $V_L$ coding pair" indicates that an antibody or an antibody fragment is produced from a vector, plasmid or similar containing the $V_H$ and $V_L$ coding sequence. When a cognate $V_H$ and $V_L$ coding pair is expressed, either as a complete antibody or as a stable fragment thereof, they preserve the binding affinity and specificity of the antibody originally expressed from the cell they are derived from. A library of cognate pairs is also termed a repertoire or collection of cognate pairs, and may be kept individually or pooled.

The term "CDR"—complementarity determining region is as defined in Lefranc et al (2003) IMGT unique numbering for immunoglobulin and T cell receptor variable domains and Ig superfamily V-like domains. Dev. Comp Immunol 27, 55-77.

The terms "a distinct member of a recombinant polyclonal protein" denotes one protein molecule of a protein composition comprising different, but homologous protein molecules, where each protein molecule is homologous to the other molecules of the composition, but also contains one or more stretches of variable polypeptide sequence, which is/are characterized by differences in the amino acid sequence between the individual members of the polyclonal protein.

The term "head-to-head promoters" refers to a promoter pair being placed in close proximity so that transcription of two gene fragments driven by the promoters occurs in opposite directions. A head-to-head promoter can also be constructed with a stuffer composed of irrelevant nucleic acids between the two promoters. Such a stuffer fragment can easily contain more than 500 nucleotides. Head-to-head promoters can also be termed bi-directional promoters.

The term "immunoglobulin" commonly is used as a collective designation of the mixture of antibodies found in blood or serum, but may also be used to designate a mixture of antibodies derived from other sources.

The term "immunoglobulin molecule" denotes an individual antibody molecule, e.g., as being a part of immunoglobulin, or part of any polyclonal or monoclonal antibody composition.

The term "a library of variant nucleic acid molecules of interest" is used to describe the collection of nucleic acid molecules, which collectively encode a "recombinant polyclonal protein of interest". When used for transfection, the library of variant nucleic acid molecules of interest is contained in a library of expression vectors. Such a library typically have at least 2, 3, 5, 10, 20, 50, 1000, $10^4$, $10^5$ or $10^6$ distinct members.

The term "mass transfer" is used to describe the transfer of nucleic acid sequences of interest from one population of vectors to another population of vectors and doing so for each DNA simultaneously without resorting to isolation of the individual DNA's of interest. Such populations of vectors can be libraries containing for example variable regions, promoters, leaders or enhancing elements of interest. These sequences can then be moved without prior isolation from for example a phage vector to a mammalian expression vector. Especially for antibody sequences this technique ensures that the linkage between $V_H$ and $V_L$ diversity is not lost while moving libraries from, for example, a selection vector (e.g., a phage display vector) to a mammalian expression vector. Hereby the original pairing of $V_H$ and $V_L$ is retained.

As used herein, the term "operably linked" refers to a segment being linked to another segment when placed into a functional relationship with the other segment. For example, DNA encoding a signal sequence is operably linked to DNA encoding a polypeptide if it is expressed as a leader that participates in the transfer of the polypeptide to the endoplasmic reticulum. Also, a promoter or enhancer is operably linked to a coding sequence if it stimulates the transcription of the sequence.

The term "polyclonal antibody" describes a composition of different antibody molecules which is capable of binding to or reacting with several different specific antigenic determinants on the same or on different antigens. Usually, the variability of a polyclonal antibody is thought to be located in the so-called variable regions of the polyclonal antibody. However, in the context of the present invention, polyclonality can also be understood to describe differences between the individual antibody molecules residing in so-called constant regions, e.g., as in the case of mixtures of antibodies containing two or more antibody isotypes such as the human isotypes IgG1, IgG2, IgG3, IgG4, IgA1, and IgA2, or the murine isotypes IgG1, IgG2a, IgG2b, IgG3, and IgA. For purposes of the present invention such a polyclonal antibody may also be termed "an antibody composition".

The term "epitope" is commonly used to describe a proportion of a larger molecule or a part of a larger molecule (e.g. antigen or antigenic site) having antigenic or immunogenic activity in an animal, preferably a mammal, and most preferably in a human. An epitope having immunogenic activity is a portion of a larger molecule that elicits an antibody response in an animal. An epitope having antigenic activity is a portion of a larger molecule to which an antibody immunospecifically binds as determined by any method well known in the art, for example, by the immunoassays described herein. Antigenic epitopes need not necessarily be immunogenic. An antigen is a substance to which an antibody or antibody fragment immunospecifically binds, e.g. toxin, virus, bacteria, proteins or DNA. An antigen or antigenic site often has more than one epitope, unless they are very small, and is often capable of stimulating an immune response. Epitopes may be linear or conformational. A linear epitope consists of about 6 to 10 adjacent amino acids on a protein molecule that is recognized by an antibody. In contrast, conformational epitope consists of amino acids that are not arranged sequentially. Here the antibody recognizes only the 3-dimensional structure. When a protein molecule folds into a three dimensional structure the amino acids forming the epitope are juxtaposed enabling the antibody to recognize the sequence. In a denatured protein only the linear epitope may be recognized. A conformational epitope, by definition, must be on the outside of the folded protein. An antibody that recognizes the conformational epitope may only bind under mild, non-denaturing procedures. Antibodies binding to different epitopes on the same antigen can have varying effects on the activity of the antigen they bind depending on the location of the epitope. An antibody binding to an epitope in an active site of the antigen may block the function of the antigen completely, whereas another antibody binding at a different epitope may have no or little effect on the activity of the antigen alone. Such antibodies may however still activate complement and thereby result in the elimination of the antigen, and may result in synergistic effects when combined with one or more antibodies binding at different epitopes on the same antigen. In the present invention, the epitope is preferably a proportion of the extracellular domain of EGFR. Antigens of the present invention are preferably extracellular domain EGFR proteins, polypeptides or fragments thereof to which an antibody or antibody fragment immunospecifically binds. An EGFR associated antigen may also be an analog or derivative of the extracellular domain of EGFR polypeptide or fragment thereof to which an antibody or antibody fragment immunospecifically binds.

Antibodies capable of competing with each other for binding to the same antigen may bind the same or overlapping epitopes or may have a binding site in the close vicinity of one another, so that competition is mainly caused by steric hindrance. Methods for determining competition between antibodies are described in the examples.

As used herein, the term "polyclonal protein" or "polyclonality" refers to a protein composition comprising different, but homologous protein molecules, preferably selected from the immunoglobulin superfamily. Thus, each protein molecule is homologous to the other molecules of the composition, but also contains one or more stretches of variable polypeptide sequence, which is/are characterized by differences in the amino acid sequence between the individual members of the polyclonal protein. Known examples of such polyclonal proteins include antibody or immunoglobulin molecules, T cell receptors and B cell receptors. A polyclonal protein may consist of a defined subset of protein molecules, which has been defined by a common feature such as the shared binding activity towards a desired target, e.g., in the case of a polyclonal antibody against the desired target antigen.

By "protein" or "polypeptide" is meant any chain of amino acids, regardless of length or post-translational modification. Proteins can exist as monomers or multimers, comprising two or more assembled polypeptide chains, fragments of proteins, polypeptides, oligopeptides, or peptides.

The term "RFLP" refers to "restriction fragment length polymorphism", a method whereby the migratory gel pattern of nucleic acid molecule fragments are analyzed after cleavage with restriction enzymes.

The term "scrambling" describes situations where two or more distinct members of a polyclonal protein comprised of two different polypeptide chains, e.g. from the immunoglobulin superfamily, are expressed from an individual cell. This situation may arise when the individual cell has integrated, into the genome, more than one pair of gene segments, where each pair of gene segments encode a distinct member of the polyclonal protein. In such situations unintended combinations of the polypeptide chains expressed from the gene segments can be made. These unintended combinations of polypeptide chains might not have any therapeutic effect.

The term "$V_H$-$V_L$ chain scrambling" is an example of the scrambling defined above. In this example the $V_H$ and $V_L$ encoding gene segments constitute a pair of gene segments. The scrambling occurs when unintended combinations of $V_H$ and $V_L$ polypeptides are produced from a cell where two different $V_H$ and $V_L$ encoding gene segment pairs are integrated into the same cell. Such a scrambled antibody molecule is not likely to retain the original specificity, and thus might not have any therapeutic effect.

The term "transfection" is herein used as a broad term for introducing foreign DNA into a cell. The term is also meant to cover other functional equivalent methods for introducing foreign DNA into a cell, such as e.g., transformation, infection, transduction or fusion of a donor cell and an acceptor cell.

The terms "variable polypeptide sequence" and "variable region" are used interchangeably.

The term "distinct epitopes" means that when two different antibodies bind distinct epitopes, there is less than 100% competition for antigen binding, preferably less than 50% competition for antigen binding, more preferably essentially no competition for antigen binding. An analysis for "distinct epitopes" of antibody pairs is typically determined by binding experiments under saturating antibody conditions with either FACS analysis on cells expressing EGFR and individually fluorescent labelled antibodies, or Surface Plasmon Resonance using EGFR antigen captured or conjugated to a flow cell surface as described in the examples.

The term being capable of "inhibiting EGF binding" when applied to one antibody molecule means that the antibody molecule exhibits an IC 50 value with respect to EGF binding to EGFR of less than 10 nM, preferably less than 8 nM, more preferably less than 7 nM, more preferably less than 5 nM, more preferably less than 4 nM, more preferably less than 3 nM, more preferably less than 2 nM, more preferably less than 2 nM, more preferably less than 1 nM.

The terms "epidermal growth factor receptor" "EGFR" and "EGFR antigen" are used interchangeably herein, and include variants, isoforms and species homologs of human EGFR. In a preferred embodiment, binding of an antibody of the invention to the EGFR-antigen inhibits the growth of cells expressing EGFR (e.g., a tumor cell) by inhibiting or blocking binding of EGFR ligand to EGFR. The term "EGFR ligand" encompasses all (e.g., physiological) ligands for EGFR, including but nor limited to EGF, TGF-alpha, heparin binding EGF (HB-EGF), amphiregulin (AR), heregulin, betacellulin, and epiregulin (EPI). In another preferred embodiment, binding of an antibody of the invention to the EGFR-antigen mediates effector cell phagocytosis and/or killing of cells expressing EGFR.

EGFR domain structure: The extracellular part of the mature EGFR (SwissProt acc.#P00533) consists of 621 amino acids and four receptor domains: Domain I encompasses residues 1-165, domain II residues 166-312, domain III residues 313-481 and domain IV 482-621 (Cochran et al. 2004 J immunol. Methods 287, 147-158). Domains I and III have been suggested to contribute to the formation of high affinity binding sites for ligands. Domains II and IV are cysteine rich, laminin-like regions that stabilize protein folding and contain a possible EGFR dimerization interface.

As used herein, the term "inhibits growth" (e.g., referring to cells) is intended to include any measurable decrease in the proliferation (increase in number of cells) or metabolism of a cell when contacted with an anti-EGFR antibody as compared to the growth of the same cells not in contact with an anti-EGFR antibody, e.g, the inhibition of growth of a cell culture by at least about 10%, 20%, 30%, 40%, 50%, 60%, 70%, 80%, 90%, 99%, or 100%.

As used herein, the terms "inhibits binding" and "blocks binding" (e.g., referring to inhibition/blocking of binding of EGFR ligand to EGFR) are used interchangeably and encompass both partial and complete inhibition/blocking. The inhibition/blocking of EGFR ligand to EGFR preferably reduces or alters the normal level or type of cell signaling that occurs when EGFR ligand binds to EGFR without inhibition or blocking. Inhibition and blocking are also intended to include any measurable decrease in the binding affinity of EGFR ligand to EGFR when in contact with an anti-EGFR antibody as compared to the ligand not in contact with an anti-EGFR antibody, e.g., the blocking of EGFR ligands to EGFR by at least about 10%, 20%, 30%, 40%, 50%, 60%, 70%, 80%, 90%, 99%, or 100%.

The term "recombinant antibody" is used to describe an antibody molecule or several molecules that is/are expressed from a cell or cell line transfected with an expression vector comprising the coding sequence of the antibody which is not naturally associated with the cell.

Cancer—Cancer (medical term: malignant neoplasm) is a class of diseases in which a group of cells display uncontrolled growth (division beyond the normal limits), invasion (intrusion on and destruction of adjacent tissues), and sometimes metastasis (spread to other locations in the body via lymph or blood). These three malignant properties of cancers differentiate them from benign tumors, which are self-limited, do not invade or metastasize. Most cancers form a tumor but some, like leukemia, do not. Cancer may also be termed neoplastic growth, and hyperproliferative disorders.

Adjuvant therapy: Treatment given after the primary treatment to increase the chances of a cure. Adjuvant therapy may include chemotherapy, radiation therapy, hormone therapy, or biological therapy.

Chemotherapy: Treatment with small molecule drugs.

Radiation therapy: Treatment with radiation.

First line therapy: The first treatment for a disease or condition. In patients with cancer, first-line therapy can be surgery, chemotherapy, radiation therapy, antibody therapy, or a combination of these therapies. Also called primary therapy and primary treatment.

Second line therapy: Treatment that is given when initial treatment (first-line therapy) doesn't work, or stops working.

Third line therapy: Treatment given when the sedond-line therapy does not work or stops working.

TKIs—inhibitors of tyrosine inhibitors

Progression: In medicine, the course of a disease, such as cancer, as it becomes worse or spreads in the body.

Resistant cancer: Cancer that does not respond to treatment. The cancer may be resistant at the beginning of treatment or it may become resistant during treatment. Also called refractory cancer. In contrast to this, an effective treatment causes tumour eradication.

Partially resistant cancer: A partially resistant cancer responds to the treatment but the treatment does not cause tumour eradication. In a partically resistant cancer, tumour growth may be inhibited partially or completely, but the tumour does not regress or regresses only insignificantly.

Resistance or partial resistance to an anti-EGFR antibody selected from the group consisting of Cetuximab, panitumumab, Zalutumumab, nimotuzumab, ICR62, mAb425, Matuzumab, and antibodies capable of binding the same epitope as any of these can be observed in a patient receiving one or more of the antibodies, or be measured in an in vitro assay, e.g. by determining expression of EGFR and non-binding or low binding of the monoclonal antibody, or in a proliferation assay such as described in Example 21.

Gate 1: Live cells (FSC/Propidium Iodide plot). (Lower left panel)

Gate 2: Plasma cells are gated as CD43 pos/CD138 pos. (lower right panel)

Gate 3: doublet discrimination (upper right panel)

Figure 2:
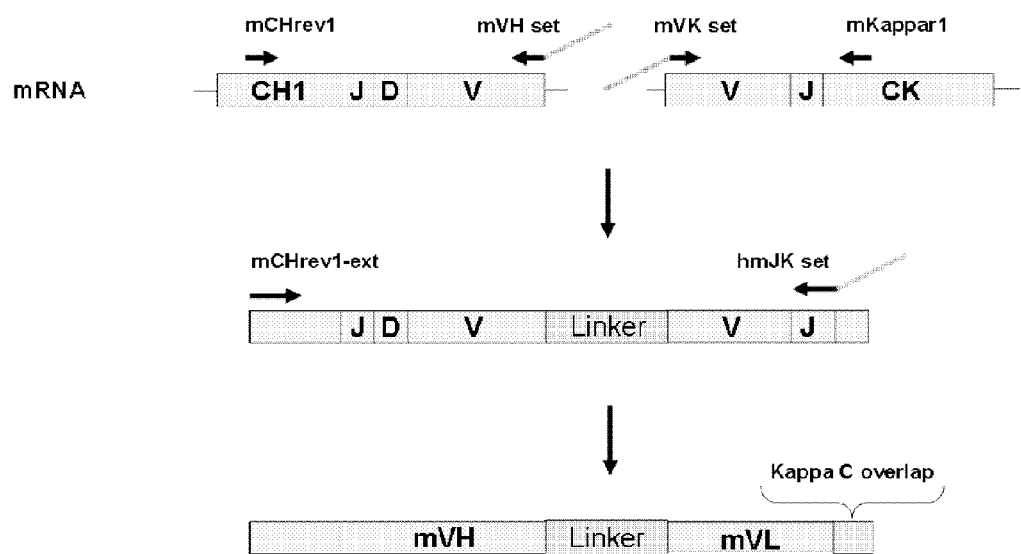

FIG. 2: Murine—mSymplex™ PCR. Multiplex overlap extension RT-PCR for the amplification and cognate linkage of heavy and light chain antibody genes from a single cell. For details refer to Example 1.

Figure 3:
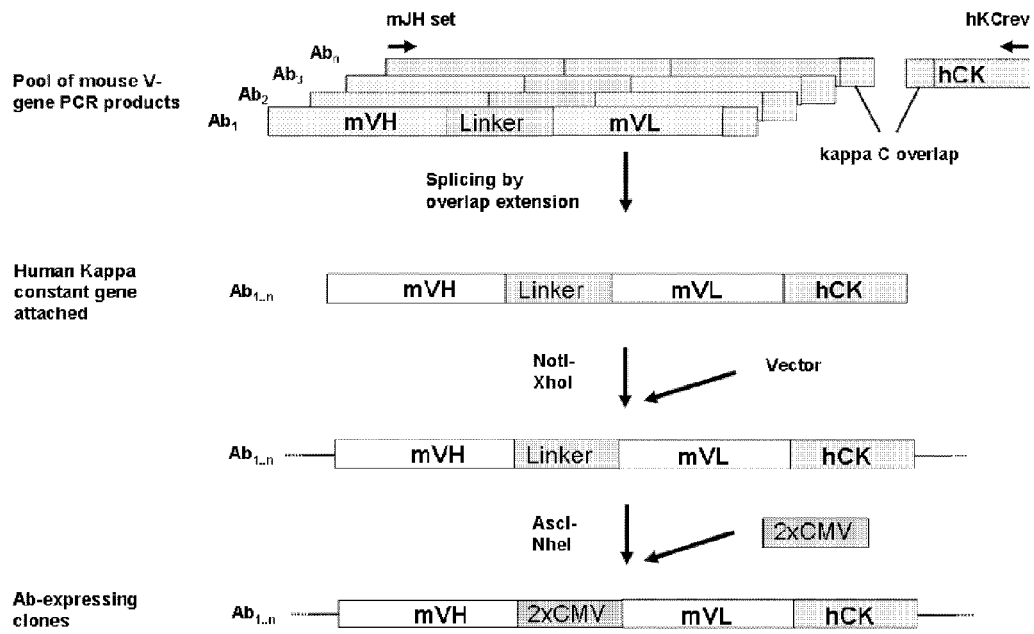

FIG. 3: Murine repertoire cloning. A pool of mSymplex™ PCR products encoding VH/VL gene pairs from single plasma cells were spliced to the gene encoding human kappa constant light chain by splicing by overlap extension. The pool of genes, encoding complete human-mouse chimeric antibodies, was inserted in an expression vector followed by an insertion of a bi-directional promoter cassette (2×CMV).

Figure 4:
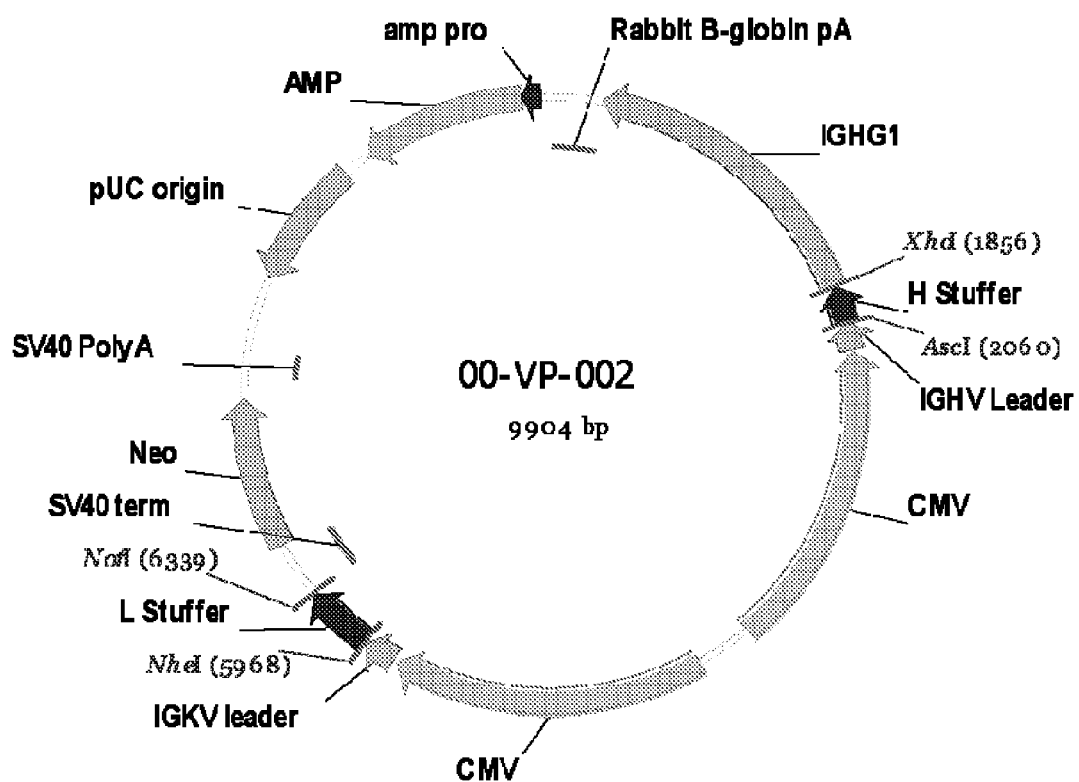

FIG. 4: A schematic representation of the mammalian full-length antibody expression vector 00-VP-002. Amp and Amp pro, ampicillin resistance gene and its promoter; pUC origin, pUC origin of replication; CMV, mammalian promoter driving the expression of the light chain and the heavy chain; IGHV Leader, genomic human heavy chain leader; H stuffer, insert that is exchanged for the heavy chain variable region encoding sequence; IGHG1, sequence coding for genomic immunoglobulin isotype G1 heavy chain constant region (sequence is shown in Appendix 2); Rabbit B-globin A, rabbit beta-globin polyA sequence; IGKV Leader, murine kappa leader; L Stuffer, insert that is exchanged for the light chain encoding sequence; SV40 term, simian virus 40 terminator sequence; FRT, Flp recognition target site; Neo, neomycin resistance gene; SV40 poly A, simian virus 40 poly A signal sequence.

Figure 5:
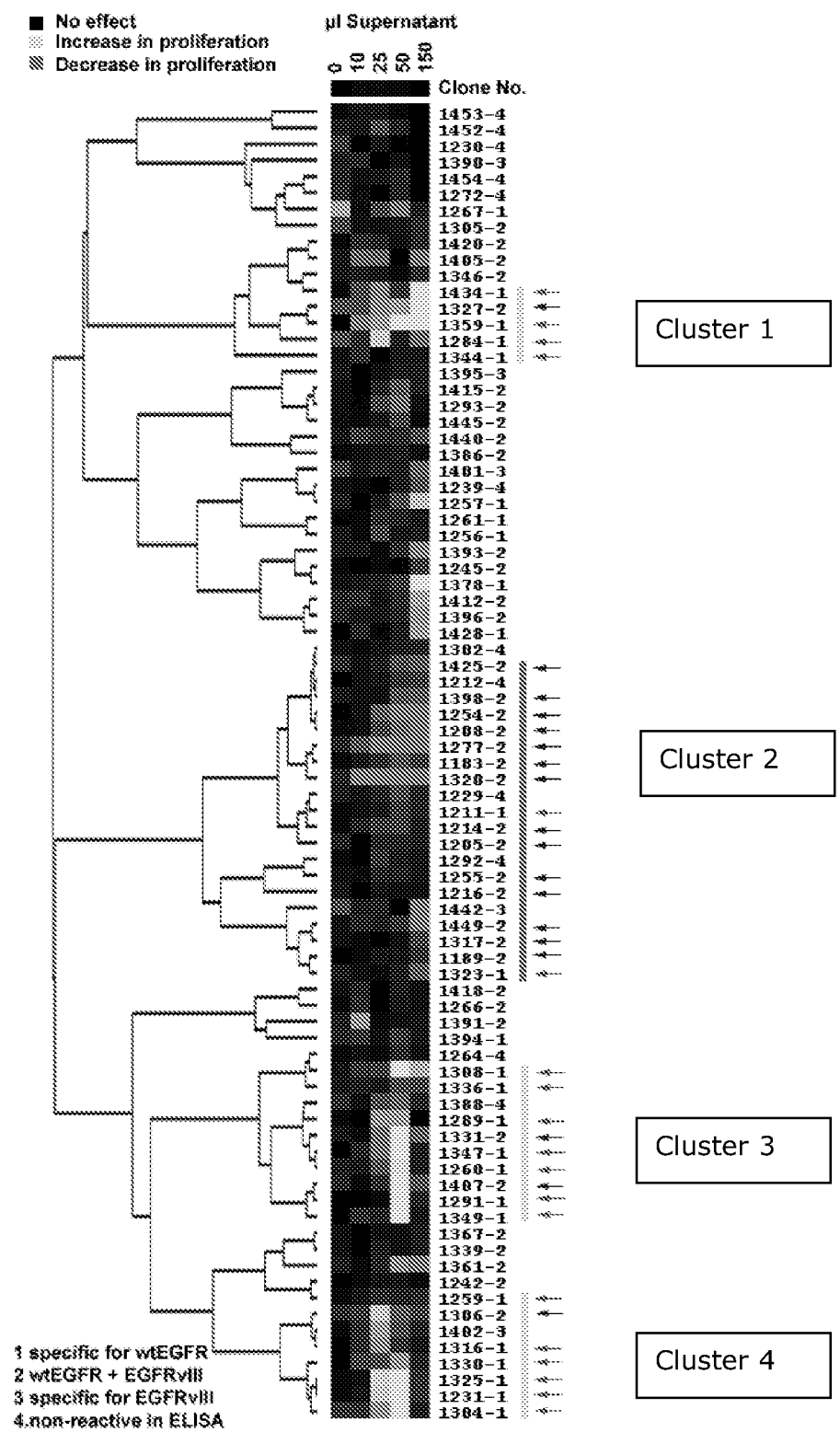

FIG. 5: Cluster analysis of the absorbance difference at 450-620 nm. Supernatants are clustered by reactivity as indicated by the number (1 to 4) following the clone no. Dark grey indicates a decrease in the number of metabolically active cells, whereas light grey indicate an increase in the number of metabolically active cells. Black indicates supernatants with no effect on the number of metabolically active cells.

FIG. 6: Degree of inhibition of Anti-EGFR antibodies with listed reference antibodies directed against specific EGFR domains as determined in a competition ELISA. A) Calculation of inhibition. B) Scoring of inhibition as follows: 25-49%: Moderate competition (+); 50-74%: Strong competition (++); 75-100%: Very strong competition (+++). Boxes displaying significant inhibition (50-100%) are shaded in gray. Erbitux and Vectibix are shown in duplicates (four independent experiments) to illustrate the reproducibility of the assay. Ab2 (225) is the murine precursor that lead to Erbitux.

Figure 7:
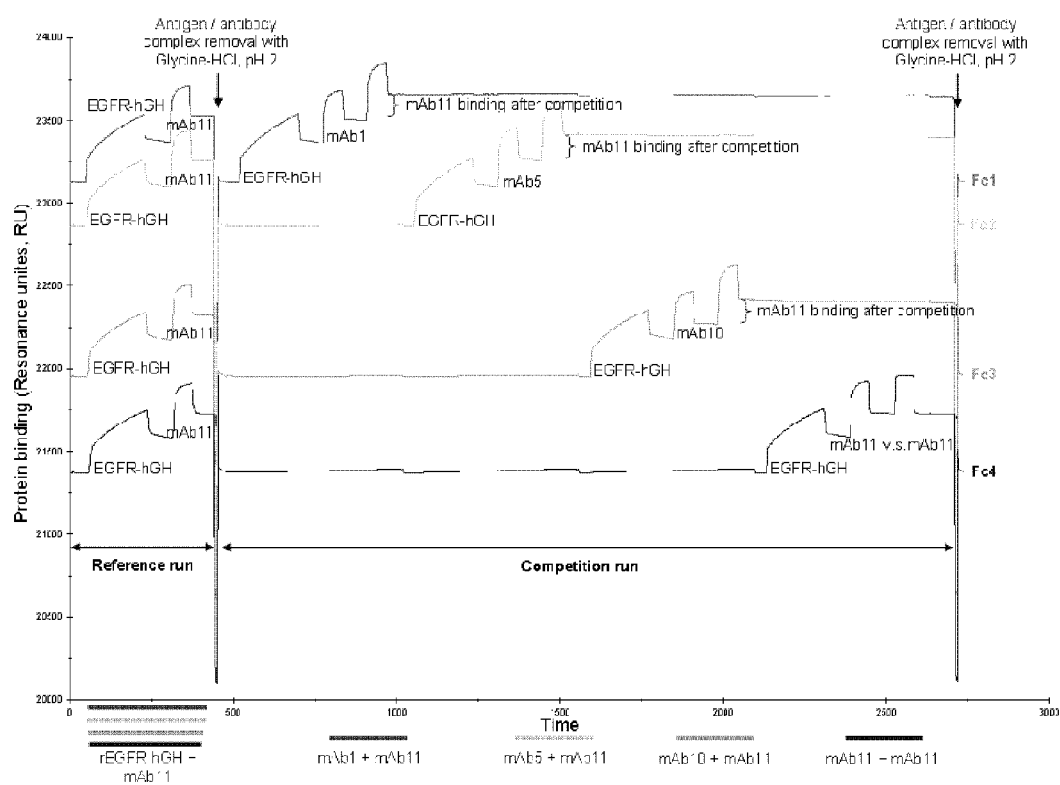

FIG. 7: Illustration of one epitope mapping cycle performed on the Biacore 3000 SPR machine, where a sample mAb is competed for binding to the extracellular domain of EGFR with four different reference antibodies.

FIG. 8: Degree of inhibition of Anti-EGFR antibodies with listed reference antibodies directed against specific EGFR domains as determined by competition analysis with SPR technology. A) Calculation of inhibition. B) Scoring of inhibition as follows: 25-49%: Moderate competition (+); 50-74%: Strong competition (++); 75-100%: Very strong competition (+++). Cells displaying significant inhibition (50-100%) are shaded in gray. Clone 1229 marked * did not bind in the Biacore assay.

FIG. 9: Determination of epitope clusters within the Anti-EGFR antibody repertoire by SPR competition analysis of Anti-EGFR antibody pairs. Antibodies are grouped according to presumed EGFR domain recognition. Cells in which antibody combinations were found to bind overlapping epitopes resulting in more than 50% inhibition are shaded in grey. Cells in which determinations were not done are colored in black. A) Calculation of inhibition. B) Scoring of inhibition as follows: 25-49%: Moderate competition (+); 50-74%: Strong competition (++); 75-100%: Very strong competition (+++).

Figure 10A:
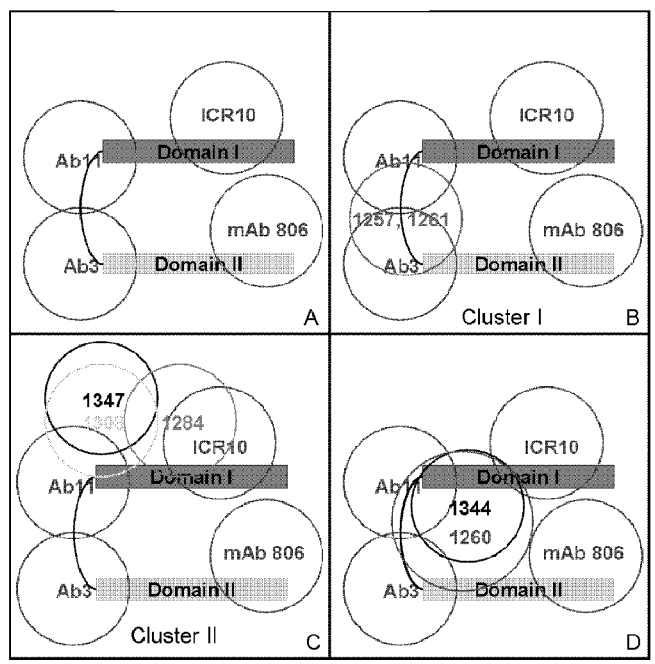
Figure 10B:
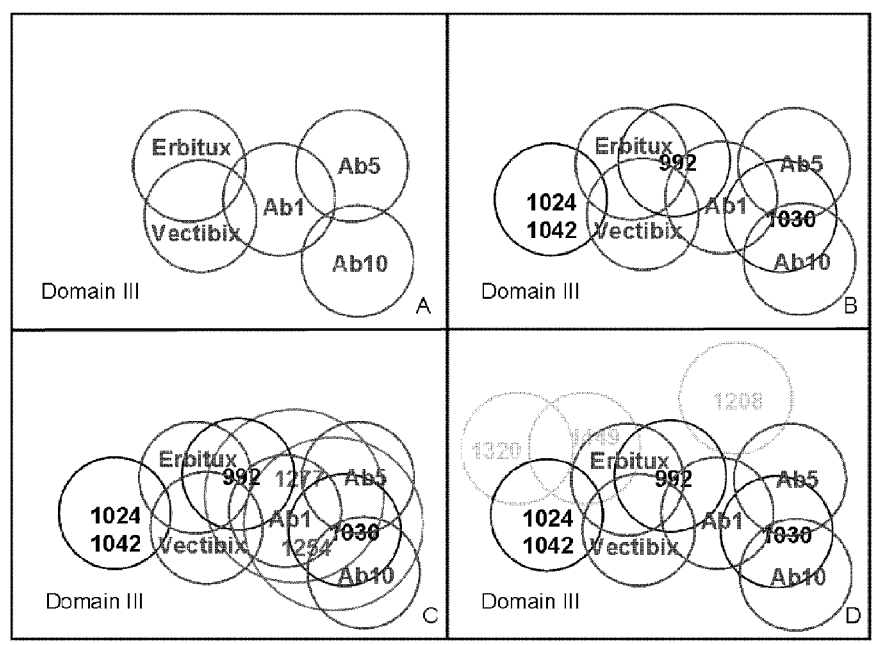

FIG. 10: Epitope maps of reference antibodies and Anti-EGFR antibodies directed against the extra cellular domain of EGFR as determined by Biacore analysis. A) Epitope map of antibodies directed against domain I or domain I/II of EGFR Extra-Cellular Domain (ECD). B) Epitope map of antibodies directed against domain III of EGFR ECD.

FIG. 11: Investigation of the simultaneous binding of an oligoclonal mix of antibodies directed against non overlapping epitopes on EGFR. A) Sequential addition of antibodies against domain III, domain I or unknown specificity. Inhibition values of single sample mAbs tested against different mAb mixtures or single mAb are shown in shaded boxes. The Ru max values used to calculate inhibition are also shown. B) Competition analysis of six distinct sample mAbs directed against non-overlapping epitopes on EGFR and an antibody mixture containing the six tested antibodies. Antibody mixes where the tested sample antibody was not included served as a positive control. Inhibition values of single sample mAbs tested against different mAb mixtures are shown in shaded boxes. The Ru max values used to calculate inhibition are also shown. C) Corresponding sensograms from the analysis in B illustrating antibody blockage and in some cases antibody enhancement of binding. D) Test of additional antibodies directed against domain I, I/II and unknown specificity against the six mAb antibody mixture.

FIG. 12: Determination of antibody mediated EGF ligand blockage by antibody titration on full length EGFR and detection of biotinylated EGF ligand binding with a streptavidin HRP reagent. Erbitux, Vectibix and Synagis IgG (palivizumab) were used as positive and negative controls respectively. After blockage of recognized antibody epitope with tested antibodies, the degree of EGF ligand competition was visualized by addition of 0.1 µg/ml biotinylated EGF ligand and a secondary Streptavidin-HRP conjugate for detection.

Figure 13A:
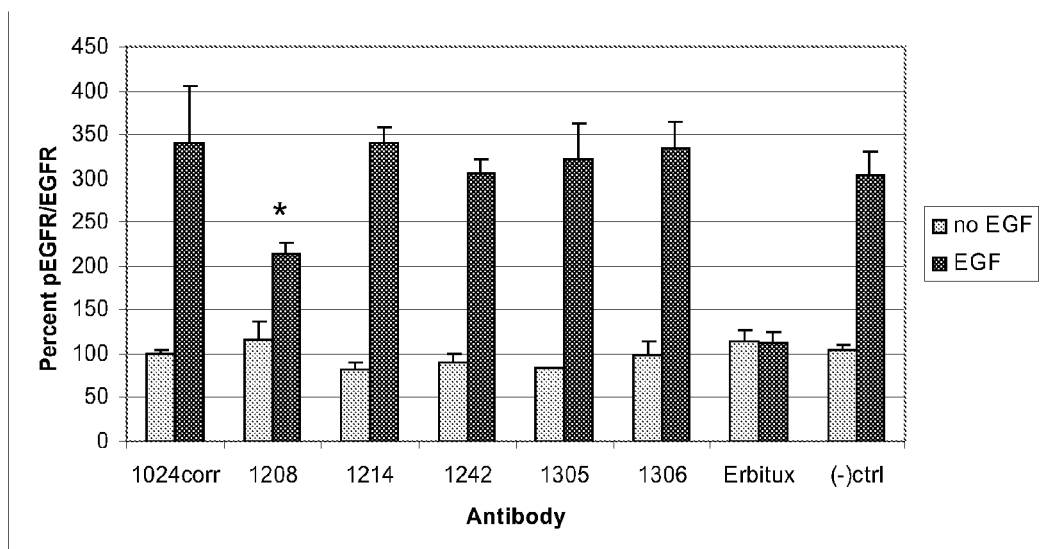
Figure 13B:
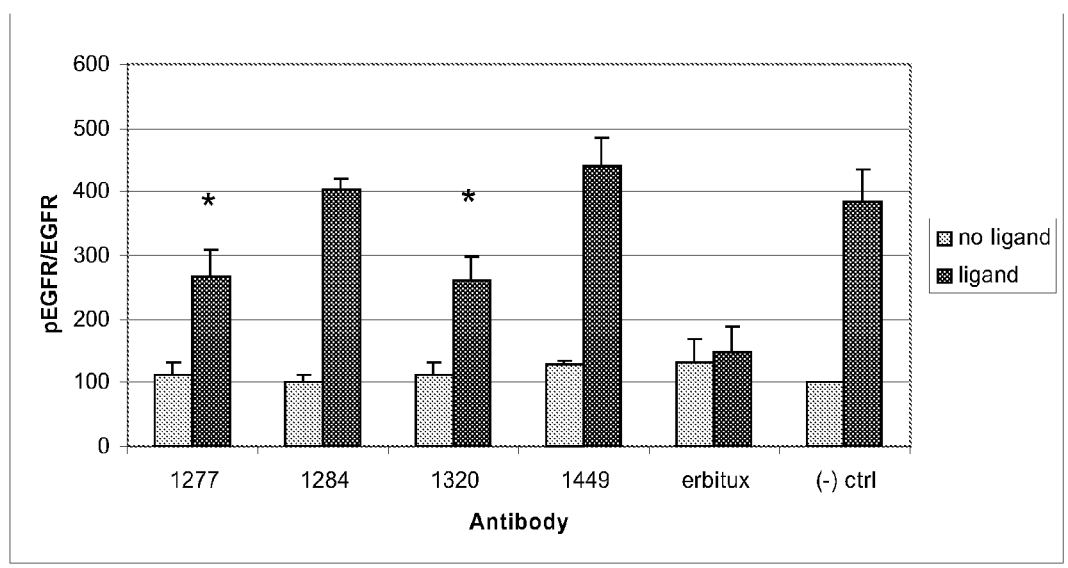

FIG. 13: Effect of pretreatment with the indicated antibodies on EGF (50 ng/ml) induced EGFR phosphorylation in HN5 cells. The antibodies (10 µg/ml) as named in the graph were incubated with the cells for 30 min prior to addition of the EGF for 7.5 min. Data sets marked * were significantly different from the control ((−)ctrl) data set (p<0.05). A. 1208 had a significant protective effect on EGFR phosphorylation. B. 1277 and 1320 significantly protects against EGF induced phosphorylation. Error bars represent standard deviations of three independent experiments.

Figure 14:
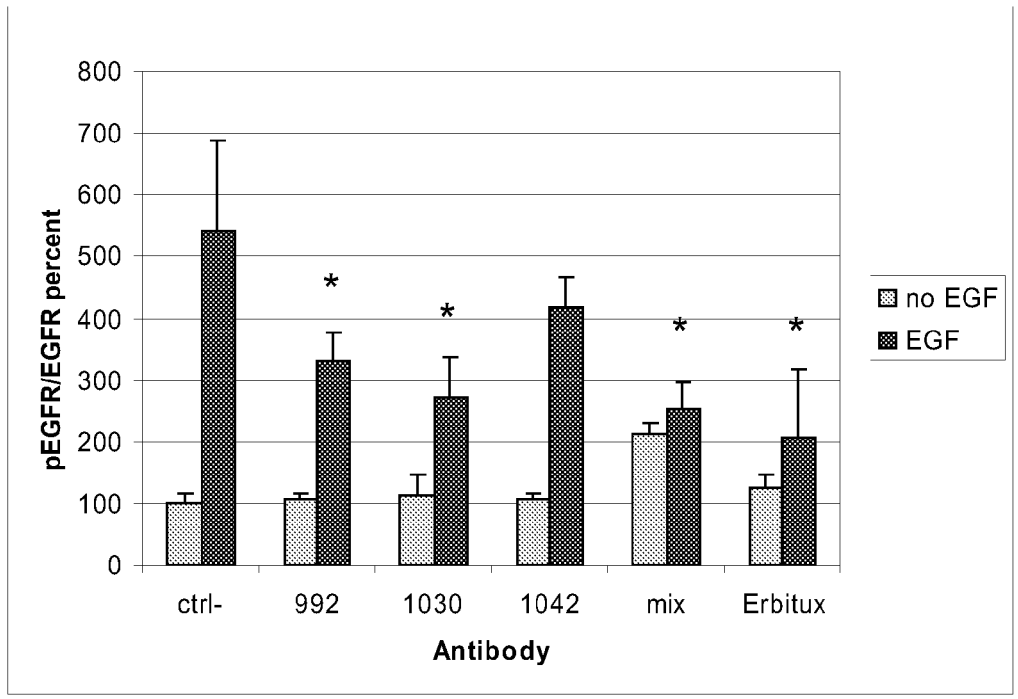

FIG. 14: In cell western analysis of phosphorylated EGFR (pEGFR) and EGFR in HN5 cells. Mix denotes the equimolar mixture of 992, 1030 and 1042 antibodies to a final concentration of 10 µg/ml, the other antibodies were used in a concentration of 10 µg/ml each. 50 µg/ml of EGF was added for 7.5 min prior to fixation to stimulate EGFR phosphorylation. Error bars represent standard deviations of 6 separate (ctlr−), or 3 separate data points (992, 1030, 1042, mix or erbitux). The 992, 1030, mix and erbitux had a significant (*=p<0.05) protective effect on phosphorylation.

Figure 15:
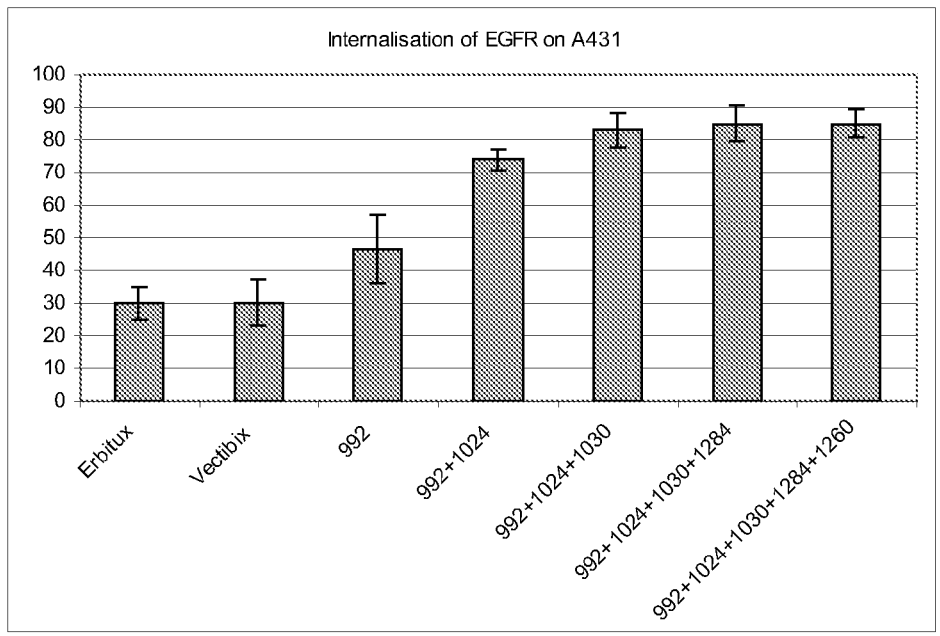

FIG. 15: The effect of incubation of antibodies on internalisation of EGFR. Data are shown as the percent of receptors removed from the cell surface relative to initial staining. Error bars corresponds to SEM.

FIG. 16: Growth curves of A431-NS cells in the presence of varying concentrations of the antibodies 992, 1030 and 1042 and mixes hereof as measured by the percent metabolically active cells as compared to untreated control. 1001 is a non-functional antibody with similar isotype used as negative control.

Figure 17:
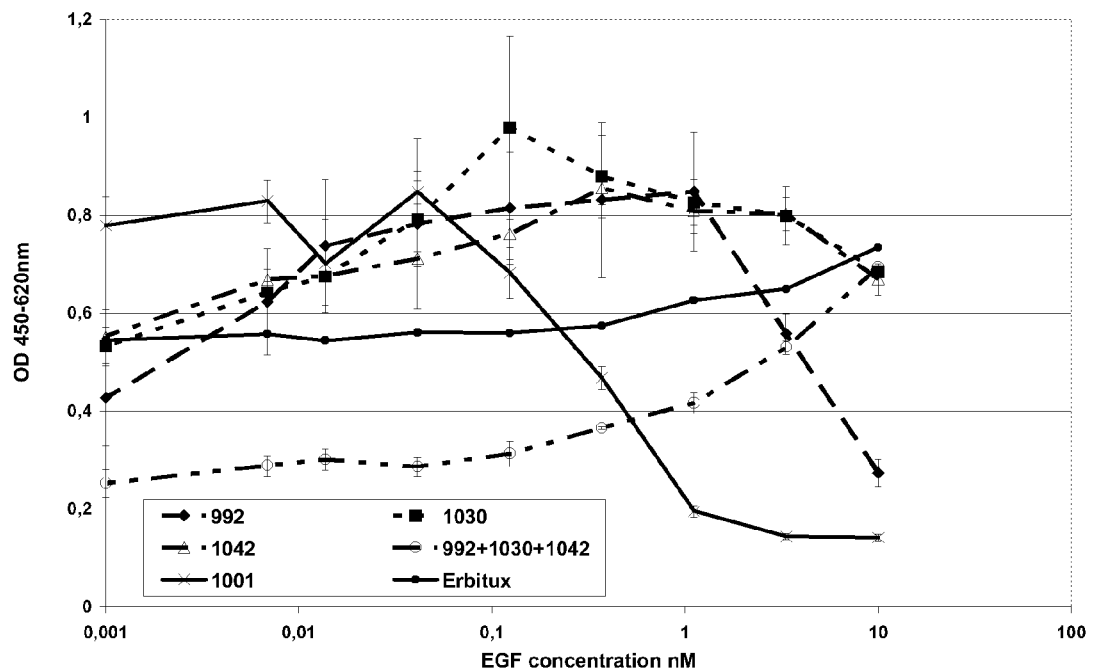

FIG. 17: Growth curves of A431-NS cells in the presence of 10 µg/ml of the antibodies 992, 1030 and 1042 and mixes hereof and varying concentrations of the EGFR ligand EGF as measured by the absorbance at 450 nm. 1001 is a non-functional antibody with similar isotype used as negative control.

Figure 18:
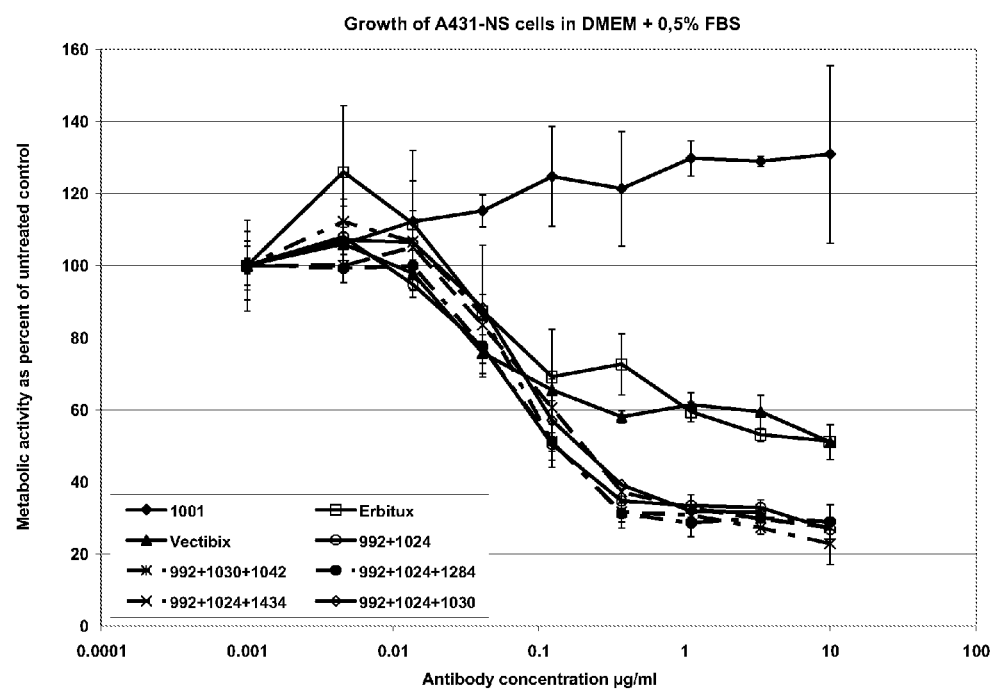

FIG. 18: Growth curves of A431-NS cells in the presence of varying concentrations of the antibody 992 and mixes of 992 and antibodies with non-overlapping epitopes present in domain I, II or III. 1001 is a non-functional antibody with similar isotype used as negative control.

Figure 19:
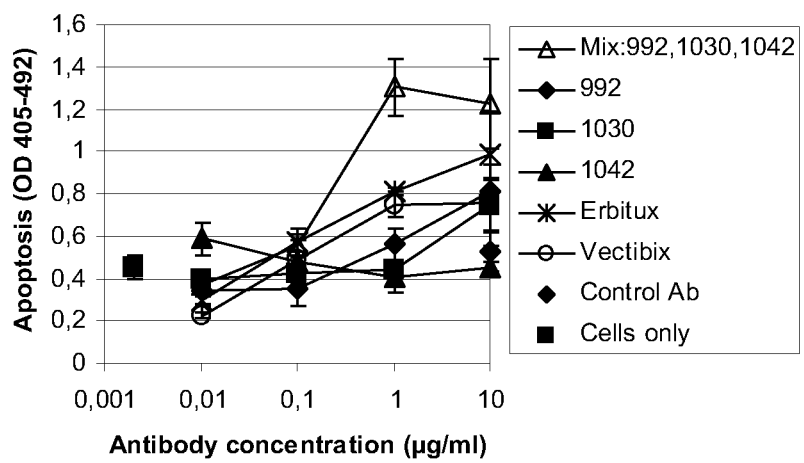

FIG. 19: Apoptosis in A431NS cells. The EGFR-mix, individual monoclonal antibodies, Erbitux and Vectibix were tested in 10-fold dilutions. Histone-DNA complex from apoptotic cells were measured using an ELISA-kit from Roche.

Figure 20:
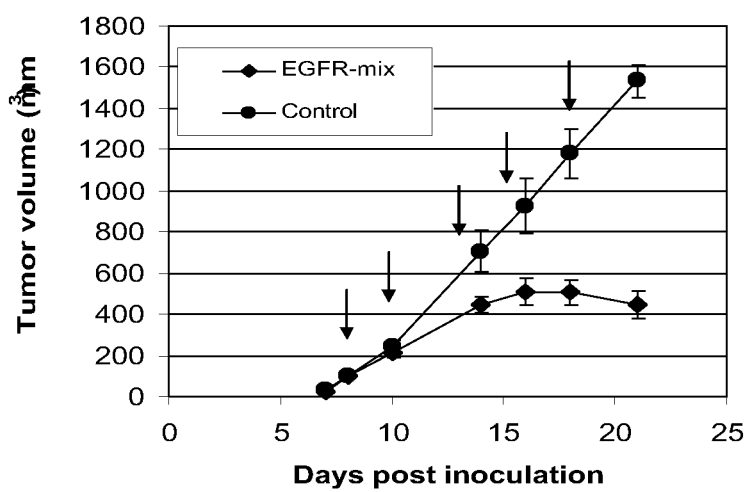

FIG. 20: Four groups of 10 nude Balb/C Nu/Nu mice were inoculated with $1 \times 10^6$ A431NS cells. When tumours were approximately 100 mm$^3$, treatment was initiated. Groups were injected with 1 mg/ml antibodies five times during the experiment as indicated with arrows. Tumour diameters were measured with digital callipers. Results are shown as the mean tumour volume (+/−SEM).

Figure 21:
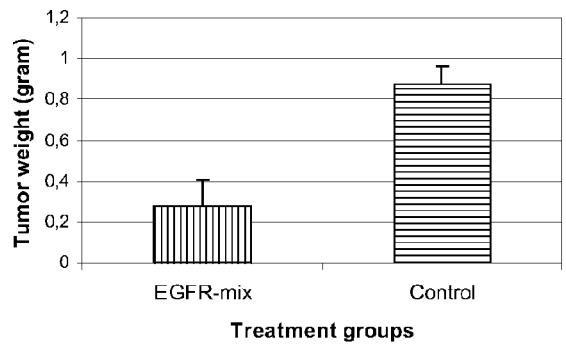

FIG. 21: When individual mice were killed in the experiment shown in FIG. 20, tumours were excised and weighted. Mean values+/−SEM are shown. Stars indicate significance at P<0.05.

Figure 22:
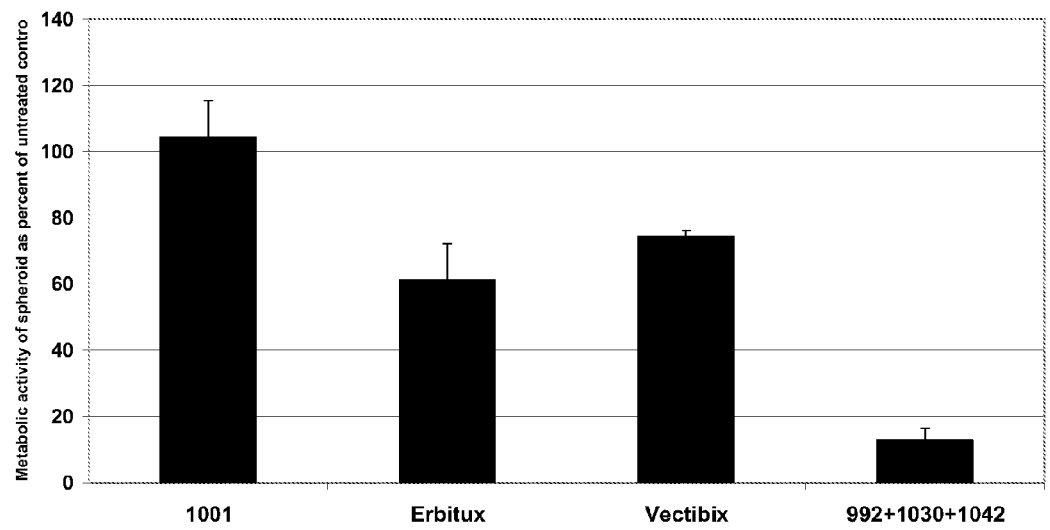

FIG. 22: Growth of A431-NS spheroids in the presence of 10 µg/ml of the antibodies 1001, Erbitux, Vectibix and a mix of three antibodies with non-overlapping epitopes 992+1030+1042. 1001 is a non-functional antibody with similar isotype used as negative control.

FIG. 23: DNA (SEQ ID No. 100) and protein sequence (SEQ ID NO. 101) of extra-cellular domain of Cynomolgus EGFR cloned from cDNA derived from Cynomolgus monkey skin epidermis.

FIG. 24: Alignment of obtained protein sequence of Cynomolgus EGFR ECD (SEQ ID NO. 101) with human EGFR ECD (SEQ ID NO 108) obtained from GENBANK accession number X00588. Also shown is a consensus sequence (SEQ ID NO 109).

Figure 25:
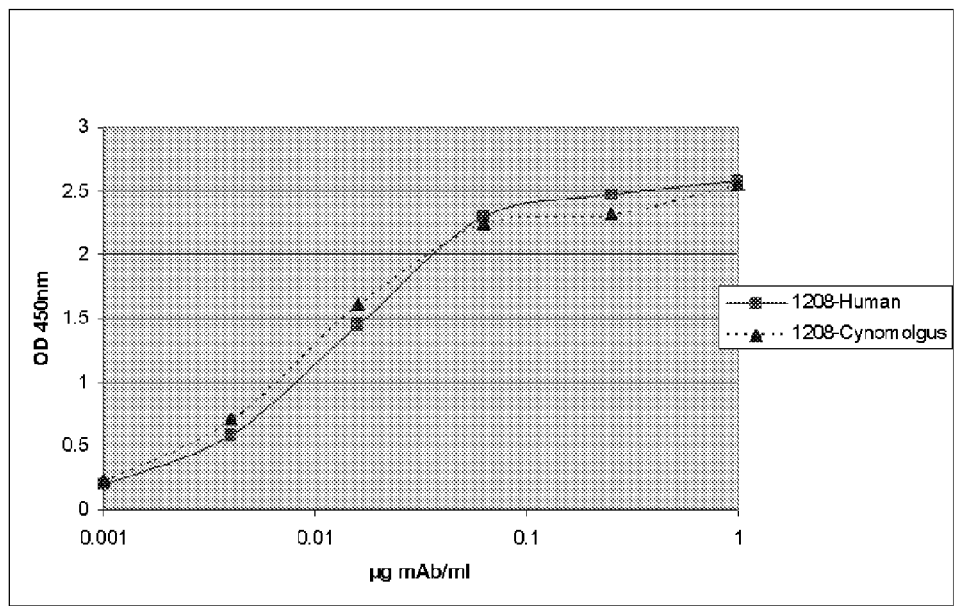
Figure 25:
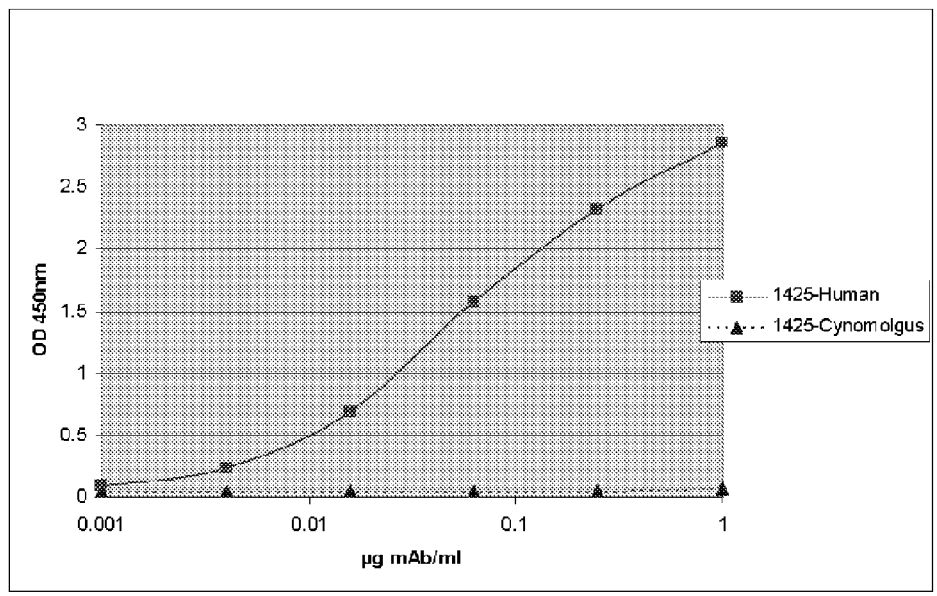

FIG. 25: Example of ELISA assay discrimination between cross reactive and species specific antibodies binding either Human or Cynomolgus EGFR ECD or both.

Figure 26:
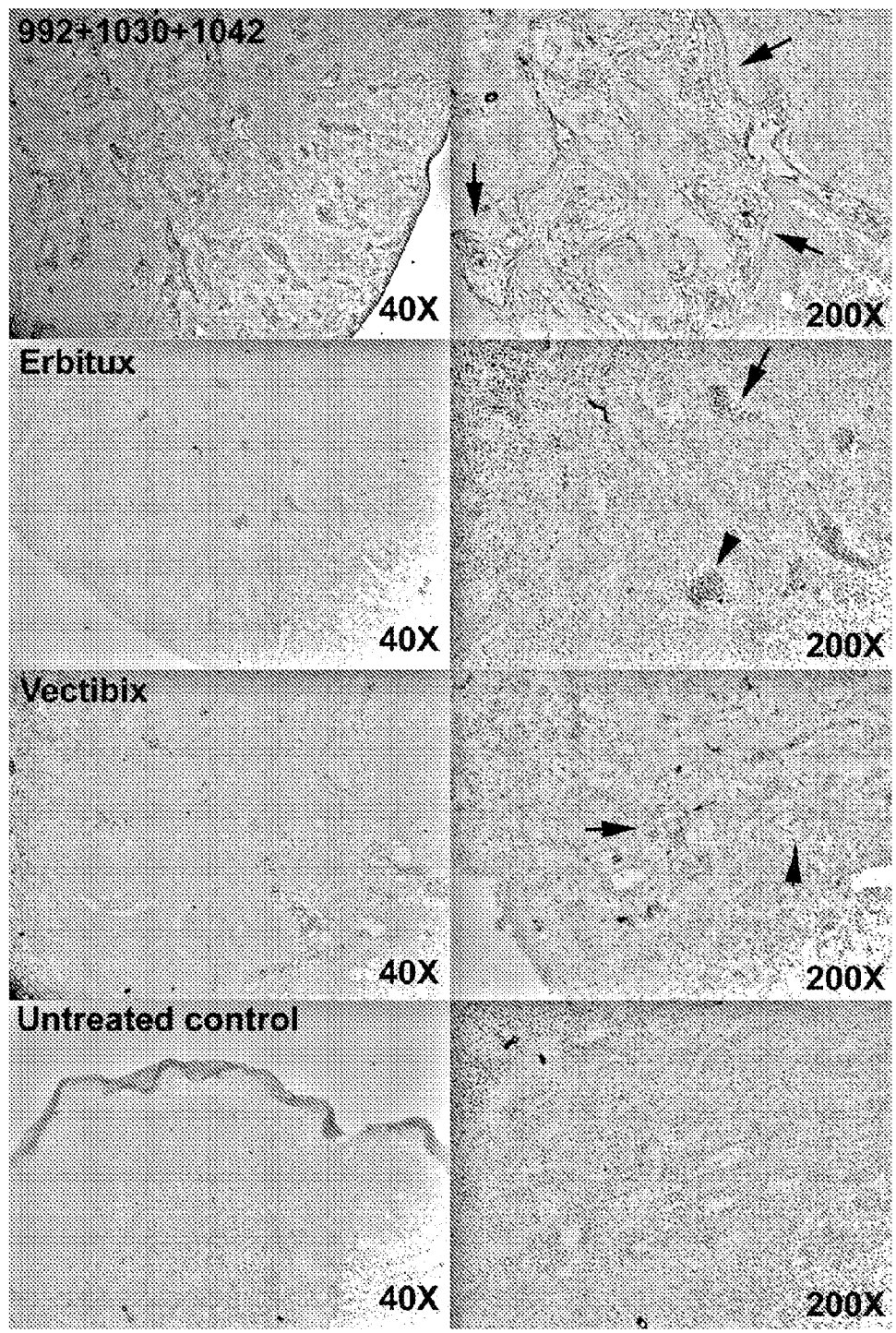

FIG. 26: Photomicrographs of representative tumor sections from each of the four experimental groups of xenografted mice. At a magnification of 200×, arrows point to foci of terminal differentiation of A431 cells in vivo. Note the markedly larger and more numerous foci of terminal differentiation in the tumour treated with a mixture of three anti-EGFR clones (992+1030+1042), upper two panels.

Figure 27:
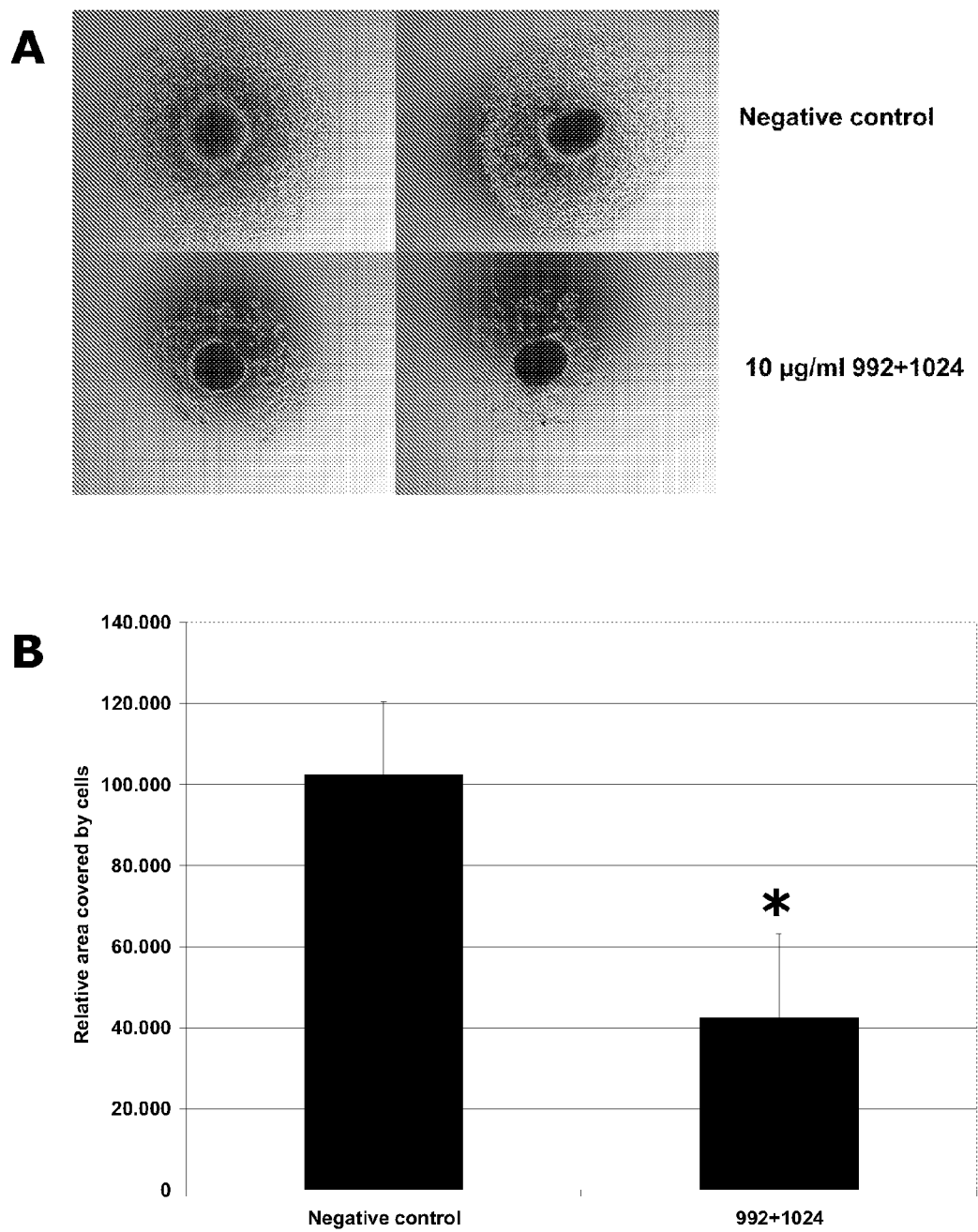

FIG. 27: A) Images taken at 40× magnification of HN5 spheroids 24 hours after addition of 10 μg/ml of the control antibody. (Rituximab, anti CD-20) or the anti EGFR antibody mix of 992 and 1024. B) Quantification of the area covered by cells using the software Image J ($*p<0.01$).

Figure 28:
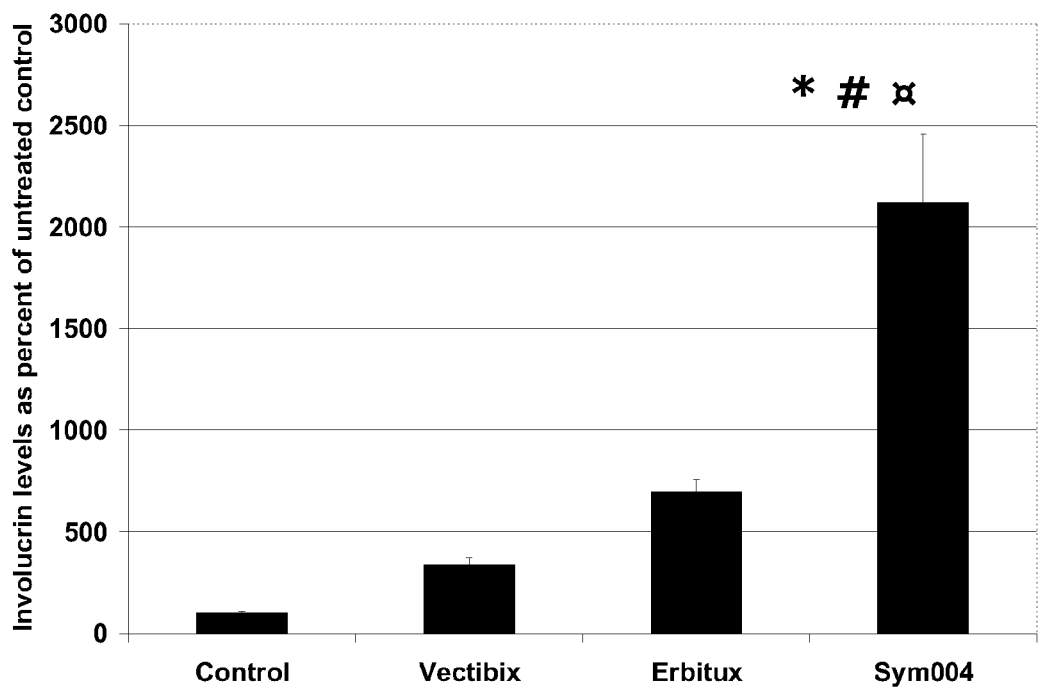

FIG. 28: Diagram showing the Involucrin levels in the four treatment groups as percent of the untreated control group ($*\#¤p<0.005$ as compared to Erbitux, Vectibix and the Negative control group respectively).

FIG. 29: A) Images taken at 60× magnifications of HN5 and A431NS cells incubated with 10 μg/ml Alexa-488 labeled Erbitux or 992+1024 for 2 hours. B) Images taken at 60× magnifications with a small pin-hole of A431NS cells incubated with 10 μg/ml Alexa-488 labeled Erbitux or 992+1024 for 2 hours.

FIG. 30: A) Images taken at 60× magnifications of HN5 cells incubated with 10 μg/ml Alexa-488 labeled Erbitux or 992+1024 for the indicated periods of time.

Figure 31A:
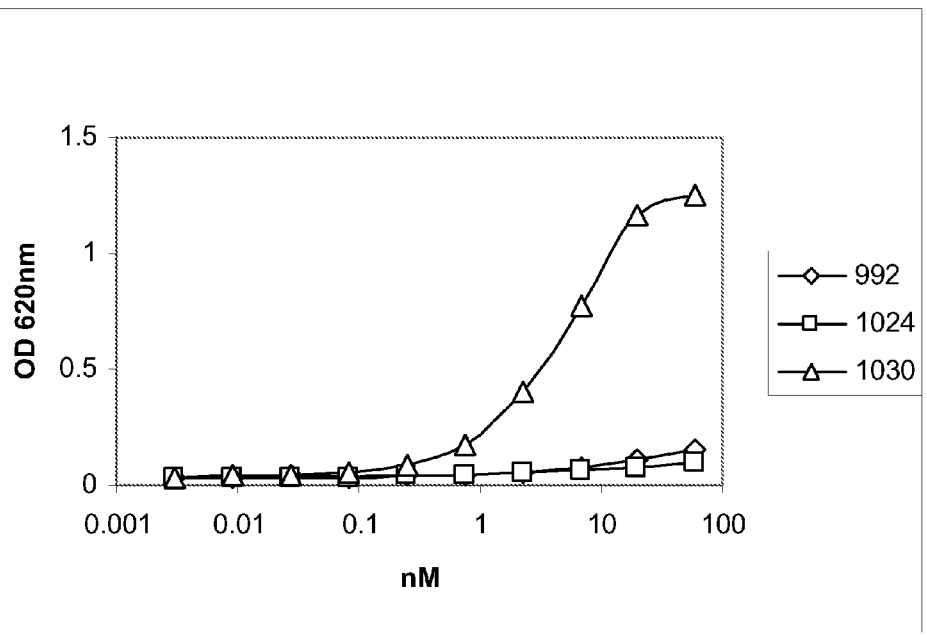
Figure 31B:
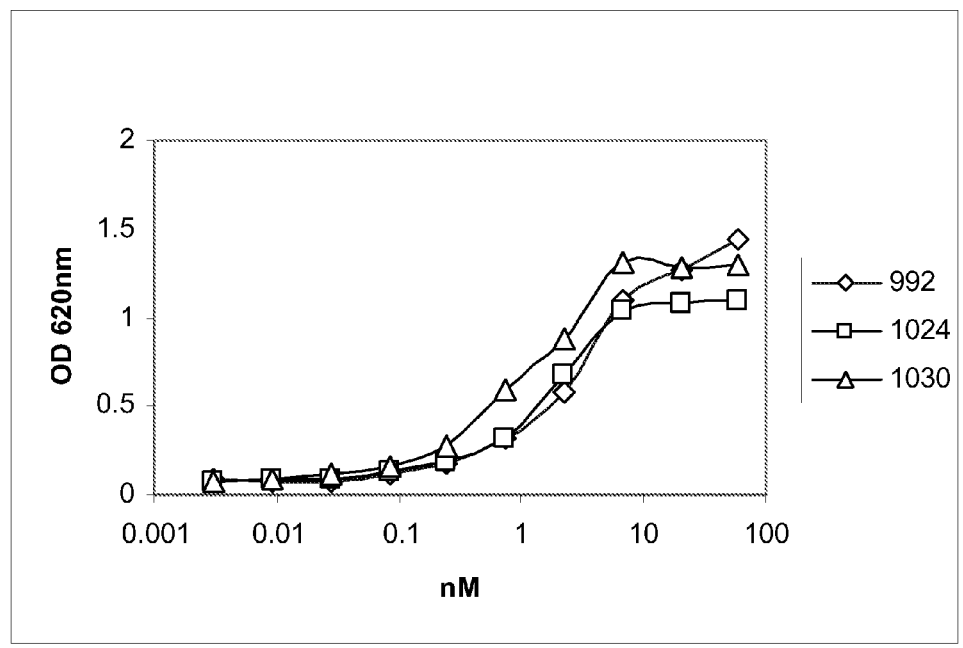

FIG. 31: Determination of antigen presentation specificity of Fabs 992, 1024 & 1030 by serial antibody titrations on A431-NS cells and purified full length EGFR in ELISA. Bound Fab antibodies were visualized by a secondary Goat anti-Human Fab specific HRP conjugate. A) Fab antibodies tested against purified full length EGFR from A431 cells. B) Fab antibodies tested against EGFR expressed on the surface of A431-NS cells.

Figure 32A:
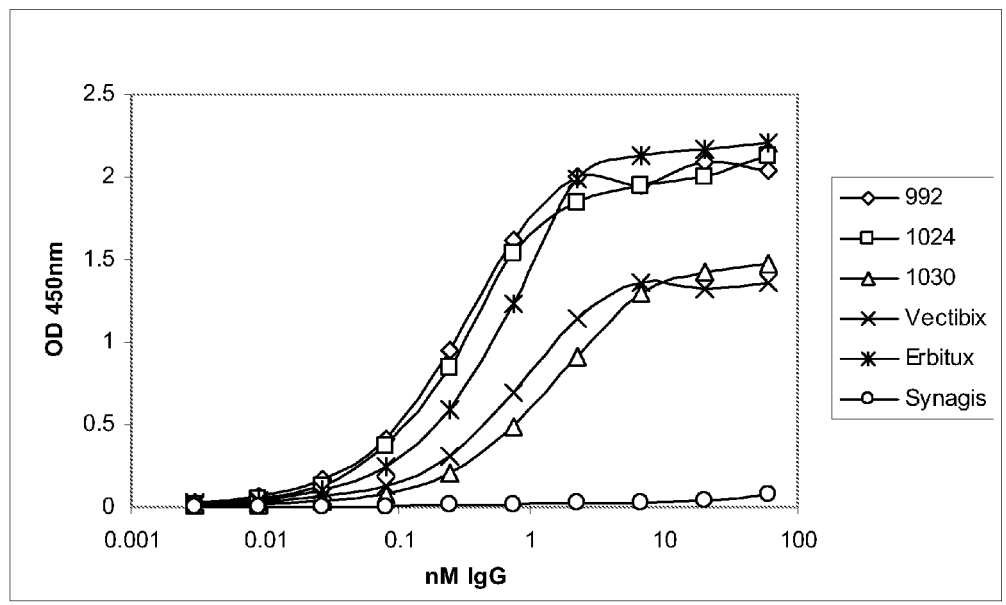
Figure 32B:
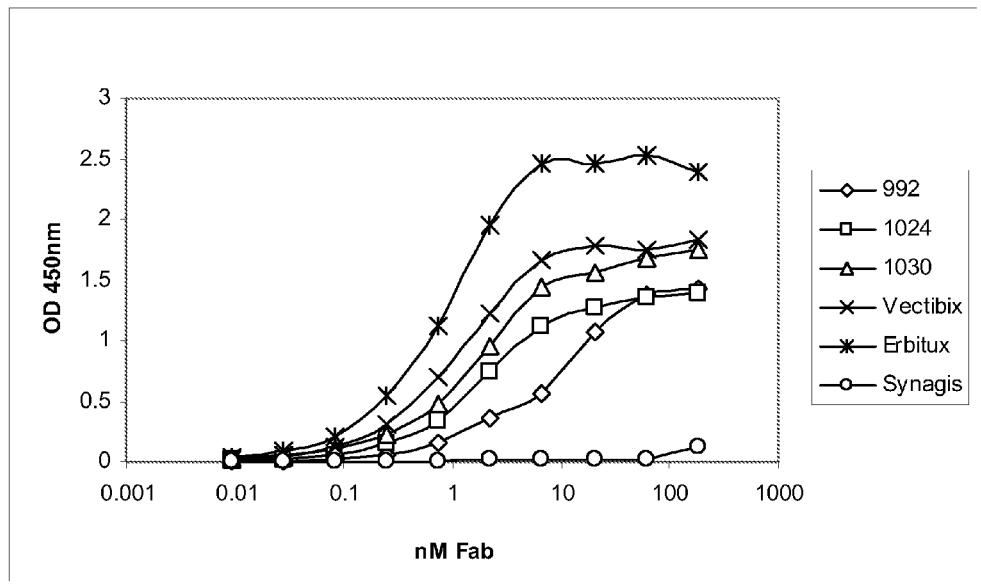

FIG. 32: Determination of the functional affinity of IgG and Fab fragments of antibodies 992, 1024, 1030, Erbitux & Vectibix by serial titration on paraformaldehyde fixed A431-NS cells in ELISA. Bound Fab and IgG antibodies were visualized by a secondary Goat anti-Human Fab specific HRP conjugate. The anti-RSV protein F antibody Synagis was employed as a negative control antibody, and did not show any binding in the employed ELISA assay. A) Functional binding of IgG antibodies to A431-NS cells. B) Functional binding of Fab antibodies to A431-NS cells.

Figure 33A:
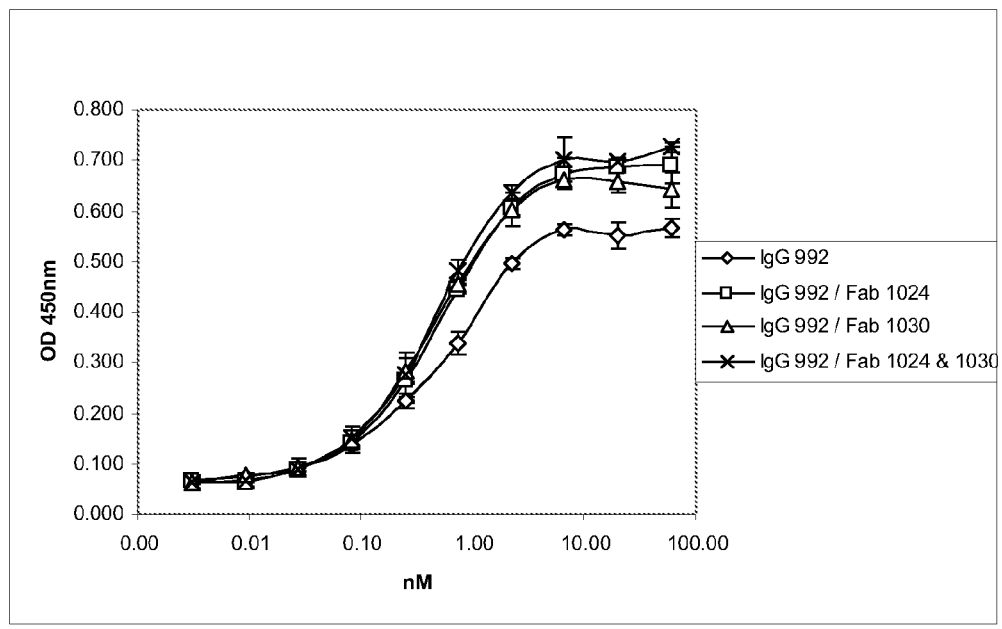
Figure 33B:
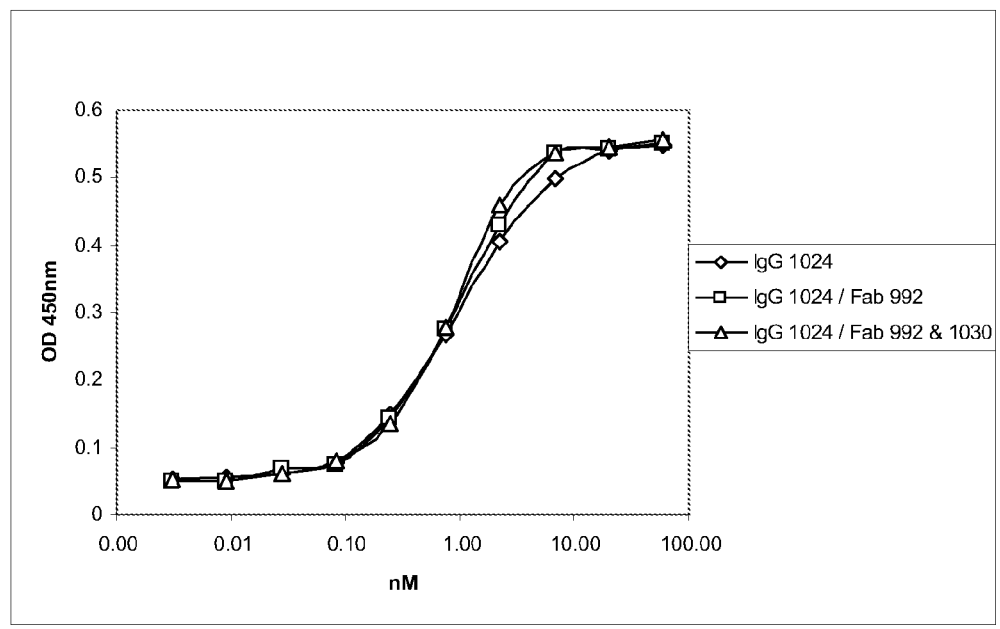
Figure 33C:
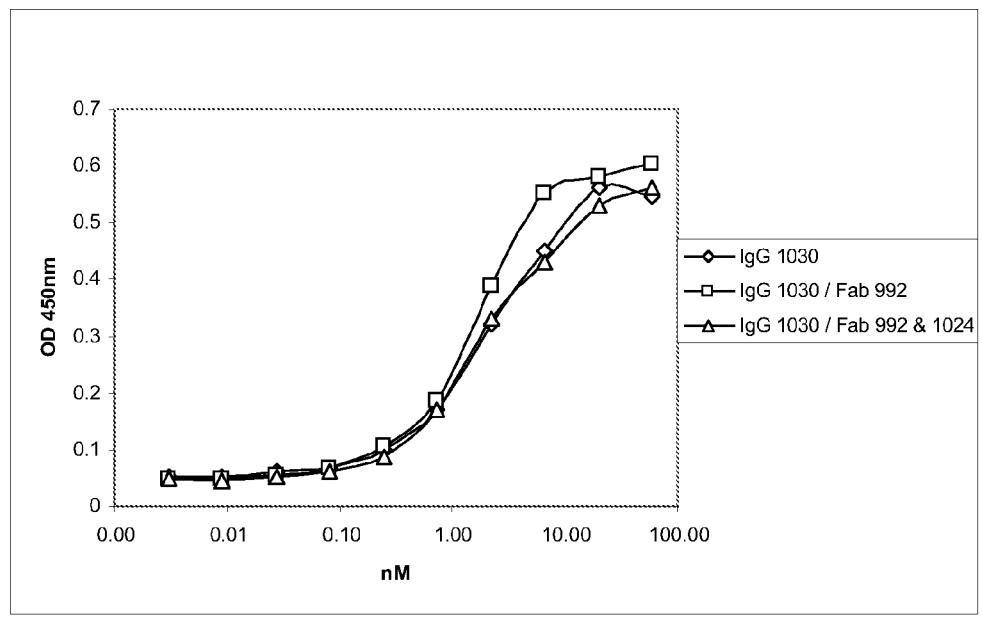

FIG. 33: Determination of enhancement of IgG binding to EGFR on A431-NS cells upon prior receptor saturation with Fab fragments binding non overlapping epitopes. Indicated Fab fragments were allowed to saturate recognized EGFR epitope on A431-NS cells for 30 min after which specified IgG antibodies were serially titrated and bound IgG with or with out Fab addition visualized by a secondary Mouse anti-Human Fc HRP conjugate. A) Binding characteristics of IgG 992 to A431-NS cells with or without prior receptor saturation with indicated Fab fragments. B) Binding characteristics of IgG 1024 to A431-NS cells with or without prior receptor saturation with indicated Fab fragments. C) Binding characteristics of IgG 1030 to A431-NS cells with or without prior receptor saturation with indicated Fab fragments.

FIG. 34: Cynomolgus full length EGFR cDNA (FIG. 34A; SEQ ID NO 102) and encoded protein (FIG. 34B; SEQ ID NO 103).

Figure 35:
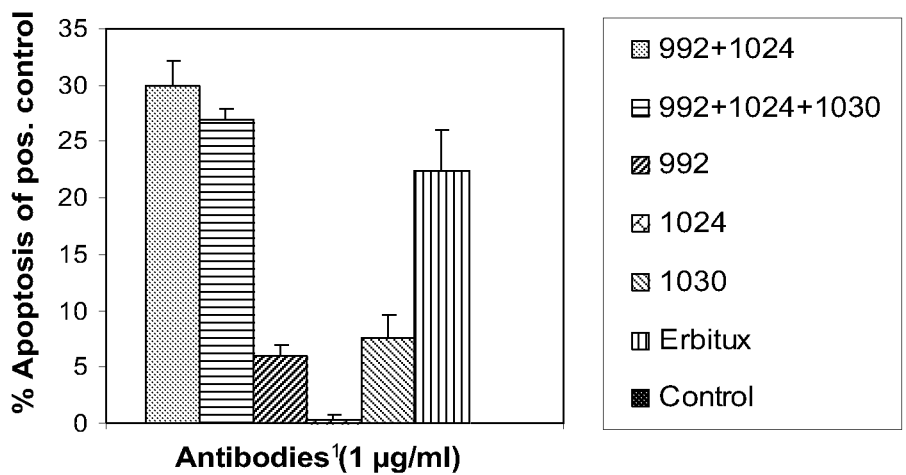

FIG. 35: Apoptosis obtained in A431NS with 1 μg/ml of the indicated antibodies/combinations. Histone-DNA complexes were detected in an ELISA kit from Roche. Levels of apoptosis were related to a positive control (maximal apoptosis).

Figure 36:
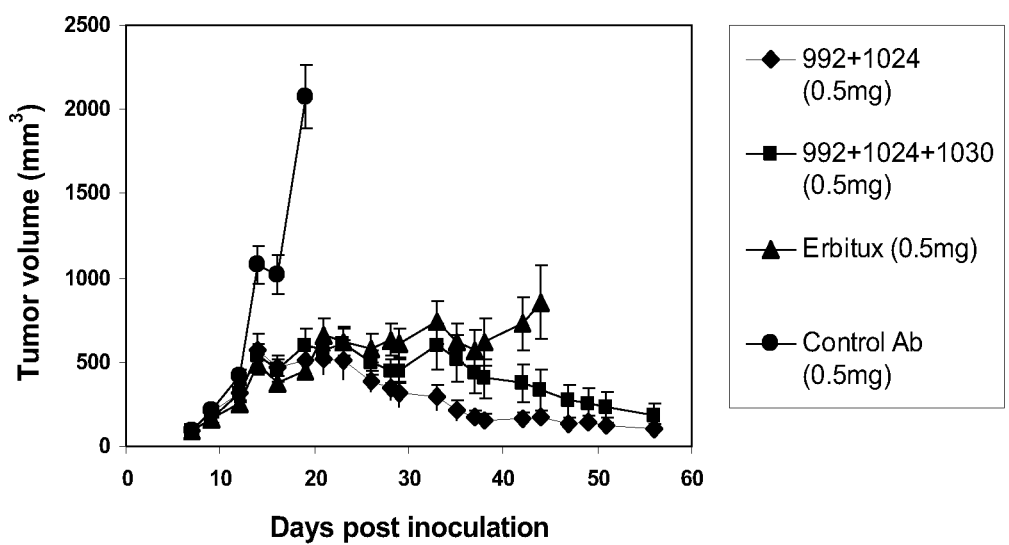

FIG. 36: Balb/C nu/nu mice were injected with $1×10^6$ A431NS cells. When tumors were approximately 100 $mm^3$ in average, treatments were initiated. Mice received 17 injections with antibody. The first treatment starting at day 8 and the last at day 34. Antibody/compositions were injected at 0.5 mg/dose or 0.17 mg/dose. Mean values of tumour volume+/−SEM are shown.

Figure 37:
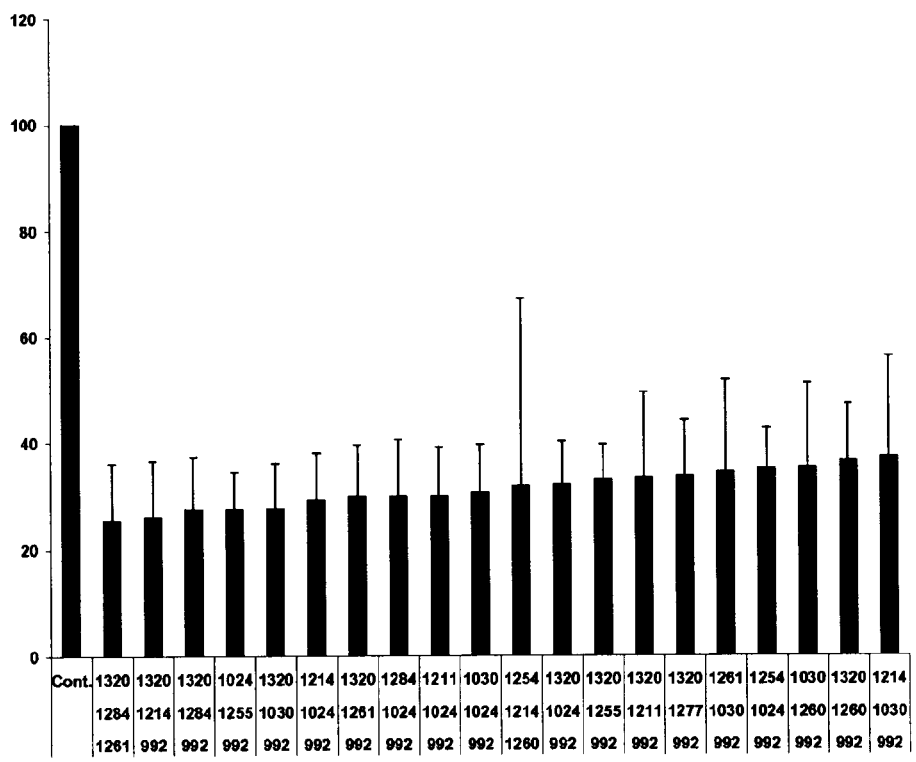

FIG. 37: Inhibition of proliferation of A431NS. The X axis shows different representative combinations of 3 antibodies of the invention. The Y axis shows Metabolic activity as percent of untreated control (control). Errorbars represent +/−SEM. For additional details see Example 6.

Figure 38:
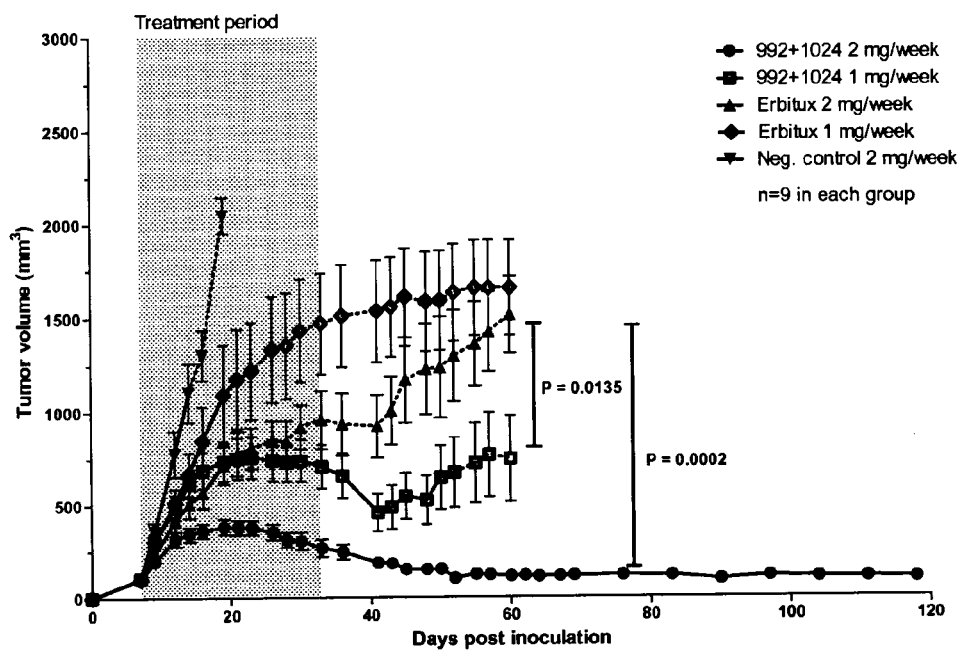

FIG. 38: Growth inhibitory effect of two different doses of 992+1024 mix compared to Erbitux in A431NS human tumor xenografts. BALB/c nu/nu mice were inoculated with $10^6$ A431NS cells. When tumors reached an average size of 100 $mm^3$ (day 8) the mice were randomized into groups of 9 and treatment was started. Indicated antibodies were injected at 0.5 mg/dose or 1 mg/dose, twice weekly for a total of 9 injections. The light grey area on the graph indicates the treatment period. The start of a dotted line designate the time point at which the first mouse in a given group was euthanized due to excessive tumor size. The statistically significant differences between 2 mg/week 992+1024 vs. 2 mg/week Erbitux and 1 mg/week 992+1024 vs. 2 mg/week Erbitux has been calculated on day 60 where all except the 992+1024 2 mg/week group were terminated. The tumor size of animals excluded prior to day 60 was carried through, thus; the graph shows the accumulated tumor volume of all mice in a given group. Mean values+/−SEM are shown.

Figure 39:
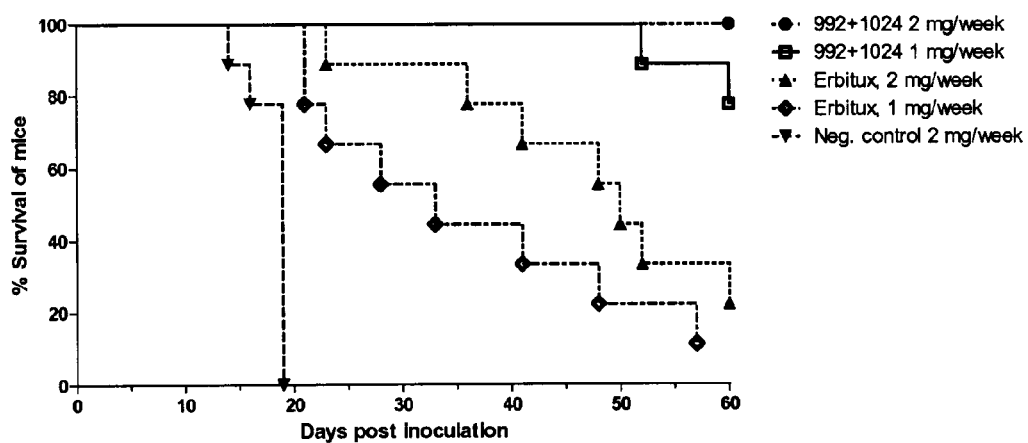

FIG. 39: Kaplan-Meyer plot of survival of mice treated with the 992+1024 antibody mix, Erbitux or control antibody (same experiment as shown in FIG. 38). Results presented as percent survival of treated mice. A significant difference between the percent survival of mice in the high dose (2 mg/week, P=0.0008)) and low dose (1 mg/week, P=0.0004) groups was observed when comparing 992+1024 and Erbitux. Also, low dose 992+1024 was significantly better when compared to high dose Erbitux (P=0.0087). The statistical difference was calculated using a Log-rank (Mantel-Cox) test.

FIG. 40: Analysis of cross reactivity of IgGs 992, 1024 & 1320 against full length Human and Cynomolgus EGFR transfected CHO cells by FACS analysis. Bound antibody was detected with a PE labelled goat $F(ab')_2$ anti-human IgG FC. Gating was performed on uniform cells (SCC/FCS properties) expressing EGFR. Binding is expressed as % maximal antibody binding at 1 nM concentration.

FIG. 41: Clustalw2 alignment of the amino acids sequences of the variable regions of the murine (chi) and humanized (hu) candidate variable regions of both heavy and light chains of 992 (A) and 1024 (B). The CDR regions as defined by IMGT are underlined; gaps presented by (−), identical amino acids by (*), conservative mutations as (:), semi-conservative (.). The bold amino acid indicates amino acid positions where back-mutations to the original identified murine residue will be performed if the fully human frame work variants display decreased binding affinity. Sequence ID numbers as follows: Humanized 992 VH (SEQ ID NO 104). Humanized 992 VL (SEQ ID NO 105). Humanized 1024 VH (SEQ ID NO 106). Humanized 1024 VL (SEQ ID NO 107). Chimeric 992 VH (aa 3-124 of SEQ ID NO 40). Chimeric 992 VL (aa 3-109 of SEQ ID No 72). Chimeric 1024 VH (aa 3-120 of SEQ ID NO 41). Chimeric 1024 VL (aa 3-114 of SEQ ID NO 73).

Figure 42A:
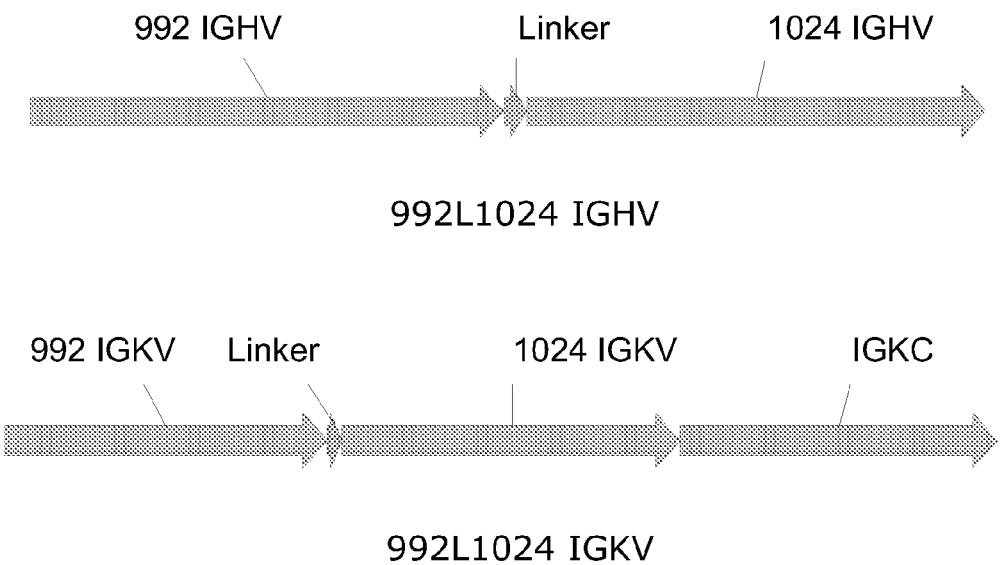

FIG. 42A: Schematic representation of the dual variable domain encoding genes for 992L1024; 992L1024 IGHV (751 bp) is represented from the 5' AscI restriction site followed by 992 IGHV, the ASTKGP linker, 1024 IGHV and ending at the 3' XhoI restriction site, 992L1024 IGKV (1071 bp) is represented from the 5' NheI restriction site followed by 992 IGKV, the TVAAP linker, 1024 IGKV, IGKC and ending at the 3' NotI restriction site.

Figure 42B:
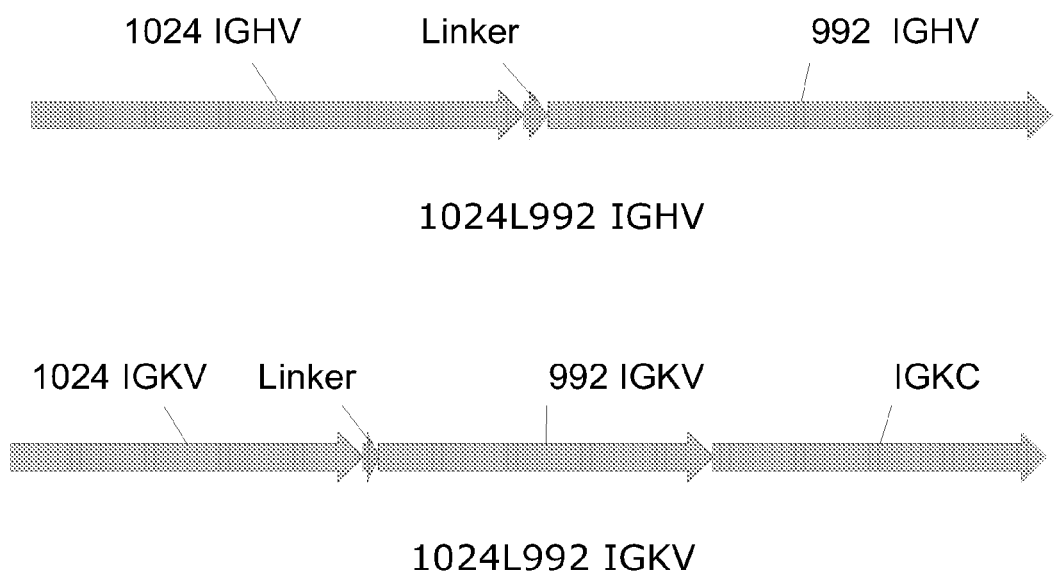

FIG. 42B: Schematic representation of the dual variable domain encoding genes for 1024L992; 1024L992 IGHV (751 bp) is represented from the 5' AscI restriction site followed by 1024 IGHV, the ASTKGP linker, 992 IGHV and ending at the 3' XhoI restriction site, 1024L992 IGKV (1071 bp) is represented from the 5' NheI restriction site followed by 1024 IGKV, the TVAAP linker, 992 IGKV, IGKC and ending at the 3' NotI restriction site.

Figure 43:
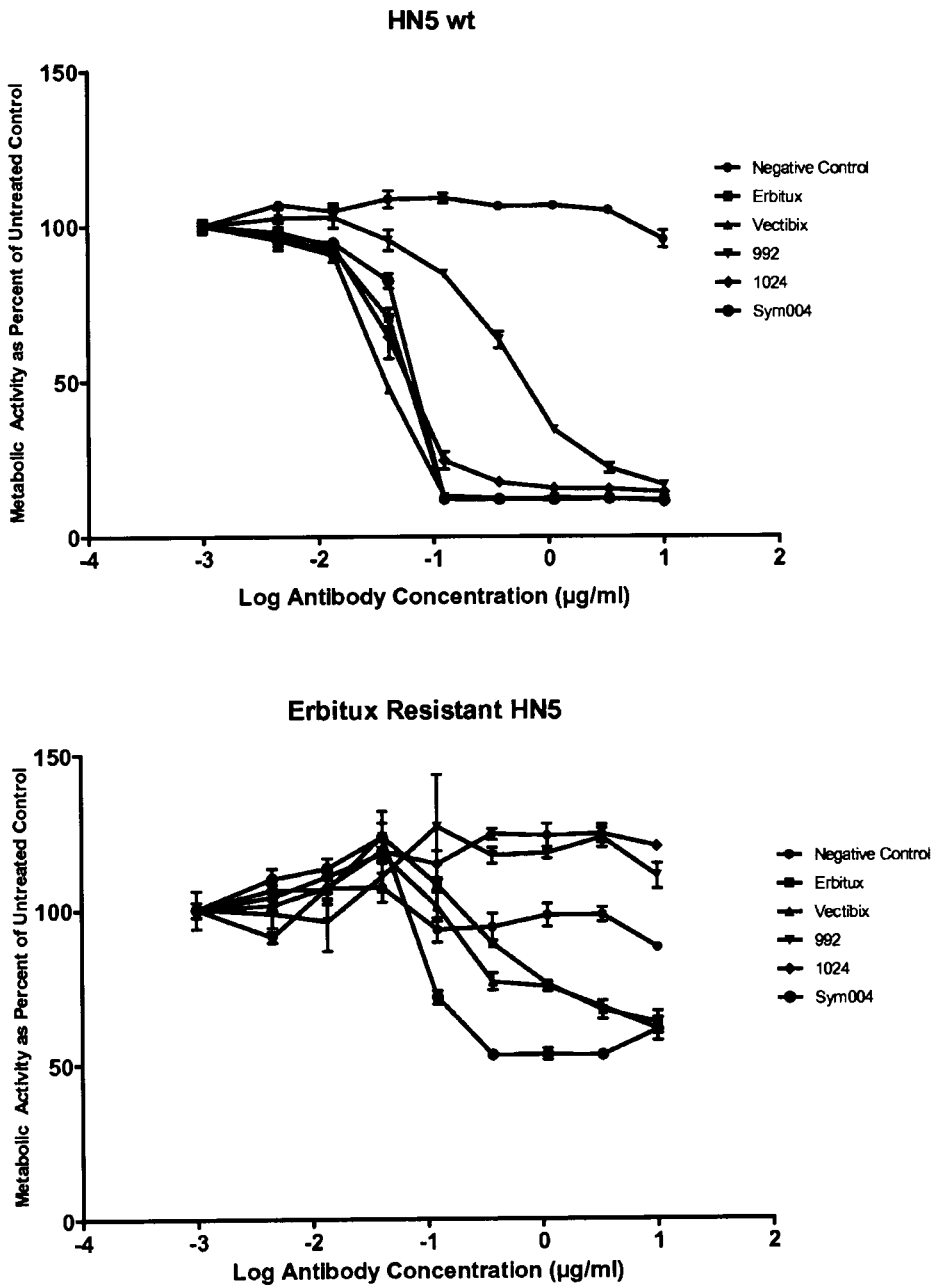

FIG. 43: Metabolic activity of HN5 wt cells in 0.5% FBS (Top) and Erbitux resistant HN5 cells (Bottom) in the presence of the varying concentrations of the indicated antibodies. Legend: antibodies 992 and 1024 are as defined in the present application. Sym004 is an antibody composition with antibodies 992 and 1024.

Figure 44:
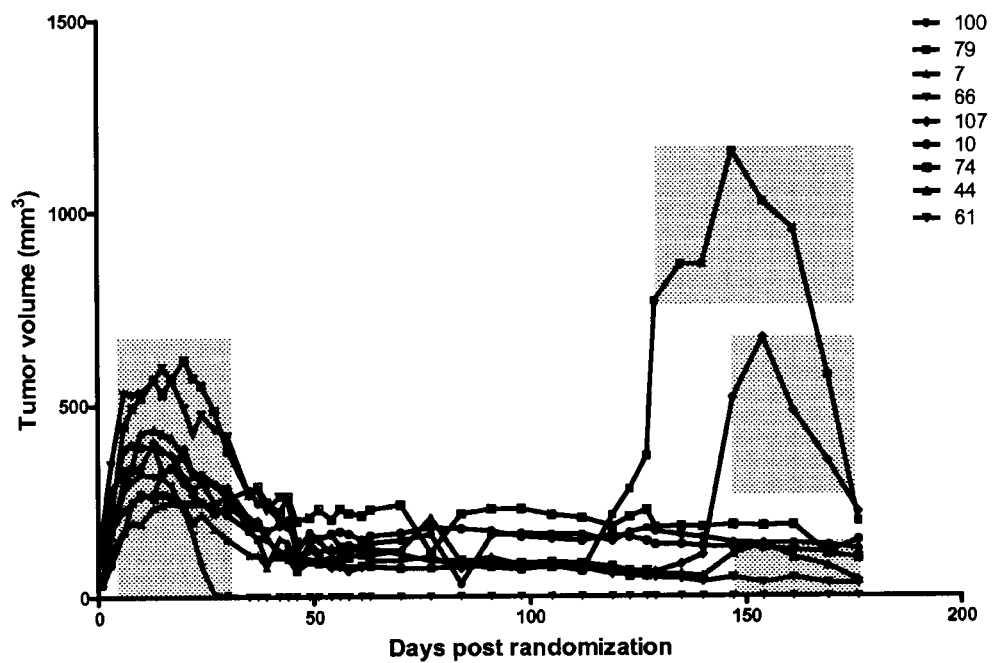

FIG. 44: Tumor growth curves of individual A431NS tumors following the initial treatment with 1 mg of an antibody composition with antibodies 992+1024 for a total of nine injections (left grey box). All tumors responded to the therapy but more than 80 days post treatment, three of the tumors started to grow again. Re-treatment of these tumors with an antibody composition with antibodies 992+1024 induced tumor regression (right grey boxes).

Figure 45:
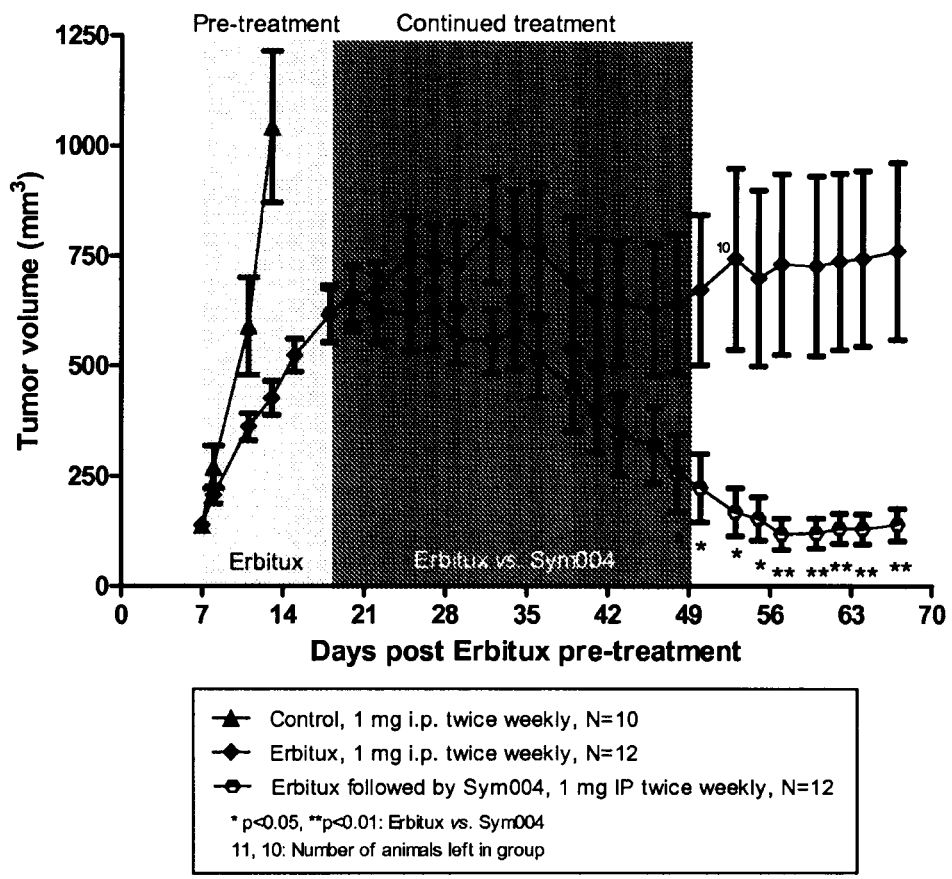

FIG. 45: BALB/c nu/nu mice with A431NS xenograft tumors were pretreated with Erbitux and subsequently randomized to continue on Erbitux treatment or switched to an antibody composition with antibodies 992+1024 (Sym004 in Figure legend) treatment when the tumors had an average tumor size of approximately 500 mm$^3$. A significant decreased tumor burden was seen in the group switched to an antibody composition with antibodies 992+1024 treatment as compared to the group continuing on Erbitux treatment.

Figure 46:
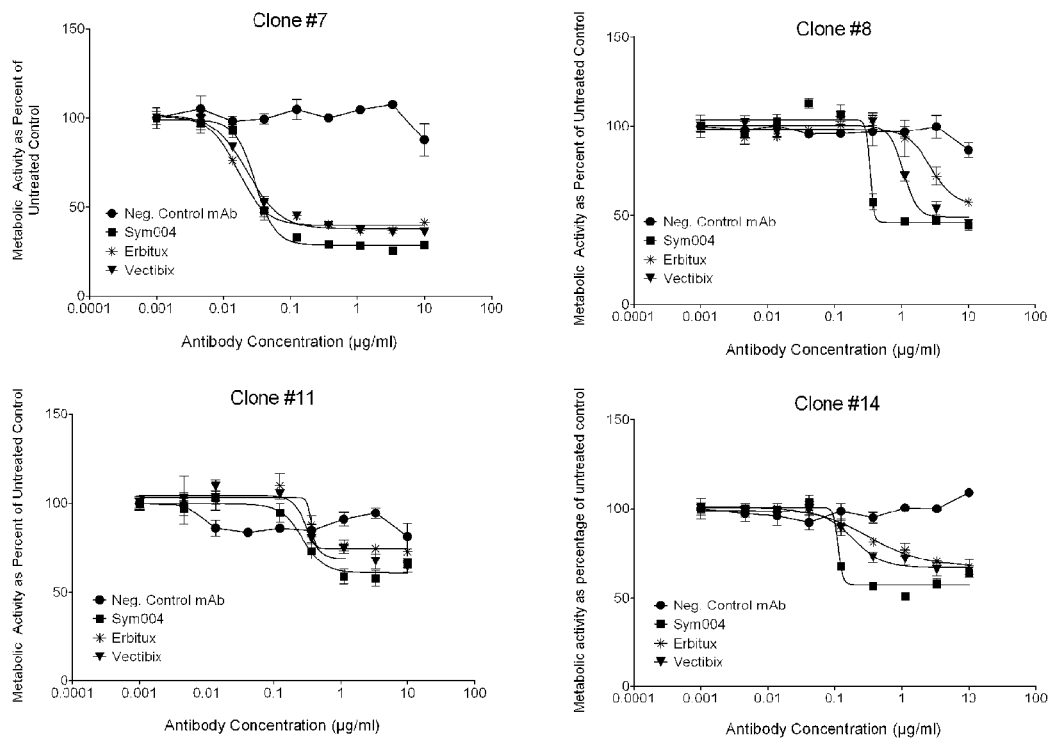

FIG. 46: Metabolic activity of Erbitux resistant HN5 clones in 0.5% FBS in the presence of the varying concentrations of the indicated antibodies.

Figure 47:
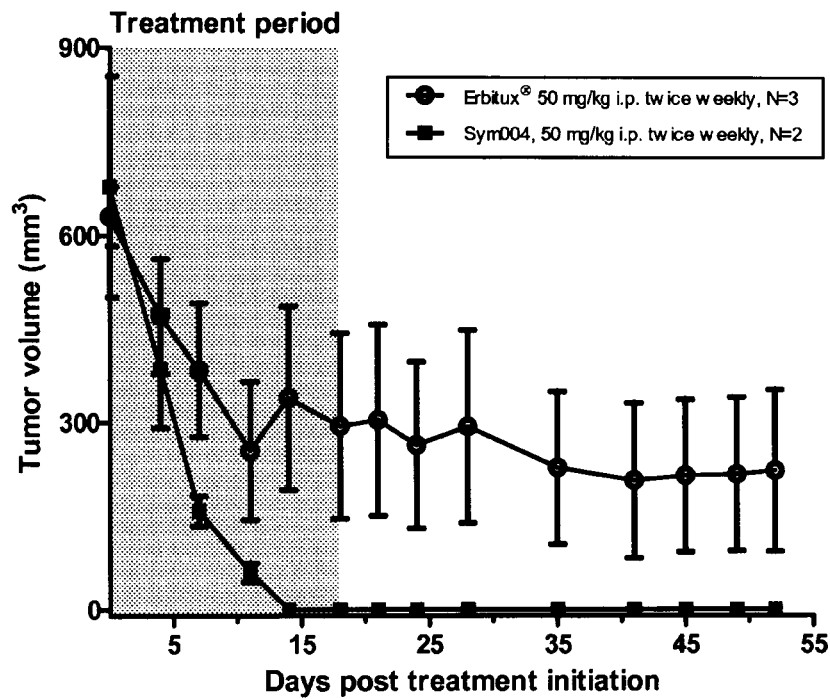

FIG. 47: Growth of Erbitux resistant HN5 clone #7 tumor xenografts treated with 50 mg/kg Sym004 or Erbitux. Standard error of mean is indicated on the graph.

DETAILED DESCRIPTION OF THE INVENTION

Antibody Mixtures

The invention relates to an antibody composition for use in a method of treatment of cancer in a subject that has been subjected to prior treatment regimen involving an anti human EGFR antibody or wherein said cancer is resistant or partially resistant to treatment with at least one other anti-EGFR antibody, said antibody composition comprising at least 2 distinct anti-human EGFR antibody molecules. In the present invention the at least 2 distinct anti-human EGFR antibodies binds to non-overlapping epitopes. The non-overlapping nature of the antibodies is preferably determined using differently labelled antibodies in a FACS analysis with EGFR expressing cells or by using Surface Plasmon Resonance using EGFR antigen captured or conjugated to a flow cell surface. ELISA based methods as described in the examples may also be used. A composition binding two or more non-overlapping EGFR epitopes can be used against a wider range of EGFR dependent cancer types as it may be less vulnerable to differences in EGFR conformation and less vulnerable to mutations compared to composition of monoclonal antibodies targeting one or two epitopes. Furthermore, the antibody composition binding two or more non-overlapping EGFR epitopes may provide superior efficacy compared to composition targeting only one epitope. In particular, the antibody composition may provide superior efficacy with respect to terminal differentiation of cancer cells in vivo. For a monoclonal anti-EGFR antibody therapy a certain proportion of patients will not respond effectively to the antibody treatment. For some of the patients, this may be due to rapid clearing of the antibody or because the antibody generates an immune response in the patient against the antibody. For some patients, the lack of response may be because their particular EGFR dependent cancer expresses EGFR in a conformation where the monoclonal antibody cannot bind its epitope. This could be because of differences in glycosylation, because of domain deletion, or because of mutations and/or SNP(s).

Also for some cancers the autocrine EGFR-stimulation caused by the cancer cells' production of ligand is of importance, while in other cases the EGFR expressed by the cancer cells does not need ligand stimulation. For the latter cancer types, an antibody capable of inhibiting ligand binding may not be effective.

An antibody composition wherein the antibodies are capable of binding at least two distinct epitopes on EGFR will be more broadly applicable, since the likelihood that both epitopes are changed compared to the epitope(s) recognised by the antibodies is diminished. Furthermore, the likelihood that all antibodies are either cleared by the patient is much smaller. Superiority has been shown most clearly in terms of induction of terminal differentiation of the cancer cells using two Domain III antibodies with non-overlapping epitopes. Such efficient antibody-induced terminal differentiation of cancer cells has not been reported before and represents a significant step forward in designing efficient antibody-based cancer therapies. Later results have shown that similar or even superior results can be obtained with a particular combination of two antibodies.

For improved clinical efficacy and broader utility against a wider range of EGFR dependent cancer types, the number of antibodies in the composition can be increased. Thus, the composition may comprise antibodies capable of binding three non-overlapping epitopes. The composition may comprise antibodies capable of binding four non-overlapping epitopes. The composition may comprise antibodies capable of binding five non-overlapping epitopes. The composition may comprise antibodies capable of binding six non-overlapping epitopes. The examples of the present application show that at least six distinct antibodies can bind to EGFR at one time (Example 3). This does not exclude that it is possible or even advantageous to design a composition comprising antibodies capable of binding more than six, such as seven or eight non-overlapping epitopes by carefully selecting antibodies.

There may be advantages of including antibodies with overlapping epitopes as this increases the likelihood that the epitope is bound. One rationale behind this is that the epitope in some patients and/or in some cancer cells may be changed due to conformational changes or mutations or SNPs. While this may affect the binding of one antibody, it may not affect the binding of another antibody binding an overlapping epitope. Furthermore, there is a risk that one of the antibodies is cleared by the patients, because it is seen as an antigen. By including two antibodies binding different but overlapping epitopes the consequence of clearance of one of the two antibodies and the consequence of a mutation in an epitope is diminished.

Superior results have been obtained with specific combinations of antibodies capable of binding two non-overlapping EGFR epitopes. These preferred "two antibody" compositions are described in more detail below together with guidance relating to how to design antibody compositions of the invention. It has turned out that compared to the three antibody composition comprising antibodies 992, 1030, and 1042 similar or even improved efficacy could be obtained when using a composition with only two antibodies: 992 and 1024. As antibodies 1024 and 1042 belong to the same cluster and therefore have the same binding specificity, in effect, the results observed for the three antibody composition including the effect on terminal differentiation may be attributed to only two of the binding specificities (992 and 1024/1042) in the composition.

The antibodies of the composition may be chimeric antibodies with non-human variable chains and human constant chains. The non-human variable chains may be from mouse, rat, sheep, pig, chicken, non-human primate or other suitable animal. In order to obtain fully human antibodies the antibodies can be generated in a transgenic animal with human antibody genes. The antibodies may also be so-called humanised antibodies, where the non-human CDR sequences have been grafted into human framework sequences.

Preferably the human constant chain is IgG1 or IgG2 isotype. More preferably all antibodies in the composition have the same isotype for ease of manufacturing. However, it may be advantageous to include in the composition antibodies of different isotype.

Preferably the antibody compositions of the invention comprise antibodies capable of binding to EGFR selected from the group consisting of human EGFR, mutated human EGFR, and deletion variants of human EGFR. Preferably the antibodies are capable of binding both human and non-human primate EGFR, so that they can be tested in relevant toxicology studies prior to clinical experiments. Preferably, the non-human primate is cynomolgous monkey (*Macaca fascicularis*).

In order to support the above identified concept of treating EGFR dependent cancer using antibodies binding two or more distinct epitopes, the present inventors have identified, manufactured, and characterised a series of chimeric mouse/human antibodies directed against EGFR. These chimeric antibodies have been compared individually and in mixtures to state of the art monoclonal antibodies, exemplified with Erbitux™ and Vectibix™.

Table 1 shows a summary of the individual chimeric antibodies and the features associated with these. Antibody no is a reference number used throughout the present application. Specificity is the EGFR domain to which the antibody binds as evidenced in Example 3. deltaEGFR is the ability of the antibody to bind to EGFR mutant (EGFRvIII) as described in example 1. Cynomolgous EGFR is the ability of the antibody to bind cynomolgous EGFR (example 10). EGF inhib is the ability of the antibody to inhibit EGF binding (Example 4) Proliferation is the ability of the antibody to inhibit proliferation of cancer cell lines, A431 and HN-5 (Example 6).

TABLE 1

Antibodies of the invention

| Antibody no. | Specificity | deltaEGFR | Cynomolgous EGFR | EGF inhib | Proliferation |
|---|---|---|---|---|---|
| 992 | Domain III | no/weak | yes | yes/weak | Yes |
| 1030 | Domain III | yes | yes | yes | yes |
| 1024 | Domain III | yes | yes | | yes |
| 1042 | Domain III | weak | yes | (yes) | yes |
| 1277 | Domain III | yes | Yes | yes | HN5 |
| 1254 | Domain III | yes | Yes | yes | HN5 |
| 1208 | Domain III | yes | yes | yes | yes HN5+/−992 |
| 1320 | Domain III | weak | No | yes | yes |
| 1257 | Domain I/II | no | yes | no | yes |
| 1261 | Domain I | no | Yes | no | yes |
| 1229 | Not domain I/II | yes | No | no | yes (A431) |
| 1284 | Domain I | no | Yes | yes | yes |
| 1344 | Domain I/II | no | yes | nd | HN5 w/992 |
| 1260 | Domain I/II | no | Yes | yes | A431 |
| 1308 | Domain I | no | yes | nd | HN5 w/992 |
| 1347 | Domain I | no | yes | nd | HN5 w/992 |
| 1428 | Domain I & II | no | Yes | yes | HN5 w/992 |

From the data generated with the chimeric antibodies tested alone and in combination in proliferation, binding, receptor degradation/inactivation, and motility assays, and in animal models, a number of conclusions can be drawn.

The results obtained with two cancer cell lines, HN-5 and A431 (Example 6) have been repeated with different cancer cell lines (MDA-MB-468 a breast cancer cell line; DU145—prostate cancer cell line). What is evident from these experiments is that combinations of antibodies provided by the present inventors display efficacy against a very wide range of cancer cell lines, supporting the efficacy of the antibody compositions against a range of EGFR conformations.

It has also been shown that the superiority of antibody mixes is higher in proliferation assays where physiological concentrations of ligand (EGF) is added to the growth medium than when EGF is not added (FIG. 17). According to literature (Hayashi and Sakamoto 1998 J Pharmacobiodyn 11; 146-51) serum contains approximately 1-1.8 ng/ml or 0.2-0.3 nM EGF while gastic juice is reported to contain 0.3 ng/ml (ca. 0.05 nM) (Pessonen et al. 1987 Life Sci. 40; 2489-94). In an in vivo setting, EGF and other EGFR ligands are likely to be present and the ability of the antibody mix to be effective in the presence of EGFR ligand is therefore an important feature of the antibody mixes of the present invention.

The chimeric mouse/human antibodies of the present invention provide better results when used in combination than when used alone. This is exemplified in several experiments (see e.g. Example 6)), where antibodies when tested alone show only moderate antiproliferative effects on a cancer cell line (A431-NS), but when used in either combination, show remarkably superior results. These results have been confirmed with numerous combinations of the chimeric antibodies of the present invention. Particularly superior results have been obtained with a composition comprising antibodies 992 and 1024.

For example several of the antibodies have been tested in an antiproliferation assay with A431-NS and HN-5 together with either of antibodies 992, 1208, 1254, and 1277.

Receptor binding studies have shown that some antibodies may actually stimulate the binding of further antibodies, such that a particular antibody binds in higher quantities to the receptor after receptor saturation with one or several antibodies. The binding of antibody 992, directed against domain III, clearly benefits from this synergistic effect obtained by prior receptor saturation with one or more antibodies binding non-overlapping epitopes. Another example of this co-operative effect is seen when antibody 1396 directed against an unknown epitope is tested against EGFR saturated with antibodies binding non-overlapping epitopes.

Receptor binding studies have also shown that it is possible to bind at least 6 antibodies to the extracellular domain of EGFR simultaneously. These 6 antibodies represent 3 Domain III antibodies, one Domain I antibody, one Domain I/II antibody, and one antibody binding an unknown epitope. Interestingly, binding of the three Domain III antibodies seems to facilitate the subsequent binding of further antibodies. This clearly supports the concept of providing antibody compositions with several antibodies binding distinct epitopes.

When designing the composition of an antibody composition against EGFR, antibodies with non-overlapping epitopes are preferably used as these provide a higher synergistic effect.

Domain III of EGFR is of importance for ligand binding to the receptor. Furthermore, antibody binding to Domain III may stabilise EGFR in the tethered monomeric conformation, which does not lead to receptor signalling. For these reasons it is preferable that the antibody composition contains at least two antibodies with specificity for Domain III. Preferred Domain III antibodies include antibodies 992, 1024, 1030, 1208, 1254, 1277, and 1320. The antibody composition may preferably comprise more than two Domain III antibody such as at least 3 domain III antibodies, for example at least 4 domain III antibodies, such as at least 5 domain III antibodies, for example at least 6 domain III antibodies.

In another preferred embodiment, the antibody composition comprises at least one Domain I antibody. Preferably the at least one Domain I antibody is selected from the group consisting of antibodies 1284, 1308, 1344, and 1347. More preferably the at least one Domain I antibody is selected from the group consisting of antibodies 1284, and 1347.

In another preferred embodiment, the antibody composition comprises at least one Domain I/II antibody. Preferably the at least one Domain I/II antibody is selected from the group consisting of antibodies 1257, 1260, 1261, 1428, and 1434. More preferably the at least one Domain I/II antibody is selected from the group consisting of antibodies 1261 and 1260.

Preferred mixes with three antibodies include: Antibodies 992+1320+1024; 992+1024+1030; 992+1255+1024; 992+1024+1214; 992+1024+1284; 992+1024+1211; 992+1024+1030.

Preferred mixes with four antibodies include: Antibodies 992+1320+1024+1030; 992+1024+1030+1284.

Preferred mixes with five antibodies include: 992+1030+1024+1260+1347; 992+1030+1024+1261+1347; 992+1030+1024+1261+1284.

One preferred mix with eight antibodies includes: 992+1030+1024+1277+1254+1320+1260+1261+1284+1347.

Furthermore, in order to be able to perform a toxicology study in a non-human primate, it is preferable that all antibodies in the composition bind to human as well as to at least one further primate EGFR, such as EGFR from chimpanzee, Macaca mulatta, Rhesus monkey and other monkeys, or cynomolgous monkey. Cynomolgous monkey is a relatively small animal, and very well suited for toxicology studies, Therefore, the further primate EGFR is preferably cynomolgous EGFR. Preferably the antibodies bind with approximately the same affinity to human and non-human primate EGFR.

The present invention has shown superior results in one or more functional assays when combining 2, 3, 4, 5, 6, 7, and 8 antibodies in one composition. While these data provide guidance on selection of the number of antibodies in the composition, they are in now way to be interpreted in a limiting way. The composition may comprise more than 8 antibodies, even though the experimental data only show simultaneous binding of 6 antibodies. There may be other reasons for including more than 6 antibodies in the composition, such as e.g. differences in clearing rate of the antibody members.

A further preferred feature of the antibodies of the compositions is protein homogeneity, so that the antibodies can be purified easily. For the individual antibody members, an ion exchange chromatography profile with one distinct peak is preferred for ease of characterisation. A clear ion exchange chromatography profile is also preferred for ease of characterisation of the final antibody composition. It is also preferable when combining the antibodies that they can be distinguished using ion exchange chromatography, so that the composition with all the antibodies can be characterised in one run.

The antibodies may be of any origin such as human, murine, rabbit, chicken, pig, lama, sheep. The antibodies may also be chimeric as described in the examples or may be humanised, superhumanised or reshaped versions thereof using well-known methods described in the art.

A Preferred Antibody Composition

As shown in the appended examples, the anti-EGFR composition based on antibodies 992 and 1024 has unique and distinct properties. The binding of antibody 992 is enhanced by binding of other antibodies including 1024. In contrast to commercial antibodies, both 992 and 1024 bind preferentially to conformational epitopes presented on cells (Examples 14 and 15). The epitopes of 992 and 1024 both overlap with but are distinct from the Erbitux and Vectibix epitope(s). In contrast to a number of other two-antibody compositions where the individual antibodies bind to non-overlapping epitopes, the composition based on the binding specificities of antibodies 992 and 1024 triggers receptor internalization rapidly and effectively. A novel mechanism of action involving terminal differentiation accompanied with increased involucrin expression and the appearance of keratin pearls is observed in an animal model after treatment with antibody compositions based on antibodies 992 and 1024. This unique mechanism of action leads to more effective and sustained growth inhibition in vitro and in vivo. This is most clearly seen in the in vivo examples where the tumours continue to diminish after termination of treatment. In the control group receiving Erbitux, tumours start growing soon after termination of treatment. This clearly indicates a different mechanism of action.

It is believed that the novel mechanism of action is achieved by using the combination of two binding specificities displayed by antibodies 992 and 1024 in one antibody composition. This mechanism of action is also seen when a third antibody which does not compete with antibodies 992 and 1024 is used, e.g. in the triple combination of antibodies 992, 1024, and 1030.

These observations have let to the design of an antibody composition comprising at least 2 distinct anti-human EGFR antibody molecules, wherein a first distinct anti-EGFR antibody molecule is selected from the group consisting of antibody 992, an antibody comprising the VL (amino acids 3-109 of SEQ ID NO 72) and VH (amino acids 3-124 of SEQ ID NO 40) sequences of antibody 992, an antibody having the CDR3s of antibody 992 (SEQ ID NO 116 and 111), an antibody binding to the same epitope as antibody 992, and an antibody capable of inhibiting the binding of antibody 992 to human EGFR; and wherein a second distinct anti-EGFR antibody molecule is selected from the group consisting of antibody 1024, an antibody comprising the VL (amino acids 3-114 of SEQ ID NO 73) and VH (amino acids 3-120 of SEQ ID NO 41) sequences of antibody 1024, an antibody having the CDR3s of antibody 1024 (SEQ ID NO 120 and 114), an antibody binding to the same epitope as antibody 1024, and an antibody capable of inhibiting the binding of antibody 1024 to human EGFR.

Preferably, said first distinct anti-EGFR antibody molecule is selected from the group consisting of antibody 992, an antibody comprising the VL and VH sequences of antibody 992, an antibody having the CDR3s of antibody 992, and an antibody binding to the same epitope as antibody 992; and said second distinct anti-EGFR antibody molecule is selected from the group consisting of antibody 1024, an antibody comprising the VL and VH sequences of antibody 1024, an antibody having the CDR3s of antibody 1024, and an antibody binding to the same epitope as antibody 1024.

The present invention contemplates mutations in the CDR3 sequences of antibodies 992 and 1024 to provide antibodies with the same binding specificity. Therefore in one embodiment an antibody having the same binding specificity as antibody 992 comprises a CDRH3 having the following formula: $CTX_1X_2X_3X_4X_5X_6X_7X_8X_9X_{10}X_{11}X_{12}X_{13}X_{14}X_{15}W$ where $X_1$ to $X_{15}$ are selected individually from the groups of amino acids listed below:

$X_1$=R or K;
$X_2$=N, D, E or Q;
$X_3$=G, A, V, or S;
$X_4$=D, E, N or Q;
$X_5$=Y, F, W or H;
$X_6$=Y, F, W or H;
$X_7$=V, I, L or A;
$X_8$=S, T, G or A;
$X_9$=S, T, G or A;
$X_{10}$=G, A, V, or S;
$X_{11}$=D, E, N or Q;
$X_{12}$=A, G, V, or S;
$X_{13}$=M, L, I or V
$X_{14}$=D or E; and
$X_{15}$=Y, or F;

and a CDRL3 described by the following formula: $CX_1X_2X_3X_4X_5X_6PPTF$ where $X_1$ to $X_6$ are selected individually from the groups of amino acids listed below:

$X_1$=Q or H;
$X_2$=H, E or Q;
$X_3$=Y, F, W or H;
$X_4$=N, Q or H;
$X_5$=T, S, G or A; and
$X_6$=V, I, L or A.

In one embodiment an antibody having the same binding specificity as antibody 1024 comprises a CDRH3 having the following formula: $CVX_1X_2X_3X_4X_5X_6X_7X_8X_9X_{10}X_{11}W$ where $X_1$ to $X_{11}$ are selected individually from the groups of amino acids listed below:

$X_1$=R or K;
$X_2$=Y, F, W or H;
$X_3$=Y, F, W or H;
$X_4$=G, A, V, or S;
$X_5$=Y, F, W or H;
$X_6$=D, E, N or Q;
$X_7$=E or D;
$X_8$=A, G, V, or S;
$X_9$=M, L, I or V;
$X_{10}$=D, E, N or Q; and
$X_{11}$=Y, or F;

and a CDRL3 described by the following formula: $CX_1X_2X_3X_4X_5X_6PX_7TF$ where $X_1$ to $X_7$ are selected individually from the groups of amino acids listed below:

$X_1$=A, G, or V;
$X_2$=Q or H;
$X_3$=N, Q or H;
$X_4$=L, I, M or V;
$X_5$=E, D, N or Q;
$X_6$=L, I, M or V; and
$X_7$=Y, F, W or H.

Antibodies with mutated CDR3s can be made using standard techniques and be expressed and tested for binding using methods described herein.

The antibodies according to this aspect of the invention may be chimeric, human, humanised, reshaped or superhumanised. This may be done by using methods known in the art. For example antibodies 992 and 1024 may be humanised using methods described in Example 18. Methods for "superhumanisation" are described in U.S. Pat. No. 6,881,557.

More preferably said first distinct anti-EGFR antibody molecule is selected from the group consisting of antibody 992, an antibody comprising the VL and VH sequences of antibody 992, and an antibody having the CDR3s of antibody 992; and said second distinct anti-EGFR antibody molecule is selected from the group consisting of antibody 1024, an antibody comprising the VL and VH sequences of antibody 1024, and an antibody having the CDR3s of antibody 1024.

More preferably said first distinct anti-EGFR antibody molecule is selected from the group consisting of antibody 992, and an antibody comprising the VL and VH sequences of antibody 992; and said second distinct anti-EGFR antibody molecule is selected from the group consisting of antibody 1024, and an antibody comprising the VL and VH sequences of antibody 1024.

Most preferably the composition comprises antibodies 992 and 1024.

As described, the first and second anti-EGFR antibodies preferably do not inhibit the binding to human EGFR of each other. Even more preferably, at least one of the antibodies is capable of increasing the maximum binding capacity of the other antibody with respect to human EGFR. This effect is observed for antibodies 992 and 1024 (Example 16).

The ratio between the two antibodies need not be exactly a 1:1 ration. Consequently, the proportion of the first antibody relative to the second antibody in the composition may be between 5 and 95%, such as between 10 and 90%, preferably between 20 and 80%, more preferably between 30 and 70, more preferably between 40 and 60, such as between 45 and 55, such as approximately 50%.

Preferably the first and second antibodies are of isotype IgG1, or IgG2.

Examples of antibodies binding to the same epitope as antibody 992 identified by the present inventors are antibodies from the antibody cluster comprising clones 1209, 1204, 992, 996, 1033, and 1220.

Examples of antibodies binding to the same epitope as antibody 1024 identified by the present inventors are antibodies from the antibody cluster comprising clones 1031, 1036, 1042, 984, 1024, 1210, 1217, 1221, and 1218.

The CDR3 determine the binding specificity of the antibodies. In preferred embodiments, the antibody comprising the CDR3 of antibody 992 additionally comprises the CDR1 and CDR2 of VH and VL of antibody 992. Likewise the antibody comprising the CDR3 of antibody 1024 additionally preferably comprises the CDR1 and CDR2 of VH and VL of antibody 1024. CDR sequences of the antibodies can be found in Table 12, example 17.

In other embodiments, the antibody competing with antibody 992 is selected from the group consisting of antibodies 1208, 1254, and 1277. Likewise, the antibody competing with antibody 1024 may be selected from the group consisting of antibodies 1042 and 1320.

In one embodiment, the composition does not contain further antibodies in addition to said first and second antibodies, more preferably not further anti-EGFR antibodies.

In other embodiments, the composition further comprises a third distinct anti-EGFR antibody, wherein said third distinct anti-EGFR antibody molecule is selected from the group consisting of antibody 1030, an antibody comprising the VL (amino acids 3-113 of SEQ ID NO 74) and VH (amino acids 3-120 of SEQ ID NO 42) sequences of antibody 1030, an antibody having the CDR3s of antibody 1030 (SEQ ID NOs 112 and 119), an antibody binding to the same epitope as antibody 1030, and an antibody capable of inhibiting the binding of antibody 1030 to human EGFR. Said third antibody preferably results in an enhanced binding to human EGFR of said first and/or second antibody. In one embodiment, the composition does not contain further antibodies in addition to said first, second, and third antibodies, more preferably not further anti-EGFR antibodies.

The antibody binding to the same epitope as antibody 1030 may be selected from the antibody cluster consisting of clones 1195, 1030, 1034, 1194, 980, 981, 1246, and 1223.

The antibody comprising the CDR3 of antibody 1030 may additionally comprise the CDR1 and CDR2 of VH and VL of antibody 1030.

The antibodies may be formulated in one container for administration. However, they may be manufactured, purified and characterised individually and be provided in two or three separate containers as a kit of parts, with one antibody in each container. As such they may be administered simultaneously, successively or separately.

In a further aspect the two binding specificities of antibodies 992 and 1024 are combined in one bi-specific binding molecule. Preferably the bispecific binding molecule comprises the CDRs of antibodies 992 and 1024, more preferably the VH and VL sequences of antibodies 992 and 1024. The bi-specific binding molecule may be a dual-variable-domain antibody as described in example 19. A bi-specific binding molecule may also be designed in the form of a bispecific Fab-fragment, a bispecific scFV, or a diabody as described in literature.

Antibody compositions based on the binding specificities pf antibodies 992 and 1024 preferably leads to one or more of receptor internalisation, to regression of A431NS tumours in vivo, to induction of terminal differentiation in A431NS cells in vivo, and to up-regulation of tumour involucrin expression in vivo.

The present application provides several examples of antibodies having the same or similar effects as the combination of antibodies 992 and 1024. Examples of these include antibodies obtained from the same immunisation and belonging to the same clusters and antibodies competing individually with one of the two antibodies. Antibody compositions with the same or similar effect may be designed based on the VL and VH sequences of antibodies 992 and 1024 and also based on the CDRs of these antibodies, in particular the CDR3s of the two antibodies.

Further antibody compositions with the same or similar effects may be made by carrying out immunisation and screening essentially as described in the examples. Antibodies with the same binding specificity as antibody 992 and 1024 may be identified in two separate competition assays as described herein. Finally, antibody compositions where one antibody enhances the binding of the other antibody may be identified by carrying out binding experiments essentially as described in Example 16. The antibody compositions may be screened further as described in the examples for effects on receptor internalisation, in vitro and in vivo efficacy, binding affinity etc.

Uses of the Antibody Compositions of the Invention

For use in in vivo treatment and prevention of diseases related to EGFR expression (e.g., over-expression), antibodies of the invention are administered to patients (e.g., human subjects) at therapeutically effective dosages (e.g., dosages which result in growth inhibition, phagocytosis, reduction of motility, terminal differentiation, and/or killing of tumour cells expressing EGFR) using any suitable route of administration, such as injection and other routes of administration known in the art for antibody-based clinical products.

Typical EGFR-related diseases which can be treated, ameliorated, and/or prevented using the antibodies of the invention include, but are not limited to, autoimmune diseases and cancers. For example, cancers which can be treated ameliorated, and/or prevented include cancer of the bladder, breast, uterine/cervical, colon, kidney, ovary, prostate, renal cell, pancreas, colon, rectum, stomach, squamous cell, lung (non-small cell), esophageal, head and neck, skin. Autoimmune diseases which may be treated include, for example, psoriasis.

In yet another embodiment, the invention relates to a method for the treatment, amelioration, and/or prevention of glioblastoma, including glioblastoma multiforme; astrocytoma, including childhood astrocytoma; glioma; neuroblastoma; neuroendocrine tumors of the gastrointestinal tract; bronchoalveolar carcinoma; follicular dendritic cell sarcoma; salivary gland carcinoma; ameloblastoma; malignant peripheral nerve sheet tumor; endocrine pancreatic tumors; or testicular germ cell tumors, including seminoma, embryonal carcinoma, yolk sac tumor, teratoma and choriocarcinoma.

Isolation and Selection of Variable Heavy Chain and Variable Light Chain Coding Pairs The process of generating an anti-EGFR recombinant antibody composition involves the isolation of sequences coding for variable heavy chains ($V_H$) and variable light chains ($V_L$) from a suitable source, thereby generating a repertoire of $V_H$ and $V_L$ coding pairs. Generally, a suitable source for obtaining $V_H$ and $V_L$ coding sequences are lymphocyte containing cell fractions such as blood, spleen or bone marrow samples from a non-human animal immunized/vaccinated with a human EGFR polypeptide or peptide or with EGFR proteins derived from a cell expressing human EGFR or with cells expressing human EGFR or fractions of such cells. Preferably, lymphocyte containing fractions are collected from non-human mammals or transgenic animals with human immunoglobulin genes. The collected lymphocyte containing cell fraction may be enriched further to obtain a particular lymphocyte population, e.g. cells from the B lymphocyte linage. Preferably, the enrichment is performed using magnetic bead cell sorting (MACS) and/or fluorescence activated cell sorting (FACS), taking advantage of lineage-specific cell surface marker proteins for example for B cells, plasma blast and/or plasma cells. Preferably, the lymphocyte containing cell fraction is enriched or sorted with respect to B cells, plasma blasts and/or plasma cells. Even more preferably, cells with high expression of CD43 and CD138 are isolated from spleen or blood. These cells are sometimes termed circulating plasma cells, early plasma cells or plasma blasts. For ease, they are just termed plasma cells in the present invention, although the other terms may be used interchangeably.

The isolation of $V_H$ and $V_L$ coding sequences can either be performed in the classical way where the $V_H$ and $V_L$ coding sequences are combined randomly in a vector to generate a combinatorial library of $V_H$ and $V_L$ coding sequences pairs. However, in the present invention it is preferred to mirror the diversity, affinity and specificity of the antibodies produced in a humoral immune response upon EGFR immunisation. This involves the maintenance of the $V_H$ and $V_L$ pairing originally present in the donor, thereby generating a repertoire of sequence pairs where each pair encodes a variable heavy chain ($V_H$) and a variable light chain ($V_L$) corresponding to a $V_H$ and $V_L$ pair originally present in an antibody produced by the donor from which the sequences are isolated. This is also termed a cognate pair of $V_H$ and $V_L$ encoding sequences and the antibody is termed a cognate antibody. Preferably, the $V_H$ and $V_L$ coding pairs of the present invention, combinatorial or cognate, are obtained from mice donors, and therefore the sequences are murine.

There are several different approaches for the generation of cognate pairs of $V_H$ and $V_L$ encoding sequences, one approach involves the amplification and isolation of $V_H$ and $V_L$ encoding sequences from single cells sorted out from a lymphocyte-containing cell fraction. In order to obtain a repertoire of $V_H$ and $V_L$ encoding sequence pairs which resemble the diversity of $V_H$ and $V_L$ sequence pairs in the donor, a high-throughput method with as little scrambling (random combination) of the $V_H$ and $V_L$ pairs as possible, is preferred, e.g. as described in WO 2005/042774 (hereby incorporated by reference).

The $V_H$ and $V_L$ encoding sequences may be amplified separately and paired in a second step or they may be paired during the amplification (Coronella et al. 2000. Nucleic Acids Res. 28: E85; Babcook et al 1996. PNAS 93: 7843-7848 and WO 2005/042774). A second approach involves in-cell amplification and pairing of the $V_H$ and $V_L$ encoding sequences (Embleton et al. 1992. Nucleic Acids Res. 20: 3831-3837; Chapal et al. 1997. BioTechniques 23: 518-524). A third approach is selected lymphocyte antibody method (SLAM) which combines a hemolytic plaque assay with cloning of $V_H$ and $V_L$ cDNA (Babcook et al. 1996. PNAS 93:7843-7848). Another method that can be used with mice is standard hybridome technique, followed by screening and selection of lead candidates and subsequent cloning of the encoded antibodies.

In a preferred embodiment of the present invention a repertoire of $V_H$ and $V_L$ coding pairs, where the member pairs mirror the gene pairs responsible for the humoral immune response resulting from a EGFR immunisation, is generated according to a method comprising the steps i) providing a lymphocyte-containing cell fraction from an animal donor immunized with human EGFR; ii) optionally enriching B cells or plasma cells from said cell fraction; iii) obtaining a population of isolated single cells, comprising distributing cells from said cell fraction individually into a plurality of vessels; iv) amplifying and effecting linkage of the $V_H$ and $V_L$ coding pairs, in a multiplex overlap extension RT-PCR procedure, using a template derived from said isolated single cells and v) optionally performing a nested PCR of the linked $V_H$ and $V_L$ coding pairs. Preferably, the isolated cognate $V_H$ and $V_L$ coding pairs are subjected to a screening procedure as described below.

Once the $V_H$ and $V_L$ sequence pairs have been generated, a screening procedure to identify sequences encoding $V_H$ and $V_L$ pairs with binding reactivity towards an EGFR associated antigen is performed. Preferably, the EGFR associated antigen is comprises an extracellular part of EGFR such as domain III, II, I, and/or IV, fragments of the domains or the complete extracellular domain. Other antigens include mutants such as deletion mutants of EGFR or SNPs, or fragments thereof. If the $V_H$ and $V_L$ sequence pairs are combinatorial, a phage display procedure can be applied to enrich for $V_H$ and $V_L$ pairs coding for antibody fragments binding to EGFR prior to screening.

In order to mirror the diversity, affinity and specificity of the antibodies produced in a humoral immune response upon immunization with EGFR, the present invention has developed a screening procedure for the cognate pairs, in order to obtain the broadest diversity possible. For screening purposes the repertoire of cognate $V_H$ and $V_L$ coding pairs are expressed individually either as antibody fragments (e.g. scFv or Fab) or as full-length antibodies using either a bacterial or mammalian screening vector transfected into a suitable host cell. The repertoire of Fabs/antibodies may be screened—without limitation—for reactivity to EGFR, for antiproliferative activity against a cancer cell line expressing EGFR, and for the ability to inhibit ligand (e.g. EGF) binding to EGFR, for inhibition of phosphorylation, induction of apoptosis, EGFR internalisation.

In parallel, the repertoire of Fabs/antibodies is screened against selected antigens such as human and optionally cynomolgous or chimpanzee or rhesus monkey EGFR peptides. The antigenic peptides can for example be selected from human EGFR extracellular domain, human mutant EGFR extracellular domain, and cynomolgous EGFR extracellular domain or fragments thereof. The peptides may be biotinylated to facilitate immobilization onto beads or plates during screening. Alternative immobilization means may be used as well. The antigens are selected based on the knowledge of the EGFR biology and the expected neutralizing and/or protective effect antibodies capable of binding to these antigens potentially can provide. This screening procedure can likewise be applied to a combinatorial phage display library.

The recombinant EGFR proteins used for screening may be expressed in bacteria, insect cells, mammalian cells or another suitable expression system. For correct processing (including glycosylation) the proteins are expressed in mammalian cells. The EGFR-ECD protein may either be expressed as a soluble protein (without the transmembrane and intracellular region) or they may be fused to a third protein, to increase stability. If the EGFR protein is expressed with a fusion tag, the fusion partner may be cleaved off prior to screening. In addition to the primary screening described above, a secondary screening may be performed, in order to ensure that none of the selected sequences encode false positives.

Generally, immunological assays are suitable for the screening performed in the present invention. Such assays are well know in the art and constitute for example ELISPOT, ELISA, FLISA, membrane assays (e.g. Western blots), arrays on filters, and FACS. The assays can either be performed without any prior enrichment steps, utilizing polypeptides produced from the sequences encoding the $V_H$ and $V_L$ pairs. In the event that the repertoire of $V_H$ and $V_L$ coding pairs are cognate pairs, no enrichment by e.g. phage display is needed prior to the screening. However, in the screening of combinatorial libraries, the immunoassays are preferably performed in combination with or following enrichment methods such as phage display, ribosome display, bacterial surface display, yeast display, eukaryotic virus display, RNA display or covalent display (reviewed in FitzGerald, K., 2000. Drug Discov. Today 5, 253-258).

The $V_H$ and $V_L$ pair encoding sequences selected in the screening are generally subjected to sequencing, and analyzed with respect to diversity of the variable regions. In particular the diversity in the CDR regions is of interest, but also the $V_H$ and $V_L$ family representation is of interest. Based on these analyses, sequences encoding $V_H$ and $V_L$ pairs representing the overall diversity of the EGFR binding antibodies isolated from one or more animal donors are selected. Preferably, sequences with differences in all the CDR regions (CDRH1, CDRH2, CDRH3 and CDRL1, CDRL2 and CDRL3) are selected. If there are sequences with one or more identical or very similar CDR regions which belong to different $V_H$ or $V_L$ families, these are also selected. Preferably, at least the CDR3 region of the variable heavy chain (CDRH3) differs among the selected sequence pairs. Potentially, the selection of $V_H$ and $V_L$ sequence pairs can be based solemnly on the variability of the CDRH3 region. During the priming and amplification of the sequences, mutations may occur in the framework regions of the variable region, in particular in the first framework region. Preferably, the errors occurring in the first framework region are corrected in order to ensure that the sequences correspond completely or at least 98% to those of the germline origin, e.g. such that the $V_H$ and $V_L$ sequences are fully murine.

When it is ensured that the overall diversity of the collection of selected sequences encoding $V_H$ and $V_L$ pairs is highly representative of the diversity seen at the genetic level in a humoral response to an EGFR immunisation, it is expected that the overall specificity of antibodies expressed from a collection of selected $V_H$ and $V_L$ coding pairs also are representative with respect to the specificity of the antibodies produced in the EGFR immunised animals. An indication of whether the specificity of the antibodies expressed from a collection of selected $V_H$ and $V_L$ coding pairs are representative of the specificity of the antibodies raised by donors can be obtained by comparing the antibody titers towards the selected antigens of the donor blood with the specificity of the antibodies expressed from a collection of selected $V_H$ and $V_L$ coding pairs. Additionally, the specificity of the antibodies expressed from a collection of selected $V_H$ and $V_L$ coding pairs can be analyzed further. The degree of specificity correlates with the number of different antigens towards which binding reactivity can be detected. In a further embodiment of the present invention the specificity of the individual antibodies expressed from a collection of selected $V_H$ and $V_L$ coding pairs is analyzed by epitope mapping.

Epitope mapping may be performed by a number of methodologies, which do not necessarily exclude each other. One way to map the epitope-specificity of an antibody molecule is to assess the binding to peptides of varying lengths derived from the primary structure of the target antigen. Such peptides may be both linear and conformational and may be used in a number of assay formats, including ELISA, FLISA and surface plasmon resonance (SPR, Biacore, FACS). Furthermore, the peptides may be rationally selected using available sequence and structure data to represent e.g. extracellular regions or conserved regions of the target antigen, or the may be designed as a panel of overlapping peptides representing a selected part or all of the antigen (Meloen R H, Puijk W C, Schaaper W M M. Epitope mapping by PEPSCAN. In: Immunology Methods Manual. Ed Iwan Lefkovits 1997, Academic Press, pp 982-988). Specific reactivity of an antibody clone with one or more such peptides will generally be an indication of the epitope specificity. However, peptides are in many cases poor mimics of the epitopes recognized by antibodies raised against proteinaceous antigens, both due to a lack of natural or specific conformation and due to the generally larger buried surface area of interaction between an antibody and a protein antigen as compared to an antibody and a peptide. A second method for epitope mapping, which allows for the definition of specificities directly on the protein antigen, is by selective epitope masking using existing, well defined antibodies. Reduced binding of a second, probing antibody to the antigen following blocking is generally indicative of shared or overlapping epitopes. Epitope mapping by selective masking may be performed by a number of immunoassays, including, but not restricted to, ELISA and Biacore, which are well known in the art (e.g. Ditzel et al. 1997. J. Mol. Biol. 267:684-695; Aldaz-Carroll et al. 2005. J. Virol. 79: 6260-6271). Yet another potential method for the determination of the epitope specificity of anti-EGFR antibodies is the selection of escape mutants in the presence of antibody. This can e.g. be performed using an alanine-scan. Sequencing of the gene(s) of interest from such escape mutants will generally reveal which amino acids in the antigen(s) that are important for the recognition by the antibody and thus constitute (part of) the epitope.

Production of an Anti-EGFR Antibody Composition from Selected $V_H$ and $V_L$ Coding Pairs An antibody composition of the present invention may be produced from a polyclonal expression cell line in one or a few bioreactors or equivalents thereof. Following this approach the anti-EGFR antibodies can be purified from the reactor as a single preparation without having to separate the individual members constituting the anti-EGFR antibody composition during the process. If the antibody composition is produced in more than one bioreactor, the purified anti-EGFR antibody composition can be obtained by pooling the antibodies obtained from individually purified supernatants from each bioreactor.

One way of producing a recombinant antibody composition is described in WO 2004/061104 and WO 2006/007850 (these references are hereby incorporated by reference). The method described therein, is based on site-specific integration of the antibody coding sequence into the genome of the individual host cells, ensuring that the $V_H$ and $V_L$ protein chains are maintained in their original pairing during production. Furthermore, the site-specific integration minimises position effects and therefore the growth and expression properties of the individual cells in the polyclonal cell line are expected to be very similar. Generally, the method involves the following: i) a host cell with one or more recombinase recognition sites; ii) an expression vector with at least one recombinase recognition site compatible with that of the host cell; iii) generation of a collection of expression vectors by transferring the selected $V_H$ and $V_L$ coding pairs from the screening vector to an expression vector such that a full-length antibody or antibody fragment can be expressed from the vector (such a transfer may not be necessary if the screening vector is identical to the expression vector); iv) transfection of the host cell with the collection of expression vectors and a vector coding for a recombinase capable of combining the recombinase recognition sites in the genome of the host cell with that in the vector; v) obtaining/generating a polyclonal cell line from the transfected host cell and vi) expressing and collecting the antibody composition from the polyclonal cell line.

When a small number (2-3 or more) of antibodies are used for one composition these may be expressed and purified individually in a way similar to manufacture of monoclonal antibodies, for example as described in WO 2004/085474. The purified antibodies can be mixed after purification or be packaged in separate vials for mixing prior to administration or for separate administration.

Preferably mammalian cells such as CHO cells, COS cells, BHK cells, myeloma cells (e.g., Sp2/0 or NSO cells), fibroblasts such as NIH 3T3, and immortalized human cells, such as HeLa cells, HEK 293 cells, or PER.C6, are used. However, non-mammalian eukaryotic or prokaryotic cells, such as plant cells, insect cells, yeast cells, fungi, E. coli etc., can also be employed. A suitable host cell comprises one or more suitable recombinase recognition sites in its genome. The host cell should also contain a mode of selection which is operably linked to the integration site, in order to be able to select for integrants, (i.e., cells having an integrated copy of an anti-EGFR Ab expression vector or expression vector fragment in the integration site). The preparation of cells having an FRT site at a pre-determined location in the genome was described in e.g. U.S. Pat. No. 5,677,177. Preferably, a host cell only has a single integration site, which is located at a site allowing for high expression of the integrant (a so-called hot-spot).

A suitable expression vector comprises a recombination recognition site matching the recombinase recognition site(s) of the host cell. Preferably the recombinase recognition site is linked to a suitable selection gene different from the selection gene used for construction of the host cell. Selection genes are well known in the art, and include glutamine synthetase gene (GS), dihydrofolate reductase gene (DHFR), and neomycin, where GS or DHFR may be used for gene amplification of the inserted $V_H$ and $V_L$ sequence. The vector may also contain two different recombinase recognition sites to allow for recombinase-mediated cassette exchange (RMCE) of the antibody coding sequence instead of complete integration of the vector. RMCE is described in (Langer et al 2002; Schlake and Bode 1994). Suitable recombinase recognition sites are well known in the art, and include FRT, lox and attP/attB sites. Preferably the integrating vector is an isotype-encoding vector, where the constant regions (preferably including introns) are present in the vector prior to transfer of the $V_H$ and $V_L$ coding pair from the screening vector (or the constant regions are already present in the screening vector if screening is performed on full-length antibodies). The constant regions present in the vector can either be the entire heavy chain constant region ($CH_2$ to $CH_3$ or to $CH_4$) or the constant region encoding the Fc part of the antibody ($CH_2$ to $CH_3$ or to $CH_4$). The light chain Kappa or Lambda constant region may also be present prior to transfer. The choice of the number of constant regions present, if any, depends on the screening and transfer system used. The heavy chain constant regions can be selected from the isotypes IgG1, IgG2, IgG3, IgG4, IgA1, IgA2, IgM, IgD and IgE. Preferred isotypes are IgG1, IgG2, and/or IgG3. Further, the expression vector for site-specific integration of the anti-EGFR antibody-encoding nucleic acid contains suitable promoters or equivalent sequences directing high levels of expression of each of the $V_H$ and $V_L$ chains. FIG. 4 illustrates one possible way to design the expression vector, although numerous other designs are possible.

The transfer of the selected $V_H$ and $V_L$ coding pairs from the screening vector can be performed by conventional restriction enzyme cleavage and ligation, such that each expression vector molecule contain one $V_H$ and $V_L$ coding pair. Preferably, the $V_H$ and $V_L$ coding pairs are transferred individually, they may, however, also be transferred in-mass if desired. When all the selected $V_H$ and $V_L$ coding pairs are transferred to the expression vector a collection or a library of expression vectors is obtained. Alternative ways of transfer may also be used if desired. If the screening vector is identical to the expression vector, the library of expression vectors is constituted of the $V_H$ and $V_L$ sequence pairs selected during screening, which are situated in the screening/expression vector.

Methods for transfecting a nucleic acid sequence into a host cell are known in the art. To ensure site-specific integration, a suitable recombinase must be provided to the host cell as well. This is preferably accomplished by co-transfection of a plasmid encoding the recombinase. Suitable recombinases are for example Flp, Cre or phage φC31 integrase, used together with a host cell/vector system with the corresponding recombinase recognition sites. The host cell can either be transfected in bulk, meaning that the library of expression vectors is transfected into the cell line in one single reaction thereby obtaining a polyclonal cell line. Alternatively, the collection of expression vectors can be transfected individually into the host cell, thereby generating a collection of individual cell lines (each cell line produce an antibody with a particular specificity). The cell lines generated upon transfection (individual or polyclonal) are then selected for site specific integrants, and adapted to grow in suspension and serum free media, if they did not already have these properties prior to transfection. If the transfection was performed individually, the individual cell lines are analyzed further with respect to their grow properties and antibody production. Preferably, cell lines with similar proliferation rates and antibody expression levels are selected for the generation of the polyclonal cell line. The polyclonal cell line is then generated by mixing the individual cell lines in a predefined ratio. Generally, a polyclonal master cell bank (pMCB), a polyclonal research cell bank (pRCB) and/or a polyclonal working cell bank (pWCB) are laid down from the polyclonal cell line. The polyclonal cell line is generated by mixing the individual cell lines in a predefined ratio. The polyclonal cell line is distributed into ampoules thereby generating a polyclonal research cell bank (pRCB) or master cell bank (pMCB) from which a polyclonal working cell bank (pWCB) can be generated by expanding cells from the research or master cell bank. The research cell bank is primarily for proof of concept studies, in which the polyclonal cell line may not comprise as many individual antibodies as the polyclonal cell line in the master cell bank. Normally, the pMCB is expanded further to lay down a pWCB for production purposes. Once the pWCB is exhausted a new ampoule from the pMCB can be expanded to lay down a new pWCB.

One embodiment of the present invention is a polyclonal cell line capable of expressing a recombinant anti-EGFR antibody composition of the present invention.

A further embodiment of the present invention is a polyclonal cell line wherein each individual cell is capable of expressing a single $V_H$ and $V_L$ coding pair, and the polyclonal cell line as a whole is capable of expressing a collection of $V_H$ and $V_L$ encoding pairs, where each $V_H$ and $V_L$ pair encodes an anti-EGFR antibody. Preferably the collection of $V_H$ and $V_L$ coding pairs are cognate pairs generated according to the methods of the present invention.

A recombinant antibody composition of the present invention may be manufactured by culturing one ampoule from a pWCB in an appropriate medium for a period of time allowing for sufficient expression of antibody and where the polyclonal cell line remains stable (The window is approximately between 15 days and 50 days). Culturing methods such as fed batch or perfusion may be used. The recombinant antibody composition is obtained from the culture medium and purified by conventional purification techniques. Affinity chromatography combined with subsequent purification steps such as ion-exchange chromatography, hydrophobic interactions and gel filtration has frequently been used for the purification of IgG. Following purification, the presence of all the individual members in the polyclonal antibody composition is assessed, for example by ion-exchange chromatography. The characterization of such an antibody composition is described in detail in WO 2006/007853 (hereby incorporated by reference).

An alternative method of expressing a mixture of antibodies in a recombinant host is described in WO 2004/009618. This method produces antibodies with different heavy chains associated with the same light chain from a single cell line. This approach may be applicable if the anti-EGFR antibody composition is produced from a combinatorial library.

Therapeutic Compositions

Another aspect of the invention is a pharmaceutical composition comprising as an active ingredient an anti-EGFR antibody composition or anti-EGFR recombinant Fab or another anti-EGFR recombinant antibody fragment composition, or a bi-specific binding molecule of the invention. Preferably, the active ingredient of such a composition is an anti-EGFR recombinant antibody composition as described in the present invention. Such compositions are intended for amelioration and/or prevention and/or treatment of cancer. Preferably, the pharmaceutical composition is administered to a human, a domestic animal, or a pet.

The pharmaceutical composition further comprises a pharmaceutically acceptable excipient.

Anti-EGFR antibody composition or fragments of the antibodies thereof may be administered within a pharmaceutically-acceptable diluent, carrier, or excipient, in unit dosage form. Conventional pharmaceutical practice may be employed to provide suitable formulations or compositions to administer to patients with cancer. In a preferred embodiment the administration is therapeutic, meaning that it is administered after a cancer condition has been diagnosed. Any appropriate route of administration may be employed, for example, administration may be parenteral, intravenous, intra-arterial, subcutaneous, intramuscular, intraperitoneal, intranasal, aerosol, suppository, or oral administration. For example, pharmaceutical formulations may be in the form of, liquid solutions or suspensions. For oral administration, need to be protected against degradation in the stomach. For intranasal formulations, antibodies may be administered in the form of powders, nasal drops, or aerosols.

The pharmaceutical compositions of the present invention are prepared in a manner known per se, for example, by means of conventional dissolving, lyophilizing, mixing, granulating or confectioning processes. The pharmaceutical compositions may be formulated according to conventional pharmaceutical practice (see for example, in Remington: The Science and Practice of Pharmacy (20th ed.), ed. A. R. Gennaro, 2000, Lippincott Williams & Wilkins, Philadelphia, Pa. and Encyclopedia of Pharmaceutical Technology, eds. J. Swarbrick and J. C. Boylan, 1988-1999, Marcel Dekker, New York, N.Y.).

Preferably solutions or suspensions of the active ingredient, and especially isotonic aqueous solutions or suspensions, are used to prepare pharmaceutical compositions of the present invention. In the case of lyophilized compositions that comprise the active ingredient alone or together with a carrier, for example mannitol, such solutions or suspensions may, if possible, be produced prior to use. The pharmaceutical compositions may be sterilized and/or may comprise excipients, for example preservatives, stabilizers, wetting and/or emulsifying agents, solubilizers, salts for regulating the osmotic pressure and/or buffers, and are prepared in a manner known per se, for example by means of conventional dissolving or lyophilizing processes. The said solutions or suspensions may comprise viscosity-increasing substances, such as sodium carboxymethylcellulose, carboxymethylcellulose, dextran, polyvinylpyrrolidone or gelatin.

The injection compositions are prepared in customary manner under sterile conditions; the same applies also to introducing the compositions into ampoules or vials and sealing of the containers.

The pharmaceutical compositions comprise from approximately 1% to approximately 95%, preferably from approximately 20% to approximately 90%, active ingredient. Pharmaceutical compositions according to the invention may be, for example, in unit dose form, such as in the form of ampoules, vials, suppositories, tablets, pills, or capsules. The formulations can be administered to human individuals in therapeutically or prophylactically effective amounts (e.g., amounts which prevent, eliminate, or reduce a pathological condition) to provide therapy for a disease or condition. The preferred dosage of therapeutic agent to be administered is likely to depend on such variables as the severity of the cancer, the overall health status of the particular patient, the formulation of the compound excipients, and its route of administration.

Therapeutic Uses of the Compositions According to the Invention

The pharmaceutical compositions according to the present invention may be used for the treatment or amelioration of a disease in a mammal. Conditions that can be treated or prevented with the present pharmaceutical compositions include prevention, and treatment of patients cancer can preferably be subjected to therapeutic treatment with a pharmaceutical composition according to the present invention.

One embodiment of the present invention is a method of preventing, treating or ameliorating one or more symptoms associated with cancer in a mammal, comprising administering an effective amount of an anti-EGFR recombinant antibody composition of the present invention to said mammal.

A further embodiment of the present invention is the use of an anti-EGFR recombinant antibody composition of the present invention for the preparation of a composition for the treatment, amelioration or prevention of one or more symptoms associated with cancer in a mammal.

Preferably, the mammal in the embodiments above is a human, domestic animal or a pet.

Antibodies in accordance with the present invention are indicated in the treatment of certain solid tumours. Based upon a number of factors, including EGFR expression levels, among others, the following tumour types appear to present preferred indications: breast, ovarian, colon, rectum, prostate, bladder, pancreas, head and neck, and non-small cell lung cancer.

Further examples of cancer include carcinoma and sarcoma. Carcinoma includes at least the following:
Epithelial neoplasms, NOS
Squamous cell neoplasms
Squamous cell carcinoma, NOS
Basal cell neoplasms
Basal cell carcinoma, NOS
Transitional cell papillomas and carcinomas
Adenomas and Adenocarcinomas (glands)
Adenoma, NOS
Adenocarcinoma, NOS
Linitis plastica
Insulinoma, NOS
Glucagonoma, NOS
Gastrinoma, NOS
Vipoma
Cholangiocarcinoma Hepatocellular carcinoma, NOS
Adenoid cystic carcinoma
Carcinoid tumor, NOS, of appendix
Prolactinoma
Oncocytoma
Hurthle cell adenoma
Renal cell carcinoma
Grawitz tumor
Multiple endocrine adenomas
Endometrioid adenoma, NOS
Adnexal and Skin appendage Neoplasms
Mucoepidermoid Neoplasms
Cystic, Mucinous and Serous Neoplasms
Cystadenoma, NOS
Pseudomyxoma peritonei
Ductal, Lobular and Medullary Neoplasms
Acinar cell neoplasms
Complex epithelial neoplasms
Warthin's tumor
Thymoma, NOS
Specialized gonadal neoplasms
Sex cord-stromal tumor
Thecoma, NOS
Granulosa cell tumor, NOS
Arrhenoblastoma, NOS
Sertoli-Leydig cell tumor
Paragangliomas and Glomus tumors
Paraganglioma, NOS
Pheochromocytoma, NOS
Glomus tumor
Nevi and Melanomas
Melanocytic nevus
Malignant melanoma, NOS
Melanoma, NOS
Nodular melanoma
Dysplastic nevus
Lentigo maligna melanoma
Superficial spreading melanoma
Acral lentiginous melanoma, malignant Examples of sarcoma include. Sarcomas are given a number of different names, based on the type of tissue from which they arise. For example, osteosarcoma arises from bone, chondrosarcoma arises from cartilage, and leiomyosarcoma arises from smooth muscle. Soft tissue sarcomas, such as leiomyosarcoma, chondrosarcoma, and gastrointestinal stromal tumor (GIST), are more common in adults than in children.

In connection with each of these indications, three clinical pathways appear to offer distinct potentials for clinical success:

Adjunctive therapy: In adjunctive therapy, patients would be treated with antibodies in accordance with the present invention in combination with a chemotherapeutic or antineoplastic agent and/or radiation therapy. The primary targets listed above will be treated under protocol by the addition of antibodies of the invention to standard first and second line therapy or third line therapy. Protocol designs will address effectiveness as assessed by reduction in tumour mass as well as the ability to reduce usual doses of standard chemotherapy. These dosage reductions will allow additional and/or prolonged therapy by reducing dose-related toxicity of the chemotherapeutic agent. Prior art anti-EGFR antibodies have been, or are being, utilized in several adjunctive clinical trials in combination with the chemotherapeutic or antineoplastic agents adriamycin (Erbitux: advanced prostrate carcinoma), cisplatin (Exbitux: advanced head and neck and lung carcinomas), taxol (Erbitux: breast cancer), and doxorubicin (Erbitux).

The invention provides pharmaceutical articles comprising an antibody composition of the invention and at least one compound capable inducing differentiation of cancer cells as a combination for the simultaneous, separate or successive administration in cancer therapy. By combining the antibody compositions of the invention with agents known to induce terminal differentiation of cancer cells, the effect can be improved further.

The at least one compound may be selected from the group consisting of retinoic acid, trans-retinoic acids, cis-retinoic acids, phenylbutyrate, nerve growth factor, dimethyl sulfoxide, active form vitamin D(3), peroxisome proliferator-activated receptorgamma, 12-O-tetradecanoylphorbol 13-acetate, hexamethylene-bis-acetamide, transforming growth factor-beta, butyric acid, cyclic AMP, and vesnarinone. Preferably the compound is selected from the group consisting of retinoic acid, phenylbutyrate, all-trans-retinoic acid, active form vitamin D.

Pharmaceutical articles comprising an antibody composition of the invention and at least one chemotherapeutic or antineoplastic compound may be used as a combination for the simultaneous, separate or successive administration in cancer therapy. The chemotherapeutic compound may be selected from the group consisting of adriamycin, cisplatin, taxol, doxorubicin, topotecan, fluoropyrimidine, oxaliplatin, and irinotecan.

Monotherapy: In connection with the use of the antibodies in accordance with the present invention in monotherapy of tumours, the antibodies may be administered to patients without a chemotherapeutic or antineoplastic agent. Preclinical results generated through use of antibodies in accordance with the present invention and discussed herein have demonstrated positive results as a stand-alone therapy.

Imaging Agent: Through binding a radionuclide (e.g., yttrium ($^{90}$Y)) to antibodies in accordance with the present invention, it is expected that radiolabeled antibodies in accordance with the present invention can be utilised as a diagnostic, imaging agent. In such a role, antibodies of the invention will localize to both solid tumours, as well as, metastatic lesions of cells expressing EGFR. In connection with the use of the antibodies of the invention as imaging agents, the antibodies can be used in assisting surgical treatment of solid tumors, as both a pre-surgical screen as well as a post operative follow to determine what tumour remain and/or returns. An ($^{111}$In) Erbitux antibody has been used as an imaging agent in a Phase I human clinical trial in patients having unresectable squamous cell lung carcinomas. (Divgi et al. J. Natl. Cancer Inst. 83:97-104 (1991). Patients were followed with standard anterior and posterior gamma camera. Preliminary data indicated that all primary lesions and large metastatic lestions were identified, while only one-half of small metastatic lesions (under 1 cm) were detected.

Tyrosine kinase inhibitors (TKIs) are synthetic, mainly quinazoline-derived, low molecular weight molecules that interact with the intracellular tyrosine kinase domain of receptors and inhibiting ligand-induced receptor phosphorylation by competing for the intracellular Mg-ATP binding site. Several TKIs in clinical development including Gefitinib (Iressa, ZD1839), Erlobtinib (Tarceva, OSI-774), Lapatinib, (Tykerb, GW572016), Canertinib (CI-1033), EKB-569 and PKI-166 are targeting the EGFR. Combination treatment of TKIs and anti-EGFR has shown to be beneficial both in vivo and in vitro against EGFR-dependent cancer cells. Pharmaceutical articles comprising an antibody composition of the invention and at least one TKI targeting EGFR may be used as a combination for the simultaneous, separate or successive administration in cancer therapy. Further small molecule inhibitors include: Sorafinib (raf and multiple RTKs), Sunitinib (Multiple RTKs), Temsirolimus (mTOR), RAD001 (mTOR), and AZD217 (VEGFR2).

In other embodiments, the antibody compositions of the present invention are used in combination with other antibody therapeutics. Examples of these include e.g. antibodies against HER2 (Herceptin) and VEGF (avastin). In yet other embodiments, the antibody compositions of the present invention are used in combination with an agent known to stimulate cells of the immune system, such combination treatment leading to enhanced immune-mediated enhancement of the efficacy of the antibody compositions of the invention. Examples of such immune-stimulating agents include but are not limited to recombinant interleukins (e.g. IL-21 and IL-2)

Dose and Route of Administration

While specific dosing for antibodies in accordance with the invention has not yet been determined, certain dosing considerations can be determined through comparison with the similar product (ImClone C225 (Erbitux)) that has been approved. The C225 antibody is typically being administered with doses in the range of 5 to 400 mg/m$^2$, with the lower doses used only in connection with the safety studies. Accordingly, we would expect that dosing in patients with antibodies in accordance with the invention can be in this range or lower, perhaps in the range of 50 to 300 mg/m$^2$, and still remain efficacious. Dosing in mg/m$^2$, as opposed to the conventional measurement of dose in mg/kg, is a measurement based on surface area and is a convenient dosing measurement that is designed to include patients of all sizes from infants to adults.

The prescribing information available for Erbitux (Cetuximab) includes an initial 120 minutes IV infusion of 400 mg/m$^2$, followed by weekly 60 min infusions of 250 mg/m$^2$. These dosages are recommended for stand alone treatment as well as for combination with radiation therapy. For Vectibix (panitumumab) the recommended dose is 6 mg/kg administered over 60 minutes every 14 days.

The expected clinical dosage of Genmab's HuMaxEGFr antibody (zalutumumab) is an initial dose of 8 mg/kg of HuMax-EGFr, followed by weekly infusions of a maintenance dose until disease progression. The maintenance dose will be adjusted as necessary until the patient develops a dose limiting skin rash, up to a maximum dose of 16 mg/kg of HuMax-EGFr (Dosages for pivotal Phase III study, available from Genmab's product description).

The clinical dosing of antibody compositions of the present invention are likely to be limited by the extent of skin rash as observed with monoclonal anti-EGFR antibodies (Erbitux and Vectibix) used in the clinic today. Data from a six week toxicology study in Cynomolgus monkeys showed no signs of skin rash when an antibody composition of the invention was administered at a dose equivalent to what is used for treatment with one of the monoclonal antibodies used in the clinic (example 20). Thus, antibody compositions of the invention can be administered intravenously and with a weekly dosing of 250 mg/m$^2$ which translates into 7.5 mg/kg for a human with body surface of 1.8 m$^2$ and 60 kg body weight. Furthermore, an initial loading dose of 400 mg/m$^2$ (translates into 12 mg/kg for a human with body surface of 1.8 m$^2$ and 60 kg body weight) may be given before the subsequent weekly dosing.

Three distinct delivery approaches are expected to be useful for delivery of the antibodies in accordance with the invention. Conventional intravenous delivery will presumably be the standard delivery technique for the majority of tumours. However, in connection with tumours in the peritoneal cavity, such as tumours of the ovaries, biliary duct, other ducts, and the like, intraperitoneal administration may prove favourable for obtaining high dose of antibody at the tumour and to minimize antibody clearance. In a similar manner certain solid tumours possess vasculature that is appropriate for regional perfusion. Regional perfusion will allow the obtention of a high dose of the antibody at the site of a tumour and will minimise short term clearance of the antibody.

As with any protein or antibody infusion based therapeutic, safety concerns are related primarily to (i) cytokine release syndrome, i.e., hypotension, fever, shaking, chills, (ii) the development of an immunogenic response to the material (i.e., development of human antibodies by the patient to the antibody therapeutic, or HAHA or HACA response), and (iii) toxicity to normal cells that express the EGF receptor, e.g., hepatocytes which express EGFR. Standard tests and follow up will be utilised to monitor each of these safety concerns. In particular, liver function will be monitored frequently during clinical trails in order to assess damage to the liver, if any.

Diagnostic Use

Another embodiment of the invention is directed to diagnostic kits. Kits according to the present invention comprise an anti-EGFR antibody composition prepared according to the invention which protein may be labeled with a detectable label or non-labeled for non-label detection. The kit may be used to identify individuals inflicted with cancer associated with overexpression of EGFR.

EXAMPLES

Example 1

Cloning of Anti-EGFR Antibodies

Immunizations

Female BALB/c, strain A, or C57B16 mice (8-10 weeks old) were used for immunizations by injections with different purified proteins in addition to EGFR overexpressing cells.

Commercially available EGFR proteins (R&D systems cat#1095-ER or Sigma #E3641) were used for some of the immunizations. For other of the immunizations recombinant human EGFR and EGFRvIII produced as fusion proteins were used consisting of the ECD of EGFR or EGFRvIII and human growth hormone (hGH), also including a Tobacco Etch Virus (TEV)-cleavage site in addition to a His-tag described in Example 10b. In some cases the ECD of EGFR was isolated by TEV-protease cleavage and subsequent purification on a Nickel column.

The human head-and-neck cancer cell line, HN5 (Easty D M, Easty G C, Carter R L, Monaghan P, Butler L J. Br J. Cancer. 1981 June; 43(6):772-85. Ten human carcinoma cell lines derived from squamous carcinomas of the head and neck.) expressing approximately 10$^7$ receptors/cell were used for cell based immunizations. Cells were cultured in DMEM medium supplemented with 10% FBS (Fetal Bovine Serum), 3 mM Glycerol, 5 mM Sodium Pyruvate and 1% Penicillin Streptomycin. Before each immunization the cells were washed in PBS, trypsinized with TryPLE and resuspended in growth medium. Subsequently the cell suspensions was washed twice in PBS by centrifugation at 250×g for 5 min, dislodging and resuspension in 15 ml sterile PBS.

Cells or antigen were diluted in PBS and then mixed 1:1 with Freund's Adjuvant. Adjuvant is used to enhance and modulate the immune response. For the first immunizations Complete Freund's Adjuvant (CFA) was used whereas Incomplete Freund's Adjuvant (IFA) was used for the subsequent immunizations. IFA is an oil-in-water emulsion composed of mineral oils and CFA is IFA to which heat-killed, dried Mycobacterium species are added. Both adjuvants have a depot effect. CFA gives rise to long-term persistence of the immune response and is used for the first immunizations to boost the immune response and IFA is used for subsequent immunizations. The emulsions were tested by adding a drop on the surface of a glass with water. If the drop remains as one drop, the emulsion is stable and the injections can be performed. Only stable emulsions were administered to mice.

Depending on the schedule (see Table 2), 25-100 µg antigen or $10^7$ cells were used for each injection. In total, mice received 4 injections. All mice were injected with either 300 µl or 200 µl emulsion. Depending on the schedule, injections were performed subcutaneously (s.c.), intraperitoneally (i.p.) or intravenous (i.v.).

At termination, the mice were sacrificed by cervical dislocation, and the spleens were removed and transferred to a 74 µm cell strainer (Corning#136350-3479). The cells were macerated through the filter, resuspended in cold RPMI 1640 with 10% FBS and centrifuged at 300×g for 5 minutes. The cell pellet was resuspended in RPMI 1640 with 1% FBS, filtered through a 50 µm syringe filter (BD#340603) and collected by centrifugation. The cell pellet was cryopreserved after resuspension in FCS with 10% DMSO and frozen cells stored at −80° C. until FACS sorting.

FACS Sorting of Murine Plasma Cells

Figure 1:
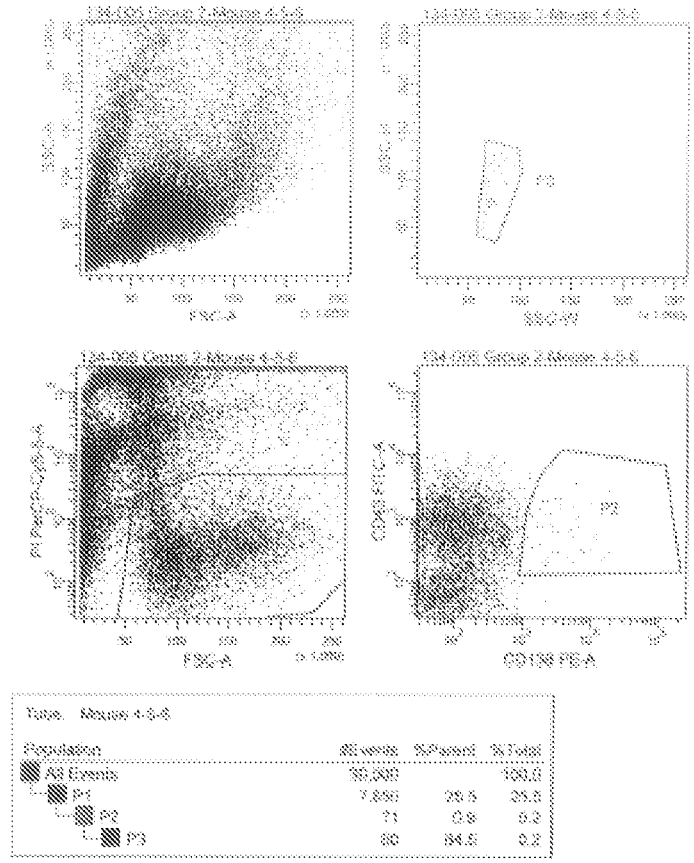
FIG. 1: Sorting of splenocytes (for details see Example 1). The following gates are made (depicted)

Vials with frozen splenocytes were thawed at 37° C. and transferred to 15 ml tube with ice still present. 10 ml Ice-cold RPMI, 10% FBS (foetal bovine serum) was drop-wise added to the tube while swirling. After one wash in 10 ml FACS PBS, 5 ml FCS PBS is added before filtering the cells through 50 µm Filcon. Cells were then pelleted and resuspended in 1 ml PBS with 2% FBS (final volume) and stained with anti-CD43-FITC and anti-CD138-PE according to the specific dilution to a final concentration of app. 5 µg/ml. Cells were incubated at 4° C. for 20 min in the dark. Subsequently, cells were washed 2 times with 2 ml FACS buffer. Up to 15 ml FACS PBS were added. Propidium Iodide (PI) was added at 1:100 (1 part PI to 100 parts FACS PBS buffer), and cells were subsequently sorted into 96 well PCR-plates, containing PCR reaction buffer (see below), and spun down for 2 min 400×g before the plates were frozen at −80° C. Plasma cells were gated as CD43-positive/CD-138 positive as shown in FIG. 1.

Linkage of Cognate $V_H$ and $V_L$ Pairs

The linkage of $V_H$ and $V_L$ coding sequences was performed on the single cells gated as plasma cells, facilitating cognate pairing of the $V_H$ and $V_L$ coding sequences. The procedure utilized a two step PCR procedure based on a one-step multiplex overlap-extension RT-PCR followed by a nested PCR. The primer mixes used in the present example only amplify Kappa light chains. Primers capable of amplifying Lambda light chains could, however, be added to the multiplex primer mix and nested PCR primer mix if desired. If Lambda primers are added, the sorting procedure should be adapted such that Lambda positive cells are not excluded. The principle for linkage of cognate $V_H$ and $V_L$ sequences is illustrated in FIG. 2.

The 96-well PCR plates produced were thawed and the sorted cells served as template for the multiplex overlap-extension RT-PCR. The sorting buffer added to each well before the single-cell sorting contained reaction buffer (OneStep RT-PCR Buffer; Qiagen), primers for RT-PCR (see Table 3) and RNase inhibitor (RNasin, Promega). This was supplemented with OneStep RT-PCR Enzyme Mix (25× dilution; Qiagen) and dNTP mix (200 µM each) to obtain the given final concentration in a 20-µl reaction volume. The plates were incubated for 30 min at 55° C. to allow for reverse transcription of the RNA from each cell. Following the RT, the plates were subjected to the following PCR cycle: 10 min at 94° C., 35×(40 sec at 94° C., 40 sec at 60° C., 5 min at 72° C.), 10 min at 72° C.

The PCR reactions were performed in H20BIT Thermal cycler with a Peel Seal Basket for 24 96-well plates (ABgene) to facilitate a high-throughput. The PCR plates were stored at −20° C. after cycling.

For the nested PCR step, 96-well PCR plates were prepared with the following mixture in each well (20-µl reactions) to obtain the given final concentration: 1× FastStart buffer (Roche), dNTP mix (200 µM each), nested primer mix (see Table 4), Phusion DNA Polymerase (0.08 U; Finnzymes) and FastStart High Fidelity Enzyme Blend (0.8 U; Roche). As template for the nested PCR, 1 µl was transferred from the multiplex overlap-extension PCR reactions. The nested PCR plates were subjected to the following thermocyling: 35×(30 sec at 95° C., 30 sec at 60° C., 90 sec at 72° C.), 10 min at 72° C.

Randomly selected reactions were analyzed on a 1% agarose gel to verify the presence of an overlap-extension fragment of approximately 890 basepairs (bp).

The plates were stored at −20° C. until further processing of the PCR fragments.

The repertoires of linked $V_H$ and $V_L$ coding pairs from the nested PCR were pooled, without mixing pairs from different donors, and were purified by preparative 1% agarose gel electrophoresis. The human kappa constant light chain encoding sequence was spliced by overlap extension to the $V_L$ coding region of the pooled PCR products of linked $V_H$ and $V_L$ coding pairs (FIG. 3). The human kappa constant light chain encoding sequence was amplified from a plasmid containing the coding sequence of a human antibody with a kappa light chain in a reaction containing: Phusion Enzyme (2 U; Finnzymes), 1× Phusion buffer, dNTP mix (200 µM each), hKCforw-v2 primer and Kappa3′ primer (Table 5), and plasmid template pLL138 (10 ng/µl) in a total volume of 50 µl. The reaction was subjected to the following thermocycling: 25×(30 sec at 95° C., 30 sec at 55° C., 45 sec at 72° C.), 10 min at 72° C. The resulting PCR fragment was purified by preparative 1% agarose gel electrophoresis.

The purified pooled PCR fragments of each repertoire was spliced to the amplified and purified PCR fragment of the human kappa constant encoding region (Appendix 2) by the following splicing by overlap extension PCR (50 µl total volume) containing: human kappa constant encoding region fragment (1.4 ng/µl), purified pooled PCR fragment (1.4 ng/µl), Phusion DNA Polymerase (0.5 U; Finnzymes) and FastStart High Fidelity Enzyme Blend (0.2 U; Roche), 1× FastStart buffer (Roche), dNTP mix (200 µM each), mhKCrev primer and mJH set primers (see Table 5). The reaction was subjected to the following thermocycling: 2 min at 95° C., 25×(30 sec at 95° C., 30 sec at 55° C., 1 min at 72° C.), 10 min at 72° C. The resulting PCR fragment (approx. 1070 bp) was purified by preparative 1% agarose gel electrophoresis.

Insertion of Cognate $V_H$ and $V_L$ Coding Pairs into a Screening Vector

In order to identify antibodies with binding specificity to EGFR, the $V_H$ and $V_L$ coding sequences obtained were expressed as full-length antibodies. This involved insertion of the repertoire of $V_H$ and $V_L$ coding pairs into an expression vector and transfection into a host cell.

A two-step cloning procedure was employed for generation of a repertoire of expression vectors containing the linked $V_H$ and $V_L$ coding pairs. Statistically, if the repertoire of expression vectors contains ten times as many recombinant plasmids as the number of cognate paired $V_H$ and $V_L$ PCR products used for generation of the screening repertoire, there is 99% likelihood that all unique gene pairs are represented. Thus, if 400 overlap-extension V-gene fragments were obtained, a repertoire of at least 4000 clones was generated for screening.

Briefly, the purified PCR product of the repertoires of linked $V_H$ and $V_L$ coding pairs, spliced to the human kappa constant coding region, were cleaved with XhoI and NotI DNA endonucleases at the recognition sites introduced into the termini of PCR products. The cleaved and purified fragments were ligated into an XhoI/NotI digested mammalian IgG expression vector, OO-VP-002 (FIG. 4) by standard ligation procedures. The ligation mix was electroporated into E. coli and added to 2×YT plates containing the appropriate antibiotic and incubated at 37° C. over night. The amplified repertoire of vectors was purified from cells recovered from the plates using standard DNA purification methods (Qiagen). The plasmids were prepared for insertion of promoter-leader fragments by cleavage using AscI and NheI endonucleases. The restriction sites for these enzymes were located between the $V_H$ and $V_L$ coding gene pairs. Following purification of the vector, an AscI-NheI digested bi-directional mammalian promoter-leader fragment was inserted into the AscI and NheI restriction sites by standard ligation procedures. The ligated vector was amplified in E. coli and the plasmid was purified using standard methods. The generated repertoire of screening vectors was transformed into E. coli by conventional procedures. Colonies obtained were consolidated into 384-well master plates and stored. The number of arrayed colonies exceeded the number of input PCR products by at least 3-fold, thus giving 95% percent likelihood for presence of all unique V-gene pairs obtained.

Screening for Binding to EGFR Extracellular Domain

In general, the screening was made as a two step procedure. The antibody-libraries were screened for reactivity to recombinant EGFR protein in ELISA after which FMAT (FLISA) was used as a cell based approach, with the NR6 wtEGFR cell line, for detection of EGFR-antibodies binding to cell-surface expressed EGFR. For the 101 and 108/109 libraries (Table 2) the ELISA was performed with recombinant EGFR representing the extracellular domain of the EGFR.

Briefly for the ELISA, Nunc maxisorb plates (cat no 464718) were coated with 1 μg/ml protein (in house produced), diluted in PBS at 4 C over night. Prior to blocking in 50 μl 2%-Milk-PBS-T the plates were washed once with PBS+0.05% Tween 20 (PBS-T). The plates were washed once with PBS-T, 20 μl of 2%-milk-PBS-T and 5 μl supernatants from FreeStyle CHO-S transfectants (see below) were added and incubated for 1½ hour at R.T after which the plates were washed once with PBS-T 20 μl per well. Secondary antibody (HRP-Goat-anti-human IgG, Jackson, cat no 109-035-097) diluted 1:10000 in 2% milk-PBS-T was added to detect the antibodies bound to the wells and incubated for 1 hour at Room Temperature. The plates were washed once in PBS-T before addition of 25 μl substrate (Kem-en-tec Diagnostics, cat no 4390) that was incubated for 5 min. 25 μl 1M sulfuric acid was added after the incubation to stop the reaction. Specific signal was detected on an ELISA reader at 450 nm.

For the cell based FMAT detection of anti-EGFR antibodies, SKBR-3 (ATCC #HTB-30) or NR6 wtEGFR (Welsh et al, 1991, J Cell Biol, 114, 3, 533-543) cells were kept in growth medium as described. The cells were counted and diluted to 125,000 cells/ml with the Alexa-647 conjugated goat-anti-human IgG (H-L) antibody (Molecular probes No. A21445, lot no. 34686A) diluted 1:40,000. A total of 20 μl of this suspension was transferred to 384 well clear bottom Nunc plates. Subsequently 10 μl transfection supernatant was added to the cells. The FMAT signal from the reaction was measured after 6-10 hour of incubation.

The data from the screening indicates that 221 (4.8%) of the total clones were positive in the ELISA. 93 (2.0%) of those clones were also positive in FMAT. In total 220 (4.8%) of the clones were positive in the FMAT and among those 127 (220-93) uniquely positive for the cell surface antigen. The 111 library was screened in a similar fashion, but since the immunization procedure was made to generate antibodies specific for the deletion mutant EGFR receptor EGFRvIII, the ELISA screenings included assays to detect both wild-type EGFR and EGFRvIII. Seven clones were identified to be specific for the EGFRvIII in the ELISA and interestingly those clones were negative for staining of wtEGFR expressing cells in the FMAT. 13 clones were identified to be positive for the wtEGFR in FMAT and ELISA but not for the EGFRvIII, which were unique for this library compared to the 101 and 108/109 libraries. All the ELISA positive clones were selected for further analysis.

Sequence Analysis and Clone Selection

The clones identified as EGFR-specific in ELISA were retrieved from the original master plates (384-well format) and consolidated into new plates. DNA was isolated from the clones and submitted for DNA sequencing of the V-genes. The sequences were aligned and all the unique clones were selected. Multiple alignments of obtained sequences revealed the uniqueness of each particular clone and allowed for identification of unique antibodies. Following sequence analysis of 220 clones, 70 genetically distinct antibody sequence clusters were identified. Each cluster of related sequences have probably been derived through somatic hypermutations of a common precursor clone. Overall, one to two clones from each cluster was chosen for validation of sequence and specificity. Sequences of selected antibody variable sequences are shown in Appendix 1. The nucleotide sequences include restriction sites in both terminals. Consequently, the corresponding translated amino acid sequences (using the third reading frame of the DNA sequence) include in the N-terminal, two amino acids which do not form part of the VH and VL sequences according to the IMGT definition (Lefranc et al (2003) IMGT unique numbering for immunoglobulin and T cell receptor variable domains and Ig superfamily V-like domains. Dev. Comp Immunol 27, 55-77). The VL sequences shown all include the same human Kappa Constant region, which starts with amino acids—TVAAP– and ends at the C-terminal –NRGEC. For the purposes of the present invention the term VL sequence when referring to a specific antibody excludes the Kappa Constant region and the two N-terminal amino acids (LA–). The term VH sequence when referring to a specific antibody excludes the two N-terminal amino acids (RA–).

Sequence and Specificity Validation

In order to validate the antibody encoding clones, DNA plasmid was prepared and transfection of FreeStyle CHO-S cells (Invitrogen) in 2-ml scale was performed for expression. The supernatant were harvested 96 hours after transfection. Expression levels were estimated with standard anti-IgG ELISA, and the specificity was determined by EGFR- and EGFRvIII-specific ELISA. 85% of the clones were shown to have the correct specificity and sequence.

Screening for Anti-Proliferative Effects

Cellular damage will inevitably result in loss of the ability of the cell to maintain and provide energy for metabolic cell function and growth. Metabolic activity assays are based on this premise. Usually they measure mitochondrial activity. The Cell Proliferation Reagent WST-1 (Roche Cat. No. 11 644 807 001) is a ready-to-use substrate which measures the metabolic activity of viable cells. It is then assumed that the metabolic activity correlates with the number of viable cells. In this example the WST-1 assay was used to measure the number of metabolically active cells after treatment with cell culture supernatants containing different anti-EGFR antibodies.

Prior to performing the WST-1 assay different volumes of 2-ml supernatants (0, 10, 25, 50 and 150 µl) were transferred to appropriate wells in a 96 well plate. HN5 cells were then washed with 1×PBS and detached by trypsination with 3 ml trypsin solution. 17 ml of complete media were then added and the cells spun down at 300×g (1200 rcf) for 5 min. The supernatant was removed and cells re-suspended in DMEM+ 0.5% FBS. Cells were counted and their concentration adjusted and 1500 cells were added to the wells with supernatants so that each well contained 200 µl media in total. The plates were incubated for 4 days in a humidified incubator at 37° C. Then 20 µl WST-1 reagent was added pr. well and the plates incubated for one hour at 37° C. Plates were then transferred to a orbital plate shaker and left another hour. The absorbance was measured at 450 and 620 nm (reference wavelength) on an ELISA reader. The difference in the levels of metabolically active cells (MAC) was calculated as percent of the control supernatants as follows:

$$\% \, MAC = \left(1 - \frac{(ODexp. - ODmedia)}{(ODuntreat. - ODmedia)}\right) \times 100$$

These values were then used as the basis for a supervised hierarchical cluster analysis (clustered based on reactivity in ELISA) performed using the free software Cluster and TreeView.

It is preferable to be able to screen for functional antibodies at an early stage in the antibody selection process. The culture supernatants from 83 2-ml transfections were used to screen for growth inhibitory functions in a proliferation assay performed using HN5 cells in 0.5% FBS. Results were visualized by simple hierarchical cluster analysis. As can be seen in the cluster analysis (FIG. 5) a number of supernatants were found to decrease the number of metabolically active HN5 cells (dark grey) in a concentration dependent manner (Cluster 2). Similarly, some supernatants increased the number of metabolically active HN5 cells (light grey) in a concentration dependent manner (Clusters 1, 3 and 4). An interesting observation was that supernatants, which decreased the number of metabolically active HN5 cells, had reactivity 2 (black arrows) whereas supernatants which increased the number of metabolically active HN5 cells had reactivity 1 (grey arrows). Supernatants with reactivity 2 were positive in both wtEGFR and EGFRvIII ELISAs, while supernatants with reactivity 1 only had reactivity towards wtEGFR. Thus, such analyses may provide relationships between antibody reactivity in ELISA and functionality in cellular assays.

Clone Repair

When using a multiplex PCR approach, a certain degree of intra- and inter-V-gene family cross-priming is expected due to primer degeneracy and the high degree of homology. The cross-priming introduces amino acids that are not naturally occurring in the immunoglobulin framework with several potential consequences, e.g. structural changes and increased immunogenicity, all resulting in a decreased therapeutic activity.

In order to eliminate these drawbacks and to ensure that selected clones mirror the natural humoral immune response, such cross-priming mutations were corrected in a process called clone repair.

In the first step of the clone repair procedure, the $V_H$ sequence was PCR amplified with a primer set containing the sequence corresponding to the $V_H$-gene the clone of interest originated from, thereby correcting any mutations introduced by cross-priming. The PCR fragment was digested with XhoI and AscI and ligated back into the XhoI/AscI digested mammalian expression vector (FIG. 4) using conventional ligation procedures. The ligated vector was amplified in $E.\ coli$ and the plasmid was purified by standard methods. The $V_H$ sequence was sequenced to verify the correction and the vector was digested with NheI/NotI to prepare it for insertion of the light chain.

In the second step the complete light chain was PCR amplified with a primer set containing the sequence corresponding to the $V_L$-gene the clone of interest originated from, thereby correcting any mutations introduced by cross-priming. The PCR fragment was digested with NheI/NotI and ligated into the $V_H$ containing vector prepared above. The ligation product was amplified in $E.\ coli$ and the plasmid was purified by standard methods. Subsequently, the light chain was sequenced to verify the correction.

In the case where the Kappa constant region of a selected clone contains mutations, introduced during the amplification of the genes, it is replaced by an unmutated constant region. This is done in an overlap PCR where the repaired $V_L$-gene (amplified without the constant region) was fused to a constant region with correct sequence (obtained in a separate PCR). The whole sequence is amplified and cloned into the $V_H$ containing vector as described above and the repaired light chain is sequenced to verify the correction.

TABLE 2

Immunization schedules used to generate starting material for anti-EGFR cloning

| Schedule, Mouse group | Strain | Injection 1 | Injection 2 | Injection 3 | Injection 4 | Termination |
|---|---|---|---|---|---|---|
| 101 | Balb/c | Day 1 25 µg rhEGFR (R&D systems 1095-ER) CFA s.c. | Day 35 25 µg rhGH-EGFR (Symphogen) IFA s.c | Day 56 25 µg rhEGFR* (Symphogen) IFA s.c | Day 70 25 µg rhEGFR* (Symphogen) IFA s.c | Day 73 |
| 108 | Balb/c | Day 1 1 × 10⁷ HN5 cells | Day 28 25 µg rhEGFR* | Day 42 1 × 10⁷ HN5 cells IFA i.p. | Day 56 25 µg rhEGFR*, | Day 59 |

TABLE 2-continued

Immunization schedules used to generate starting material for anti-EGFR cloning

| Schedule, Mouse group | Strain | Injection 1 | Injection 2 | Injection 3 | Injection 4 | Termination |
|---|---|---|---|---|---|---|
| 109 | Balb/c | Day 1<br>1 × 10⁷ HN5 cells<br>CFA i.p. | CFA i.p. (Symphogen) IFA s.c.<br>Day 28<br>25 µg rhEGFR* (Symphogen) IFA s.c. | Day 42<br>1 × 10⁷ HN5 cells IFA i.p. | (Symphogen) IFA s.c.<br>Day 56<br>25 µg rhEGFR* (Symphogen) IFA s.c. | Day 59 |
| 111 | Balb/c | Day 1<br>25 µg rhEGFR* (Symphogen) CFA s.c. | Day 28<br>25 µg rhEGFR+ rhEGFRvIII** (Symphogen) IFA s.c. | Day 42<br>25 µg rhEGFR+ rhEGFRvIII** (Symphogen) IFA s.c. | PBS i.v.<br>Day 56<br>25 µg rhEGFR+ rhEGFRvIII** (Symphogen) IFA s.c. | Day 59 |
| 118 | Balb/c | Day 1<br>1 × 10⁷ HN5 cells<br>CFA i.p. | Day 29<br>100 µg rhGH-EGFR (Symphogen) IFA s.c. | Day 44<br>1 × 10⁷ HN5 cells IFA i.p. | Day 58<br>25 µg rhEGFR, (Sigma E3641) IFA s.c. | Day 61 |
| 119 | C57B | Day 1<br>1 × 10⁷ HN5 cells<br>CFA i.p. | Day 29<br>100 µg rhGH-EGFR (Symphogen) IFA s.c. | Day 44<br>1 × 10⁷ HN5 cells IFA i.p. | Day 58<br>25 µg rhEGFR, (Sigma E3641) IFA s.c. | Day 61 |

TABLE 3

RT-PCR multiplex overlap-extension primer mix

| Primer name | Conc. (nM) | Sequence | SEQ ID |
|---|---|---|---|
| mHCre | 0.2 | GACSGATGGGCCCTTGGTGG | 1 |
| mKapp | 0.2 | GCTGTAGGTGCTGTCTTTGC | 2 |
| mVH | | | |
| mVH A | 0.04 | TATTCCCATGGCGCGCCSAGGTCCARCTGCARCAGYCTG | 3 |
| mVH B | 0.04 | TATTCCCATGGCGCGCCGARGTGMAGCTKGTKGAGTC | 4 |
| mVH C | 0.04 | TATTCCCATGGCGCGCCSAGGTGCAGCTKMAGGAGTC | 5 |
| mVH 8 | 0.04 | TATTCCCATGGCGCGCCCAGGTTACTCTGAAAGAGTC | 6 |
| mVH 9 | 0.04 | TATTCCCATGGCGCGCCCAGATCCAGTTGGTGCAGTCTG | 7 |
| mVK | | | |
| mVK D | 0.04 | GGCGCGCCATGGGAATAGCTAGCCGAYATCCAGATGACHCARWCT | 8 |
| mVK E | 0.04 | GGCGCGCCATGGGAATAGCTAGCCRACATTGTGMTGACHCAGTC | 9 |
| mVK F | 0.04 | GGCGCGCCATGGGAATAGCTAGCCSAMATTGTKCTSACCCARTCTC | 10 |
| mVK 1- | 0.04 | GGCGCGCCATGGGAATAGCTAGCCGATRTTGTGATGACBCARRCT | 11 |

W = A/T,
R = A/G,
S = G/C,
Y = C/T,
K = G/T,
M = A/C,
H = ACT,
B = GCT;
Conc. - final concentration.

TABLE 4

Nested primer set

| Primer name | Conc. (nM) | Sequence | SEQ ID |
|---|---|---|---|
| mHCrev | 0.2 | GGACAGGGMTCCAKAGTTCCADKT | 16 |
| hmJK | | | |
| hmJK1- | 0.2 | GACAGATGGTGCAGCCACAGTTCGTTTGATTTCCAGCTTGGTG | 17 |
| hmJK2- | 0.2 | GACAGATGGTGCAGCCACAGTTCGTTTTATTTCCAGCTTGGTC | 18 |
| hmJK4- | 0.2 | GACAGATGGTGCAGCCACAGTTCGTTTTATTTCCAACTTTGTC | 19 |
| hmJK5- | 0.2 | GACAGATGGTGCAGCCACAGTTCGTTTCAGCTCCAGCTTGGTC | 20 |

K = G/T,
M = A/C,
D = AGT;
Conc. - final concentration.

TABLE 5

Kappa constant splicing primer set

| Primer | Conc. (nM) | Sequence | SEQ ID |
|---|---|---|---|
| | | Human kappa constant amplification | |
| hKCforw-v2 | 0.2 | GAACTGTGGCTGCACCATCTGTC | 21 |
| Kappa3' | 0.2 | ACCGCCTCCACCGGCGGCCGCTTATTAACACTCTCCCCTGTTG | 22 |
| | | Splicing by overlap extension | |
| mhKCrev | 0.2 | ACCGCCTCCACCGGCGGCCGCTTATTAACACTCTCCCCTGTTGAAGCTCTT | 23 |
| mJH set | | | |
| mJH1 | 0.2 | GGAGGCGCTCGAGACGGTGACCGTGGTCCC | 12 |
| mJH2 | 0.2 | GGAGGCGCTCGAGACTGTGAGAGTGGTGCC | 13 |
| mJH3 | 0.2 | GGAGGCGCTCGAGACAGTGACCAGAGTCCC | 14 |
| mJH4 | 0.2 | GGAGGCGCTCGAGACGGTGACTGAGGTTCC | 15 |

Example 2

Mammalian Production of Anti-EGFR Antibodies

The FreeStyle MAX CHO expression system (Invitrogen) was used for transient expression of anti-EGFR antibodies. Antibodies were expressed in 200-2000 ml volume.

Approximately 24 hours before transfection CHO-S cells were passaged to reach a cell concentration of $0.5 \times 10^6$ cells/ml. Plasmid (1.25 μg per ml cell culture media) was diluted into OptiPro serum-free medium and mixed with a solution of FreeStyle MAX Transfection reagent as recommended by the supplier. The transfection reagents were transferred to the cell culture and supernatant were harvested 6 days later.

The expressed antibodies were purified from the culture supernatant using an affinity chromatography step employing a Protein A-Sepharose column (MabSelect Sure, GE Health Care) for purification of IgG1 molecules. The antibodies were eluted from the column using 0.1M Glycine, 2.7. The fractions containing antibodies, determined by absorbance measurements at 280 nm, were pooled and dialyzed against 5 mM sodium acetate, 150 mM NaCl, pH 5. The purified antibody samples were tested for the presence of endototoxin by the LAL assay.

Example 3

Determination of Epitope Specificities

Competition ELISA with Reference Antibodies

By using reference antibodies binding to known domains of EGFR as published in (J. R. Cochran et. al., JIM 2004: 287; 147-158), a competition ELISA was developed that could distinguish between the binding epitopes of anti-EGFR antibodies by incubation with a secondary reagent that was specific for the human Fc region of Anti-EGFR antibodies and exhibiting no cross reactivity to mouse or rat IgG Fc. The ELISA was adapted from the descriptions published in Ditzel et al, 1995, The Journal of Immunology, Vol 154, Issue 2 893-906.

An epitope blocking ELISA was performed by diluting full length EGFR receptor antigen to 0.5 μg/ml in PBS; and coating 50 μl/ELISA well overnight at 4° C. The next morning wells were washed twice with PBS-T and blocked for one hour with PBS-T-1% BSA at room temperature followed by wash twice in PBS-T. Next 25 μl murine or Rat reference mAbs were added to independent ELISA wells in a dilution known from previous experiments to give 200 times maximal antigen binding. After 15 min, 25 μl Anti-EGFR antibodies were added in a concentration of 2 μg/ml to wells preincubated with reference antibodies or wells containing 25 μl PBS. This gave a final concentration of 1 μg/ml Anti-EGFR antibody and 100 times maximal antigen binding of reference antibodies after mixture. Antibodies were incubated for 45 min. at room temperature after which wells were washed four times with PBS-T. A secondary Goat-anti-Human IgG HRP conjugate was diluted 1:3000, and 50 μl was added to each well followed by 30 min incubation at room temperature. Finally wells were washed four times with PBS-T and plates were developed by adding 50 μl/well TMB and read at 620 nm every 5-15-30 min. The degree of inhibition was calculated from the formula: % inhibition=(1−(OD competition/OD no competition (PBS)))×100.

ELISA Reagents:
1) Coating buffer: 1×PBS; Gibco cat:20012-019
2) Antigens: Wild type full length EGFR purified from A431 cells; Sigma E3641
3) ELISA plate: NUNC Maxisorp; cat: 442404
4) Blocking/Dilution buffer: 1% BSA in PBS-T (PBS-T-1% BSA)
5) Washing buffer: 1×PBS/0.05% Tween 20 (PBS-T)
6) Positive control: Erbitux (Merck KGaA, 64271 Darmstadt, Germany, Catalogue #: 018964; Cetuximab), Vectibix (Amgen Inc, One Amgen Center Drive, Thousand Oaks Calif. 91320-1799, USA, Cat #3241400; Panitumumab)
7) Reference antibodies:
   ICR10 (rat), Abcam, Ab231
   199.12 (murine), Lab Vision Ab-11, MS-396-PABX
   EGFR.1 (murine), Lab Vision Ab-3, MS-311-PABX
   H11 (murine), Lab Vision Ab-5, MS-316-PABX
   B1D8 (murine), Lab Vision Ab-16, MS-666-PABX
   111.6 (murine), Lab Vision Ab-10, MS-378-PABX
   225 (murine), Lab Vision Ab-2, MS-269-PABX
   528 (murine), Lab Vision Ab-1, MS-268-PABX
8) Goat-anti-Human IgG HRP conjugate; Serotec, Star 106P
9) TMB Plus; KemEnTec, cat #4390L
10) 1M $H_2SO_4$ The result of the competition ELISA is shown in FIG. 6. ELISA competition assays were employed to rank Anti-EGFR antibody supernatants according to the domain specificity of used reference antibodies raised against the EGFR extra cellular domain. Inhibition values from 50-100% were taken as an indication of significant competition between antibody pairs binding overlapping epitopes or epitopes in close proximity on the antigen, while inhibition values below 50% indicated that the recognized epitopes by the antibody pairs were not in close proximity resulting in decreased steric hindrance. The Anti-EGFR antibodies were found to bind a variety of epitopes on EGFR ECD including domain I, II & III. For some antibodies this analysis could not distinguish whether the specific mAb was directed against domain I or domain II. Such specificities were labeled domain I/II. Further some antibodies appeared to bind unique epitopes which could not be further deduced in the employed competition ELISA (E.g. clones 1229 & 1320, FIG. 6). It is possible that some of these antibodies are directed against domain IV for which we did not have any reference antibody reactivities. Interestingly the domain III antibodies could further be divided in four subgroups based on the different competition patterns obtained with the tested murine reference antibodies against this domain. Group I consisted of only mAb 992 which was found to compete for binding with reference antibodies Ab1 & Ab2. Group II consisted of mAbs 1024 & 1042 which were both derived from the same Ig rearrangement and consequently showed very close sequence homology at the DNA and amino acid level. These two antibodies were found to only compete for binding with Ab2. Group III consisted of mAbs 1030, 1208 & 1277 which competed for binding with reference antibodies Ab1, Ab5 & Ab10. Finally group IV consisted of mAb 1254, which competed for binding with all the used domain III reference antibodies Ab1, Ab2, Ab5 & Ab10.

Competition Analysis for Distinct Epitopes with Reference or Same Species Antibodies Using Surface Plasmon Resonance Technology SPR analysis was performed on a Biacore 3000 machine containing four flow cells. A CM5 Biacore chip was conjugated with 10,000 Resonance units (Ru) polyclonal anti-His antibody to flow cells 1-4 according to the manufacturer's instructions. Using a flow rate of 5 μl/min, 15 μl 6×His EGFR ECD at a concentration of 20 μg/ml was injected and captured on all four flow cells to which anti-His polyclonal antibody had been conjugated. Immediately after antigen injection the maximal binding of the Anti-EGFR mAb without competition was established in each flow cell during a reference run. Briefly 5 μl antibody at a concentration of 40 μg/ml was injected over all flow cells with captured EGFR followed by stripping of the antibody/antigen complex with a low pH acid wash (10 sec. contact time with 10 mM Glycine-HCl, pH2). After the determination of Anti-EGFR antibody maximal binding to each flow cell, a competition run was performed during the same Biacore cycle. Flow cells were first saturated with EGFR ECD antigen followed by injection of different reference antibodies or Anti-EGFR antibodies into separate flow cells using the same antigen saturating conditions as outlined above. This step was immediately followed by a second injection of Anti-EGFR antibody over the flow cell saturated with EGFR antigen and competition antibody to minimize the dissociation of either antigen or blocking antibody. Then the antibody/antigen complexes were stripped off with a low pH acid wash (10 sec. contact time with 10 mM Glycine-HCl, pH 2) and the whole cycle beginning with the reference run was repeated with a new Anti-EGFR antibody. The degree of inhibition of tested Anti-EGFR antibodies were determined by comparing the Ru max value of the individual Anti-EGFR antibody before and after competition by introduction of report points recorded two seconds before and after injection of each sample. An example of one Biacore cycle is shown in FIG. 7.

Reagents:
1. CM5 chip; Biacore, Cat. No. BR-1000-14
2. NHS; Biacore BR-1000-50
3. EDC; Biacore BR-1000-50
4. 10 mM Acetate buffer pH 4.5; Biacore, Cat. No. BR-1003-50
5. Tetra-His antibody (BSA free); Qiagen, Cat. No. 34670
6. Ethanolamine, 1.0M pH 8.5; Biacore BR-1000-50
7. 10×HBS-EP running buffer: 0.01M HEPES pH 7.4, 0.15 M NaCl, 3 mM EDTA, 0.005% v/v Surfactant P20
8. Antigen: Inhouse produced recombinant human EGFR extracellular domain with 6×His.
9. 10 mM Glycine HCl pH 2.0
10. Reference antibodies:
    ICR10 (rat), Abcam, Ab231
    199.12 (murine), Lab Vision Ab-11, MS-396-PABX
    EGFR.1 (murine), Lab Vision Ab-3, MS-311-PABX H11 (murine), Lab Vision Ab-5, MS-316-PABX
B1 D8 (murine), Lab Vision Ab-16, MS-666-PABX
111.6 (murine), Lab Vision Ab-10, MS-378-PABX
225 (murine), Lab Vision Ab-2, MS-269-PABX
528 (murine), Lab Vision Ab-1, MS-268-PABX To confirm the epitope analysis obtained in competition ELISA and to perform further epitope analysis by competition between same species Anti-EGFR antibody pairs, a competition assay based on antibody binding measured in real time by surface plasmon resonance was established. The obtained epitope map of Anti-EGFR clones tested against the panel of reference antibodies is shown in FIG. 8 below. Inhibition values from 50-100% were taken as an indication of significant competition between antibody pairs binding overlapping epitopes or epitopes in close proximity on the antigen, while inhibition values below 50% indicated that the recognized epitopes by the antibody pairs were not in close proximity resulting in decreased steric hindrance. Inhibition values below 25% were not included in the analysis for overlapping epitopes, because they were judged to represent non-significant inhibition. All tested antibodies except 1320 were found to compete with one or more of the employed reference antibodies, indicating that 1320 was directed against an unknown epitope for which we did not have any reference antibody reactivities. The fully human or humanized antibodies Vectibix and Erbitux were included in the analysis and were found to bind overlapping epitopes. The data obtained from both the competitive ELISA and competitive SPR analysis generally correlated well with respect to the established domain specificity of the Anti-EGFR antibodies. However, slight differences in the competition pattern between individual reference antibodies were sometimes observed in the two assays, perhaps due to the fact that the ELISA competition assay employed full length EGFR receptor antigen while the SPR competition assay used recombinant extra cellular domain EGFR.

After the epitope mapping of Anti-EGFR antibodies had been confirmed in two different competition assays, competition analysis of same species combinations of Anti-EGFR antibody pairs were investigated to resolve which antibody pairs were recognizing distinct epitopes, and if antibody pairs recognizing overlapping epitopes could be further divided into epitope clusters. The result of this analysis is shown in FIG. 9. Again in this analysis, inhibition values from 50-100% were taken as an indication of significant competition between antibody pairs binding overlapping epitopes. This criterion seemed valid, since antibodies tested against them selves, and consequently recognizing complete overlapping epitopes resulted in values between 70%-100% inhibition as shown in FIG. 9. Further, this observation illustrated that dissociation of either antigen or antibody pairs within the time frame of the analysis did not appear to have an impact on the outcome of the experiment for the antibodies tested. By grouping the antibodies according to the presumed EGFR ECD domain specificity determined in the previous sections, antibodies binding exclusively to domain I or to either domain I or II (I/II) were found to mainly cluster with antibody members with same specificities, and not antibody members recognizing domain III. Likewise domain III antibodies were found to compete for binding only with antibody members recognizing domain III and not antibodies recognizing EGFR domain I or I/II. While the two domain III antibodies 1024 & 1042 derived from the same Ig rearrangement were found to recognize overlapping epitopes, pair wise combinations of either 1024 or 1042 with either 992 or 1030 were importantly not found to result in significant competition. Consequently it was concluded that antibodies 992, 1030 & 1024/1042 were recognizing three non-overlapping epitopes on the domain III of EGFR ECD. Finally mAb 1320 was found to compete for binding with mAbs 1024 and 1449, both directed against domain III, and not other domain III antibodies tested (competition of 1320 with 1042 not determined). Consequently, it was assumed that mAb 1320 was binding in the periphery of domain III on the extracellular domain of EGFR. An overview of the epitope specificities can be seen in FIG. 10, where epitope maps of antibodies directed against EGFR ECD domain I, I/II or III are illustrated.

After the finding that pair wise combinations of 992, 1030 & 1024/1042 did not result in significant antibody competition as determined by SPR, new Biacore experiments were designed to examine how many antibodies that could bind to the receptor antigen simultaneously. First it was investigated what impact saturation of Domain III with the three antibodies 992, 1024 and 1030 had on the binding of antibodies directed against other EGFR specificities that were not domain III. The result from this analysis is shown in FIG. 11A. The inhibitions of single antibodies were established by testing them in combinations with either single antibody or antibody mixtures of up to three antibodies generated by sequential addition of one extra antibody during each Biacore cycle. To assure complete blockage of the recognized epitope, antibodies were tested in individual concentrations of 40 μg/ml. As shown in FIG. 11A, the three domain III antibodies 992, 1024 & 1030 were found to bind simultaneously to the receptor without any inhibition of binding. The observed negative inhibition values increasing for each antibody added further suggested a synergy in binding for the next antibody added. Importantly, once domain III was incubated with the three antibodies, other antibodies directed against non-overlapping epitopes on domain I/II (mAb 1261), domain I (1347) or an unknown specificity (1361) appeared to be binding without epitope blockage from the three mAb mixture. Further, these tested antibodies had small negative inhibition values indicating that they were binding better after receptor saturation with the three mAb mixture. Consequently this experiment suggested that the six tested antibodies could bind to the ECD of EGFR simultaneously. To further test this observed phenomenon, an antibody mix consisting of all the tested antibodies (1261, 1347, 992, 1024, 1030 & 1361) was made and tested for inhibition of each individual sample antibody in the mix. Antibody mixes where the tested sample antibody had not been included were also tested to serve as a positive control. As presented in FIG. 11B/C, all six tested antibodies were found to be inhibited from 80-116% when tested for binding to the EGF receptor incubated with the full mix of antibodies. However, when individual sample antibodies were removed from this mixture, no significant inhibition of the particular sample antibody was noted, illustrating that the antibodies in the mixture were only blocked for binding to the EGF receptor by themselves. This experiment clearly illustrated that at least six antibodies recognizing non-overlapping epitopes can bind to EGFR simultaneously. As a final experiment it was investigated if other antibodies directed against domain I (1284), I/II (1257) or unknown specificity cluster (1183, 1255) could bind to the EGFR, when this was incubated with the six antibody mixture. As presented in FIG. 11D none of the tested antibodies were able to bind significantly to the EGFR upon prior incubation with the six antibody mixture. This may be because the collection of antibodies does not include antibodies against any of the sites left unoccupied by the six bound antibodies. Alternatively, it is possible that in fact all sites on the tested domains were blocked with antibody.

TABLE 6

Commercially available antibodies with documented specificities against EGFR extracellular domains.

| Clone | Species | Domain I | Domain II | Domain III |
|---|---|---|---|---|
| ICR10 | Rat | X | | |
| 199.12/Ab11 | Mouse | X | | |
| EGFR.1/Ab3 | Mouse | | X | |
| H11/Ab5 | Mouse | | | X |
| 111.6/Ab10 | Mouse | | | X |
| 528/Ab-1 | Mouse | | | X |
| 225/Ab-2 | Mouse | | | X |

Example 4

EGFR Activation Inhibition

Determination of Antibody Mediated Blockage of EGF Ligand Binding to EGFR Receptor by Competitive ELISA To verify that tested Anti-EGFR antibodies bound to the EGFR receptor and simultaneously blocked the binding of Biotinylated EGF ligand, ELISA wells were coated with 80 µl/well of full length EGFR at a concentration of 0.5 µg/ml in PBS overnight at 4° C. The next morning wells were washed twice with PBS-T and blocked for one hour with 150 µl PBS-T-1% BSA at room temperature, followed by wash twice in PBS-T. Next 80 µl of serially diluted Anti-EGFR antibodies and control antibodies were added to wells and incubated 30 min at room temperature. After antibody incubation 20 µL biotinylated EGF ligand at a concentration of 0.5 µg/ml was added to all wells containing Anti-EGFR antibody dilutions or to wells containing only PBS-T 1% BSA, and incubated at room temperature for 1 hour. Subsequently wells were washed five times with PBS-T, followed by incubation with 100 µl/well Streptavidin-HRP secondary reagent diluted 1:1000 in blocking buffer and incubation at room temperature for 30 min. Finally wells were washed five times with PBS-T and plates were developed by adding 100 µL/well TMB substrate and incubated for 60 min. After incubation the reaction was stopped by addition of 1M $H_2SO_4$; 100 µl/well and plates were read at OD 450 nm.

Figure 12A:
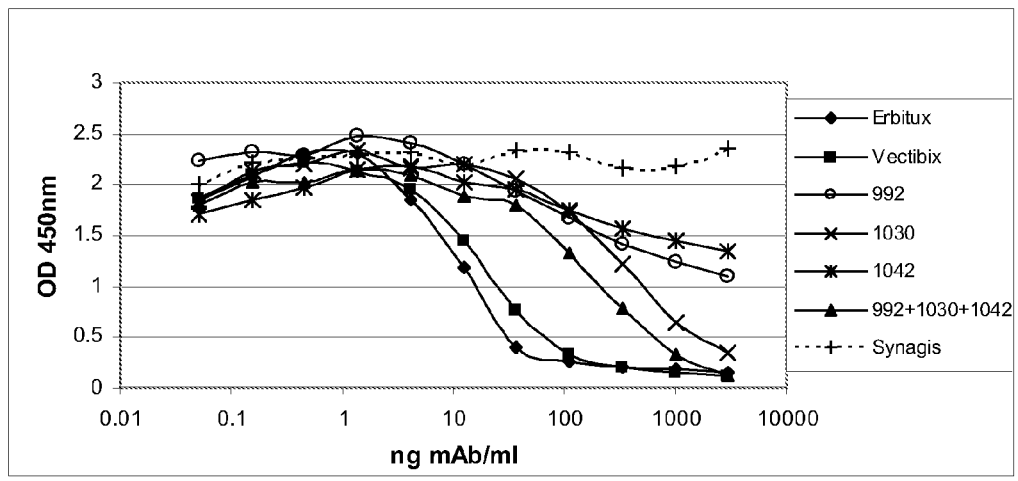
Figure 12B:
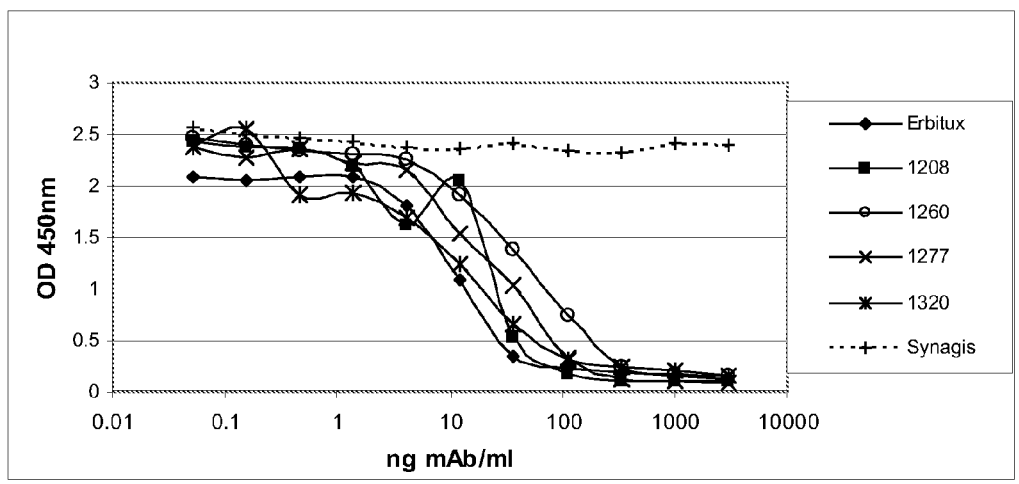

ELISA Reagents:
1) Coating buffer: 1×PBS; Gibco cat:20012-019
2) Antigen: Wild type full length EGFR purified from A431 cells; Sigma E2645
3) ELISA plate: NUNC Maxisorp; cat: 442404
4) Blocking/Dilution buffer: 1% BSA in PBS-T (PBS-T-1% BSA)
5) Washing buffer: 1×PBS/0.05% Tween 20 (PBS-T)
6) Positive control: Erbitux, Vectibix
7) Negative control: Synagis (Medimmune Inc, Palivizumab, cat. #NDC 60574-4111-1)
8) Biotinylated EGF ligand; Invitrogen, cat E3477
9) Streptavidin-HRP, ultra sensitive: Sigma S 2438
10) TMB Plus; KemEnTec, cat #4390L
11) 1M $H_2SO_4$ ELISA competition assays were employed to rank the ability of Anti-EGFR antibodies to inhibit the binding of biotinylated EGF ligand to full length EGFR receptor coated to ELISA wells. As presented in FIG. 12, both Erbitux and Vectibix appeared to very potently block EGF ligand binding while the negative control antibody Synagis, which is not directed against EGFR did not inhibit EGF ligand binding. As shown in FIG. 12A, the three antibodies 992, 1030 and 1042 directed against domain III and recognizing non overlapping epitopes were tested alone or in an equimolar mixture for their ability do inhibit EGF ligand binding. Of the three tested antibodies only mAb 1030 showed a modest EGF ligand inhibiting activity when compared to Erbitux and Vectibix. The equimolar mixture of mAbs 992, 1030 and 1042 appeared to be more efficient in inhibiting EGF ligand binding than the single antibodies tested alone. At a total IgG concentration of 1 µg/ml, the equimolar mixture was found to inhibit EGF ligand binding approximately two times more efficiently than mAb 1030 and four times more efficiently than mAbs 992 & 1042 tested alone, showing a synergistic effect of mixing three domain III antibodies recognizing non overlapping epitopes. As shown in FIG. 12B the Anti-EGFR clones 1208, 1260, 1277 & 1320 were also tested in this assay. These four clones were able to inhibit EGF ligand binding in a dose dependant manner that was more efficient than observed for clones 992, 1030 and 1042 when comparing to the Erbitux control. At concentrations above 0.33 µg/ml the Anti-EGFR clones 1208, 1260, 1277 & 1320 appeared to be just as efficient at blocking EGF ligand binding as Erbitux tested at same concentrations.

Ability to Inhibit EGF Induced EGFR Phosphorylation in HN5 Cells

Anti-EGFR antibodies were tested for reactivity on EGFR phosphorylation in an in cell western analysis. The in cell western procedure enables the detection of EGFR and phosphorylated EGFR (pEGFR) from the same sample, this in turn makes it possible to compare the ratio of EGFR to pEGFR expression for each antibody treatment and data set. HN5 cells were cultivated according to the instructions provided by ATCC in DMEM supplemented with 10% FCS and pen/strep. 43,000 HN5 cells were seeded in 96 well plates from Nunc (cat no 167008) 24 h before starvation. Cells were starved in DMEM 16 h before addition of the antibodies. Antibodies were added at a final concentration of 10 µg/ml in 200 µl DMEM and the mixture was pipetted up and down at least five times to mix. After 30 min of antibody treatment EGF was added at a concentration of 50 µg/ml to appropriate wells and left for 7.5 min. In cell westerns were performed essentially to the instructions provided by the manufacturer of the in-cell western kit (Odyssey, LI-COR biosciences).

The cells were fixed in 3.7% formaldehyde (Sigma F-8775, lot 71K500, containing ~1% methanol) for 20 min after EGF stimulation. Five PBS-Triton X-100 (0.1%) 5 min washes were used in order to permeabilize the cells membranes prior to blocking in the LI-COR blocking buffer (927-40000). Primary antibodies were added in concentrations corresponding to the instructions provided and incubated with gentle shaking at RT for 2.5 h (total EGFR mouse, 1:500 dilution biosource international, cat no AHR5062 and Phospho-EGFR Tyr1173, Rabbit 1:100 dilution, biosource, Cat no 44-794G).

Following incubation with the primary antibodies the cells were washed five times for five minutes in PBS-T (0.1% tween-20) after which the secondary antibodies were added (goat-anti-rabbit IRDye 680, 1:200 dilution, LI-COR cat no 926-32221 and goat-anti-mouse, IRDye 800CW 1:800 dilution; LI-COR cat no 926-32210) and incubated for 1 h at RT with gentle shaking of the plate covered in aluminium foil.

Prior to measurement on the Tecan fluorescence reader the plate was washed five times for five min in PBS-T. All washes were terminated by an abruptly aborted throwing motion of the plates, open side down, to dispel the washing solution, followed by knocking of the plate against paper towels. (Identical to the treatment of ELISA plates, the important thing is the notion that the cells remain on the plate during this treatment and that the wash solution can be removed by this procedure rather than by suction, that will disturb the integrity of the cell monolayer). Any residual washing solution left from the last wash was removed by gentle suction at the side of the wells with a multichannel pipette. The fluorescent signal was measured for the 680 nm channel (excitation 675 nm and emission 705 nm, both 10 nm bandwidth) and for the 800 nm channel (excitation 762 nm and emission 798 nm, both 10 nm bandwidth).

Using the in-cell Western analysis it becomes evident that the three antibodies are significantly ($p<0.05$) affecting the pEGFR status of HN5 cells; the 1208, 1277 and 1320 antibodies (FIG. 13)

The anti-EGFR mix (992, 1030 and 1042) of anti-EGFR antibodies and the individual antibodies therein were tested for effect in an in cell western analysis of inhibition of EGF induced EGFR phosphorylation. As seen in FIGS. 14, 992 and 1030 and the anti-EGFR antibody mix significantly inhibited EGF induced EGFR phosphorylation ($p<0.05$).

Example 5

Internalisation of EGF Receptors in A431NS cells

A431NS cells (ATCC# CRL-2592) were trypsinised from an 80-90% confluent T175 culture flask using TrypLE. Detached cells were washed in PBS and suspended in DMEM without serum. Cells were split into portions of 1-2 ml and incubated 30 min on ice with the antibodies examined. The antibody concentration were 10 µg/ml. Cells were washed three times in DMEM (250 g, 4 min, 4° C.) and re-suspended in 1.8 ml DMEM. Each portion were split into six FACS tubes containing each 300 µl cell suspension. Three tubes of each portion are placed in 37° C. water bath in exactly 40 min and the other three are put on ice immediately. After incubation, cells are washed twice at (250 g, 4 min, 4° C.) and pellets re-dissolved in 100 µl Rabbit anti human IgG Fcγ F(ab)$_2$-FITC in DMEM. Cells are incubated for 30 min at 4° C. before washed three times in 4° C. DMEM and analysed on FACSCalibur.

Results are shown in FIG. 15. Incubation with Erbitux and Vectibix showed an equal level of internalisation of receptor of around 30% leaving 70% of initial surface staining. Incubation with 992 alone leads to around 45% receptor downregulation. Incubation with antibody mixtures containing two additional antibodies with non-overlapping epitopes leads to an increase in receptor downregulation: 992+1024, 74%; 992+1024+1030, 83%. Addition of additional antibodies did not lead to further increase in receptor internalisation. Thus, at least three antibodies appear to be required to achieve the maximal level of internalisation in A431 cells.

Example 6

Proliferation Assays

Cellular damage will inevitably result in loss of the ability of the cell to maintain and provide energy for metabolic cell function and growth. Metabolic activity assays are based on this premise. Usually they measure mitochondrial activity. The Cell Proliferation Reagent WST-1 (Roche Cat. No. 11 644 807 001) is a ready-to-use substrate which measures the metabolic activity of viable cells. It is then assumed that the metabolic activity correlates with the number of viable cells. In this example the WST-1 assay was used to measure the number of metabolically active cells after treatment with different antibodies in different concentrations.

Prior to performing the WST-1 assay the appropriate antibodies and antibody mixes were diluted to a final total antibody concentration of 20 µg/ml in DMEM supplemented with 0.5% of FBS and 1% P/S yielding a final antibody concentration of 10 µg/ml in the well with the highest antibody concentration. 150 µl of these solutions were then added to wells in column 2 of a 96-well plate and a three-fold serial dilution were made down to column 9 so that each well contains 100 µl of antibody solution. 100 µl of media were added to column 11. 200 µl of media were added to Rows 1 and 8 as well as column 1 and 12 to the decrease effect of media evaporation in the experimental wells.

A431-NS cells are then washed with 1×PBS and detached by trypsination with 3 ml trypsin solution. 17 ml of complete media are then added and the cells spun down at 300×g (1200 rcf) for 5 min. The supernatant is removed and cells re-suspended in DMEM+0.5% FBS. Cells are the counted and their concentration adjusted to 15,000 cells/ml. 100 µl of the cell suspension (1500 cells/well) are then added to experimental wells in columns 2-11. The plates are incubated for 4 days in a humidified incubator at 37° C. Then 20 µl WST-1 reagent is added pr. well and the plates incubated for one hour at 37° C. Plates are then transferred to a orbital plate shaker and left another hour. The absorbance is measured at 450 and 620 nm (reference wavelength) on an ELISA reader. The amount of metabolically active cells (MAC) is calculated as percent of the untreated control as follows:

$$\% \ MAC = \left( \frac{(ODexp.-ODmedia)}{(ODuntreat.-ODmedia)} \right) \times 100$$

For the EGF titration studies, the ligand was diluted to concentration of 20 nM/ml in DMEM+0.5% FBS, yielding a final concentration of 10 nM/ml in the well with the highest EGF concentration. 150 µl of this solution was then added to wells in column 2 of a 96-well plate and a three-fold serial dilution were made down to column 9 so that each well contains 100 µl of EGF solution. 100 µl of media were added to column 11. 200 µl of media were added to Rows 1 and 8 as well as column 1 and 12 to the decrease effect of media evaporation in the experimental wells. The appropriate antibodies and antibody mixes were diluted to a final total antibody concentration of 40 µg/ml in DMEM supplemented with 0.5% of FBS and 1% P/S yielding a final antibody concentration of 10 µg/ml in the wells. 50 µl of these solutions were then added to wells in column 2-9 of the 96-well plate.

A431-NS cells are then washing with 1×PBS and detached by trypsination with 3 ml trypsin solution. 17 ml of complete media are then added and the cells spun down at 300×g (1200 rcf) for 5 min. The supernatant is removed and cells re-suspended in DMEM+0.5% FBS. Cells are the counted and their concentration adjusted to 40,000 cells/ml. 50 µl of the cell suspension (2000 cells/well) are then added to experimental wells in columns 2-11. The plates are incubated for 4 days in a humidified incubator at 37° C. Then 20 µl WST-1 reagent is added pr. well and the plates incubated for one hour at 37° C. Plates are then transferred to a orbital plate shaker and left another hour. The absorbance is measured at 450 and 620 nm (reference wavelength) on an ELISA reader. The amounts of metabolically active cells are indicated by the absorbance at 450 nm subtracted the absorbance at the reference wavelength of 620 nm.

The amount of metabolically active cells (MAC) is calculated as percent of the untreated control as follows:

$$\% \, MAC = \left( \frac{(ODexp. - ODmedia)}{(ODuntreat. - ODmedia)} \right) \times 100$$

Results

Figure 16A:
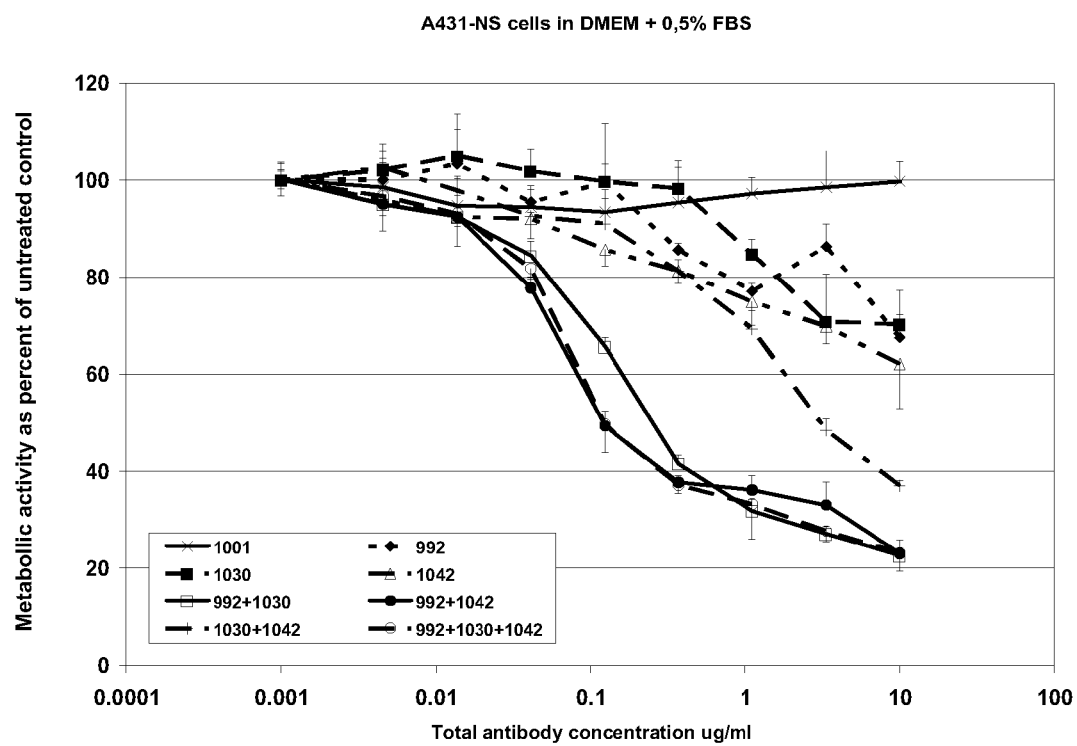

To show that a mixture of three anti-EGFR antibodies with non-overlapping epitopes within domain III is superior to the antibodies alone an experiment was performed which investigated the inhibition of A431-NS growth. As can be seen in FIG. 16A, the antibodies are poor inhibitors of A431-NS growth on their own, but when combined a synergistic inhibitory effect on 431-NS growth is obtained. Although mixes of 992 with either 1042 or 1030 is also very potent, the mix of all three is superior to these over all antibody concentration ranges.

The effects of individual antibodies and antibody mixes on the growth of A431-NS cells stimulated with varying concentrations of EGF were investigated and the results are shown in FIG. 17. As can be seen in FIG. 17 EGF concentrations above 0.1 nM in the absence of antibodies are toxic to the cells. However it is evident that a mix of three antibodies with non-overlapping epitopes within domain III of EGFR (992, 1030 and 1042) acts synergistically to inhibit growth of the A431-NS cells in the presence of EGF when tested up to at least 0.3 nM of EGF and the mix is superior to all monoclonal antibodies.

Next we demonstrate that the synergistic inhibitory effect on A431-NS growth also can be obtained by combining two antibodies with non-overlapping epitopes in domain III of EGFR with antibodies with epitopes within either domain I or II of EGFR. As can be seen in FIG. 18 combinations of the antibody 992 and 1024 which are both domain III of EGFR, with either an antibody reactive with domain I (1284) or with domain I/II (1434) of EGFR are as potent as three antibodies reacting with non-overlapping epitopes within domain III of EGFR (992+1024+1030). In addition, these mixes of antibodies are more potent at inhibiting the growth of A431-NS than the therapeutic anti EGFR antibodies Erbitux and Vectibix.

Figure 16B:
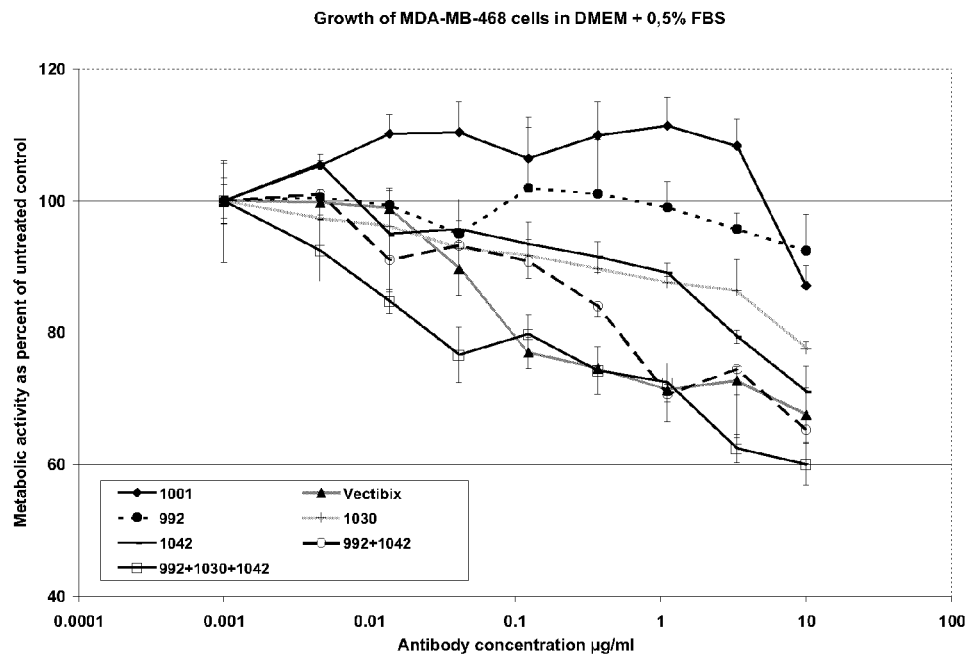
Figure 16C:
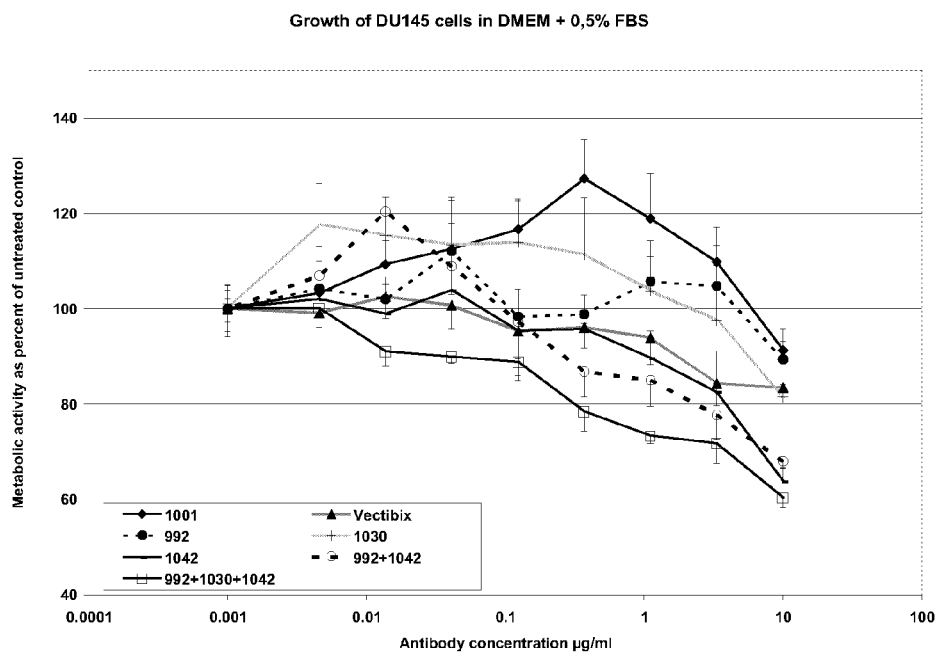

Similar assays were performed using two other cancer cell lines, DU145 (ATCC#HTB-81) and MDA-MB-468 (ATCC#HTB-132). Results from these proliferation assays are shown in FIGS. 16B and 16C. In both cases, a mix of three antibodies (992, 1030 and 1042) was superior to mixes of two antibodies and single antibodies. In DU145 cells the mix of three antibodies was superior to Vectibix at all concentrations, and in MDA-MB-468 at high concentrations.

Using a method similar to the one described above we tested different combinations of three anti-EGFR antibodies. Results The effects of different combinations of three antibodies were investigated in the A431NS cell line. The growth inhibitory activity of the twenty most potent of these is shown in FIG. 37. All the combinations inhibited the proliferation of the A431NS cell line more than 60% compared to a non-treated control. Another interesting observation is than with the exception of the combinations (992+1024+1254 and 992+1024+1320 and 992+1277+1320) the combinations contain antibodies with non-overlapping epitopes. This shows that it is possible to design several combinations of three antibodies binding distinct epitopes.

Example 7

Apoptosis

Apoptosis is a biological mechanism that leads to death of the cell. This mechanism has been reported previously by use of anti-EGFR antibodies, such as Erbitux (Baselga J. The EGFR as a target for anticancer therapy—focus on cetuximab. Eur J. Cancer. 2001 September: 37, Suppl 4:S16-22). It was therefore investigated to which extent the individual anti-EGFR antibodies 992, 1042, and 1030 as well as the mix (992+1042+1030) were able to induce apoptosis.

$1 \times 10^4$ A431NS cells were incubated in DMEM supplemented with 0.5% of FBS and antibiotics in triple determinations in 96 wells culture plates in the presence of the EGFR mix (equal parts of 992, 1030, 1042), 992, 1030, 1042, Erbitux or Vectibix, in concentrations ranging from 0.01 µg/ml to 10 µg/ml. Cells and antibodies were incubated for 22 h. Then supernatants were harvested and measured in an ELISA-kit from Roche, Cat No: 11774425001 (Basel, Switzerland), for the presence of histone-DNA complexes.

The effect of the mix was compared with each of the monoclonal antibodies alone as well as with the reference antibodies Vectibix and Erbitux using A431NS cells (results in FIG. 19). The antibodies were tested in 10-fold dilution. The mix is significantly (P<0.05) more efficient compared to the individual monoclonal antibodies as well as Vectibix when tested at concentrations of 1 µg/ml and 10 µg/ml. The mix increased apoptosis statistically significant (p<0.05) compared to Erbitux at 1 µg/ml.

Example 7b

In addition to example 7, the mixture of 992+1024 as well as the mixture of 992+1024+1030 were investigated for apoptotic activity according to the same method as described in example 7 (FIG. 35). The factual level of apoptosis was related to a maximum positive control. Both of the two mixtures were compared with Erbitux and the individual monoclonal antibodies 992, 1024 and 1030 as well as a control antibody in 1 µg/ml using A431NS cells. The mixture of 992+1024 was significantly better than Erbitux and the individual monoclonal antibodies (all P<0.05).

Example 8

In Vivo Efficacy

The anti-EGFR-mix consisting of the antibodies 992, 1030 and 1042 was investigated for in vivo efficacy in the nude mouse xenograft model using A431NS cells. This is a widely used model for investigating the potency of monoclonal anti-cancer antibodies, including anti-EGFR antibodies. Nude mice are immunocompromised and lack T-cells. This allows growth of human cells in the mice.

Two groups of nude mice 6-8 weeks were injected subcutaneously with $1 \times 10^6$ A431NS cells. When the average tumor size reached 100 mm$^3$, treatment was initiated. Mice received five injections of 1 mg antibody, intraperitonally, with 2-3 days interval. Tumour sizes were measured in two diameters using digital callipers and the volume was calculated using the formula: Tumour volume (mm$^3$)=L×W$^2$×0.5, where L is the longest diameter and W is the shortest diameter (Teicher B A, Tumor Models in Cancer Research. Humana Press, NJ, USA 2002, p 596). By the end of the experiment, tumours were excised and weighted.

Synagis was used as control antibody. The experiment also included treatment with Erbitux and Vectibix in the same amount an using the same schedule as for the anti-EGFR-mix (antibodies 992, 1030, and 1024).

As seen in FIG. 20, the mix of 992, 1030 and 1042 significantly inhibited tumour growth of A431NS(P<0.05). The average weights are shown in FIG. 21. The result correlated with the measured tumour sizes. There are significant difference between the treatment group and the control group.

Example 8b

In Vivo Efficacy

In addition to the described in vivo experiment in example 8, the mixtures of 992+1024 and 992+1024+1030 were investigated in the A431NS xenograft model described above (FIG. 36). Four groups each of 9 nude mice, 6-8 weeks, were injected subcutaneously with $1\times10^6$ A431NS cells. When the average tumour size reached 100 $mm^3$, mice received the first antibody injection. The three groups received either the mixture of 992+1024, 992+1024+1030, Erbitux or the control antibody, Synagis. In all, mice received 17 injections of 0.5 mg 4 times a week. The first injection was given on day 8 and the last injection was given on day 34. Tumour sizes were measured for 56 days. After termination of the antibody treatment, the tumours of the mice receiving Erbitux started expanding in size, whereas tumours continued to decreased in size for mice in the two groups receiving the mix of either 992+1024 or 992+1024+1030. No expansion in tumour size was observed for the 992+1024 group at day 91 (57 days following termination of treatment). The average tumour size for the combination of 992+1024 was significantly smaller (P<0.01) at day 56 than the average tumor size for mice receiving Erbitux.

The survival of mice in the experiment was also monitored. Mice were scored as dead when tumors reached the maximum allowed sizes. The table below shows the number of survived mice 56 days after inoculation of tumor cells. An improved survival is seen for both of the combinations compared to Erbitux.

| Group | 992 + 1024 | 992 + 1024 + 1030 | Erbitux | Control Ab |
| --- | --- | --- | --- | --- |
| Initial number of mice | 9 | 9 | 9 | 9 |
| Mice remaining at day 56 | 9 | 9 | 2 | 0 |

Additional Experiments

Preliminary data on tumour lysates from the xenograft experiment described in example 8 shows that the combination of 992+1042+1030 induces potent down regulation of VEGF production by A431NS, the former being an important mediator of angiogenesis. Increased formation of blood vessels is a phenomena seen in many solid tumours, a mechanism that participate in the sustained supply of nutrients etc., thereby affecting the survival conditions.

Furthermore, other preliminary data shows that an increased level of the antibody combination of 992+1042+1030 can be observed in the tumour lysates from the xenograft experiment described in example 8, when compared to Erbitux and Vectibix.

Example 8c

Enhanced In Vivo Tumor Cell Differentiation

Terminal differentiation of cells is a complex process that includes activation of cell-type specific gene expression programs, leading in a multistep process to an irreversible loss of their proliferative capacity. In malignant disease, cancer cells are often in a dedifferentiated state characterized by an increased rate of proliferation, and it has been suggested that drugs capable of inducing terminal differentiation of cancer cells would be able to eliminate the malignant cells and reestablish normal cellular homeostasis (Pierce G B, Speers W C: Tumors as caricatures of the process of tissue renewal: prospects for therapy by directing differentiation. Cancer Res 48:1996-2004, 1988). Under certain experimental conditions, anti-EGFR monoclonal antibodies have previously been reported to be able to increase the rate of terminal differentiation of human squamous cancer cells grown as xenograft tumors in immunocompromised mice (Miles L, Mason K, Hunter N, Petersen S, Yamakawa M, Ang K, Mendelsohn J, Fan Z: In vivo enhancement of tumor radioresponse by C225 antiepidermal growth factor receptor antibody. Clin Cancer Res 6:701-8, 2000; Modjtahedi H, Eccles S, Sandie J, Box G, Titley J, Dean C: Differentiation or immune destruction: two pathways for therapy of squamous cell carcinomas with antibodies to the epidermal growth factor receptor. Cancer Res 54:1695-701, 1994).

We examined histologically the extent of terminal differentiation in anti-EGFR treated A431NS cells grown as xenografts in mice. The histological study included 3 randomly selected mouse xenograft tumors from each of the four experimental groups from the experiment described in example 8.

The tissues were dissected and snap frozen, then mounted with Tissue-Tek on a cryomicrotome (Leitz, model 1720), cut into 5 μm sections and sampled on superfrost plus slides, then processed for hematoxylin/eosin staining. Two independent observers then conducted a microscopic examination of all tissue sections in a blinded fashion, scoring keratinized areas ("keratin pearls") as a measure of the extent of terminal differention (Modjtahedi et al., 1994). Table 7 lists the result obtained. Mice treated with a mixture of three anti-EGFR antibodies (992+1024+1030, group 1) had markedly larger and more numerous foci of terminally differentiated cancer cells as compared to mice treated with reference antibodies Erbitux and Vectibix (Groups 2 and 3, respectively). No terminal differentiation was detected in the control group receiving PBS instead of antibody (group 4). Representative microscope images were acquired using a microscope fitted with a digital camera, see FIG. 26.

In conclusion, a combination of three anti-EGFR antibodies with non-overlapping epitopes within domain III (clones 992, 1030 and 1042) showed an unexpected enhanced differentiation-inducing effect on tumour cells in vivo as compared to Erbitux and Vectibix monoclonal antibodies. The observed effects on terminal differentiation leads to the conclusion that the antibody compositions of the invention can be used in combination therapy with other differentiation inducing agents, such as retinoic acid, 4-phenyl butyrate.

TABLE 7

| Group | Tumour No. | Scoring of No. of keratin pearls | Comments |
| --- | --- | --- | --- |
| 1 | 16 | ++++ | Large keratin pearls |
| 1 | 17 | +++ | Large keratin pearls |
| 1 | 54 | ++++ | Large keratin pearls |
| 2 | 14 | ++ | Small keratin pearls |
| 2 | 45 | ++ | Small keratin pearls |
| 2 | 49 | ++ | Small keratin pearls |
| 3 | 11 | ++ | Small keratin pearls |
| 3 | 34 | ++ | Small keratin pearls |

TABLE 7-continued

| Group | Tumour No. | Scoring of No. of keratin pearls | Comments |
|---|---|---|---|
| 3 | 56 | ++ | Small keratin pearls |
| 4 | 43 | − | |
| 4 | 60 | − | |
| 4 | 31 | − | |

Example 8d

Sustained Growth Inhibitory Effect of an Antibody Composition of the Invention

A repeat of the tumor xenograft experiment presented in examples 8 and 8b was performed to investigate the in vivo efficacy of the 992+1024 antibody mix. In brief, BALB/c nu/nu mice were injected subcutaneously with $10^6$ A431NS cells into the flank. Tumor xenografts were allowed to grow to an average tumor size of 100 mm$^3$ (day 7) at which point mice were randomized into five groups of nine animals and antibody treatments were initiated. The five groups received either high (2 mg/week) or low (1 mg/week) dose of the 992+1024 mixture or reference antibody Erbitux, or high dose (2 mg/week) control antibody Synagis. All mice received a total of 9 injections of 0.5 or 1 mg antibody twice weekly starting on day 7 and ending on day 33.

High dose (2 mg/week) 992+1024 mix was very efficient at controlling initial tumor growth and at inducing long-term tumor regression when compared to Erbitux (P=0.0002, FIG. 38). None of the animals receiving 2 mg/week 992+1024 mix were terminated in the study period (118 days after the start of the experiment, FIGS. 38 and 39) a significantly better outcome than in the high dose Erbitux 2 mg/week group where only one of nine animal was left at day 60 (P=0.0008, FIG. 39). This shows the sustained effect of 992+1024 treatment on long-term survival. Although less efficient than the high dose, low dose 992+1024 mix (1 mg/week) was also able to control tumor growth and was significantly better compared to high dose 2 mg/week Erbitux when looking at both tumor suppression (P=0.0135, FIG. 38) and survival (P=0.0087, FIG. 39). These results demonstrate the superior potency of the 992+1024 combination when compared to Erbitux even at the low dosage. The results also demonstrate the sustained growth inhibition caused by the 992+1024 combination compared to an approved monoclonal antibody.

Example 9

Spheroid Growth

For the spheroid study, a round-bottomed 96-well plate is added 35 µl of 120 mg/ml Poly-HEMA solution and left to evaporate overnight in a flow-hood. Poly-HEMA prevents cell attachment. A431-NS cells are treated as above, counted and their concentration adjusted to 100,000 cells/ml. 50 µl of the cell suspension (5,000 cells/well) are then added to experimental wells in columns 2-11 together with 50 µl of a 5% matrigel solution. 200 µl of media were added to Rows 1 and 8 as well as column 1 and 12 to the decrease effect of media evaporation in the experimental wells. The plates are centrifuged at 300×g for 5 minutes and left to form overnight in a humidified incubator at 37° C. The following day the appropriate antibodies and antibody mixes were diluted to a final total antibody concentration of 20 µg/ml in an empty 96-well plate. This is done in DMEM supplemented with 0.5% of FBS and 1% P/S yielding a final antibody concentration of 10 µg/ml in the well with the highest antibody concentration. 150 µl of these solutions were then added to wells in column 2 of a 96-well plate and a three-fold serial dilution were made down to column 9 so that each well contains 100 µl of antibody solution. 100 µl of media were added to column 11. 100 µl of these solutions are then transferred to the plate containing the spheroids and left to incubate for 7 days. Then 20 µl WST-1 reagent is added pr. well and the plates incubated for one hour at 37° C. Plates are then transferred to a orbital plate shaker and left another hour. The absorbance is measured at 450 and 620 nm (reference wavelength) on an ELISA reader. The amount of metabolically active cells (MAC) is calculated as percent of the untreated control as follows:

$$\% \ MAC = \left( \frac{(ODexp. - ODmedia)}{(ODuntreat. - ODmedia)} \right) \times 100$$

A mix of three antibodies with non-overlapping epitopes within domain III (992+1030+1042) effectively inhibits the growth of A431-NS spheroids and are more potent that the monoclonal therapeutic anti EGFR antibodies Erbitux and Vectibix (FIG. 22).

Example 10

Binding to Cynomolgus EGFR ECD

Cloning of Cynomolgus EGFR Extra Cellular Domain.

The extra cellular domain of Cynomolgus EGFR excluding signal peptide was cloned from Cynomolgus cDNA isolated from epidermis by using nested PCR and sequence specific primers derived from the published sequence of full length human EGFR (GENBANK X00588, Ullrich, A. et. al. Nature 309(5967), 418-425 (1984)).

PCR Reagents:
Cynomolgous Monkey cDNA Isolated from Normal Skin Epidermis:
CytoMol Unimed, Cat. No: ccy34218, Lot No: A711054.
Phusion reaction buffer (5×): Finnzymes, Cat. no: F-518, Lot. No: 11.
Phusion enzyme: Finnzymes, F-530S (2 U/µL).
dNTP 25 mM: Bioline, Cat. No: B10-39029, Lot. No: DM-103F.
Primers for Amplification of Cynomolgus EGFR ECD Including Partial Signal Sequence and Transmembrane Domain:

```
5' ATG primer:
                               (SEQ ID NO 135)
5'-TCTTCGGGAAGCAGCTATGC-3'

3' Tm 2 primer:
                               (SEQ ID NO 136)
5'-TTCTCCACTGGGCGTAAGAG-3'
```

Primers for Nested PCR Amplifying Cynomolgus EGFR ECD Bp 1-1863 and Incorporating XbaI, MluI Restriction Sites and Stop Codon Before Transmembrane Domain:

```
5' EGFR XbaI:
                               (SEQ ID NO 137)
5'-ATCTGCATTCTAGACTGGAGGAAAAGAAAGTTTGCCAAGGC-3'

3' EGFR MluI:
                               (SEQ ID NO 138)
5'-TACTCGATGACGCGTTTAGGATGGGATCTTAGGCCCGTTCC-3'
```

PCR Conditions:
30 cycles: 98° C./30 sec melting, 55° C./30 sec annealing, 72° C./60 sec elongation. After 30 cycles PCR products were allowed to elongate for additional 5 min.

PCR reactions were performed with 1 µl template and 2 units Phusion Enzyme in a total volume of 50 µL reaction buffer containing 0.2 mM dNTP, 0.5 µM primer.

A final PCR band with an apparent length of approximately 1800-1900 Bp was obtained and cloned into expression vector. The DNA and protein sequence of the cloned extracellular domain of Cynomolgus EGFR is shown in FIG. 23 and the protein sequence of Cynomolgus EGFR ECD aligned to human EGFR ECD is shown in FIG. 24. The alignment of the human EGFR ECD and Cynomolgus EGFR ECD DNA sequences showed 97.6% sequence identity, while the alignment of the corresponding protein sequences showed 98.6% sequence identity.

Demonstration of Antibody Cross Reactivity Between Extra Cellular Domain of Human and Cynomolgus EGFR in ELISA.

To verify that tested Anti-EGFR antibodies bound equally well to both Human and Cynomolgus EGFR ECD and accordingly warranting toxicology studies in Cynomolgus monkies, serial four fold dilutions of antibodies beginning from 1 µg/ml were tested by ELISA for binding to recombinant Human and Cynomolgus EGFR ECD proteins. Antibodies showing identical binding profiles in this assay were taken as indication for good species EGFR cross reactivity. ELISA wells were coated with 50 µl/well of full length EGFR at a concentration of 1 µg/ml in PBS overnight at 4° C. The next morning wells were washed twice with PBS-T and blocked for one hour with 100 µl PBS-T-1% BSA at room temperature, followed by wash twice in PBS-T. Next 50 µl of serially diluted Anti-EGFR antibodies and control antibodies were added to wells and incubated for one hour at room temperature. After antibody incubation wells were washed five times with PBS-T, followed by incubation with 50 µl/well Streptavidin-HRP secondary reagent diluted 1:3000 in blocking buffer and incubation at room temperature for 30 min. Finally wells were washed five times with PBS-T and plates were developed by adding 50 µL/well TMB substrate and incubated at room temperature. After incubation the reaction was stopped by addition of 1M $H_2SO_4$; 100 µl/well and plates were read at OD 450 nm.

ELISA Reagents:
1. ELISA plate; NUNC Maxisorp; cat: 442404
2. Antigen: Human rEGFR ECD; Cynomolgus rEGFR ECD
3. Coating buffer: 1×PBS; Gibco cat:20012-019
4. Washing buffer: 1×PBS/0.05% Tween 20 (PBS-T)
5. Blocking/Dilution buffer: 1% BSA in PBS-T
6. Goat-anti-Human IgG HRP conjugate: Serotec, Star 106P
7. TMB Plus (KemEnTec cat #4390L)
8. (1M $H_2SO_4$)

As shown in FIG. 25, the described ELISA assay could discriminate between cross reactive Human and Cynomolgus anti-EGFR ECD antibodies (FIG. 25 A) and species specific antibodies only recognizing the Human EGFR ECD used for mice immunizations (FIG. 25B).

Example 11

Inhibition of Motility

Most cancer deaths derive from the dissemination of tumor cells and subsequent growth in distant locations. Local invasion of adjacent normal tissue compromise homeostatic functions and prevent surgical or radiological excision of the tumor. Recent investigations have highlighted the central role that induced motility plays in promoting this spread. The EGFR is known to facility cell motility and spreading and therefore inhibition of EGFR mediated motility an important mechanism of EGFR targeted drugs.

The effect of a mixture of the two antibodies 992 and 1024 on the motility of the head and neck carcinoma cell line were investigated. Spheroids consisting of 10,000 cells were prepared overnight as described in example 9. The spheroids were then transferred to NUNC T25 cell culture flasks and adhering allowed overnight. 10 µg/ml of the antibody mix 992+1024 or a negative control antibody were then added and the spheroids were incubated for another 24 hours. Images were then taken at 40× magnification and the area covered by cells measured using the software Image J.

Results: As can be seen in FIG. 27A addition of the EGFR specific antibodies 992 and 1024 leads to a significant decrease in the area covered by tumor cells. The motility is quantified in FIG. 27B, which show that the motility is decreased approximately 60% as compared to the negative control antibody. This decrease in motility is highly significant $p<0.01$.

Thus a combination of the antibodies 992 and 1024 potently inhibits EGFR mediated tumor cell motility, which indicates that combinations of anti EGFR antibodies could be used for the treatment of disseminated disease.

Example 12

Upregulation of Involucrin by Sym004 Antibody Composition

Involucrin is a marker of early squamous cell differentiation and a protein that is involved in formation of the cornified envelope. Involucrin levels can therefore be used as measure of the number of tumor cells that have differentiated. The levels of Involucrin was estimated in protein lysates from A431NS xenograft tumors either untreated or treated with Erbitux, Vectibix or a mix of the antibodies 992+1030+1042 using a commercially available Involucrin ELISA kit (Biomedical Technologies). Tumor lysates were prepared by homogenizing 30-40 mg of tumor tissues in 1 ml of RIPA buffer using the TissueLyzer from Qiagen. The protein concentration in each cleared lysate was determined using the BCA protein assay kit from Pierce and the involucrin level estimated using the ELISA assay in 0.4 µg of protein from each sample.

Results: As can be seen in FIG. 27 Involucrin is found in significantly higher levels in the 992+1030+1042 treatment group as compared to the negative control and Erbitux or Vectibix treatment groups. Thus a combination of the antibodies 992, 1030 and 1042 increases the levels of involucrin in the A431NS xenograft tumors and therefore presumably induces a higher degree of A431NS differentiation. A result that correlates well with the high number of keratin pearls found in this particular treatment group (See example 8).

Example 13

Internalisation of EGFR by Sym004 Antibody Composition

Some antibodies function by inducing internalization of their surface target. The EGFR is known to undergo internalization when activated by ligand such as EGF.

The ability of a mixture of the two antibodies 992 and 1024 to induce EGFR internalization was investigated using confocal microscopy. A431NS and HN5 cells were seeded in 8-well chamber slides from LabTek and incubated overnight in DMEM containing 0.5% FBS. Cells were then added 10 µg/ml of Alexa-488 labeled antibody mix of 992+1024 or the control antibody Erbitux and then incubated for different periods of time. Images were then taken at 60× magnification using a Biorad confocal microscope with either a large pin-hole or a small pin-hole.

Results: As shown in FIG. 29A addition of the Alexa-488 labeled EGFR specific antibodies 992 and 1024 for 2 hours leads to accumulation of the antibodies in intracellular vesicles in both the A431NS and HN5 cell lines. Erbitux in contrast is mainly found at the cell surface. FIG. 29B shows images of A431NS cells using a smaller pin-hole, which results in images of thinner sections of the cells. It is clear from these images that the antibodies 992+1024 are located inside the cells whereas Erbitux is mainly found at the cell surface. FIG. 30 shows a timeframe of the 992+1024 mediated internalization and as earlier as 30 minutes after addition of antibodies they can be found in intracellular vesicles. After 4 hours almost all of the antibodies 992+1024 are found inside the cells with low or very weak surface staining. Erbitux in contrast remains at the cell surface. Evidence has also been obtained showing that the internalization induced by 992+1024 leads to a sustained degradation and removal of EGFR in the cells.

Thus a combination of the antibodies 992 and 1024 rapidly and potently induce EGFR internalization whereas Erbitux does not.

Example 14

Measurement of Antibody Affinities with Surface Plasmon Resonance

Measurement of monovalent affinities of Sym004 IgG antibodies against recombinant soluble EGFR ECD.

Kinetic analysis of the full length IgG antibodies of the invention was performed on a BIAcore 2000, employing an assay as described in (Canziani, Klakamp, et al. 2004, Anal. Biochem, 325:301-307) allowing measurement of monovalent affinities of whole IgG molecules against soluble antigen. Briefly approximately 10,000 Ru of a polyclonal anti-human IgG Fc antibody was conjugated to a CM5 chip surface according to the manufacturers instructions, followed by capture of 25 µg of individual anti-EGFR antibodies of the invention or Synagis negative control on the anti-Fc Chip surface. The density of captured IgG was optimized for each clone, so that the binding of the highest antigen concentration employed in the assay did not exceed 25 Ru. Next 250 µL soluble human EGFR ECD, previously shown to contain only monovalent protein by gel exclusion chromatography, was injected at a flow rate of 25 µL/min in serial two fold dilutions in HBS-EP buffer to generate response curves. The chip surface was regenerated in between cycles by stripping the captured antibody/antigen complexes with a 10 second injection of 100 mM $H_3PO_4$. Kinetic analysis was performed by first subtracting the response of the flow cell containing the negative control antibody Synagis followed by subtraction of the response generated by injection of HBS-EP buffer only ("double referencing"). The association rate constant (ka) and dissociation constant (kd) were evaluated globally from the generated sensograms with the BIA evaluation software 4.1 provided by the manufacturer.

Reagents:
1. CM5 chip: Biacore, Cat. No. BR-1000-14
2. NHS: Biacore BR-1000-50
3. EDC: Biacore BR-1000-50
4. 10 mM Acetate buffer pH 4.5: Biacore, Cat. No. BR-1003-50
5. Goat anti-Human IgG Fc: Caltag, Cat. No. H10500
6. Ethanolamine, 1.0 M pH 8.5: Biacore BR-1000-50
7. 10×HBS-EP running buffer: 0.01M HEPES pH 7.4, 0.15 M NaCl, 3 mM EDTA, 0.005% v/v Surfactant P20
8. Antigen: Human EGFR extracellular domain with 6×His.
9. 100 mM $H_3PO_4$ The calculated monovalent affinities of the full length IgG's of the invention against soluble Human EGFR ECD are shown in Table 8 below.

TABLE 8

Measured affinities of anti-EGFR IgG antibodies against soluble receptor. Antibody measurements were performed by Surface Plasmon Resonance on a BIAcore 2000 employing evaluation software provided by the manufacturer.

| IgG | $k_{ON}$ (M$^{-1}$ s$^{-1}$) | koff (1/s) | $t_{1/2}$ (min) | $K_D$ (nM) |
|---|---|---|---|---|
| 992* | NA | NA | 0.2 | 170.0 |
| 1024 | 1.8E+05 | 4.9E−03 | 2.4 | 26.7 |
| 1030 | 1.3E+04 | 3.7E−04 | 31.1 | 29.2 |
| 1254 | 8.1E+04 | 1.0E−03 | 11.3 | 12.7 |
| 1260 | 3.7E+04 | 1.6E−04 | 74.1 | 4.2 |
| 1261 | 1.7E+05 | 3.2E−03 | 3.6 | 18.6 |
| 1277 | 1.3E+05 | 5.3E−05 | 217.6 | 0.4 |
| 1284 | 3.2E+04 | 1.5E−04 | 78.1 | 4.6 |
| 1320 | 1.2E+05 | 2.8E−03 | 4.1 | 24.2 |
| 1347 | 2.4E+04 | 5.0E−04 | 22.9 | 21.4 |

*The affinity of 992 was determined by Scatchard Analysis.
NA. Not applicable.

Most tested Sym004 antibodies recognized soluble human EGFR ECD with affinities in the 10-20 nM range, except 1260, 1277, and 1284 which had higher affinities of 4.2 nM, 0.4 nM, and 4.6 nM respectively. Finally 992 was found to bind soluble EGFR ECD with a much lower affinity than the other tested antibodies. Consequently the kinetic analysis of this antibody had to be determined by Scatchard analysis which revealed an affinity of 170 nM against soluble human EGFR ECD.

Measurement of affinities of Sym004 Fab antibodies against immobilized recombinant EGFR ECD.

To investigate possible differences in antigen presentation between EGFR ECD presented in soluble and immobilized form, a new affinity measurement on an immobilized chimeric EGFR receptor antigen termed EGFR-Fc (R&D Systems, 344-ER), consisting of Human EGFR ECD fused to Human IgG Fc was performed. For this purpose Fab fragments of the IgG antibodies 992, 1024 & 1030 were generated to allow measurement of monovalent affinities.

Fab Production:

Fab fragments of 992, 1024 and 1030 were produced by Papain digestion using a Fab preparation Kit from Pierce and following the manufactures instructions. Briefly 2 mg of each IgG antibody was buffer exchanged on NAP-5 columns (Amersham Biosciences) with freshly prepared digestion buffer containing 20 mM Cystein-HCl, pH 7.0 following the instructions of the manufacturer. Then a 350 µl slurry of Papain beads was washed twice in the same digestion buffer before the beads were spun down and the supernatant discarded. Antibodies were digested by adding 1 ml buffer exchanged IgG antibody to the beads and incubating overnight at 37° C. with shaking at 1000 rpm. The next morning, undigested IgG was separated from crude Fab by depletion of full length IgG on HiTrap Protein A columns (Ge Healthcare). The produced Fab was finally dialyzed against PBS overnight and analyzed with SDS-PAGE under reducing and nonreducing conditions. A protein band of approximately 50 kDa under nonreducing conditions was taken as an indication of successful Fab production.

Reagents:
1. ImmunoPure Fab preparation Kit; Pierce; cat. No. 44885
2. NAPS desalting column; Amersham, Cat. No. 17-0853-02
3. PBS pH 7.2; Gibco; #20012-019
4. HiTrap Protein A HP, 1 ml column; GE Healthcare; #17-0402-01
5. NuPAGE 4-12% Novex Bis-Tris Gel; Invitrogen; #NP0322BOX
6. Molecular marker; Seeblue Plus 2; Invitrogen; #LC5925
7. Anti-EGFR antibodies—2.0 mg of each Kinetic analysis of the Fab antibodies of the invention was performed on a Biacore 2000, using recombinant antigen immobilized onto the sensor surface at a very low density to avoid limitations in mass transport. Briefly a total of 285 Ru recombinant EGFR ECD-Fc chimera (R&D Systems, Cat. No. 344-ER) was conjugated to a CM5 chip surface according to the manufacturer's instructions. Then Fab fragments derived from the antibodies of the invention were tested in serial two fold dilutions, starting at an optimized concentration that did not result in Ru max values above 25 when tested on the chip with immobilized EGFR. Kinetic analysis was performed by first subtracting the response generated by injection of HBS-EP buffer only. The association rate constant (ka) and dissociation constant (kd) were evaluated globally from the generated sensograms with the BIA evaluation software 4.1 provided by the manufacturer.

The calculated affinities of the tested Fab fragments of the invention against immobilized Human EGFR ECD are shown in Table 9 below.

TABLE 9

Measured affinities of anti-EGFR Fab antibodies against immobilized receptor. Antibody measurements were performed by Surface Plasmon Resonance on a BIAcore 2000 employing evaluation software provided by the manufacturer.

| Fab | $k_{ON}$ (M$^{-1}$ s$^{-1}$) | koff (1/s) | $t_{1/2}$ (min) | $K_D$ (nM) |
|---|---|---|---|---|
| Fab 992* | N.A. | N.A. | 0.2 | 150.0 |
| Fab 1024 | 1.9E+05 | 4.9E−03 | 2.3 | 25.6 |
| Fab 1030 | 8.7E+04 | 2.0E−04 | 57.5 | 2.3 |

*The affinity of 992 was determined by Scatchard Analysis.
NA. Not applicable

As presented in Table 9 above the Fab fragments of 992 and 1024 were found to have affinities of 150 nM and 26 nM respectively in agreement with the affinities presented in the previous example, illustrating minor differences in the antibody recognition against soluble and immobilized EGFR for these two antibodies. However, antibody 1030 exhibited a ten fold higher affinity of 2.3 nM against immobilized antigen as compared to soluble receptor and consequently preferentially recognized an epitope exposed on immobilized antigen.

Example 15

Investigation of EGFR Antigen Presentation and Ranking of Functional Affinities on A431-NS Cells Comparison between antigen presentation on A431-NS cells and purified full length EGFR receptor.

Since the kinetic analysis revealed that antibody 992 recognized recombinant EGFR ECD with an affinity between 150-170 nM, it was investigated if this weak affinity was due to the fact that mAb 992 preferentially bound native conformations of EGFR as expressed on A431-NS cells as opposed to conformations presented on recombinant EGFR ECD or full length EGFR purified from A431 cells. To investigate differences in the EGF receptor antigen presentations, concurrent ELISA binding studies of a subpopulation of the antibodies of the invention was performed with Fab fragments to avoid avidity effects on tested A431-NS cells and purified full length EGFR from the same cells.

Fab production: Production of Fab fragments was performed as described in example 14.

Indirect ELISA: For the indirect ELISA, full length EGFR (Sigma E2645) was coated at 1 µg/ml in Carbonate buffer (50 µl/well) overnight at 4° C. The next morning, wells were washed twice with PBS-T and blocked for one hour with PBS-T containing 1% BSA at room temperature followed by wash twice in PBS-T. Next 50 µl serial dilutions of Fab antibodies in DMEM containing 1% BSA were added to independent ELISA wells and incubated for 1 hour at room temperature, after which wells were washed four times with PBS-T. Next 50 µl of a secondary Goat-anti-Human (Fab specific) HRP conjugate diluted 1:5000 in DMEM containing 1% BSA was added and incubated on ice for 30 min. Finally, wells were washed four times with PBS-T and plates developed by adding 50 µl/well TMB substrate and read at 620 nm every 5-15-30 min. After incubation with substrate, the reaction was stopped by addition of 1M $H_2SO_4$ and absorbance read at 450 nm.

Reagents, Indirect ELISA:
1) Coating buffer: 50 mM Carbonate buffer, pH 9.8
2) Antigens: Wild type full length EGFR purified from A431 cells; Sigma E2645
3) ELISA plate: NUNC Maxisorp; Cat. No: 442404
4) Washing buffer: 1×PBS/0.05% Tween 20 (PBS-T)
5) Blocking/Dilution buffer: 1% BSA in PBS-T (PBS-T-1% BSA)
6) Antibody dilution buffer: DMEM containing 1% BSA
7) Goat-anti-Human (Fab specific) HRP conjugate: Jackson, Cat. No. 109-035-097
8) TMB Plus substrate: KemEnTec, Cat. No. 4390L
9) 1M $H_2SO_4$ Cell ELISA: The relative binding affinities defined as the molar concentration giving the half maximal OD (ED50) were determined by antibody titrations on A431-NS cells. Briefly, 10,000 A431-NS cells were grown in 96 well ELISA plates containing DMEM with added 0.5% FCS and 1% P/S at 37° C., 5% $CO_2$ overnight. The next morning confluent cells (approximately 20,000/Well) were washed twice with PBS and fixed by incubation with a 1% paraformaldehyde solution for 15 min at room temperature followed by wash four times with PBS. Next, tested EGFR antibodies and the negative control antibody Synagis were serially diluted in DMEM containing 1% BSA and 50 µl of each dilution added to the wells and incubated for 1 hour at room temperature, after which wells were washed four times with PBS. Then 50 µl of a secondary Goat-anti-Human (Fab specific) HRP conjugate diluted 1:5000 in DMEM containing 1% BSA was added and incubated on ice for 30 min. Finally wells were washed four times with PBS and plates developed by adding 50 µl/well TMB Plus substrate and read at 620 nm every 5-15-30 min. After incubation with substrate the reaction was stopped by addition of 1M $H_2SO_4$ and absorbance read at 450 nm. The functional affinity expressed as ED50 values were calculated by subtraction of the average background binding with secondary reagent only, followed by normalization of the binding curves by plotting % maximal binding relative to each antibody tested.

Reagents, Cell ELISA:
1) DMEM media: Gibco, Cat. No 41966-029
2) FCS: Gibco, Cat. No. 10099-141
3) Pen strep (P/S): Gibco, Cat. No. 15140-122
4) ELISA plate: Costar, Cat. No. 3595
5) Wash buffer (PBS): Gibco cat. 20012-019
6) Antibody dilution buffer: DMEM containing 1% BSA
7) Cell fixation solution: BD Biosciences, Cat. No. 340181
8) Goat-anti-Human (Fab specific) HRP conjugate: Jackson, Cat. No. 109-035-097
9) TMB Plus substrate: KemEnTec, Cat. No. 4390L
10) 1M $H_2SO_4$ Differences in the antigen presentation on EGF receptor expressed on A431-NS cells and on purified receptor from the same cells were determined with concurrent ELISA binding studies, employing same secondary antibody reagent and incubation times. The results are shown in FIG. 31. The experiment clearly showed that Fab antibodies 992 and 1024 bound weakly to purified full length EGFR coated to ELISA wells when compared to the binding of same concentrations of Fab 1030. However, this weak binding activity of 992 and 1024 was restored when the antibodies were tested on A431-NS cells against which all three Fabs showed strong binding activity. The comparison of the two different ELISAs clearly illustrated a preference of Fabs 992 and 1024 for binding native EGFR conformations as expressed on cell surfaces as opposed to conformations presented on purified antigen in ELISA wells. The result also suggested that the apparent weak affinity of 992 measured with surface plasmon resonance on recombinant soluble and immobilized EGFR ECD was due to unfavorable presentation of the 992 antibody epitope in the tested systems.

Ranking of functional affinities on A431-NS cells.

Cell ELISAs performed as described above were used to rank the functional affinities of IgG and Fab fragments of 992, 1024, 1030, Vectibix and Erbitux by calculation of the half maximal OD values expressed as ED50 values. The result of this analysis is shown in FIG. 32 and calculated ED50 values are presented in Table 10 below.

TABLE 10

Ranking of functional affinities expressed as ED50 values based on avidity effects of IgG or monovalent affinity of Fab.

| | IgG Avidity | | | | Fab Affinity | | |
|---|---|---|---|---|---|---|---|
| IgG | Log ED50 | ED50 nM | SD | Fab | Log ED50 | ED50 nM | SD |
| 992 | −0.56 | 0.3 | 0.04 | 992 | 1.00 | 9.9 | 0.11 |
| 1024 | −0.49 | 0.3 | 0.05 | 1024 | 0.30 | 2.0 | 0.02 |
| 1030 | 0.17 | 1.5 | 0.02 | 1030 | 0.27 | 1.8 | 0.05 |
| Vectibix | −0.15 | 0.7 | 0.04 | Vectibix | 0.08 | 1.2 | 0.04 |
| Erbitux | −0.23 | 0.6 | 0.04 | Erbitux | −0.07 | 0.8 | 0.06 |

ED50 values were determined by serial antibody titrations on A431-NS cells.
SD: Standard deviation of curve fitting.

The experiment clearly showed that when avidity effects were taken into account IgG 992 and 1024 appeared to be binding A431-NS cells with higher avidity than both Erbitux and Vectibix, while IgG 1030 had the lowest affinity of the tested IgG antibodies. However, when the monovalent affinity on cells was determined using Fab fragments, 992 had the lowest affinity of approximately 10 nM. Nonetheless, this monovalent functional affinity was still at least 15 fold lower than tested with BIAcore.

Example 16

Investigation of Antibody Induced Binding Enhancement

The BIAcore competition experiment performed on antibody pairs of the invention revealed that the binding of 992 and 1024 were enhanced approximately 55% and 58% respectively (FIG. 9A), when these antibodies were tested against each other in both directions. To investigate this phenomenon further, a cell ELISA using unfixed cells was designed to investigate the effect of IgG binding of one antibody clone upon prior receptor saturation with the Fab fragment of an antibody binding a non overlapping epitope.

Cell ELISA: The ELISA was performed essentially as described in example 15 with modifications. Cells were left unfixed to allow conformational EGFR flexibility after antibody additions. Briefly, 10,000 A431-NS cells were grown in 96 well ELISA plates containing DMEM with added 0.5% FCS and 1% P/S at 37° C., 5% $CO_2$ overnight. The next morning confluent cells (approximately 20,000/Well) were washed twice with PBS, and wells for investigation of antibody induced binding enhancements were preincubated with 25 µl of 40 nM single Fab fragments of either 992, 1024 or 1030, or 12.5 µl of 80 nM of each single Fab in double combinations previously shown to give saturated binding. 25 µl DMEM containing 1% BSA was added to wells used for testing of IgG antibodies without added Fab fragments. Following Fab and media addition, ELISA wells were incubated for 30 min at room temperature, after which 25 µl of serial three fold dilutions of IgGs of the invention or Synagis negative control, beginning at a concentration of 360 nM were added to wells and incubated on ice for one hour. Next, wells were washed four times with PBS and 50 µl of a secondary monoclonal Mouse-anti-Human (Fc specific) HRP conjugate diluted 1:5000 in DMEM containing 1% BSA was added and incubated on ice for 30 min. Finally wells were washed four times with PBS and plates developed by adding 50 µl/well TMB substrate and read at 620 nm every 5-15-30 min. After incubation with substrate the reaction was stopped by addition of 1M $H_2SO_4$ and absorbance read at 450 nm. The functional affinity expressed as ED50 values were calculated by subtraction of the average background binding with secondary reagent only, followed by normalization of the binding curves by plotting % maximal binding relative to each antibody tested.

Reagents, cell ELISA:
1) DMEM media: Gibco, Cat. No 41966-029
2) FCS: Gibco, Cat. No. 10099-141
3) Pen strep (P/S): Gibco, Cat. No. 15140-122
4) ELISA plate: Costar, Cat. No. 3595
5) Wash buffer (PBS): Gibco cat. 20012-019
6) Antibody dilution buffer: DMEM containing 1% BSA
7) Mouse-anti-Human (Fc specific) HRP conjugate: Ab-direct, Cat. No. MCA647P
8) TMB Plus substrate: KemEnTec, Cat. No. 4390L
9) 1M $H_2SO_4$ Investigations of antibody induced binding enhancements were determined by concurrent ELISA binding studies, employing same secondary antibody reagent and incubation times. The result of the study is shown in FIG. 33 and calculated ED50 values in Table 11 below.

TABLE 11

Ranking of functional affinities expressed as ED50 values based on avidity effects of IgG with or without prior receptor saturation with listed Fab fragments.

| IgG | Log ED50 | ED50 nM | SD |
|---|---|---|---|
| IgG 992 | −0.24 | 0.6 | 0.07 |
| IgG 992/Fab 1024 | −0.31 | 0.5 | 0.02 |
| IgG 992/Fab 1030 | −0.38 | 0.4 | 0.05 |
| IgG 992/Fab 1024 & 1030 | −0.34 | 0.5 | 0.04 |
| IgG 1024 | −0.01 | 1.0 | 0.01 |
| IgG 1024/Fab 992 | −0.05 | 0.9 | 0.04 |
| IgG 1024/Fab 992 & 1030 | −0.08 | 0.8 | 0.02 |
| IgG 1030 | 0.33 | 2.2 | 0.06 |
| IgG 1030/Fab 992 | 0.20 | 1.6 | 0.03 |
| IgG 1030/Fab 992 & 1024 | 0.34 | 2.2 | 0.06 |

ED50 values were determined by serial antibody IgG titrations on A431-NS cells.
SD: Standard deviation of curve fitting.

As presented in FIG. 33 and Table 11 above, IgG 992 showed a clear enhancement of binding upon prior receptor saturation with Fab fragments of either 1024 or 1030 or 1024 together with 1030. The incubation with Fab fragments resulted in decreased ED50 values of 0.5; 0.4 & 0.5 nM respectively compared to 0.6 nM when IgG 992 was tested alone. Likewise IgG 1024 and 1030 also showed increased binding when cells were first saturated with Fab 992 and only 1024 when both Fab 992 and 1030 were added to cells prior to IgG. This result clearly illustrated the benefit of having more than one antibody against nonoverlapping epitopes on the same target receptor.

Slightly lower functional affinities were determined in this experiment as compared to example 2. This outcome is probably due to the fact that a different secondary reagent was used in the present example and due to the fact that tested IgGs were incubated with unfixed cells on ice to avoid internalization.

Example 16B

Cloning of Full Length Cynomolgus EGFR

The full length Cynomolgus EGFR including signal peptide was cloned from Cynomolgus cDNA isolated from epidermis by using nested PCR and sequence specific primers derived from the published sequence of full length human EGFR (GENBANK X00588, Ullrich, A. et. al. Nature 309 (5967), 418-425 (1984)).

PCR Reagents:
Cynomolgous Monkey cDNA Isolated from Normal Skin Epidermis:
CytoMol Unimed, Cat. No: ccy34218, Lot No: A711054.
FastStart reaction buffer (10×): Roche, Cat. no: 03 553 361 001
FastStart enzyme: Roche, Roche, Cat. no: 03 553 361 001
Phusion enzyme: Finnzymes, F-530S (2 U/μL).
dNTP 25 mM: Bioline, Cat. No: BIO-39029
Primers for Amplification of Full Length Cynomolgus EGFR Including Signal Sequence:

```
5' ATG primer:
                                    (SEQ ID NO 135)
5'-TCTTCGGGAAGCAGCTATGC-3'

3' STOP primer:
                                    (SEQ ID NO 139)
5'-TCATGCTCCAATAAATTCACTG-3'
```

PCR Conditions:
95° C./2 min, 40 cycles: 95° C./30 sec, 55° C./30 sec, 72° C./3 min 30 sec with a final incubation at 72° C. for 5 min.
Primers for Nested PCR Amplifying Full Length Cynomolgus EGFR and Incorporating Not and Xho Restriction Sites:

```
E579 Cyn Not5'
                                    (SEQ ID NO 140)
5'-GGAGTCGGCGGCCGCACCATGCGACCCTCCGGGACGG-3

E580 Cyn Xho5'
                                    (SEQ ID NO 141)
5'-GCATGTGACTCGAGTCATGCTCCAATAAATTCACTGC-3
```

PCR Conditions:
95° C./2 min, then 30 cycles: 95° C./30 sec melting, 55° C./30 sec annealing, 72° C./3 min elongation. After 30 cycles PCR products were allowed to elongate for additional 10 min.

PCR reactions were performed with 0.5 μl template and 0.1 μl Phusion Enzyme, 0.4 μl FastStart enzyme in a total volume of 50 μL reaction buffer with a final concentration of 1× FastStart buffer, 0.2 mM dNTP and 0.2 μM of each primer.

A PCR fragment with an apparent length of approximately 4000 bp was obtained and cloned using the TOPO TA cloning kit (Invitrogen, Part No. 4506-41) and sequenced. The DNA and protein sequence of the cloned Cynomolgus EGFR is shown in FIG. 34. An alignment of the human EGFR and Cynomolgus EGFR protein sequences showed 99.2% sequence identity.

Demonstration of Antibody Cross Reactivity Between Full Length Human and Cynomolgus EGFR by FACS Analysis.

Full length Human and Cynomolgus EGFR were expressed on the surface of CHO cells by stable transfection, and cells tested for binding to a panel of serially diluted EGFR antibodies by FACS analysis. Determinations were done under $K_D$ dependent conditions, by keeping a molar excess of antibody that was at least 5 times higher than the number of EGFR antigen molecules expressed on the cell surface of a fixed number of cells in all antibody dilution series. This setup permitted FACS analysis of antibody binding at full receptor saturation for all tested antibody concentrations.

Briefly quantitative FACS analysis was performed on a BD FACS array Bioanalyzer System to determine the number of EGFR molecules expressed on the surface of CHO cells transfected with either Human or Cynomolgus full length EGFR. The analysis was performed by titrating PE labeled Erbitux IgG on cells, and determine the number of molecules of equivalent PE by comparison to a standard curve made from Rainbow calibration particles with known PE density. The quantitative analysis revealed that the EGFR transfected CHO cells displayed approximately 350,000 molecules on the surface of each cell. Next, serial 5 fold dilutions of antibodies of the invention starting at 5 nM were compared by incubating with 10,000 EGFR transfected CHO cells in increasing volumes, permitting at least 5 fold molar excess of antibody over surface displayed EGFR antigen in each determination. Antibodies were incubated with cells for 14 hours on a shaker, to promote full antigen saturation at all antibody concentrations tested, while FACS buffer was added 0.02% $NaN_3$ and temperature kept at 4° C. to prevent receptor internalization. After incubation, cells were pelleted at 1200 RPM for 5 min at 4° C. and resuspended in 200 ul FACS buffer. Next cells were stained with a secondary Goat F(ab')$_2$ anti-Human IgG FcGamma PE diluted 1:500 and incubated for 30 min at 4° C. on a shaker. Finally cells were washed twice in FACS buffer and analyzed on a BD FACS array Bioanalyzer System with gating on EGFR expressing CHO cells displaying uniform forward/side scatter properties.

FACS Reagents:
Rainbow calibration particles: BD, cat. no: 559123
FACS buffer: 1×PBS+2% FCS+0.02% NaN$_3$
Goat F(ab')$_2$ anti-Human IgG FcGamma PE: Jackson ImmunoResearch, cat. no. 109-116-170

Figure 40A:
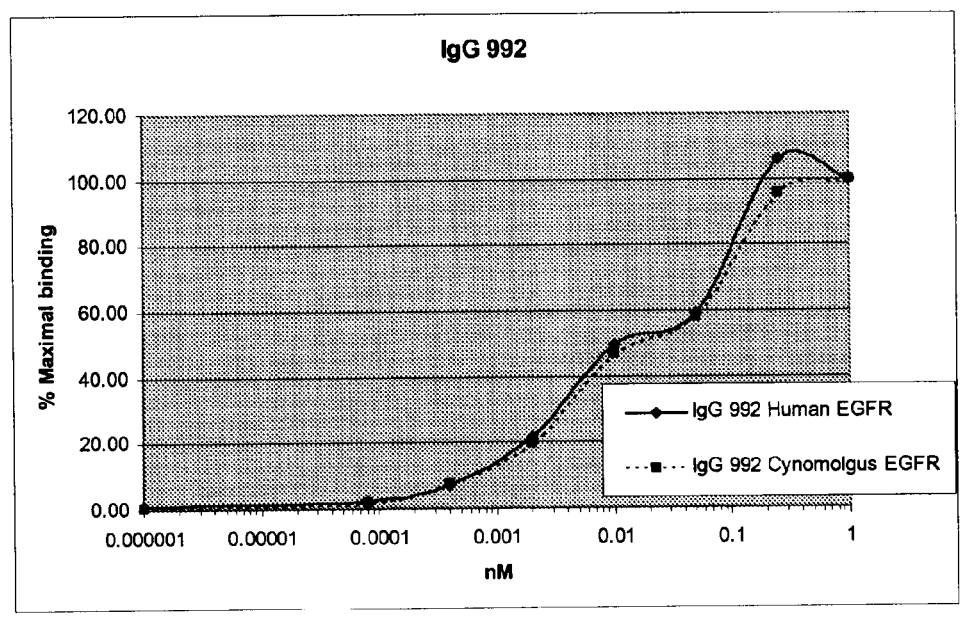
Figure 40B:
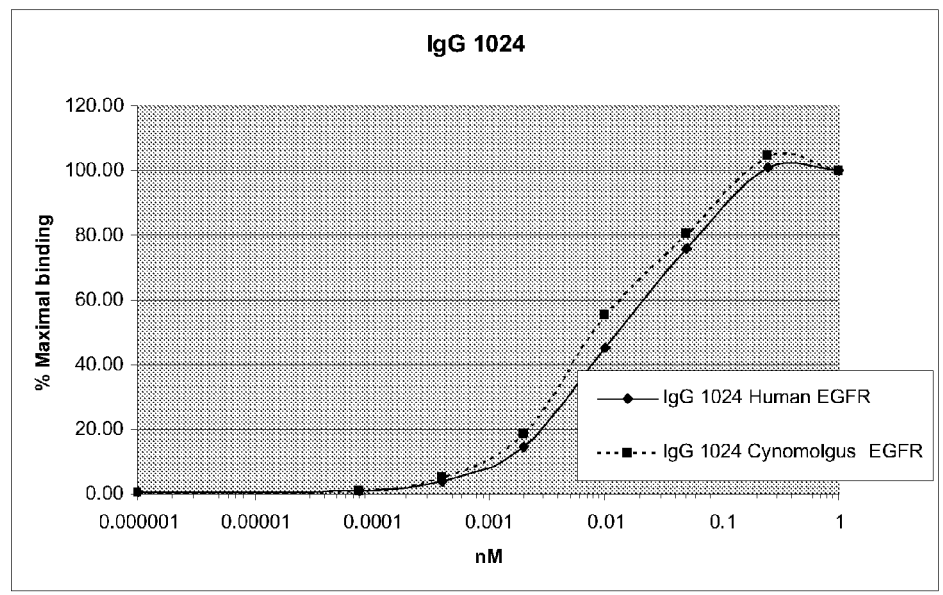
Figure 40C:
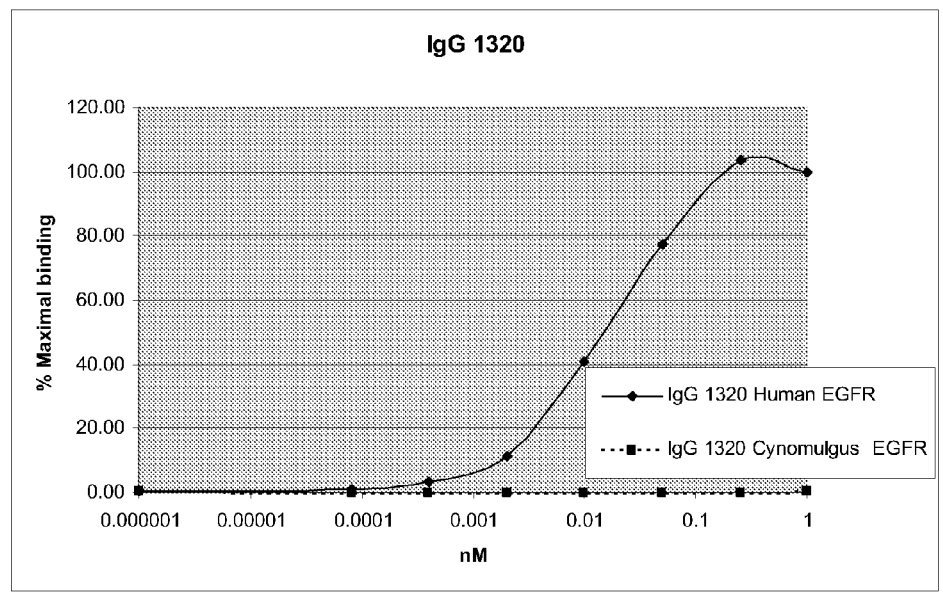

The described FACS binding assay was used for determination of the cross reactivity of the EGFR antibodies IgG 992 and 1024 and compared to a control antibody IgG 1320, which did not cross react with Cynomolgus EGFR. As shown in FIG. 40 below, the described FACS assay was very good at discriminating antibodies exhibiting good cross reactivity between Human and Cynomolgus full length EGFR (FIG. 40A, IgG 992 and FIG. 40B, IgG 1024) and species specific antibodies only recognizing the full length Human EGFR (FIG. 40C, IgG 1320). From this analysis it was concluded that both IgG 992 and 1024 exhibited excellent crossreactivity against both Human and Cynomolgus full length EGFR expressed on the surface of stable transfected CHO cells. The difference in binding between cynomolgus and human EGFR is surprising in view of the high degree of sequence similarity and underscores the importance of testing antibodies for binding to the exact target sequence in the animals used for pre-clinical toxicology studies.

Example 17

Clones Homologous to 992, 1024 and 1030

The screening for EGFR-binding Antibody-clones, based on immunosorbent assays (ELISA and cell based assays), led to the identification of clones 992, 1024, 1030 as described in the previous examples. EGFR specific clones, homologous to 992, 1024, 1030, were also identified (Table 12).

Clones belonging to the same cluster are expected to have the same binding specificity but may bind with different affinities. Therefore, clones within a cluster can replace one another in the antibody compositions of the present invention, provided that the binding affinities of the clones do not differ too much.

TABLE 12

| Cluster | Clone name | IGHV gene | IGHJ gene | CDR3 | SEQ ID NO | Number of somatic mutations | Somatic mutations |
|---|---|---|---|---|---|---|---|
| | | | | IGHV | | | |
| 992 | 1209 | IGHV1S22*01 | IGHJ4*01 | CTRNGDYYISSGDAMDYW | 110 | 4 | H46P, G61R, G76A, H90Q |
| | 1204 | IGHV1S22*01 | IGHJ4*01 | CTRNGDYYVSSGDAMDYW | 111 | 5 | H46P, G59D, G61R, G76A, H90Q |
| | 992 | IGHV1S22*01 | IGHJ4*01 | CTRNGDYYVSSGDAMDYW | 111 | 4 | H46P, G61R, G76A, H90Q |
| | 996 | IGHV1S22*01 | IGHJ4*01 | CTRNGDYYVSSGDAMDYW | 111 | 4 | H46P, G61R, G76A, H90Q |
| | 1033 | IGHV1S22*01 | IGHJ4*01 | CTRNGDYYVSSGDAMDYW | 111 | 4 | H46P, G61R, G76A, H90Q |
| | 1220 | IGHV1S22*01 | IGHJ4*01 | CTRNGDYYVSSGDAMDYW | 111 | 4 | H46P, G61R, G76A, H90Q |
| 1030 | 1195 | IGHV5S9*01 | IGHJ4*01 | CARGSDGYFYAMDYW | 112 | 12 | K14R, M39L, T55S, S58G, G59V, Y62T, T63Y, Y66-, Y67F, I78M, K84R, T86I |
| | 1030 | IGHV5S9*01 | IGHJ4*01 | CARGSDGYFYAMDYW | 112 | 12 | M39L, K48R, T55S, S58G, G59V, Y62T, T63Y, Y66-, Y67F, I78M, K84R, T86I |
| | 1034 | IGHV5S12*01 | IGHJ4*01 | CARGSDGYFYAMDYW | 112 | 12 | M39L, T55S, I56T, S58G, G59V, Y62T, T63Y, Y66-, Y67F, I78M, K84R, T86I |
| | 1194 | IGHV5S9*01 | IGHJ4*01 | CARGSDGYFYAMDYW | 112 | 12 | M39L, T55S, S58G, G59V, Y62T, T63Y, Y66-, Y67F, D69G, I78M, K84R, T86I |
| | 980 | IGHV5S12*01 | IGHJ4*01 | CARGSDGYFYAMDYW | 112 | 11 | M39L, T55S, S58G, G59V, Y62T, T63Y, Y66-, Y67F, I78M, K84R, T86I |
| | 981 | IGHV5S9*01 | IGHJ4*01 | CARGSDGYFYAMDYW | 112 | 11 | M39L, T55S, S58G, G59V, Y62T, T63Y, Y66-, Y67F, I78M, K84R, T86I |
| | 1246 | IGHV5S9*01 | IGHJ4*01 | CARGSDGYFYAMDYW | 112 | 11 | M39L, T55S, S58G, G59V, Y62T, T63Y, Y66-, Y67F, I78M, K84R, T86I |
| | 1223 | IGHV5S9*01 | IGHJ4*01 | CARGSDGYFYAMDYW | 112 | 12 | S32N, M39L, T55S, S58G, G59V, Y62T, T63Y, Y66-, Y67F, I78M, K84R, T86I |
| 1024 | 1031 | IGHV1S128*01 | IGHJ4*01 | CARYYGYDDAMDYW | 113 | 6 | Y33H, K43Q, N57H, S74N, S84P, P94L |
| | 1036 | IGHV1S128*01 | IGHJ4*01 | CARYYGYDDAMDYW | 113 | 6 | Y33H, K43Q, N57H, S74N, S84P, P94L |
| | 1042 | IGHV1S128*01 | IGHJ4*01 | CARYYGYDDAMDYW | 113 | 6 | Y33H, K43Q, N57H, S74N, S84P, P94L |
| | 984 | IGHV1S128*01 | IGHJ4*01 | CARYYGYDDAMDYW | 113 | 7 | Y33H, K43Q, N57H, S74N, T79A, S84P, P94L |
| | 1024 | IGHV1S128*01 | IGHJ4*01 | CVRYYGYDEAMDYW | 114 | 7 | K14E, A17G, Y33H, N60S, T63N, L91F, P94L |
| | 1210 | IGHV1S128*01 | IGHJ4*01 | CVRYYGYDEVMDYW | 115 | 7 | K14E, A17G, Y33H, N60S, T63N, L91F, P94L |
| | 1217 | IGHV1S128*01 | IGHJ4*01 | CVRYYGYDEVMDYW | 115 | 7 | K14E, A17G, Y33H, N60S, T63N, L91F, P94L |
| | 1221 | IGHV1S128*01 | IGHJ4*01 | CVRYYGYDEVMDYW | 115 | 7 | K14E, A17G, Y33H, N60S, T63N, |

TABLE 12-continued

| Cluster | Clone name | IGHV gene | IGHJ gene | CDR3 | SEQ ID NO | Number of somatic mutations | Somatic mutations |
|---|---|---|---|---|---|---|---|
| | | | | | | | L91F, P94L |
| | | | | IGKV | | | |
| 992 | 1209 | IGKV10-96*01 | IGKJ1*02 | CQHYNTVPPTF | 116 | 6 | A25T, S30G, Y87F, S92N, L94V, I99V |
| | 1204 | IGKV10-96*01 | IGKJ1*02 | CQHYNTVPPTF | 116 | 6 | A25T, S30G, Y87F, S92N, L94V, I99V |
| | 992 | IGKV10-96*01 | IGKJ1*02 | CQHYNTVPPTF | 116 | 6 | A25T, S30G, Y87F, S92N, L94V, I99V |
| | 996 | IGKV10-96*01 | IGKJ1*02 | CQHYNTVPPTF | 116 | 7 | T8A, A25T, S30G, Y87F, S92N, L94V, I99V |
| | 1033 | IGKV10-94*03 | IGKJ2*01 | CQQFTTSPFTF | 117 | 8 | A25T, I29V, S30G, Y87F, N93S, L94M, P96G, I99V |
| | 1220 | IGKV10-96*01 | IGKJ1*02 | CQHYNTVPPTF | 118 | 6 | A25T, S30G, Y87F, S92N, L94V, I99V |
| 1030 | 1195 | IGKV3-12*01 | IGKJ2*01 | CQHSREFPLTF | 119 | 3 | K27Q, Y36F, Q44L |
| | 1030 | IGKV3-12*01 | IGKJ2*01 | CQHSREFPLTF | 119 | 2 | Y36F, Q44L |
| | 1034 | IGKV3-12*01 | IGKJ2*01 | CQHSREFPLTF | 119 | 2 | Y36F, Q44L |
| | 1194 | IGKV3-12*01 | IGKJ2*01 | CQHSREFPLTF | 119 | 2 | Y36F, Q44L |
| | 980 | IGKV3-12*01 | IGKJ2*01 | CQHSREFPLTF | 119 | 3 | Y36F, Q44L, Q48R |
| | 981 | IGKV3-12*01 | IGKJ2*01 | CQHSREFPLTF | 119 | 3 | Y36F, Q44L, H92Y |
| | 1246 | IGKV3-12*01 | IGKJ2*01 | CQHSREFPLTF | 119 | 2 | Y36F, Q44L |
| | 1223 | IGKV3-12*01 | IGKJ2*01 | CQHSREFPLTF | 119 | 2 | Y36F, Q44L |
| 1024 | 1031 | IGKV2-109*01 | IGKJ2*01 | CAQNLELPYTF | 120 | 0 | |
| | 1036 | IGKV2-109*01 | IGKJ2*01 | CAQNLELPYTF | 120 | 1 | T85A |
| | 1042 | IGKV2-109*01 | IGKJ2*01 | CAQNLELPYTF | 120 | 1 | G84R |
| | 984 | IGKV2-109*01 | IGKJ2*01 | CAQNLELPYTF | 120 | 0 | |
| | 1024 | IGKV2-109*01 | IGKJ2*01 | CAQNLELPYTF | 120 | 0 | |
| | 1210 | IGKV2-109*01 | IGKJ2*01 | CAQNLELPYTF | 120 | 1 | T17A |
| | 1217 | IGKV2-109*01 | IGKJ2*01 | CAQNLELPYTF | 120 | 0 | |
| | 1221 | IGKV2-109*01 | IGKJ2*01 | CAQNLELPYTF | 120 | 1 | S32N |
| | 1218 | IGKV2-109*01 | IGKJ2*01 | CAQNLELPYTF | 120 | 0 | |

Example 18

Humanization of Antibodies 922 and 1024

All antibodies contain the potential for eliciting a human anti-antibody response. The response correlates to some extent with the degree of "humanness" of the applied therapeutic antibody. It is not possible to predict the immunogenicity and thereby the human anti-antibody but there is a tendency towards preferring antibodies with a high degree of humanness for clinic use. The humanness of the antibodies described in the present invention can be increased by a humanization process [Reichert J M. Monoclonal antibodies in the clinic. Nature Biotechnol, 2001; 19:819-822; Reichert J M, Rosensweig C J, Faden L B and Dewitz M C. Monoclonal antibody successes in the clinic. Nature Biotechnol, 2005; 23:1073-1078].

Humanization of a murine mAb is in principle achieved by grafting the complementarity determining regions (CDRs) onto human framework regions (FRs) of the IGHV and IGKV domains with closely related sequence by a procedure commonly referred to as CDR grafting (Jones P T, Dear P H, Foote J, Neuberger M S and Winter G. Replacing the complementarity-determining regions in a human antibody with those from a mouse. Nature, 1986; 321:522-525). However, simple CDR grafting of only the hyper variable regions can results in decreased affinity because some framework amino acids or regions make crucial contacts to the antigen or support the conformation of the antigen binding CDR loops [Queen C, Schneider W P, Selick H E, Payne P W, Landolfi N F, Duncan J F, Avdalovic N M, Levitt M, Junghans R P and Waldmann T A. A humanized antibody that binds to the interleukin 2 receptor. Proc Natl Acad Sci USA, 1989; 86:10029-10033; Al-Lazikani B, Lesk A M and Chothia C. Standard conformations for the canonical structures of immunoglobulins. Mol Biol, 1997; 273:927-948]. Consequently antibody humanization should involve both grafting of CDR loops from the murine derived variable regions onto a closely homologous human framework while retaining key murine frame work residues with documented influence on antigen binding activity (Winter, G. and W. J. Harris. "Humanized antibodies." Immunol. Today 14.6 (1993): 243-46). Several methods have been developed and successfully applied to achieved humanization while retaining the antibody affinity and function (reviewed in Almagro, J. C. and J. Fransson. "Humanization of antibodies." Front Biosci. 13 (2008): 1619-33.). Humanization can be achieved by rational methods e.g. CDR grafting, resurfacing, superhumanization, human string content optimization which all rely on construction of a few humanized antibody candidates. The amino acids sequence of the candidates is based on insight and prediction in antibody structure and the contribution of the individual amino acids to antigen binding both directly and indirectly through stabilizing the overall structure of the antigen interacting regions. Usually the candidates have to be refined and some amino acids back-mutated to the original murine residue because each antibody has some unforeseen individual constraints. Common for the methods is that several successive rounds of design, testing and redesign may be required to retain the affinity and functions. Alternatives are the more empirical methods where large combinatorial libraries are generated and the antibodies with the desired features are enriched from the pool of variants by a selection by methods such as yeast or phage display or alternative screening methods.

Anti-EGFR antibodies described in the present invention may be humanised by CDR grafting into the human V regions. In the preferred scenario the human V region is selected based on the homology to the original murine V region. Human V gene regions with other desires features such as low immunogenicity may also be used. The present example describes a method to be used for humanization of 992 and 1024 anti-EGFR chimeric antibodies. The humanized sequences given in FIG. 41A have been generated by grafting the IMGT defined CDR regions from 992 IGHV into IGHV1-46/IGHJ4 and 992 IGKV into IGKV1-27/IGKJ1-01. The amino acid sequences given in FIG. 41B have been generated in silico by grafting the IMGT defined CDR regions from 1024 IGHV into IGHV1-2*02/IGHJ6*02 and 1024 IGKV into IGKV2-28*01/IGKJ2*01. Artificial genes encoding the specified humanized antibodies are synthesized and inserted into the mammalian expression vector. Antibodies are expressed, purified and tested for activity as described in Example 3. After initial testing, the binding kinetics of humanized antibodies may be determined by surface plasmon resonance as described in Example 14. Similarly binding to hEGFR expressed on the surface of cells can be determined as described in Example 15.

If the binding activity of the humanized amino acids is significantly lower than observed for the original antibodies a sequential back-mutation scheme will be employed for regeneration of the affinity, starting with the humanized framework residues located in the Vernier zone or residues proposed to support the structure if the CDR regions (Foote, J. and G. Winter. "Antibody framework residues affecting the conformation of the hypervariable loops." J. Mol. Biol. 224.2 (1992): 487-99; Padlan, E. A. "Anatomy of the antibody molecule." Mol. Immunol 31.3 (1994): 169-217.). These residues are in IMGT numbering for 992 IGHV amino acid number 13, 45, and 80; 992 IGKV amino acids 25; 1024 IGHV amino acids 13, 45, 80 and 82; 1024 IGKL amino acid 78. These mutants may be constructed by using PCR mediated site-directed mutagenesis using standard molecular biology methods. The constructed mutants will be tested as described above. It is expected that these sets of candidates will result in humanized antibodies with retained antigen binding properties. However additional back mutations or affinity maturation by introducing amino acid substitutions in the CDR regions by site directed mutagenesis cannot be excluded.

Example 19

Dual Variable Domain Antibody

A dual variable domain (DVD) antibody protein is engineered by fusing the IGHV domains of 992 and 1024 in tandem by a 6 amino acid linker (ASTKGP) and the IGKV domains of 992 and 1024 by a 5 amino acid linker (TVAAP) [Wu C, Ying H, Grinnell C, Bryant S, Miller R, Clabbers A, Bose S, McCarthy D, Zhu R R, Santora L, vis-Taber R, Kunes Y, Fung E, Schwartz A, Sakorafas P, Gu J, Tarcsa E, Murtaza A and Ghayur T. Simultaneous targeting of multiple disease mediators by a dual-variable-domain immunoglobulin. Nature Biotechnol, 2007; 25:1290-1297]. The dual IGHV and IGKV domain fusions are followed by the IGHC and IGKC domains, respectively. In one full length DVD antibody (992L1024), the 992 IGHV and IGKV is N-terminal, followed by the linker and the 1024 IGHV and IGKV, respectively. In a second full length DVD antibody (1024L992), the 1024 IGHV and IGKV is N-terminal, followed by the linker and the 992 IGHV and IGKV, respectively. Plasmid DNA encoding the 992 and the 1024 antibody is used as template for a two step PCR mediated construction of the DVD encoding genes. The two variable domain encoding regions of IGHV and IGKV are first amplified separately so that they contain overlap extension regions at the position of the linker encoding region (for template and primer combinations see Table 13 and Table 14). The IGKV gene encoding the C-terminus proximal variable domain is amplified so that the human light chain constant domain encoding gene (IGKC) is included in the coding sequence. Coding sequences and amino acids sequences of the subunits of the dual variable domain antibodies are shown in Appendix 3.

The first PCR is prepared with the following mixture in each tube (50-µl reactions) to obtain the given final concentration: 1× FastStart buffer (Roche), dNTP mix (200 µM each), primers (10 pmol each) (see Table 14), FastStart High Fidelity Enzyme Blend (2.2 U; Roche) and 100 ng plasmid template (see Table 14). The PCR were subjected to the following thermo cycle: 2 min. at 95° C., 20×(30 sec. at 95° C., 30 sec. at 55° C., 1 min. at 72° C.), 10 min. at 72° C. The resulting PCR products with the correct size from the first PCR reaction (see Table 14) are purified by preparative agarose gel electrophoresis and used in a second step where the two variable domains are spliced by overlap extension PCR. The second PCR, splicing of DNA fragments by overlap extension PCR, is prepared with the following mixture in each tube (50-µl reactions) to obtain the given final concentration: 1× FastStart buffer (Roche), dNTP mix (200 µM each), primers (10 pmol each, see Table 15), FastStart High Fidelity Enzyme Blend (2.2 U; Roche) and template (100 ng PCR fragment, see Table 15). The PCR were subjected to the thermo cycle as defined above. The resulting products from the second PCR step are purified by preparative agarose gel electrophoresis and treated with restriction enzymes, AscI and XhoI for the dual IGHV and NheI and NotI for the dual IGKV (IGKC included). The fragments are ligated consecutively into a mammalian IgG expression vector, 00-VP-002 (FIG. 4), by standard restriction enzyme digestion and ligation procedures. The resulting expression plasmid vector is amplified in *E. coli* and the plasmid preparation is purified by standard methods. The DVD antibodies are expressed and purified as in Example 2 and characterized for activity as in Example 3-13.

Other linkers can be tested if the resulting antibodies show reduced or no binding to target hEGFr.

TABLE 13

Primers for constructing DVD antibodies from 992 and 1024

| SEQ ID NO | Primer name | Sequence |
|---|---|---|
| 121 | 3'JH | GGAGGCGCTCGAGACGGTGACTGAGGTTCCTTGAC |
| 122 | 992_5'VH | CCAGCCGGGGCGCGCCGAGGTCCAACTGCAGCAACCTGGGTCTGAGCTGGTG |

TABLE 13-continued

Primers for constructing DVD antibodies from 992 and 1024

| SEQ ID NO | Primer name | Sequence |
|---|---|---|
| 123 | 1024_5'VH | CCAGCCGGGGCGCGCCCAGGTCCAACTGCAGCAGCCTGGGGCTGAACTG |
| 124 | 992_5'VK | catgggaatagctagccGACATTCAGATGACTCAGACTACATCCTCCCTG |
| 125 | 1024_5'VK | catgggaatagctagccGACATCGTGATGACACAAGCTGCATTCTCCAATC |
| 126 | Kappa3' | ACCGCCTCCACCGGCGGCCGCTTATTAACACTCTCCCCTGTTG |
| 127 | 992H_O3' | CTGGGGGCCCTTGGTGCTGGCTGACGAGACGGTGACTGAGGTTC |
| 128 | 1024H_O5' | GCCAGCACCAAGGGCCCCCAGGTCCAACTGCAGCAGC |
| 129 | 1024H_O3' | CGGGGCCCTTGGTGCTGGCTGACGAGACGGTGACTGAG |
| 130 | 992H_O5' | GCCAGCACCAAGGGCCCCGAGGTCCAACTGCAGCAAC |
| 131 | 992K_O3' | GTCTGGTGCAGCCACAGTTCGTTTGATTTCCAGCTTGGTG |
| 132 | 1024K_O5' | CGAACTGTGGCTGCACCAGACATCGTGATGACACAAGC |
| 133 | 1024K_O3' | GTCTGGTGCAGCCACAGTTCGTTTTATTTCCAGCTTGGTCC |
| 134 | 992K_O5' | CGAACTGTGGCTGCACCAGACATTCAGATGACTCAGACTAC |

TABLE 14

Primer and template combinations for 1st PCR step for constructing DVD encoding genes from 992 and 1024

| DVD | Template for PCR | Primers for IGHV gene amplification | | Primers for IGKV gene amplification | |
|---|---|---|---|---|---|
| | | 1st PCR step | 1st PCR product (size bp) | 1st PCR step | 1st PCR product (size bp) |
| 992L1024 | 992 | 992_5'VH 992H_O3' | 992HO (406 bp) | 992_5'VK 992K_O3' | 992KO (359 bp) |
| | 1024 | 1024H_O5' 3'JH | HO1024 (381 bp) | 1024K_O5' Kappa3' | KO1024* (702 bp) |
| 1024L992 | 992 | 992H_O5' 3'JH | HO992 (393 bp) | 992K_O5' Kappa3' | KO992 (687 bp) |
| | 1024 | 1024_5'VH 1024H_O3' | 1024HO (392 bp) | 1024_5'VK 1024K_O3' | 1024KO* (374 bp) |

*The amplified coding sequence includes the IGKC-gene

TABLE 15

Primer and template combinations for 2nd PCR step, splicing by overlap extension, for constructing DVD encoding genes from 992 and 1024

| | IGHV | | | IGKV | | |
|---|---|---|---|---|---|---|
| DVD | Template | Primers | Product (bp) | Template | Primers | Product (bp) |
| 992L1024 | 992HO HO1024 | 992_5'VH 3'JH | 766 | 992KO KO1024 | 992_5'VK Kappa3' | 1040 |
| 1024L992 | HO992 1024HO | 1024_5'VH 3'JH | 766 | KO992 1024KO | 1024_5'VK Kappa3' | 1040 |

Example 20

6 Week Intravenous Administration Toxicity Study in Combination with Erbitux in the Cynomolgus Monkey Objective of study: The objective of the study was to determine the toxicity of the test article, 992+1024, following once weekly intravenous administration to the cynomolgus monkey for 6 weeks.

Since toxicity is a dose limiting factor in clinical practice with EGFR inhibitors like Erbitux and Vectibix it was deemed important at an early stage to assess tolerability of 992+1024 at clinically relevant dose. This emphasized by the fact that 992+1024 seems to be acting by a different mechanism than the other EGFR targeting products. This could potentially lead to new adverse effects or a worsening of the effects seen with other EGFR inhibitors. Groups of three female cynomolgus monkeys were treated with weekly IV doses of 992+1024 at 4/2.7 and 12/8 mg/kg and 12/8 mg/kg of Erbitux for 6 weeks. The first doses of 4 and 12 mg/kg being loading doses and the 2.7 and 8 mg/kg being maintenance doses administered 5 times. The 12/8 mg/kg dose is equivalent to the human clinical dose of Erbitux administered in clinical practice.

Study Design

| Group number | Group description | Dose level (mg/kg/day) | Dose volume (mL/kg) | Animal numbers Females |
|---|---|---|---|---|
| 1 | Control | 0 | 19/12# | 1-3 |
| 2 | 992 + 1024 Low | 4.2/2.7# | 19/12# | 4-6 |
| 3 | 992 + 1024 High | 12.6/8# | 19/12# | 7-9 |
| 4 | Erbitux | 12.6/8# | 19/12# | 10-12 |

First dose level is for loading dose, second dose level is for administration from Day 8 onwards The following parameters were followed during the study: Mortality, Clinical signs, Body weights, Food consumption, Haematology, Clinical chemistry, Organ weights, Macroscopic findings.

Results

Mortality: There were no unscheduled deaths during the course of the study.

Clinical signs: No treatment related adverse clinical observations

Body weights: There was no effect of treatment with either 992+1024 or Erbitux on body weight.

Food consumption: There were no obvious effects on food consumption.

Haematology: There were no effects on haematological parameters to suggest an effect of treatment with either 992+1024 or Erbitux.

Clinical chemistry: There were no changes in clinical chemistry parameters to suggest an effect of treatment with either test article.

In Week 4, one animal dosed at 4.2/2.7 mg/kg 992+1024/day had increased aspartate aminotransferase and alanine aminotransferase levels, in comparison to pretreatment values. These levels had returned to normal ranges by Week 6. In the absence of a similar effect in other treated animals, the toxicological significance of this increase in liver enzymes is unknown.

Organ weights: There were no differences of toxicological significance in organ weights between treated and control animals.

Macroscopic findings: There were no consistent observations noted at necropsy to suggest an effect of 992+1024 or Erbitux.

Preliminary conclusion: The preliminary data show that 992+1024 was well tolerated at the doses tested and no adverse effects related to treatment were observed.

Example 21

Growth Inhibition of Lung Cell Cancer Lines

Lung cancer cell lines are known to express EGFR with mutations in the tyrosine kinase domain (Steiner et al. Clin Cancer Res 13.5 (2007): 1540-51). By a method similar to the one used in example 6 the ability of a combination of the two antibodies 992 and 1024 to inhibit the growth of the lung cancer cell lines HCC827 and H1975 having different EGFR mutations were investigated.

Results

As can be seen in Table 16 and Table 17 the combination of 992 and 1024 is able to inhibit the growth of both cell lines. The combination is superior to the monoclonal antibodies 992 and 1024 and to Vectibix.

TABLE 16

IC50 values and maximum growth inhibition of the indicated antibodies against the HCC827 cell line

| HCC827 | IC50 (µg/ml) | Max inhibition |
|---|---|---|
| Erbitux | 0.013 | 80% |
| Vectibix | 0.100 | 60% |
| 992 | 0.050 | 80% |
| 1024 | 0.034 | 40% |
| 992 + 1024 | 0.031 | 80% |

TABLE 17

IC50 values and maximum growth inhibition of the indicated antibodies against the H1975 cell line

| H1975 | IC50 (µg/ml) | Max inhibition |
|---|---|---|
| Erbitux | 0.010 | 30% |
| Vectibix | 0.141 | 30% |
| 992 | 0.056 | 30% |
| 1024 | — | 0% |
| 992 + 1024 | 0.024 | 30% |

Example 21

Efficacy on Erbitux Resistant Cells

To investigate if the antibody composition with antibodies 992+1024 can inhibit Erbitux-resistant cells, Erbitux-resistant HN5 cells were generated by continued exposure of parental HN5 cells to increasing levels of Erbitux. Once an Erbitux resistant pool of cells was generated the inhibitory effects of Erbitux, Vectibix and an antibody composition with antibodies 992+1024 were tested using a WST-1 viability assay.

Method

Erbitux-resistant HN5 cells were generated from Erbitux (Cetuximab)-sensitive human head and neck cell line HN5 by prolonged exposure to increasing concentrations of Erbitux over a period of 6 months. Commencing with a starting dose corresponding to the IC50 of cetuximab (0.05 µg/ml), the exposure dose was progressively increased until the cells were successfully proliferating in media containing 10 µg/ml of Erbitux. The cells were grown in DMEM, supplemented with 10% FBS and appropriate concentrations of Erbitux, and passaged twice weekly.

The Cell Proliferation Reagent WST-1 is a ready-to-use substrate which measures the metabolic activity of viable cells, and it is assumed that the metabolic activity correlates with the number of viable cells. In this example the WST-1 assay was used to measure the number of metabolically active cells after treatment with different antibodies in different concentrations.

Prior to performing the WST-1 assay the appropriate antibodies and antibody mixes were diluted to a final total antibody concentration of 20 µg/ml in appropriate media supplemented with 0.5% of FBS and 1% P/S yielding a final antibody concentration of 10 µg/ml in the well containing the highest antibody concentration. 150 µl of these solutions were then added to wells in column 2 of a 96-well plate and a three-fold serial dilutions were made and added to subsequent columns of wells until column 9 so that each well contained 100 µl of antibody solution. 100 µl of media were added to column 11. 200 µl of media were added to Rows 1 and 8 as well as column 1 and 12 to decrease the effect of media evaporation in the experimental wells.

HN5 parental and HN5 resistant cells were then washed with 1×PBS and detached by trypsination with 3 ml trypsin solution. 17 ml of complete media were then added and the cells were spun down at 300×g (1200 rcf) for 5 min. The supernatant was removed and cells re-suspended in DMEM+ 0.5% FBS. Cells were counted and their concentration adjusted to 15000 cells/ml. 100 µl of the cell suspension (1500 cells/well) were then added to experimental wells in columns 2-11. The plates were incubated for 4 days in a humidified incubator at 37° C. Then 20 µl WST-1 reagent was added per well and the plates incubated for one hour at 37° C. Plates were then transferred to an orbital plate shaker for one hour. The absorbance was measured at 450 and 620 nm (reference wavelength) using an ELISA reader. The amount of metabolically active cells (MAC) is calculated as the percent of the untreated control using the same formula as used in Example 6.

The IC50 of each mix was calculated using Graph Pad Prism by fitting the titration curves to the equation $Y=Bottom+(Top-Bottom)/(1+10^{((Log\ IC50-X)*HillSlope)})$.

Results

Results from the titrations are shown in FIG. 43 for both the HN5 parental cells and the Erbitux-resistant cells. It is evident that the potency and efficacy of Erbitux have decreased significantly in the Erbitux-resistant cells as compared to the parental cells. The efficacy of Erbitux and Vectibix decreased about 50% and the IC50 increased more than tenfold (Table 18). In contrast, the potency of an antibody composition with antibodies 992+1024 (Sym004) only decreased by 43% and the IC50 increased by a factor of 2. These results show that an antibody composition with antibodies 992+1024 is more potent and inhibits the growth of Erbitux resistant HN5 cells with a higher efficacy than Erbitux and Vectibix.

TABLE 18

IC50 values and efficacy of inhibition of the HN5wt and HN5 Erbitux resistant cells by the indicated antibodies.

|  | IC50 (µg/ml) | | Efficacy (% of untreated) | |
| --- | --- | --- | --- | --- |
|  | HN5 parental | HN5 Erbitux Resistant | HN5 parental | HN5 Erbitux Resistant |
| Erbitux | 0.050 | 0.750 | 88.1% | 34.4% |
| Vectibix | 0.035 | 0.500 | 88.3% | 32.3% |
| 992 | 0.420 | ND | 85.5% | 1.7% |
| 1024 | 0.048 | ND | 84.8% | 1.3% |
| 992 + 1024 (Sym004) | 0.053 | 0.110 | 88.2% | 45.0% |

ND: Not determined

Example 22

In Vivo Re-Treatment Using an Antibody Composition with Antibodies 992+1024

Method $1\times10^6$ A431NS cells were injected subcutaneously in the right flank of 6-8 weeks old BALB/c nu/nu female mice. Tumors were measured one to three times per week with calipers, and the tumor volume (V) was calculated using the following formula: $V=(width)^2\times(length)\times0.5$. Treatment was started when tumors reached an average tumor volume of approximately 100 mm$^3$, and the mice were treated with 1 mg of antibodies 992+1024 intraperitoneally twice a week for a total of nine injections. After the initial treatment period the mice were followed for 159 days. If tumor growth was detected during this period, the mice were retreated with 1 mg of antibodies 992+1024 twice a week until termination of the study.

Results

All tumors responded to the initial four weeks of therapy (FIG. 44). The exponential tumor growth was stopped and the tumors regressed to tumor volumes between 0 and ~200 mm$^3$. Hereafter, the tumor volume was stable for more the 85 days before three of the nine tumors started to grow again. The three tumors, which were of varying sizes before initiation of the second round of therapy, were treated with 1 mg of antibodies 992+1024 twice a week for the rest of the study period. In all three cases, the re-treatment resulted in an immediate tumor regression, indicating that the tumors had not become resistant treatment following the initial four weeks of treatment with antibody composition with antibodies 992+1024.

Example 23

In Vivo Treatment of Partial Erbitux-Responders Using an Antibody Composition with Antibodies 992+1024

Methods $1\times10^6$ A431NS cells were injected subcutaneously in the right flank of 6-8 weeks old BALB/c nu/nu female mice. Tumors were measured three times per week with calipers and the tumor volume (V) was calculated using the following formula: $V=(width)^2\times(length)\times0.5$. When the tumors reached an average tumor volume of approximately 130 mm$^3$ the mice were divided into two groups of 10 and 30 animals. The group with 10 animals was treated with a control antibody, whereas the group with 30 animals was treated with 1 mg Erbitux for a total of 3 doses. At this point, the Erbitux treated group was randomised into two balanced groups of 12 animals with an average tumour size of 500 mm$^3$. The two groups of animals were treated with either 1 mg of antibodies 992+1024 twice a week or continued on Erbitux treatment. Six outliers were taken out of the study.

Results

The initial Erbitux treatment partially inhibited the A431NS tumor growth (FIG. 45). After 11 days of Erbitux treatment half of the animals were shifted to treatment with an antibody composition with antibodies 992+1024 (Sym004 in figure legend). In the group of mice that was switched to treatment with antibodies 992+1024, a significant tumor regression was observed as compared to the group that continued on Erbitux treatment. This clear effect of an antibody composition with antibodies 992+1024 on large tumors pretreated with Erbitux, indicates that an antibody composition with antibodies 992+1024 is more potent than Erbitux in the A431NS model and that an antibody composition with antibodies 992+1024 may be a treatment option in Erbitux partial responders.

Example 24

In Vivo Treatment of Erbitux-Resistant Cells

To further investigate if the Sym004 drug candidate can inhibit Erbitux-resistant cells, Erbitux-resistant HN5 clones were generated from the Erbitux resistant HN5 cell pool. Clones were generated by limited-dilution and once Erbitux resistant clones were generated the inhibitory effects of Erbitux, Vectibix and Sym004 was tested using a WST-1 viability assay.

Method

Erbitux-resistant HN5 clones were generated from the Erbitux-resistant cell pool (see example 21) by limiting-dilution. Cloning by limiting dilution is a procedure for separating cells based on the assumption that if a suspension of cells is diluted with enough culture medium, a concentration of cells will be produced such that an accurately measured volume of the diluted suspension will contain 1 cell. When this volume of the diluted suspension is placed into separate wells of a 96-well plate, each well should receive 1 cell/well. If this cell remains viable (feeder cell layers and/or "conditioned" medium is/are usually needed because of the obviously low cell density of 1 cell/well) and proliferates, then an isolated clone of cells will have been established in the well. The cells were grown in DMEM, supplemented with 10% FBS and appropriate concentrations of Erbitux.

The Cell Proliferation Reagent WST-1 is a ready-to-use substrate which measures the metabolic activity of viable cells, and it is assumed that the metabolic activity correlates with the number of viable cells. In this example the WST-1 assay was used to measure the number of metabolically active cells after treatment with different antibodies in different concentrations.

Prior to performing the WST-1 assay the appropriate antibodies and antibody mixes were diluted to a final total antibody concentration of 20 µg/ml in appropriate media supplemented with 0.5% of FBS and 1% P/S yielding a final antibody concentration of 10 µg/ml in the well containing the highest antibody concentration. 150 µl of these solutions were then added to wells in column 2 of a 96-well plate and a three-fold serial dilutions were made and added to subsequent columns of wells until column 9 so that each well contained 100 µl of antibody solution. 100 µl of media were added to column 11. 200 µl of media were added to Rows 1 and 8 as well as column 1 and 12 to decrease the effect of media evaporation in the experimental wells.

HN5 parental and HN5 resistant cells were then washed with 1×PBS and detached by trypsination with 3 ml trypsin solution. 17 ml of complete media were then added and the cells were spun down at 300×g (1200 rcf) for 5 min. The supernatant was removed and cells re-suspended in DMEM+ 0.5% FBS. Cells were counted and their concentration adjusted to 15000 cells/ml. 100 µl of the cell suspension (1500 cells/well) were then added to experimental wells in columns 2-11. The plates were incubated for 4 days in a humidified incubator at 37° C. Then 20 µl WST-1 reagent was added per well and the plates incubated for one hour at 37° C. Plates were then transferred to an orbital plate shaker for one hour. The absorbance was measured at 450 and 620 nm (reference wavelength) using an ELISA reader. The amount of metabolically active cells (MAC) is calculated as the percent of the untreated control as follows:

$$\% \ MAC = \left( \frac{(ODexp. - ODmedia)}{(ODuntreat. - ODmedia)} \right) \times 100$$

The IC50 of each mix was calculated using Graph Pad Prism by fitting the titration curves to the equation Y=Bottom+(Top-Bottom)/(1+10^((Log IC50-X)*HillSlope)).

Results

Results from the titrations are shown in FIG. 46 for four representative clones. It is evident that the clones have different levels of resistance to Erbitux. However, Sym004 is superior at inhibiting the growth of all four clones as compared to Erbitux and Vectibix. The superiority was evident either as an increased efficacy (clones #7, #11 and #14) and/or potency (clones #8, #11 and #14) (Table 19).

TABLE 19

IC50 values and efficacy of inhibition of the four Erbitux resistant HN5 clones by the indicated antibodies.

|  | HN5 parental | Clone #7 | Clone #8 | Clone #11 | Clone #14 |
|---|---|---|---|---|---|
|  | Potency IC$_{50}$ (µg/ml) | | | | |
| Erbitux | 0.050 | 0.016* | 1.06 | 0.366* | 0.314* |
| Vectibix | 0.035 | 0.023* | 2.70 | 0.311* | 0.190* |
| Sym004 | 0.053 | 0.029* | 0.33 | 0.267* | 0.110* |
|  | Efficacy (% maximum inhibition) | | | | |
| Erbitux | 88.1% | 60.9% | 42.5% | 35.7% | 32.0% |
| Vectibix | 88.3% | 61.1% | 51.3% | 28.6% | 33.7% |
| Sym004 | 88.2% | 70.3% | 57.5% | 38.9% | 43.5% |

*IC50 values cannot be compared because of difference in the maximum level of inhibition.

Example 25

In Vivo Treatment of Erbitux Resistant HN5 Cells Using Erbitux and an Antibody Composition with Antibodies 992+1024

Method $5*10^6$ Erbitux resistant HN5 clone #7 cells were injected subcutaneously into the right flank of six-eight week-old female athymic nude mice. Tumors were measured twice a week with calipers, and tumor volume in mm$^3$ was calculated according to the formula: (width)$^2$×(length)×0.5. Treatment was started sequentially when tumors reached an average size of ~650 mm$^3$. Mice were treated with 50 mg/kg Sym004 or Erbitux by intraperitoneal injections twice weekly for three weeks. After the three week treatment period the mice were followed for five weeks.

Results

After three weeks of Sym004 therapy, both tumors in the Sym004 group were completely eliminated (FIG. 47). Two out of the three treated mice in the Erbitux group were only partially responsive to treatment. This indicates that tumors that are partially resistant/unresponsive to Erbitux treatment can be efficiently treated with Sym004. Thus, the acquired resistance mechanism against Erbitux does not affect the efficacy of Sym004.

APPENDIX 1

Antibody variable region sequences

>992VH (Seq. no. 24)
cgcgccgaggtccaactgcagcaacctgggtctgagctggtgaggcctggagcttcagtgaagctgtcct gcaaggcttctggctacacattcaccagctactggatgcactgggtgaagcagaggcctggacaaggcct APPENDIX 1-continued Antibody variable region sequences tgagtggattgggaatatttatcctggtagtcgtagtactaactacgatgagaagttcaagagcaaggcc acactgactgtagacacatcctccagcacagcctacatgcagctcagcagcctgacatctgaggactctg cggtctattactgtacaagaaatggggattactacgttagtagcggggatgctatggactactggggtca aggaacctcagtcaccgtctcg >1024VH (Seq. no. 25)
cgcgcccaggtccaactgcagcagcctggggctgaactggtggagcctgggggttcagtgaagctgtcct
gcaaggcttctggctacaccttcaccagtcactgatgcactgggtgaagcagaggcctggacaaggcct
tgagtggataggtgagattaatcctagcagcggtcgtaataactacaatgagaagttcaagagtaaggcc
acactgactgtagacaaatcctccagcacagcctacatgcaattcagcagcctgacatctgaggactctg
cggtctattattgtgtaagatactatggttacgacgaagctatggactactggggtcaaggaacctcagt
caccgtctcg >1030VH (Seq. no. 26)
cgcgccgaagtgcagctggtggagtctgggggaggcttagtgaagcctggagggtccctgaaactctcct
gtgcagcctctggattcactttcagtagttatgccctgtcttgggttcgccagactccagagaggaggct
ggagtgggtcgcatccattagtggtgttggtagcacctactttccagacagtgtgaagggccgtttcacc
atgtccagagataatgccaggaacatcctgtacctccaaatgagcagtctgaggtctgaggacacggcca
tgtattactgtgcaagaggttctgatggttacttctatgctatggactactggggtcaaggaacctcagt
caccgtctcg >1042VH (Seq. no. 27)
cgcgcccaggtgcagcttcagcagcctggggctgaactggtgaagcctggggcttcagtgaagctgtcct
gtaaggcttctggctacaccttcaccagccactgatgcactgggtgcagcagaggcctggacaaggcct
tgagtggattggagagattcatcctagcaacggtcgtactaactacaatgagaagttcaagaacaaggcc
acactgactgtagacaaatctcccagcacagcctacatgcaactcagcagtttgacatctgaggactctg
cggtctattactgtgcaagatactatggttacgacgatgctatggactactggggtcaaggaacctcagt
caccgtctcg >1208VH (Seq. no. 28)
cgcgccgaagtgcagctggtggagtctgggggaggcttagtgaagcctggagggtccctgaaactctcct
gtgcagcctctggattcgctttcagtagctatgacatgtcttgggttcgccagactccggagaagaggct
ggagtgggtcgcatacattggtagtggtgatgataatacccactatccagactctgtgaagggccgattc
accatctccagacacaatgccaaaaacaccctatacctgcaaatgagcagtctgaagtctgaggacacag
ccatgtattactgtgcaagacagaagtatggtaactacggggacactatggactactggggtcaaggaac
ctcagtcaccgtctcg >1229\VH (Seq. no. 29)
cgcgcccaggttcagctgaaggagtcaggacctggcctggtggcgccctcacagagcctgtccatcactt
gctctgtctctggtttttcattaaccatctatggtgtacactgggttcgccagcctccaggaaagggtct
ggagtggctgggagttatgtggctggtggaaatacagattataattcggctctcatgtccagactgaac
atcagcaaggacaattccaagagccaagttttcttaaaagtgaacagtctacaaactgatgacacagcca
tgtactattgtaccagagatcccgatggttactacgtggggtggttcttcgatgtctggggcgcggggac
cacggtcaccgtctcg >1254VH (Seq. no. 30)
cgcgccgaagtgcagctggtggagtctgggggaggcttagtgaagcctggagggtccctgaaactctcct
gtgcagcctctggattcgcttacagtacctatgacatgtcttgggttcgccagactccggagaagaggct APPENDIX 1-continued Antibody variable region sequences ggagtgggtcgcatacattagtagtggtggtgatgccgcctactatcccgacactgtgaagggccgattc accatctccagagacaatgccaaaaacaccctatacctgcaaatgagcagtctgaagtctgaggacacag ccatgtattactgtgcgaggtctcgctatggaaactacggggacgctatggactactggggtcaaggaac ctcagtcaccgtctcg >1257VH (Seq. no. 31)
cgcgccgaggtccagctgcaacagtctggacctgagctggtgaaacctggggcttcagtgaagatacccct
gcaagacttctggatacactttcactgactacaacatggcctgggtgaagcagagccatggaaagagcct
tgagtggattggagatattattcctaacaatggtggtgctatctacaaccagaaattcaagggcaaggcc
actttgactgtagacaaatcctccagtacagcctccatggagctccgcagcctgacatctgaggacactg
cagtctatttctgtgcaagaaagaatatctactataggtacgacggggcaggtgctctggactactgggg
tcaaggaacctcagtcaccgtctcg >1260VH (Seq. no. 32)
cgcgcccaggtgcagctgaaggagtcaggacctggcctggtggcgccctcacagagcctgtccatcactt
gcactgtctctgggttttcattaaccacctatggggtacactgggttcgccagcctccaggaaagggtct
ggagtggctgggagtaatatgggctggtggaagcacaaattataattcggctctcatgtccagactgagc
atcaagaaagacaactccaagagccaagttttcttaaaaatgaacagtctgcaaactgatgacacagcca
tgtactactgtgccagagcctatggttacaactttgactattggggccaaggcaccactctcacagtctc
g >1261VH (Seq. no. 33)
cgcgccgaagtgcagctggtggagtctggggggaggcttagtgaagcctggagggtccctgaaactctcct
gtgcagtctctggattcactttcagtagctatgtcatgtcttgggttcgccagactccggagaagaggct
ggagtgggtcgcaaccattactagtggtggtaggaacatctactatctagacagtgtgaaggggcgattc
actatctccagagacaatgccaagaacaccctgtacctgcaaatgagcagtctgaggtctgaggacacgg
ccatgtattactgtgcaagacatgaggactataggtacgacggttactatgctatggactactggggtca
aggaacctcagtcaccgtctcg >1277VH (Seq. no. 34)
cgcgccgaagtgcagctggtggagtctggggggaggcttagtgaagcctggagagtccttgaaactctcct
gtgcagcctctggattcgctttcagttactctgacatgtcttgggttcgccagactccggagaagaggct
ggagtgggtcgcatacatgagtagtgctggtgatgtcaccttctattcagacactgtgaagggccgattc
accatctccagagacaatgccaagaacaccctgtatctgcaagtgagcagtctgaagtctgaggacacag
ccatatattactgtgtaagacaccgggacgtggctatggactactggggtcaaggaacctcagtcaccgt
ctcg >1284VH (Seq. no. 35)
cgcgcccaggtccaactgcagcagcctggggctgaactggtgaagcctgggcgcttcagtgaagctgtcct
gcaaggcttctggctacaccttcaccagcgactggatgcactggatgaaacagaggcctggacaaggcct
tgagtggattggagagattaatcctagtaacggtcgctctagctacaatgagaagttcaagagcaaggcc
acactgactgtagacaaatcctccagcacagcctacatgcaactcagcagcctgacatctgaggactctg
cggtctattactgtgcaagaataggtggtatctacgtggagacttactggggccaagggactctggtcac
tgtctcg >1308VH (Seq. no. 36)
cgcgccgaggtccagcttcagcagtctggagctgagctggtgaggcctgggtcctcagtgaagatttcct
gcaaggcttctggctatgcattcagtagctactggatgaactgggtgaggcagaggcctggacagggtct APPENDIX 1-continued Antibody variable region sequences tgagtggattggacagatttatcctggagatggtgatactaactacaatggaaagttcaagggtagagcc acactgactgcaaacaaatcctccagcacagcctacatgcagctcagcagcctaacatctgaggactctg cggtctatttctgtgcaagaagggcatcttccctctatgatgtttaccccta ctactttgactactgggg ccaaggcaccactctcacagtctcg >1320VH (Seq. no. 37)
cgcgcccaggtccaactgcagcagcctggggctgaactggtgaagcctggggcttcaatgaagctgtcct gcaaggcttctggctacacct tcaccaactactggatgcactgggtgaagcagaggcctggacaaggcct tgaatggattggagaaattaatcctagcaacggtcgtactaattacaatgagaagttcaagagcaaggcc acactgactgtagacaaatcgtccagcacagcctacatgcaactcagcagcctgacatctgaggactctg gggtctattactgtgcaaaggggggaactactatgattacgactgggactactggggccaaggcaccac tctcacagtctcg >1344VH (Seq. no. 38)
cgcgcccaggtgcagctgaaggagtcaggacctggcctggtggcgccctcacagagcctgtccatcactt gcactgtctctgggttttcattaaccatctatggtgtacactgggttcgccagcctccaggaaagggtct ggagtggctgggagtaatatgggctggtggaaacacaaattataattcggctctcatgtccagactgagc atcagcaaagacaactccaagagtcaagttttcttaaaaatgaacagtctgcaaactgatgacacagcca tgtacttctgtgccagaggctatggctacaatttagactattggggccaaggcaccactctcacagtctc g >1347VH (Seq. no. 39)
cgcgcccaggtgcagctgaaggagtcaggacctggcctggtggcgccctcacagagcctgtccatcacat gcaccgtctcaggattctcattaaccggccatggtgtaaactgggttcgccagcctccaggaaagggtct ggagtggctgggaatgatatgggg tgatggaagcacggactataattcaactctcaaatccagactgagt atcagcaaggacaactccaagagccaagttttcttaaaaatgaacagtctgcagactgatgacaccgcca ggtactactgtgccagaggctacggctacctttactactttgactactggggccaaggcaccactctcac agtctcg >992VH (Seq. no. 40)
RAEVQLQQPGSELVRPGASVKLSCKASGYTFTSYWMHWVKQRPGQGLEWIGNIYPGSRST

NYDEKFKSKATLTVDTSSSTAYMQLSSLTSEDSAVYYCTRNGDYYVSSGDAMDYWGQGTS

VTVS

>1024VH (Seq. no. 41)
RAQVQLQQPGAELVEPGGSVKLSCKASGYTFTSHWMHWVKQRPGQGLEWIGEINPSSGRN

NYNEKFKSKATLTVDKSSSTAYMQFSSLTSEDSAVYYCVRYYGYDEAMDYWGQGTSVTVS

>1030VH (Seq. no. 42)
RAEVQLVESGGGLVKPGGSLKLSCAASGFTFSSYALSWVRQTPERRLEWVASISGVGSTY

FPDSVKGRFTMSRDNARNILYLQMSSLRSEDTAMYYCARGSDGYFYAMDYWGQGTSVTVS

>1042VH (Seq. no. 43)
RAQVQLQQPGAELVKPGASVKLSCKASGYTFTSHWMHWVQQRPGQGLEWIGEIHPSNGRT

NYNEKFKNKATLTVDKSPSTAYMQLSSLTSEDSAVYYCARYYGYDDAMDYWGQGTSVTVS

>1208VH (Seq. no. 44)
RAEVQLVESGGGLVKPGGSLKLSCAASGFAFSSYDMSWVRQTPEKRLEWVAYIGSGDDNT

HYPDSVKGRFTISRHNAKNTLYLQMSSLKSEDTAMYYCARQKYGNYGDTMDYWGQGTSVT

VS

APPENDIX 1-continued

Antibody variable region sequences

>1229VH (Seq. no. 45)
RAQVQLKESGPGLVAPSQSLSITCSVSGFSLTIYGVHWVRQPPGKGLEWLGVMWAGGNTD

YNSALMSRLNISKDNSKSQVFLKVNSLQTDDTAMYYCTRDPDGYYVGWFFDVWGAGTTVT

VS

>1254VH (Seq. no. 46)
RAEVQLVESGGGLVKPGGSLKLSCAASGFAYSTYDMSWVRQTPEKRLEWVAYISSGGDAA

YYPDTVKGRFTISRDNAKNTLYLQMSSLKSEDTAMYYCARSRYGNYGDAMDYWGQGTSVT

VS

>1257VH (Seq. no. 47)
RAEVQLQQSGPELVKPGASVKIPCKTSGYTFTDYNMAWVKQSHGKSLEWIGDIIPNNGGA

IYNQKFKGKATLTVDKSSSTASMELRSLTSEDTAVYFCARKNIYYRYDGAGALDYWGQGT

SVTVS

>1260VH (Seq. no. 48)
RAQVQLKESGPGLVAPSQSLSITCTVSGFSLTTYGVHWVRQPPGKGLEWLGVIWAGGSTN

YNSALMSRLSIKKDNSKSQVFLKMNSLQTDDTAMYYCARAYGYNFDYWGQGTTLTVS

>1261VH (Seq. no. 49)
RAEVQLVESGGGLVKPGGSLKLSCAVSGFTFSSYVMSWVRQTPEKRLEWVATITSGGRNI

YYLDSVKGRFTISRDNAKNTLYLQMSSLRSEDTAMYYCARHEDYRYDGYYAMDYWGQGTS

VTVS

>1277VH (Seq. no. 50)
RAEVQLVESGGGLVKPGESLKLSCAASGFAFSYSDMSWVRQTPEKRLEWVAYMSSAGDVT

FYSDTVKGRFTISRDNAKNTLYLQVSSLKSEDTAIYYCVRHRDVAMDYWGQGTSVTVS

>1284VH (Seq. no. 51)
RAQVQLQQPGAELVKPGASVKLSCKASGYTFTSDWMHWMKQRPGQGLEWIGEINPSNGRS

SYNEKFKSKATLTVDKSSSTAYMQLSSLTSEDSAVYYCARIGGIYVETYWGQGTLVTVS

>1308VH (Seq. no. 52)
RAEVQLQQSGAELVRPGSSVKISCKASGYAFSSYWMNWVRQRPGQGLEWIGQIYPGDGDT

NYNGKFKGRATLTANKSSSTAYMQLSSLTSEDSAVYFCARRASSLYDVYPYYFDYWGQGT

TLTVS

>1320VH (Seq. no. 53)
RAQVQLQQPGAELVKPGASMKLSCKASGYTFTNYWMHWVKQRPGQGLEWIGEINPSNGRT

NYNEKFKSKATLTVDKSSSTAYMQLSSLTSEDSGVYYCAKGGNYYDYDWDYWGQGTTLTV

S

>1344VH (Seq. no. 54)
RAQVQLKESGPGLVAPSQSLSITCTVSGFSLTIYGVHWVRQPPGKGLEWLGVIWAGGNTN

YNSALMSRLSISKDNSKSQVFLKMNSLQTDDTAMYFCARGYGYNLDYWGQGTTLTVS

>1347VH (Seq. no. 55)
RAQVQLKESGPGLVAPSQSLSITCTVSGFSLTGHGVNWVRQPPGKGLEWLGMIWGDGSTD

YNSTLKSRLSISKDNSKSQVFLKMNSLQTDDTARYYCARGYGYLYYFDYWGQGTTLTVS

>992VL (Seq. no. 56)
ctagccgacattcagatgactcagactacatcctccctgtctgcctctctgggagacagagtcaccatca gttgcaggacaagtcaggacattggcaattatttaaactggtatcagcagaaaccagatggaactgttaa actcctgatctactacacatcaagattacactcaggagtcccatcaaggttcagtggcagtgggtctgga acagattttctctcaccattaacaacgtggagcaagaggatgttgccacttacttttgccaacactata atacggttcctccgacgttcggtggaggcaccaagctggaaatcaaacgaactgtggctgcaccatctgt APPENDIX 1-continued Antibody variable region sequences cttcatcttcccgccatctgatgagcagttgaaatctggaactgcctctgttgtgtgcctgctgaataac ttctatcccagagaggccaaagtacagtggaaggtggataacgccctccaatcgggtaactcccaggaga gtgtcacagagcaggacagcaaggacagcacctacagcctcagcagcaccctgacgctgagcaaagcaga ctacgagaaacacaaagtctacgcctgcgaagtcacccatcagggcctgagctcgcccgtcacaaagagc ttcaacaggggagagtgt >1024VL (Seq. no. 57)
ctagccgacatcgtgatgacacaagctgcattctccaatccagtcactcttggaacatcagcttccatct cctgcaggtctagtaagagtctcctacatagtaatggcatcacttatttgtattggtatctgcagaagcc aggccagtctcctcagctcctgatttatcagatgtccaaccttgcctcaggagtcccagacaggttcagt agcagtgggtcaggaactgatttcacactgagaatcagcagagtggaggctgaggatgtgggtgtttatt actgtgctcaaaatctagaacttccgtacacgttcggaggggggaccaagctggaaataaaacgaactgt ggctgcaccatctgtcttcatcttcccgccatctgatgagcagttgaaatctggaactgcctctgttgtg tgcctgctgaataacttctatcccagagaggccaaagtacagtggaaggtggataacgccctccaatcgg gtaactcccaggagagtgtcacagagcaggacagcaaggacagcacctacagcctcagcagcaccctgac gctgagcaaagcagactacgagaaacacaaagtctacgcctgcgaagtcacccatcagggcctgagctcg cccgtcacaaagagcttcaacaggggagagtgt >1030VL (Seq. no. 58)
ctagccgacattgtgctgactcagtctcctgcttccttagctgtatctctggggcagagggccaccattt catgcagggccagcaaaagtgtcagtacatctggctatagttttatgcactggtaccaactgaaaccagg acagccacccaaactcctcatctatcttgcatccaacctagaatctggggtccctgccaggttcagtggc agtgggtctgggacagacttcaccctcaacatccatcctgtggaagaggaggatgctgcaacctattact gtcagcacagtagggagtttccgttaacgttcggaggggggaccaagctggaaataaaacgaactgtggc tgcaccatctgtcttcatcttcccgccatctgatgagcagttgaaatctggaactgcctctgttgtgtgc ctgctgaataacttctatcccagagaggccaaagtacagtggaaggtggataacgccctccaatcgggta actcccaggagagtgtcacagagcaggacagcaaggacagcacctacagcctcagcagcaccctgacgct gagcaaagcagactacgagaaacacaaagtctacgcctgcgaagtcacccatcagggcctgagctcgccc gtcacaaagagcttcaacaggggagagtgt >1042VL (Seq. no. 59)
gatattgtgatgactcaggctgcattctccaatccagtcactcttggaacatcagcttccatctcctgca ggtctagtaagagtctcctacatagtaatggcatcacttatttgtattggtatctgcagaagccaggcca gtctcctcagctcctgatttatcagatgtccaaccttgcctcaggagtcccagacaggttcagtagcagt gggtcaagaactgatttcacactgagaatcagcagagtggaggctgaggatgtgggtgtttattactgtg ctcaaaatctagaacttccgtacacgttcggaggggggaccaagctggaaataaaacgaactgtggctgc accatctgtcttcatcttcccgccatctgatgagcagttgaaatctggaactgcctctgttgtgtgcctg ctgaataacttctatcccagagaggccaaagtacagtggaaggtggataacgccctccaatcgggtaact cccaggagagtgtcacagagcaggacagcaaggacagcacctacagcctcagcagcaccctgacgctgag caaagcagactacgagaaacacaaagtctacgcctgcgaagtcacccatcagggcctgagctcgcccgtc acaaagagcttcaacaggggagagtgt >1208VL (Seq. no. 60)
ctagccgatgttgtgatgactcagactccactctccctgcctgtcagtcttggagatcaagcctccatct cttgcagatctagtcagagccttgtacacagtaatggaaacacctatttacattggtacctgcagaagcc APPENDIX 1-continued Antibody variable region sequences aggccagtctccaaaactcctgatctacaaagtttccaaccgattttctggggtcccagacaggttcagt ggcagtggatcagggacagatttcacactcaagatcagcagagtggaggctgaggatctgggagtttatt tctgctctcaaagtacacatgttcccacgttcggaggggggaccaagctggaaatcaaacgaactgtggc tgcaccatctgtcttcatcttcccgccatctgatgagcagttgaaatctggaactgcctctgttgtgtgc ctgctgaataacttctatcccagagaggccaaagtacagtggaaggtggataacgccctccaatcgggta actcccaggagagtgtcacagagcaggacagcaaggacagcacctacagcctcagcagcaccctgacgct gagcaaagcagactacgagaaacacaaagtctacgcctgcgaagtcacccatcagggcctgagctcgccc gtcacaaagagcttcaacaggggagagtgt >1229VL (Seq. no. 61)
ctagccgacattgtgatgacccagtctcacaaattcatgtccacatcagtgggagacagggtcagcatca cctgcaaggccagtcaggatgtgactaatgccgtagcctggtatcaacaaaaaccaggacaatctcctaa actactgatttactgggcatccatccgacacactggagtccctgatcgcttcacaggcagtagatctggg acagattatactctcaccatcaacagtgtgcaggctgaagacctggcccttattattgtcagcaacatt ataacactccgctcacgttcggtgctgggaccaagctggaaataaaacgaactgtggctgcaccatctgt cttcatcttcccgccatctgatgagcagttgaaatctggaactgcctctgttgtgtgcctgctgaataac ttctatcccagagaggccaaagtacagtggaaggtggataacgccctccaatcgggtaactcccaggaga gtgtcacagagcaggacagcaaggacagcacctacagcctcagcagcaccctgacgctgagcaaagcaga ctacgagaaacacaaagtctacgcctgcgaagtcacccatcagggcctgagctcgcccgtcacaaagagc ttcaacaggggagagtgt >1254VL (Seq. no. 62)
ctagccgatgttgtgatgacacagactccactctccctgcctgtcagtcttggagatcaagcctccatct cttgcagatctagtcagagccttgtacacagtaatggtaacacctatttacattggtacctgcagaagcc aggccagtctccaaagctcctgctctacaaagtttccaaccgattttctggggtcccagacaggttcagt ggcagtggatcagggacagatttcacactcaagatcagcagagtggagtctgaggatctgggagtttatt tctgctctcaaaatacacatgtgtacacgttcggaggggggacaaagttggaaataaaacgaactgtggc tgcaccatctgtcttcatcttcccgccatctgatgagcagttgaaatctggaactgcctctgttgtgtgc ctgctgaataacttctatcccagagaggccaaagtacagtggaaggtggataacgccctccaatcgggta actcccaggagagtgtcacagagcaggacagcaaggacagcacctacagcctcagcagcaccctgacgct gagcaaagcagactacgagaaacacaaagtctacgcctgcgaagtcacccatcagggcctgagctcgccc gtcacaaagagcttcaacaggggagagtgt >1257VL (Seq. no. 63)
ctagcccaaattgtgctcacacagtctccagcaatcatgtctgcatctccaggggagaaggtcaccatga cctgcagtgccagctcaagtgtaagttacatttactggtaccagcagaagccaggatcctcccccagact cctgatttatgacgcatccaacctggcttctggagtccctgttcgcttcagtggcagtgggtctgggacc tcttactctctcacaatcagccgaatggaggctgaagatgctgccacttattactgccagcagtggagca gttacccaatcacgttcggctcggggacaaagttggaaataaaacgaactgtggctgcaccatctgtctt catcttcccgccatctgatgagcagttgaaatctggaactgcctctgttgtgtgcctgctgaataacttc tatcccagagaggccaaagtacagtggaaggtggataacgccctccaatcgggtaactcccaggagagtg tcacagagcaggacagcaaggacagcacctacagcctcagcagcaccctgacgctgagcaaagcagacta APPENDIX 1-continued Antibody variable region sequences cgagaaacacaaagtctacgcctgcgaagtcacccatcagggcctgagctcgcccgtcacaaagagcttc aacaggggagagtgt >1260VL (Seq. no. 64)
ctagccgatatccagatgactcagactacatcctccctgtctgcctctctgggagacagagtcaccatca gttgcagtgcaagtcagggcattaccaattatttaaactggtatcagcagaaaccagatggaactgttaa actcctgatctattactcatcaagtttacactcaggagtcccatcaaggttcagtggcagtgggtctggg acagattattctctcaccatcagcaacctggaacctgaagatattgccacttactattgtcagcagtata gtgagattccgtacacgttcggaggggggaccaagctggagctgaaacgaactgtggctgcaccatctgt cttcatcttcccgccatctgatgagcagttgaaatctggaactgcctctgttgtgtgcctgctgaataac ttctatcccagagaggccaaagtacagtggaaggtggataacgccctccaatcgggtaactcccaggaga gtgtcacagagcaggacagcaaggacagcacctacagcctcagcagcaccctgacgctgagcaaagcaga ctacgagaaacacaaagtctacgcctgcgaagtcacccatcagggcctgagctcgcccgtcacaaagagc ttcaacaggggagagtgt >1261VL (Seq. no. 65)
ctagcccaaattgtgctgacccagtctccagcaatcatgtctgcatctccaggggagaaggtcaccataa cctgcagtgccagctcaagtgtaagttacatgcactggttccagcagaagccaggcacttctcccaaact ctggatttatagtacatccaacctggcttctggagtccctgctcgcttcagtggcagtggatctgggacc tcttactctctcacaatcagccgaatggaggctgaagatgctgccacttattactgccagcaaaggagta gttacccatacacgttcggaggggggaccaagctggagctgaaacgaactgtggctgcaccatctgtctt catcttcccgccatctgatgagcagttgaaatctggaactgcctctgttgtgtgcctgctgaataacttc tatcccagagaggccaaagtacagtggaaggtggataacgccctccaatcgggtaactcccaggagagtg tcacagagcaggacagcaaggacagcacctacagcctcagcagcaccctgacgctgagcaaagcagacta cgagaaacacaaagtctacgcctgcgaagtcacccatcagggcctgagctcgcccgtcacaaagagcttc aacaggggagagtgt >1277VL (Seq. no. 66)
ctagccgatgttgtgatgacccagactccactctccctgcctgtcagtcttggagatcaagcctccatct cttgcagatctagtcagagccttgtacacagtaatggaaacacctatttacattggtacctgcagaagcc aggccagtctccaaagctcctgatctacaaagtttccaaccgattttctggggtcccagacaggttcagt ggcagtggatcagggacagatttcacactcaagatcagcagagtggaggctgaggatctgggagtttatt tctgctctcaaagtacacatgttccgacgttcggtggaggcaccaagctggaaatcaaacgaactgtggc tgcaccatctgtcttcatcttcccgccatctgatgagcagttgaaatctggaactgcctctgttgtgtgc ctgctgaataacttctatcccagagaggccaaagtacagtggaaggtggataacgccctccaatcgggta actcccaggagagtgtcacagagcaggacagcaaggacagcacctacagcctcagcagcaccctgacgct gagcaaagcagactacgagaaacacaaagtctacgcctgcgaagtcacccatcagggcctgagctcgccc gtcacaaagagcttcaacaggggagagtgt >1284VL (Seq. no. 67)
ctagccgacattgtgctaacacagtctcctgcttccttagctgtatctctggggcagagggccaccatct catgcagggccagcaaagtgtcagtacatctacctatagttatatgcactggtatcaacagaaatcagg acagccacccaaactcctcatcaagtatgcatccaacctagagtctggggtccctgccaggttcagtggc agtgggtctgggacagacttcaccctcaacatccatcctgtggaggaggaggatactgcaacatattact gtcagcacagtttgggagattccgtggacgttcggtggaggcaccaagctggaaatcaaacgaactgtggc APPENDIX 1-continued Antibody variable region sequences tgcaccatctgtcttcatcttcccgccatctgatgagcagttgaaatctggaactgcctctgttgtgtgc ctgctgaataacttctatcccagagaggccaaagtacagtggaaggtggataacgccctccaatcgggta actcccaggagagtgtcacagagcaggacagcaaggacagcacctacagcctcagcagcaccctgacgct gagcaaagcagactacgagaaacacaaagtctacgcctgcgaagtcacccatcagggcctgagctcgccc gtcacaaagagcttcaacaggggagagtgt >1308VL (Seq. no. 68)
ctagccgacatccagatgacacaaactacatcctccctgtctgcctctctgggagacagagtcaccatca gttgcagggcaagtcaggacattagcaattatttaaactggtatcagcagaaaccagatggaactgttaa agtcctgatctactacacatcaagattacactcaggagtcccatcaaggttcagtggcagtgggtctgga acagattattctctcaccattagcaacctggagcaagaagatattgccacttacttttgccaacagggta atacgcttccgtacacgttcggaggggggaccaagctggaaataaaacgaactgtggctgcaccatctgt cttcatcttcccgccatctgatgagcagttgaaatctggaactgcctctgttgtgtgcctgctgaataac ttctatcccagagaggccaaagtacagtggaaggtggataacgccctccaatcgggtaactcccaggaga gtgtcacagagcaggacagcaaggacagcacctacagcctcagcagcaccctgacgctgagcaaagcaga ctacgagaaacacaaagtctacgcctgcgaagtcacccatcagggcctgagctcgcccgtcacaaagagc ttcaacaggggagagtgt >1320VL (Seq. no. 69)
ctagccgacattcagatgacccagactacatcctccctgtctgcctctctgggagacagagtcaccatca gttgcagtgcaagtcaggacattagcaattatttaaactggtatcagcagaaaccagatggaactgttaa actcctgatctatcacacatcaactttacactcaggagtcccatcaaggttcagtggcagtgggtctggg acagattattctctcaccatcagcaacctggaacctgaagatattgccacttactattgtcagcaatata gtaagcttccgtggacgttcggtggaggcaccaagctggaaatcaaacgaactgtggctgcaccatctgt cttcatcttcccgccatctgatgagcagttgaaatctggaactgcctctgttgtgtgcctgctgaataac ttctatcccagagaggccaaagtacagtggaaggtggataacgccatccaatcgggtaactcccaggaga gtgtcacagagcaggacagcaaggacagcacctacagcctcagcagcaccctgacgctgagcaaagcaga ctacgagaaacacaaagtctacgcctgcgaagtcacccatcagggcctgagctcgcccgtcacaaagagc ttcaacaggggagagtgt >1344VL (Seq. no. 70)
ctagccgacattcagatgacacagactacttcctccctgtctgcctctctgggagacagagtcaccatta gttgcagtgcaagtcagggcattagtaattatttaaactggtatcagcagaaaccagatggaactgttaa actcctgatctattacacatcaagtttacactcaggagtcccatcaaggttcagtggcagtgggtctggg acagattattctctcaccatcagcaacctggaacctgaagatattgccacttactattgtcagcagtata gtaagcttccgtacacgttcggaggggggaccaagctggaaatcaaacgaactgtggctgcaccatctgt cttcatcttcccgccatctgatgagcagttgaaatctggaactgcctctgttgtgtgcctgctgaataac ttctatcccagagaggccaaagtacagtggaaggtggataacgccctccaatcgggtaactcccaggaga gtgtcacagagcaggacagcaaggacagcacctacagcctcagcagcaccctgacgctgagcaaagcaga ctacgagaaacacaaagtctacgcctgcgaagtcacccatcagggcctgagctcgcccgtcacaaagagc ttcaacaggggagagtgt >1347VL (Seq. no. 71)
ctagccgaaaatgtgctgactcagtctccagcaatcatgtctgcatctccaggggaaaaggtcaccatga cctgcagggccagctcaagtgtaagttccagttacttgcactggtaccagcaaaagtcaggtgcctcccc APPENDIX 1-continued Antibody variable region sequences caaactctggatttatagcacatccaacttggcttctggagtccctgctcgcttcagtggcagtgggtct gggacctcttactctctcacagtcaacagtgtggagactgaagatgctgccacttattactgccaccagt acagtggtttcccattcacgttcggctcggggaccaagctggagctgaaacgaactgtggctgcaccatc tgtcttcatcttcccgccatctgatgagcagttgaaatctggaactgcctctgttgtgtgcctgctgaat aacttctatcccagagaggccaaagtacagtggaaggtggataacgcccctccaatcgggtaactcccagg agagtgtcacagagcaggacagcaaggacagcacctacagcctcagcagcaccctgacgctgagcaaagc agactacgagaaacacaaagtctacgcctgcgaagtcacccatcagggcctgagctcgcccgtcacaaag agcttcaacaggggagagtgt >992VL (Seq. no. 72)
LADIQMTQTTSSLSASLGDRVTISCRTSQDIGNYLNWYQQKPDGTVKLLIYYTSRLHSGV

PSRFSGSGSGTDFSLTINNVEQEDVATYFCQHYNTVPPTFGGGTKLEIKRTVAAPSVFIF

PPSDEQLKSGTASVVCLLNNFYPREAKVQWKVDNALQSGNSQESVTEQDSKDSTYSLSST

LTLSKADYEKHKVYACEVTHQGLSSPVTKSFNRGEC

>1024VL (Seq. no. 73)
LADIVMTQAAFSNPVTLGTSASISCRSSKSLLHSNGITYLYWYLQKPGQSPQLLIYQMSN

LASGVPDRFSSSGSGTDFTLRISRVEAEDVGVYYCAQNLELPYTFGGGTKLEIKRTVAAP

SVFIFPPSDEQLKSGTASVVCLLNNFYPREAKVQWKVDNALQSGNSQESVTEQDSKDSTY

SLSSTLTLSKADYEKHKVYACEVTHQGLSSPVTKSFNRGEC

>1030VL (Seq. no. 74)
LADIVLTQSPASLAVSLGQRATISCRASKSVSTSGYSFMHWYQLKPGQPPKLLIYLASNL

ESGVPARFSGSGSGTDFTLNIHPVEEEDAATYYCQHSREFPLTFGGGTKLEIKRTVAAPS

VFIFPPSDEQLKSGTASVVCLLNNFYPREAKVQWKVDNALQSGNSQESVTEQDSKDSTYS

LSSTLTLSKADYEKHKVYACEVTHQGLSSPVTKSFNRGEC

>1042VL (Seq. no. 75)
DIVMTQAAFSNPVTLGTSASISCRSSKSLLHSNGITYLYWYLQKPGQSPQLLIYQMSNLA

SGVPDRFSSSGSRTDFTLRISRVEAEDVGVYYCAQNLELPYTFGGGTKLEIKRTVAAPSV

FIFPPSDEQLKSGTASVVCLLNNFYPREAKVQWKVDNALQSGNSQESVTEQDSKDSTYSL

SSTLTLSKADYEKHKVYACEVTHQGLSSPVTKSFNRGEC

>1208VL (Seq. no. 76)
LADVVMTQTPLSLPVSLGDQASISCRSSQSLVHSNGNTYLHWYLQKPGQSPKLLIYKVSN

RFSGVPDRFSGSGSGTDFTLKISRVEAEDLGVYFCSQSTHVPTFGGGTKLEIKRTVAAPS

VFIFPPSDEQLKSGTASVVCLLNNFYPREAKVQWKVDNALQSGNSQESVTEQDSKDSTYS

LSSTLTLSKADYEKHKVYACEVTHQGLSSPVTKSFNRGEC

>1229VL (Seq. no. 77)
LADIVMTQSHKFMSTSVGDRVSITCKASQDVTNAVAWYQQKPGQSPKLLIYWASIRHTGV

PDRFTGSRSGTDYTLTINSVQAEDLALYYCQQHYNTPLTFGAGTKLEIKRTVAAPSVFIF

PPSDEQLKSGTASVVCLLNNFYPREAKVQWKVDNALQSGNSQESVTEQDSKDSTYSLSST

LTLSKADYEKHKVYACEVTHQGLSSPVTKSFNRGEC

>1254VL (Seq. no. 78)
LADVVMTQTPLSLPVSLGDQASISCRSSQSLVHSNGNTYLHWYLQKPGQSPKLLLYKVSN

RFSGVPDRFSGSGSGTDFTLKISRVESEDLGVYFCSQNTHVYTFGGGTKLEIKRTVAAPS

VFIFPPSDEQLKSGTASVVCLLNNFYPREAKVQWKVDNALQSGNSQESVTEQDSKDSTYS

LSSTLTLSKADYEKHKVYACEVTHQGLSSPVTKSFNRGEC

APPENDIX 1-continued

Antibody variable region sequences

>1257VL (Seq. no. 79)
LAQIVLTQSPAIMSASPGEKVTMTCSASSSVSYIYWYQQKPGSSPRLLIYDASNLASGVP

VRFSGSGSGTSYSLTISRMEAEDAATYYCQQWSSYPITFGSGTKLEIKRTVAAPSVFIFP

PSDEQLKSGTASVVCLLNNFYPREAKVQWKVDNALQSGNSQESVTEQDSKDSTYSLSSTL

TLSKADYEKHKVYACEVTHQGLSSPVTKSFNRGEC

>1260VL (Seq. no. 80)
LADIQMTQTTSSLSASLGDRVTISCSASQGITNYLNWYQQKPDGTVKLLIYYSSSLHSGV

PSRFSGSGSGTDYSLTISNLEPEDIATYYCQQYSEIPYTFGGGTKLELKRTVAAPSVFIF

PPSDEQLKSGTASVVCLLNNFYPREAKVQWKVDNALQSGNSQESVTEQDSKDSTYSLSST

LTLSKADYEKHKVYACEVTHQGLSSPVTKSFNRGEC

>1261VL (Seq. no. 81)
LAQIVLTQSPAIMSASPGEKVTITCSASSSVSYMHWFQQKPGTSPKLWIYSTSNLASGVP

ARFSGSGSGTSYSLTISRMEAEDAATYYCQQRSSYPYTFGGGTKLELKRTVAAPSVFIFP

PSDEQLKSGTASVVCLLNNFYPREAKVQWKVDNALQSGNSQESVTEQDSKDSTYSLSSTL

TLSKADYEKHKVYACEVTHQGLSSPVTKSFNRGEC

>1277VL (Seq. no. 82)
LADVVMTQTPLSLPVSLGDQASISCRSSQSLVHSNGNTYLHWYLQKPGQSPKLLIYKVSN

RFSGVPDRFSGSGSGTDFTLKISRVEAEDLGVYFCSQSTHVPTFGGGTKLEIKRTVAAPS

VFIFPPSDEQLKSGTASVVCLLNNFYPREAKVQWKVDNALQSGNSQESVTEQDSKDSTYS

LSSTLTLSKADYEKHKVYACEVTHQGLSSPVTKSFNRGEC

>1284VL (Seq. no. 83)
LADIVLTQSPASLAVSLGQRATISCRASQSVSTSTYSYMHWYQQKSGQPPKLLIKYASNL

ESGVPARFSGSGSGTDFTLNIHPVEEEDTATYYCQHSWEIPWTFGGGTKLEIKRTVAAPS

VFIFPPSDEQLKSGTASVVCLLNNFYPREAKVQWKVDNALQSGNSQESVTEQDSKDSTYS

LSSTLTLSKADYEKHKVYACEVTHQGLSSPVTKSFNRGEC

>1308VL (Seq. no. 84)
LADIQMTQTTSSLSASLGDRVTISCRASQDISNYLNWYQQKPDGTVKVLIYYTSRLHSGV

PSRFSGSGSGTDYSLTISNLEQEDIATYFCQQGNTLPYTFGGGTKLEIKRTVAAPSVFIF

PPSDEQLKSGTASVVCLLNNFYPREAKVQWKVDNALQSGNSQESVTEQDSKDSTYSLSST

LTLSKADYEKHKVYACEVTHQGLSSPVTKSFNRGEC

>1320VL (Seq. no. 85)
LADIQMTQTTSSLSASLGDRVTISCSASQDISNYLNWYQQKPDGTVKLLIYHTSTLHSGV

PSRFSGSGSGTDYSLTISNLEPEDIATYYCQQYSKLPWTFGGGTKLEIKRTVAAPSVFIF

PPSDEQLKSGTASVVCLLNNFYPREAKVQWKVDNALQSGNSQESVTEQDSKDSTYSLSST

LTLSKADYEKHKVYACEVTHQGLSSPVTKSFNRGEC

>1344VL (Seq. no. 86)
LADIQMTQTTSSLSASLGDRVTISCSASQGISNYLNWYQQKPDGTVKLLIYYTSSLHSGV

PSRFSGSGSGTDYSLTISNLEPEDIATYYCQQYSKLPYTFGGGTKLEIKRTVAAPSVFIF

PPSDEQLKSGTASVVCLLNNFYPREAKVQWKVDNALQSGNSQESVTEQDSKDSTYSLSST

LTLSKADYEKHKVYACEVTHQGLSSPVTKSFNRGEC

APPENDIX 1-continued

Antibody variable region sequences

>1347VL (Seq. no. 87)
LAENVLTQSPAIMSASPGEKVTMTCRASSSVSSSYLHWYQQKSGASPKLWIYSTSNLASG

VPARFSGSGSGTSYSLTVNSVETEDAATYYCHQYSGFPFTFGSGTKLELKRTVAAPSVFI

FPPSDEQLKSGTASVVCLLNNFYPREAKVQWKVDNALQSGNSQESVTEQDSKDSTYSLSS

TLTLSKADYEKHKVYACEVTHQGLSSPVTKSFNRGEC

APPENDIX 2

Antibody constant region sequences

>Human IGKC region (Seq. no. 88)
ttcatcttcccgccatctgatgagcagttgaaatctggaactgcctctgttgtgtgcctgctgaataact tctatcccagagaggccaaagtacagtggaaggtggataacgccctccaatcgggtaactcccaggagag tgtcacagagcaggacagcaaggacagcacctacagcctcagcagcaccctgacgctgagcaaagcagac tacgagaaacacaaagtctacgcctgcgaagtcacccatcagggcctgagctcgcccgtcacaaagagct tcaacaggggagagtgttaataagcggccgccggtggaggcggt >Human IGKC region (Seq. no. 89)
TVAAPSVFIFPPSDEQLKSGTASVVCLLNNFYPREAKVQWKVDNALQSGNSQESVTEQDS

KDSTYSLSSTLTLSKADYEKHKVYACEVTHQGLSSPVTKSFNRGEC

```
Exon1     1 . . . 298
Intron  299 . . . 689
Exon2   690 . . . 734
Intron  735 . . . 852
Exon3   853 . . . 1182
Intron 1183 . . . 1279
Exon4  1280 . . . 1602
```

>human IGHG1 constant domain genomic sequence (Seq. no. 90)
agtgcctccaccaagggcccatcggtcttccccctggcaccctcctccaagagcacctctgggggcacag cggccctgggctgcctggtcaaggactacttccccgaaccggtgacggtgtcgtggaactcaggcgccct gaccagcggcgtgcacaccttcccggctgtcctacagtcctcaggactctactccctcagcagcgtggtg accgtgccctccagcagcttgggcacccagacctacatctgcaacgtgaatcacaagcccagcaacacca aggtggacaagagagttggtgagaggccagcacagggagggagggtgtctgctggaagccaggctcagcg ctcctgcctggacgcatcccggctatgcagtcccagtccagggcagcaaggcaggccccgtctgcctctt cacccggaggcctctgcccgcccactcatgctcaggagagggtcttctggcttttttcccaggctctg ggcaggcacaggctaggtgcccctaacccaggccctgcacacaaaggggcaggtgctgggctcagacctg ccaagagccatatccgggaggaccctgcccctgacctaagcccaccccaaaggccaaactctccactccc tcagctcggacaccttctctcctcccagattccagtaactcccaatcttctctctgcagagcccaaatct tgtgacaaaactcacacatgcccaccgtgcccaggtaagccagcccaggcctcgccctccagctcaaggc gggacaggtgccctagagtagcctgcatccagggacaggccccagccgggtgctgacacgtccacctcca tctcttcctcagcacctgaactcctggggggaccgtcagtcttcctcttccccccaaaacccaaggacac cctcatgatctcccggacccctgaggtcacatgcgtggtggtggacgtgagccacgaagaccctgaggtc aagttcaactggtacgtggacggcgtggaggtgcataatgccaagacaaagccgcgggaggagcagtaca acagcacgtaccgtgtggtcagcgtcctcaccgtcctgcaccaggactggctgaatggcaaggagtacaa gtgcaaggtctccaacaaagcccctcccagcccccatcgagaaaaccatctccaaagccaaaggtgggacc cgtggggtgcgagggccacatggacagaggccggctcggcccaccctctgccctgagagtgaccgctgta ccaacctctgtccctacagggcagccccgagaaccacaggtgtacaccctgcccccatcccgggaggaga

APPENDIX 2-continued

Antibody constant region sequences tgaccaagaaccaggtcagcctgacctgcctggtcaaaggcttctatcccagcgacatcgccgtggagtg ggagagcaatgggcagccggagaacaactacaagaccacgcctcccgtgctggactccgacggctccttc ttcctctatagcaagctcaccgtggacaagagcaggtggcagcaggggaacgtcttctcatgctccgtga tgcatgaggctctgcacaaccactacacgcagaagagcctctccctgtccccgggtaaatga >IGHG1 (Seq. no. 91)
SASTKGPSVFPLAPSSKSTSGGTAALGCLVKDYFPEPVTVSWNSGALTSGVHTFPAVLQSSGLYSLSSVVT
VPSSSLGTQTYICNVNHKPSNTKVDKRVEPKSCDKTHTCPPCPAPELLGGPSVFLFPPKPKDTLMISRTP
EVTCVVVDVSHEDPEVKFNWYVDGVEVHNAKTKPREEQYNSTYRVVSVLTVLHQDWLNGKEYKCKVSNKA
LPAPIEKTISKAKGQPREPQVYTLPPSREEMTKNQVSLTCLVKGFYPSDIAVEWESNGQPENNYKTTPPV
LDSDGSFFLYSKLTVDKSRWQQGNVFSCSVMHEALHNHYTQKSLSLSPGK

APPENDIX 3

Dual variable domain antibody sequences

>992L1024\IGHV (Seq. no. 92)
ggcgcgccgaggtccaactgcagcaacctgggtctgagctggtgaggcctggagcttcagtgaagctgtc ctgcaaggcttctggctacacattcaccagctactggatgcactgggtgaagcagaggcctggacaaggc cttgagtggattgggaatatttatcctggtagtcgtagtactaactacgatgagaagttcaagagcaagg ccacactgactgtagacacatcctccagcacagcctacatgcagctcagcagcctgacatctgaggactc tgcggtctattactgtacaagaaatggggattactacgttagtagcgggatgctatggactactggggt caaggaacctcagtcaccgtctcgtcagccagcaccaagggcccccaggtccaactgcagcagcctgggg ctgaactggtggagcctgggggttcagtgaagctgtcctgcaaggcttctggctacaccttcaccagtca ctggatgcactgggtgaagcagaggcctggacaaggccttgagtggataggtgagattaatcctagcagc ggtcgtaataactacaatgagaagttcaagagtaaggccacactgactgtagacaaatcctccagcacag cctacatgcaattcagcagcctgacatctgaggactctgcggtctattattgtgtaagatactatggtta cgacgaagctatggactactggggtcaaggaacctcagtcaccgtctcgag >992L1024\IGKV (Seq. no. 93)
gctagccgacattcagatgactcagactacatcctccctgtctgcctctctgggagacagagtcaccatc agttgcaggacaagtcaggacattggcaattatttaaactggtatcagcagaaaccagatggaactgtta aactcctgatctactacacatcaagattacactcaggagtcccatcaaggttcagtggcagtgggtctgg aacagattttctctcaccattaacaacgtggagcaagaggatgttgccacttacttttgccaacactat aatacggttcctccgacgttcggtggaggcaccaagctggaaatcaaacgaactgtggctgcaccagaca tcgtgatgacacaagctgcattctccaatccagtcactcttggaacatcagcttccatctcctgcaggtc tagtaagagtctcctacatagtaatggcatcacttatttgtattggtatctgcagaagccaggccagtct cctcagctcctgatttatcagatgtccaaccttgcctcaggagtcccagacaggttcagtagcagtgggt caggaactgatttcacactgagaatcagcagagtggaggctgaggatgtgggtgtttattactgtgctca aaatctagaacttccgtacacgttcggaggggggaccaagctggaaataaaacgaactgtggctgcacca tctgtcttcatcttcccgccatctgatgagcagttgaaatctggaactgcctctgttgtgtgcctgctga ataacttctatcccagagaggccaaagtacagtggaaggtggataacgccctccaatcgggtaactccca ggagagtgtcacagagcaggacagcaaggacagcacctacagcctcagcagcaccctgacgctgagcaaa APPENDIX 3-continued Dual variable domain antibody sequences gcagactacgagaaacacaaagtctacgcctgcgaagtcacccatcagggcctgagctcgcccgtcacaa agagcttcaacaggggagagtgttaataagcggccgc >1024L992\IGHV (Seq. no. 94)
ggcgcgcccaggtccaactgcagcagcctggggctgaactggtggagcctgggggttcagtgaagctgtc ctgcaaggcttctggctacaccttcaccagtcactggatgcactgggtgaagcagaggcctggacaaggc cttgagtggataggtgagattaatcctagcagcggtcgtaataactacaatgagaagttcaagagtaagg ccacactgactgtagacaaatcctccagcacagcctacatgcaattcagcagcctgacatctgaggactc tgcggtctattattgtgtaagatactatggttacgacgaagctatggactactggggtcaaggaacctca gtcaccgtctcgtcagccagcaccaagggccccgaggtccaactgcagcaacctgggtctgagctggtga ggcctggagcttcagtgaagctgtcctgcaaggcttctggctacacattcaccagctactggatgcactg ggtgaagcagaggcctggacaaggccttgagtggattgggaatatttatcctggtagtcgtagtactaac tacgatgagaagttcaagagcaaggccacactgactgtagacacatcctccagcacagcctacatgcagc tcagcagcctgacatctgaggactctgcggtctattactgtacaagaaatggggattactacgttagtag cggggatgctatggactactggggtcaaggaacctcagtcaccgtctcgag >1024L992\IGKV (Seq. no. 95)
gctagccgacatcgtgatgacacaagctgcattctccaatccagtcactcttggaacatcagcttccatc tcctgcaggtctagtaagagtctcctacatagtaatggcatcacttatttgtattggtatctgcagaagc caggccagtctcctcagctcctgatttatcagatgtccaaccttgcctcaggagtcccagacaggttcag tagcagtgggtcaggaactgatttcacactgagaatcagcagagtggaggctgaggatgtgggtgtttat tactgtgctcaaaatctagaacttccgtacacgttcggaggggggaccaagctggaaataaaacgaactg tggctgcaccagacattcagatgactcagactacatcctccctgtctgcctctctgggagacagagtcac catcagttgcaggacaagtcaggacattggcaattatttaaactggtatcagcagaaaccagatggaact gttaaactcctgatctactacacatcaagattacactcaggagtcccatcaaggttcagtggcagtgggt ctggaacagattttctctcaccattaacaacgtggagcaagaggatgttgccacttacttttgccaaca ctataatacggttcctccgacgttcggtggaggcaccaagctggaaatcaaacgaactgtggctgcacca tctgtcttcatcttcccgccatctgatgagcagttgaaatctggaactgcctctgttgtgtgcctgctga ataacttctatcccagagaggccaaagtacagtggaaggtggataacgccctccaatcgggtaactccca ggagagtgtcacagagcaggacagcaaggacagcacctacagcctcagcagcaccctgacgctgagcaaa gcagactacgagaaacacaaagtctacgcctgcgaagtcacccatcagggcctgagctcgcccgtcacaa agagcttcaacaggggagagtgttaataagcggccgc >992L1024\IGHV (Seq. no. 96)
RAEVQLQQPGSELVRPGASVKLSCKASGYTFTSYWMHWVKQRPGQGLEWIGNIYPGSRST

NYDEKFKSKATLTVDTSSSTAYMQLSSLTSEDSAVYYCTRNGDYYVSSGDAMDYWGQGTS

VTVSSASTKGPQVQLQQPGAELVEPGGSVKLSCKASGYTFTSHWMHWVKQRPGQGLEWIG

EINPSSGRNNYNEKFKSKATLTVDKSSSTAYMQFSSLTSEDSAVYYCVRYYGYDEAMDYW

GQGTSVTVS

>992L1024\IGKV (Seq. no. 97)
LADIQMTQTTSSLSASLGDRVTISCRTSQDIGNYLNWYQQKPDGTVKLLIYYTSRLHSGV

PSRFSGSGSGTDFSLTINNVEQEDVATYFCQHYNTVPPTFGGGTKLEIKRTVAAPDIVMT

QAAFSNPVTLGTSASISCRSSKSLLHSNGITYLYWYLQKPGQSPQLLIYQMSNLASGVPD

RFSSSGSGTDFTLRISRVEAEDVGVYYCAQNLELPYTFGGGTKLEIKRTVAAPSVFIFPP

APPENDIX 3-continued

Dual variable domain antibody sequences

SDEQLKSGTASVVCLLNNFYPREAKVQWKVDNALQSGNSQESVTEQDSKDSTYSLSSTLT

LSKADYEKHKVYACEVTHQGLSSPVTKSFNRGEC

>1024L992\IGHV (Seq. no. 98)
RAQVQLQQPGAELVEPGGSVKLSCKASGYTFTSHWMHWVKQRPGQGLEWIGEINPSSGRN

NYNEKFKSKATLTVDKSSSTAYMQFSSLTSEDSAVYYCVRYYGYDEAMDYWGQGTSVTVS

SASTKGPEVQLQQPGSELVRPGASVKLSCKASGYTFTSYWMHWVKQRPGQGLEWIGNIYP

GSRSTNYDEKFKSKATLTVDTSSSTAYMQLSSLTSEDSAVYYCTRNGDYYVSSGDAMDYW

GQGTSVTVS

>1024L992\IGKV (Seq. no. 99)
LADIVMTQAAFSNPVTLGTSASISCRSSKSLLHSNGITYLYWYLQKPGQSPQLLIYQMSN

LASGVPDRFSSSGSGTDFTLRISRVEAEDVGVYYCAQNLELPYTFGGGTKLEIKRTVAAP

DIQMTQTTSSLSASLGDRVTISCRTSQDIGNYLNWYQQKPDGTVKLLIYYTSRLHSGVPS

RFSGSGSGTDFSLTINNVEQEDVATYFCQHYNTVPPTFGGGTKLEIKRTVAAPSVFIFPP

SDEQLKSGTASVVCLLNNFYPREAKVQWKVDNALQSGNSQESVTEQDSKDSTYSLSSTLT

LSKADYEKHKVYACEVTHQGLSSPVTKSFNRGEC

The invention claimed is:

1. A method for treatment of cancer in a subject in need thereof that has been subjected to a prior treatment regimen using an anti-human EGFR antibody, said method comprising administering to said subject an antibody composition comprising at least a first anti-human EGFR antibody molecule and a second anti-human EGFR antibody molecule distinct from the first molecule,
 a. wherein the first anti-human EGFR antibody molecule is selected from the group consisting,
  (i) an antibody whose light chain comprises amino acids 3-216 of SEQ ID NO:72, and whose heavy chain has a variable domain (VH) comprising amino acids 3-124 of SEQ ID NO:40 and a constant region comprising the amino acid sequence of SEQ ID NO: 91;
  (ii) an antibody whose light chain has a variable domain (VL) comprising amino acids 3-109 of SEQ ID NO:72 and whose VH comprises amino acids 3-124 of SEQ ID NO:40; and
  (iii) an antibody having the light chain CDR1, CDR2, and CDR3 in SEQ ID NO: 72 and the heavy chain CDR1, CDR2, and CDR3 in SEQ ID NO: 40; and
 b. wherein the second anti-human EGFR antibody molecule is selected from the group consisting of
  (i) an antibody whose light chain comprises amino acids 3-221 of SEQ ID NO:73, and whose heavy chain has a variable domain (VH) comprising amino acids 3-120 of SEQ ID NO:41 and a constant region comprising the amino acid sequence of SEQ ID NO: 91:
  (ii) an antibody whose VL comprises amino acids 3-114 of SEQ ID NO:73 and whose VH comprises amino acids 3-120 of SEQ ID NO:41; and
  (iii) an antibody having the light chain CDR1, CDR2, and CDR3 in SEQ ID NO: 73 and the heavy chain CDR1, CDR2, and CDR3 in SEQ ID NO: 41,
 wherein the prior treatment regimen does not use the first antibody molecule, the second antibody molecule, an antibody molecule have light chain CDR1, CDR2 and CDR3 in SEQ ID NO:74 and the heavy chain CDR1, CDR2, and CDR3 in SEQ ID NO:42, or any combination of these antibody molecules.

2. The method of claim 1, wherein said prior treatment regimen used an anti-human EGFR antibody selected from the group consisting of cetuximab, panitumumab, zalutumumab, nimotuzumab, ICR62, mAb806, matuzumab, and antibodies capable of binding the same epitope as cetuximab, panitumumab, or zalutumumab.

3. The method of claim 2, wherein said anti-human EGFR antibody is selected from the group consisting of cetuximab, panitumumab, zalutumumab, and antibodies capable of binding the same epitope as any of these.

4. The method of claim 2, wherein said anti-human EGFR antibody is selected from the group consisting of cetuximab, panitumumab, and antibodies capable of binding the same epitope as either of these.

5. The method of claim 2, wherein said anti-human EGFR antibody is cetuximab or an antibody capable of binding the same epitope as cetuximab.

6. The method of claim 1, wherein said cancer is selected from the group consisting of head-and-neck cancer, colon cancer, breast cancer, renal cancer, lung cancer, ovarian cancer, prostate cancer, glioma, pancreatic cancer, bladder cancer, non-small-cell-lung-carcinoma (NSCLC), gastric cancer, cervical cancer, hepatocellular cancer, gastrophageal cancer, colorectal cancer, rectal cancer, epithelioid carcinoma, RCC, squamous cell carcinoma of the head and neck (SCCHN), esophageal cancer, glioblastoma multiforme, squamous cell carcinoma, kidney cancer, sarcoma, and melanoma.

7. The method of claim 1, wherein said composition is used as adjuvant therapy following surgery and/or radiation therapy.

8. The method of claim 1, wherein said composition is used for combination therapy together with (a) chemotherapy, (b) at least one tyrosine kinase inhibitor, (c) at least one angiogenesis inhibitor, (d) at least one hormone, (e) at least one differentiation inducing agent, or (f) any combination of (a)-(e).

9. The method of claim 1, wherein said prior treatment regimen was first-line therapy.

10. The method of claim 1, wherein said prior treatment regimen was second-line therapy.

11. The method of claim 10, wherein the second-line therapy comprised a treatment regimen with (a) chemotherapy, (b) at least one tyrosine kinase inhibitor, (c) at least one angiogenesis inhibitor, (d) at least one hormone, (e) at least one differentiation inducing agent, or (f) any combination of (a)-(e).

12. The method of claim 8 or 11, wherein the chemotherapy comprises administration of a compound selected from the group consisting of adriamycin, cisplatin, taxol, doxorubicin, topotecan, fluoropyrimidine, oxaliplatin, and irinotecan.

13. The method of claim 1, wherein the cancer of said subject had progressed during said prior treatment regimen.

14. The method of claim 1, wherein the cancer of said subject had progressed following said prior treatment regimen.

15. The method of claim 1, wherein said cancer was resistant or partially resistant to said prior treatment regimen.

16. The method of claim 1, wherein
   a. said first anti-human EGFR antibody molecule comprises a light chain comprising amino acids 3-216 of SEQ ID NO:72, and a heavy chain that has a VH comprising amino acids 3-124 of SEQ ID NO:40 and a constant region comprising the amino acid sequence of SEQ ID NO: 91; and
   b. said second anti-human EGFR antibody molecule comprises a light chain comprising amino acids 3-221 of SEQ ID NO:73, and a heavy chain that has a VH comprising amino acids 3-120 of SEQ ID NO:41 and a constant region comprising the amino acid sequence of SEQ ID NO: 91.

17. The method of claim 1, wherein
   a. the first anti-human EGFR antibody molecule whose VL comprises amino acids 3-109 of SEQ ID NO:72, and whose VH comprises amino acids 3-124 of SEQ ID NO:40; and
   b. the second anti-human EGFR antibody molecule whose VL comprises amino acids 3-114 of SEQ ID NO:73 and whose VH comprises amino acids 3-120 of SEQ ID NO:41.

18. The method of claim 1, wherein the first and second anti-human EGFR antibody molecules of said composition do not inhibit the binding to human EGFR of each other.

19. The method of claim 1, wherein at least one of the antibody molecules of said composition is capable of increasing the maximum binding capacity of the other antibody molecule with respect to human EGFR.

20. The method of claim 1, wherein the proportion of the first antibody molecule relative to the second antibody molecule in the composition is between 5 and 95%.

21. The method of claim 1, wherein the first and second antibody molecules of the composition are of isotype IgG1 or IgG2.

22. The method of claim 1, wherein the composition does not contain further anti-EGFR antibody molecules in addition to said first and second antibody molecules.

23. The method of claim 1, wherein the composition further comprises a third distinct anti-EGFR antibody molecule, wherein said third distinct anti-EGFR antibody molecule is selected from the group consisting of
   (i) an antibody whose light chain comprises amino acids 3-220 of SEQ ID NO:74, and whose heavy chain has a VH comprising amino acids 3-120 of SEQ ID NO:42 and a constant region comprising the amino acid sequence of SEQ ID NO: 91;
   (ii) an antibody whose VL comprises amino acids 3-114 of SEQ ID NO:74 and whose VH comprises amino acids 3-120 of SEQ ID NO:42; and
   (iii) an antibody having the light chain CDR1, CDR2, and CDR3 in SEQ ID NO: 74 and the heavy chain CDR1, CDR2, and CDR3 in SEQ ID NO: 42.

24. The method of claim 23, wherein said third antibody molecule results in an enhanced binding to human EGFR of said first and/or second antibody molecule.

25. The method of claim 23, wherein the composition does not contain further anti-EGFR antibody molecules in addition to said first, second, and third antibody molecules.

26. The method of claim 1, wherein the distinct antibody molecules of the composition are prepared for simultaneous, successive or separate administration.

27. The method of claim 1, wherein the composition leads to receptor internalisation.

28. The method of claim 1, wherein the composition leads to regression of A431NS tumours in vivo.

29. The method of claim 1, wherein the composition induces terminal differentiation in A431NS cells in vivo.

30. The method of claim 1, wherein the composition up-regulates tumour involucrin expression in vivo.

31. The method of claim 1, wherein the first and second anti-EGFR antibody molecules form part of a bi-specific binding molecule.

32. The method of claim 31, wherein the bi-specific binding molecule comprises the light chain CDR1, CDR2, and CDR3 in SEQ ID NOs: 72 and 73 and the heavy chain CDR1, CDR2, and CDR3 in SEQ ID NOs: 40 and 41.

33. The method of claim 31, wherein the bi-specific binding molecule is a dual-variable-domain antibody.

34. The method of claim 31, wherein the bi-specific binding molecule is a bi-specific Fab-fragment or a bi-specific scFv.

35. The method of claim 1, wherein the ratio of the first antibody molecule to the second antibody molecule is 1:1.

36. A method for treatment of cancer in a subject in need thereof, comprising administering to said subject an antibody composition comprising at least a first anti-human EGFR antibody molecule and a second anti-human EGFR antibody molecule distinct from the first molecule,
   a. wherein the first anti-human EGFR antibody molecule is selected from the group consisting of
      (i) an antibody whose light chain comprises amino acids 3-216 of SEQ ID NO:72, and whose heavy chain has a variable domain (VH) comprising amino acids 3-124 of SEQ ID NO:40 and a constant region comprising the amino acid sequence of SEQ ID NO: 91;
      (ii) an antibody whose VL comprises amino acids 3-109 of SEQ ID NO:72 and whose VH comprises amino acids 3-124 of SEQ ID NO:40; and
      (iii) an antibody having the light chain CDR1, CDR2, and CDR3 in SEQ ID NO: 72 and the heavy chain CDR1, CDR2, and CDR3 in SEQ ID NO: 40; and
   b. wherein the second anti-human EGFR antibody molecule is selected from the group consisting of
      (i) an antibody whose light chain comprises amino acids 3-221 of SEQ ID NO:73, and whose heavy chain has a variable domain (VH) comprising amino acids 3-120 of SEQ ID NO:41 and a constant region comprising the amino acid sequence of SEQ ID NO: 91;
      (ii) an antibody whose VL comprises amino acids 3-114 of SEQ ID NO:73 and whose VH comprises amino acids 3-120 of SEQ ID NO:41; and
      (iii) an antibody having the light chain CDR1, CDR2, and CDR3 in SEQ ID NO: 73 and the heavy chain CDR1, CDR2, and CDR3 in SEQ ID NO: 41,
   wherein said cancer is resistant or partially resistant to treatment with at least one other anti-EGFR antibody selected from the group consisting of cetuximab, panitumumab, zalutumumab, nimotuzumab, ICR62, mAb806, matuzumab, and antibodies capable of binding the same epitope as cetuximab, panitumumab, or zalutumumab.

37. The method of claim 36, wherein
   a. said first anti-human EGFR antibody molecule is selected from the group consisting of
      (i) an antibody whose light chain comprises amino acids 3-216 of SEQ ID NO:72, and whose heavy chain has a variable domain (VH) comprising amino acids 3-124 of SEQ ID NO:40 and a constant region comprising the amino acid sequence of SEQ ID NO: 91; and
      (ii) an antibody whose VL comprises amino acids 3-109 of SEQ ID NO:72 and whose VH comprises amino acids 3-124 of SEQ ID NO:40; and
   b. said second anti-human EGFR antibody molecule is selected from the group consisting of
      (i) an antibody whose light chain comprises amino acids 3-221 of SEQ ID NO:73, and whose heavy chain has a variable domain (VH) comprising amino acids 3-120 of SEQ ID NO:41 and a constant region comprising the amino acid sequence of SEQ ID NO: 91; and
      (ii) an antibody whose VL comprises amino acids 3-114 of SEQ ID NO:73 and whose VH comprises amino acids 3-120 of SEQ ID NO:41.

38. The method of claim 36, wherein said composition is used for first-line therapy.

39. The method of claim 36, wherein said composition is used for second-line therapy following a treatment regimen with (a) chemotherapy, (b) at least one tyrosine kinase inhibitor, (c) at least one angiogenesis inhibitor, (d) at least one hormone, (e) at least one differentiation inducing agent, or (f) any combination of (a)-(e).

40. The method of claim 36, wherein said composition is used for third-line therapy.

41. The method of claim 36, wherein said composition is used for combination therapy together with (a) chemotherapy, (b) at least one tyrosine kinase inhibitor, (c) at least one angiogenesis inhibitor, (d) at least one hormone, (e) at least one differentiation inducing agent, or (f) any combination of (a)-(e).

42. The method of claim 36, wherein said composition is used as adjuvant therapy following surgery and/or radiation therapy.

43. The method of claim 36, wherein the resistance or partial resistance has been determined by assaying a sample of cancer cells isolated from said subject.

44. A method of reducing EGFR signalling comprising administering an antibody composition to a composition of EGFR expressing cells, said cells having previously been subjected to an anti-human EGFR antibody selected from the group consisting of cetuximab, panitumumab, zalutumumab, nimotuzumab, ICR62, mAb806, matuzumab, and antibodies capable of binding the same epitope as cetuximab, panitumumab, or zalutumumab, wherein said antibody composition comprises at least a first anti-human EGFR antibody molecule and a second anti-human EGFR antibody molecule distinct from the first molecule,
   a. wherein the first anti-human EGFR antibody molecule is selected from the group consisting of
      (i) an antibody whose light chain comprises amino acids 3-216 of SEQ ID NO:72, and whose heavy chain has a variable domain (VH) comprising amino acids 3-124 of SEQ ID NO:40 and a constant region comprising the amino acid sequence of SEQ ID NO: 91;
      (ii) an antibody whose VL comprises amino acids 3-109 of SEQ ID NO:72 and whose VH comprises amino acids 3-124 of SEQ ID NO:40; and
      (iii) an antibody having the light chain CDR1, CDR2, and CDR3 in SEQ ID NO: 72 and the heavy chain CDR1, CDR2, and CDR3 in SEQ ID NO: 40; and
   b. wherein the second anti-human EGFR antibody molecule is selected from the group consisting of
      (i) an antibody whose light chain comprises amino acids 3-221 of SEQ ID NO:73, and whose heavy chain has a variable domain (VH) comprising amino acids 3-120 of SEQ ID NO:41 and a constant region comprising the amino acid sequence of SEQ ID NO: 91;
      (ii) an antibody whose VL comprises amino acids 3-114 of SEQ ID NO:73 and whose VH comprises amino acids 3-120 of SEQ ID NO:41; and
      (iii) an antibody having the light chain CDR1, CDR2, and CDR3 in SEQ ID NO: 73 and the heavy chain CDR1, CDR2, and CDR3 in SEQ ID NO: 41,
      whereby the EGFR signalling is reduced.

45. A method of killing cells expressing EGFR comprising administering an antibody composition to EGFR expressing cells, said cells having previously been subjected to an anti-human EGFR antibody selected from the group consisting of cetuximab, panitumumab, zalutumumab, nimotuzumab, ICR62, mAb806, matuzumab, and antibodies capable of binding the same epitope as cetuximab, panitumumab, or zalutumumab, wherein said antibody composition comprises at least a first anti-human EGFR antibody molecule and a second anti-human EGFR antibody molecule distinct from the first molecule,
- a. wherein the first anti-human EGFR antibody molecule is selected from the group consisting of
  - (i) an antibody whose light chain comprises amino acids 3-216 of SEQ ID NO:72, and whose heavy chain has a variable domain (VH) comprising amino acids 3-124 of SEQ ID NO:40 and a constant region comprising the amino acid sequence of SEQ ID NO: 91;
  - (ii) an antibody whose VL comprises amino acids 3-109 of SEQ ID NO:72 and whose VH comprises amino acids 3-124 of SEQ ID NO:40; and
  - (iii) an antibody having the light chain CDR1, CDR2, and CDR3 in SEQ ID NO: 72 and the heavy chain CDR1, CDR2, and CDR3 in SEQ ID NO: 40; and
- b. wherein the second anti-human EGFR antibody molecule is selected from the group consisting of
  - (i) an antibody whose light chain comprises amino acids 3-221 of SEQ ID NO:73, and whose heavy chain has a variable domain (VH) comprising amino acids 3-120 of SEQ ID NO:41 and a constant region comprising the amino acid sequence of SEQ ID NO: 91;
  - (ii) an antibody whose VL comprises amino acids 3-114 of SEQ ID NO:73 and whose VH comprises amino acids 3-120 of SEQ ID NO:41; and
  - (iii) an antibody having the light chain CDR1, CDR2, and CDR3 in SEQ ID NO: 73 and the heavy chain CDR1, CDR2, and CDR3 in SEQ ID NO: 41, wherein the EGFR expressing cells are killed.

46. A method of inducing apoptosis in cells expressing EGFR, comprising administering an antibody composition to EGFR expressing cells, said cells having previously been subjected to an anti-human EGFR antibody selected from the group consisting of cetuximab, panitumumab, zalutumumab, nimotuzumab, ICR62, mAb806, matuzumab, and antibodies capable of binding the same epitope as cetuximab, panitumumab, or zalutumumab, wherein said antibody composition comprises at least a first anti-human EGFR antibody molecule and a second anti-human EGFR antibody molecule distinct from the first molecule,
- a. wherein the first anti-human EGFR antibody molecule is selected from the group consisting of
  - (i) an antibody whose light chain comprises amino acids 3-216 of SEQ ID NO:72, and whose heavy chain has a variable domain (VH) comprising amino acids 3-124 of SEQ ID NO:40 and a constant region comprising the amino acid sequence of SEQ ID NO: 91;
  - (ii) an antibody whose VL comprises amino acids 3-109 of SEQ ID NO:72 and whose VH comprises amino acids 3-124 of SEQ ID NO:40; and
  - (iii) an antibody having the light chain CDR1, CDR2, and CDR3 in SEQ ID NO: 72 and the heavy chain CDR1, CDR2, and CDR3 in SEQ ID NO: 40; and
- b. wherein the second anti-human EGFR antibody molecule is selected from the group consisting of
  - (i) an antibody whose light chain comprises amino acids 3-221 of SEQ ID NO:73, and whose heavy chain has a variable domain (VH) comprising amino acids 3-120 of SEQ ID NO:41 and a constant region comprising the amino acid sequence of SEQ ID NO: 91;
  - (ii) an antibody whose VL comprises amino acids 3-114 of SEQ ID NO:73 and whose VH comprises amino acids 3-120 of SEQ ID NO:41; and
  - (iii) an antibody having the light chain CDR1, CDR2, and CDR3 in SEQ ID NO: 73 and the heavy chain CDR1, CDR2, and CDR3 in SEQ ID NO: 41, thereby inducing apoptosis.

47. A method of inhibiting proliferation of cells expressing EGFR comprising administering an antibody composition to EGFR expressing cells, said cells having previously been subjected to an anti-human EGFR antibody selected from the group consisting of cetuximab, panitumumab, zalutumumab, nimotuzumab, ICR62, mAb806, matuzumab, and antibodies capable of binding the same epitope as cetuximab, panitumumab, or zalutumumab, wherein said antibody composition comprises at least a first anti-human EGFR antibody molecule and a second anti-human EGFR antibody molecule distinct from the first molecule,
- a. wherein the first anti-human EGFR antibody molecule is selected from the group consisting of
  - (i) an antibody whose light chain comprises amino acids 3-216 of SEQ ID NO:72, and whose heavy chain has a variable domain (VH) comprising amino acids 3-124 of SEQ ID NO:40 and a constant region comprising the amino acid sequence of SEQ ID NO: 91;
  - (ii) an antibody whose VL comprises amino acids 3-109 of SEQ ID NO:72 and whose VH comprises amino acids 3-124 of SEQ ID NO:40; and
  - (iii) an antibody having the light chain CDR1, CDR2, and CDR3 in SEQ ID NO: 72 and the heavy chain CDR1, CDR2, and CDR3 in SEQ ID NO: 40; and
- b. wherein the second anti-human EGFR antibody molecule is selected from the group consisting of
  - (i) an antibody whose light chain comprises amino acids 3-221 of SEQ ID NO:73, and whose heavy chain has a variable domain (VH) comprising amino acids 3-120 of SEQ ID NO:41 and a constant region comprising the amino acid sequence of SEQ ID NO: 91;
  - (ii) an antibody whose VL comprises amino acids 3-114 of SEQ ID NO:73 and whose VH comprises amino acids 3-120 of SEQ ID NO:41; and
  - (iii) an antibody having the light chain CDR1, CDR2, and CDR3 in SEQ ID NO: 73 and the heavy chain CDR1, CDR2, and CDR3 in SEQ ID NO: 41, thereby inhibiting proliferation.

48. A method of inducing differentiation of tumour cells in vivo, comprising administering an antibody composition to EGFR expressing tumour cells, said cells having previously been subjected to an anti-human EGFR antibody selected from the group consisting of cetuximab, panitumumab, zalutumumab, nimotuzumab, ICR62, mAb806, matuzumab, and antibodies capable of binding the same epitope as cetuximab, panitumumab, or zalutumumab, wherein said antibody composition comprises at least a first anti-human EGFR antibody molecule and a second anti-human EGFR antibody molecule distinct from the first molecule,
- a. wherein the first anti-human EGFR antibody molecule is selected from the group consisting of
  - (i) an antibody whose light chain comprises amino acids 3-216 of SEQ ID NO:72, and whose heavy chain has a variable domain (VH) comprising amino acids 3-124 of SEQ ID NO:40 and a constant region comprising the amino acid sequence of SEQ ID NO: 91;
  - (ii) an antibody whose VL comprises amino acids 3-109 of SEQ ID NO:72 and whose VH comprises amino acids 3-124 of SEQ ID NO:40; and
  - (iii) an antibody having the light chain CDR1, CDR2, and CDR3 in SEQ ID NO: 72 and the heavy chain CDR1, CDR2, and CDR3 in SEQ ID NO: 40; and b. wherein the second anti-human EGFR antibody molecule is selected from the group consisting of
  (i) an antibody whose light chain comprises amino acids 3-221 of SEQ ID NO:73, and whose heavy chain has a variable domain (VH) comprising amino acids 3-120 of SEQ ID NO:41 and a constant region comprising the amino acid sequence of SEQ ID NO: 91;
  (ii) an antibody whose VL comprises amino acids 3-114 of SEQ ID NO:73 and whose VH comprises amino acids 3-120 of SEQ ID NO:41; and
  (iii) an antibody having the light chain CDR1, CDR2, and CDR3 in SEQ ID NO: 73 and the heavy chain CDR1, CDR2, and CDR3 in SEQ ID NO: 41, thereby inducing differentiation of the tumour cells.

49. The method of claim 48, wherein said differentiation is terminal.

50. The method of claim 48, wherein said differentiation is accompanied by an increase in involucrin expression.

51. A method for inducing internalisation of EGFR comprising administering an antibody composition to EGFR expressing cells, said cells having previously been subjected to an anti-human EGFR antibody selected from the group consisting of cetuximab, panitumumab, zalutumumab, nimotuzumab, ICR62, mAb806, matuzumab, and antibodies capable of binding the same epitope as cetuximab, panitumumab, or zalutumumab, wherein said antibody composition comprises at least a first anti-human EGFR antibody molecule and a second anti-human EGFR antibody molecule distinct from the first molecule,
  a. wherein the first anti-human EGFR antibody molecule is selected from the group consisting of
    (i) an antibody whose light chain comprises amino acids 3-216 of SEQ ID NO:72, and whose heavy chain has a variable domain (VH) comprising amino acids 3-124 of SEQ ID NO:40 and a constant region comprising the amino acid sequence of SEQ ID NO: 91;
    (ii) an antibody whose VL comprises amino acids 3-109 of SEQ ID NO:72 and whose VH comprises amino acids 3-124 of SEQ ID NO:40; and
    (iii) an antibody having the light chain CDR1, CDR2, and CDR3 in SEQ ID NO: 72 and the heavy chain CDR1, CDR2, and CDR3 in SEQ ID NO: 40; and
  b. wherein the second anti-human EGFR antibody molecule is selected from the group consisting of
    (i) an antibody whose light chain comprises amino acids 3-221 of SEQ ID NO:73, and whose heavy chain has a variable domain (VH) comprising amino acids 3-120 of SEQ ID NO:41 and a constant region comprising the amino acid sequence of SEQ ID NO: 91;
    (ii) an antibody whose VL comprises amino acids 3-114 of SEQ ID NO:73 and whose VH comprises amino acids 3-120 of SEQ ID NO:41; and
    (iii) an antibody having the light chain CDR1, CDR2, and CDR3 in SEQ ID NO: 73 and the heavy chain CDR1, CDR2, and CDR3 in SEQ ID NO: 41,
  thereby inducing internalisation of EGFR.

52. A method of reducing EGFR signalling comprising administering an antibody composition to EGFR expressing cells, said cells being resistant or partially resistant to an anti-human EGFR antibody selected from the group consisting of cetuximab, panitumumab, zalutumumab, nimotuzumab, ICR62, mAb806, matuzumab, and antibodies capable of binding the same epitope as cetuximab, panitumumab, or zalutumumab, wherein said antibody composition comprises at least a first anti-human EGFR antibody molecule and a second anti-human EGFR antibody molecule distinct from the first molecule,
  a. wherein the first anti-human EGFR antibody molecule is selected from the group consisting of
    (i) an antibody whose light chain comprises amino acids 3-216 of SEQ ID NO:72, and whose heavy chain has a variable domain (VH) comprising amino acids 3-124 of SEQ ID NO:40 and a constant region comprising the amino acid sequence of SEQ ID NO: 91;
    (ii) an antibody whose VL comprises amino acids 3-109 of SEQ ID NO:72 and whose VH comprises amino acids 3-124 of SEQ ID NO:40; and
    (iii) an antibody having the light chain CDR1, CDR2, and CDR3 in SEQ ID NO: 72 and the heavy chain CDR1, CDR2, and CDR3 in SEQ ID NO: 40; and
  b. wherein the second anti-human EGFR antibody molecule is selected from the group consisting of
    (i) an antibody whose light chain comprises amino acids 3-221 of SEQ ID NO:73, and whose heavy chain has a variable domain (VH) comprising amino acids 3-120 of SEQ ID NO:41 and a constant region comprising the amino acid sequence of SEQ ID NO: 91;
    (ii) an antibody whose VL comprises amino acids 3-114 of SEQ ID NO:73 and whose VH comprises amino acids 3-120 of SEQ ID NO:41; and
    (iii) an antibody having the light chain CDR1, CDR2, and CDR3 in SEQ ID NO: 73 and the heavy chain CDR1, CDR2, and CDR3 in SEQ ID NO: 41,
  whereby the EGFR signalling is reduced.

53. A method of killing cells expressing EGFR comprising administering an antibody composition to EGFR expressing cells, said cells being resistant or partially resistant to an anti-human EGFR antibody selected from the group consisting of cetuximab, panitumumab, zalutumumab, nimotuzumab, ICR62, mAb806, matuzumab, and antibodies capable of binding the same epitope as cetuximab, panitumumab, or zalutumumab, wherein said antibody composition comprises at least a first anti-human EGFR antibody molecule and a second anti-human EGFR antibody molecule distinct from the first molecule,
  a. wherein the first anti-human EGFR antibody molecule is selected from the group consisting of
    (i) an antibody whose light chain comprises amino acids 3-216 of SEQ ID NO:72, and whose heavy chain has a variable domain (VH) comprising amino acids 3-124 of SEQ ID NO:40 and a constant region comprising the amino acid sequence of SEQ ID NO: 91;
    (ii) an antibody whose VL comprises amino acids 3-109 of SEQ ID NO:72 and whose VH comprises amino acids 3-124 of SEQ ID NO:40; and
    (iii) an antibody having the light chain CDR1, CDR2, and CDR3 in SEQ ID NO: 72 and the heavy chain CDR1, CDR2, and CDR3 in SEQ ID NO: 40; and
  b. wherein the second anti-human EGFR antibody molecule is selected from the group consisting of
    (i) an antibody whose light chain comprises amino acids 3-221 of SEQ ID NO:73, and whose heavy chain has a variable domain (VH) comprising amino acids 3-120 of SEQ ID NO:41 and a constant region comprising the amino acid sequence of SEQ ID NO: 91;
    (ii) an antibody whose VL comprises amino acids 3-114 of SEQ ID NO:73 and whose VH comprises amino acids 3-120 of SEQ ID NO:41; and
    (iii) an antibody having the light chain CDR1, CDR2, and CDR3 in SEQ ID NO: 73 and the heavy chain CDR1, CDR2, and CDR3 in SEQ ID NO: 41, wherein the EGFR expressing cells are killed.

54. A method of inducing apoptosis in cells expressing EGFR, comprising administering an antibody composition to EGFR expressing cells, said cells being resistant or partially resistant to an anti-human EGFR antibody selected from the group consisting of cetuximab, panitumumab, zalutumumab, nimotuzumab, ICR62, mAb806, matuzumab, and antibodies capable of binding the same epitope as cetuximab, panitumumab, or zalutumumab, wherein said antibody composition comprises at least a first anti-human EGFR antibody molecule and a second anti-human EGFR antibody molecule distinct from the first molecule,
  a. wherein the first anti-human EGFR antibody molecule is selected from the group consisting of
    (i) an antibody whose light chain comprises amino acids 3-216 of SEQ ID NO:72, and whose heavy chain has a variable domain (VH) comprising amino acids 3-124 of SEQ ID NO:40 and a constant region comprising the amino acid sequence of SEQ ID NO: 91;
    (ii) an antibody whose VL comprises amino acids 3-109 of SEQ ID NO:72 and whose VH comprises amino acids 3-124 of SEQ ID NO:40; and
    (iii) an antibody having the light chain CDR1, CDR2, and CDR3 in SEQ ID NO: 72 and the heavy chain CDR1, CDR2, and CDR3 in SEQ ID NO: 40; and
  b. wherein the second anti-human EGFR antibody molecule is selected from the group consisting of
    (i) an antibody whose light chain comprises amino acids 3-221 of SEQ ID NO:73, and whose heavy chain has a variable domain (VH) comprising amino acids 3-120 of SEQ ID NO:41 and a constant region comprising the amino acid sequence of SEQ ID NO: 91;
    (ii) an antibody whose VL comprises amino acids 3-114 of SEQ ID NO:73 and whose VH comprises amino acids 3-120 of SEQ ID NO:41; and
    (iii) an antibody having the light chain CDR1, CDR2, and CDR3 in SEQ ID NO: 73 and the heavy chain CDR1, CDR2, and CDR3 in SEQ ID NO: 41, thereby inducing apoptosis.

55. A method of inhibiting proliferation of cells expressing EGFR comprising administering an antibody composition to EGFR expressing cells, said cells being resistant or partially resistant to an anti-human EGFR antibody selected from the group consisting of cetuximab, panitumumab, zalutumumab, nimotuzumab, ICR62, mAb806, matuzumab, and antibodies capable of binding the same epitope as cetuximab, panitumumab, or zalutumumab, wherein said antibody composition comprises at least a first anti-human EGFR antibody molecule and a second anti-human EGFR antibody molecule distinct from the first molecule,
  a. wherein the first anti-human EGFR antibody molecule is selected from the group consisting of
    (i) an antibody whose light chain comprises amino acids 3-216 of SEQ ID NO:72, and whose heavy chain has a variable domain (VH) comprising amino acids 3-124 of SEQ ID NO:40 and a constant region comprising the amino acid sequence of SEQ ID NO: 91;
    (ii) an antibody whose VL comprises amino acids 3-109 of SEQ ID NO:72 and whose VH comprises amino acids 3-124 of SEQ ID NO:40; and
    (iii) an antibody having the light chain CDR1, CDR2, and CDR3 in SEQ ID NO: 72 and the heavy chain CDR1, CDR2, and CDR3 in SEQ ID NO: 40; and
  b. wherein the second anti-human EGFR antibody molecule is selected from the group consisting of
    (i) an antibody whose light chain comprises amino acids 3-221 of SEQ ID NO:73, and whose heavy chain has a variable domain (VH) comprising amino acids 3-120 of SEQ ID NO:41 and a constant region comprising the amino acid sequence of SEQ ID NO: 91;
    (ii) an antibody whose VL comprises amino acids 3-114 of SEQ ID NO:73 and whose VH comprises amino acids 3-120 of SEQ ID NO:41; and
    (iii) an antibody having the light chain CDR1, CDR2, and CDR3 in SEQ ID NO: 73 and the heavy chain CDR1, CDR2, and CDR3 in SEQ ID NO: 41, thereby inhibiting proliferation.

56. A method of inducing differentiation of tumour cells in vivo, comprising administering an antibody composition to EGFR expressing tumour cells, said cells being resistant or partially resistant to an anti-human EGFR antibody selected from the group consisting of cetuximab, panitumumab, zalutumumab, nimotuzumab, ICR62, mAb806, matuzumab, and antibodies capable of binding the same epitope as cetuximab, panitumumab, or zalutumumab, any of these, wherein said antibody composition comprises at least a first anti-human EGFR antibody molecule and a second anti-human EGFR antibody molecule distinct from the first molecule,
  a. wherein the first anti-human EGFR antibody molecule is selected from the group consisting of
    (i) an antibody whose light chain comprises amino acids 3-216 of SEQ ID NO:72, and whose heavy chain has a variable domain (VH) comprising amino acids 3-124 of SEQ ID NO:40 and a constant region comprising the amino acid sequence of SEQ ID NO: 91;
    (ii) an antibody whose VL comprises amino acids 3-109 of SEQ ID NO:72 and whose VH comprises amino acids 3-124 of SEQ ID NO:40; and
    (iii) an antibody having the light chain CDR1, CDR2, and CDR3 in SEQ ID NO: 72 and the heavy chain CDR1, CDR2, and CDR3 in SEQ ID NO: 40; and
  b. wherein the second anti-human EGFR antibody molecule is selected from the group consisting of
    (i) an antibody whose light chain comprises amino acids 3-221 of SEQ ID NO:73, and whose heavy chain has a variable domain (VH) comprising amino acids 3-120 of SEQ ID NO:41 and a constant region comprising the amino acid sequence of SEQ ID NO: 91;
    (ii) an antibody whose VL comprises amino acids 3-114 of SEQ ID NO:73 and whose VH comprises amino acids 3-120 of SEQ ID NO:41; and
    (iii) an antibody having the light chain CDR1, CDR2, and CDR3 in SEQ ID NO: 73 and the heavy chain CDR1, CDR2, and CDR3 in SEQ ID NO: 41, thereby inducing differentiation of the tumour cells.

57. The method of claim 56, wherein said differentiation is terminal.

58. The method of claim 56, wherein said differentiation is accompanied by an increase in involucrin expression.

59. A method for inducing internalisation of EGFR comprising administering an antibody composition to EGFR expressing cells, said cells being resistant or partially resistant to an anti-human EGFR antibody selected from the group consisting of cetuximab, panitumumab, zalutumumab, nimotuzumab, ICR62, mAb806, matuzumab, and antibodies capable of binding the same epitope as cetuximab, panitumumab, or zalutumumab, any of these, wherein said antibody composition comprises at least a first anti-human EGFR antibody molecule and a second anti-human EGFR antibody molecule distinct from the first molecule,
  a. wherein the first anti-human EGFR antibody molecule is selected from the group consisting of
    (i) an antibody whose light chain comprises amino acids 3-216 of SEQ ID NO:72, and whose heavy chain has a variable domain (VH) comprising amino acids 3-124 of SEQ ID NO:40 and a constant region comprising the amino acid sequence of SEQ ID NO: 91;

(ii) an antibody whose VL comprises amino acids 3-109 of SEQ ID NO:72 and whose VH comprises amino acids 3-124 of SEQ ID NO:40; and
(iii) an antibody having the light chain CDR1, CDR2, and CDR3 in SEQ ID NO: 72 and the heavy chain CDR1, CDR2, and CDR3 in SEQ ID NO: 40; and b. wherein the second anti-human EGFR antibody molecule is selected from the group consisting of
(i) an antibody whose light chain comprises amino acids 3-221 of SEQ ID NO:73, and whose heavy chain has a variable domain (VH) comprising amino acids 3-120 of SEQ ID NO:41 and a constant region comprising the amino acid sequence of SEQ ID NO: 91;
(ii) an antibody whose VL comprises amino acids 3-114 of SEQ ID NO:73 and whose VH comprises amino acids 3-120 of SEQ ID NO:41; and
(iii) an antibody having the light chain CDR1, CDR2, and CDR3 in SEQ ID NO: 73 and the heavy chain CDR1, CDR2, and CDR3 in SEQ ID NO: 41, thereby inducing internalisation of EGFR.

\* \* \* \* \*

UNITED STATES PATENT AND TRADEMARK OFFICE
CERTIFICATE OF CORRECTION

PATENT NO. : 8,663,640 B2
APPLICATION NO. : 13/061417
DATED : March 4, 2014
INVENTOR(S) : Pedersen et al.

It is certified that error appears in the above-identified patent and that said Letters Patent is hereby corrected as shown below:

IN THE CLAIMS:

Column 224, claim 1, line 58: "have" should be --having--

Column 234, claim 56, line 15: delete "any of these,"

Column 234, claim 59, line 57: delete "any of these,"

Signed and Sealed this
Twenty-eighth Day of October, 2014

Michelle K. Lee
*Deputy Director of the United States Patent and Trademark Office*

SEQUENCE LISTING

<160> NUMBER OF SEQ ID NOS: 141

<210> SEQ ID NO 1
<211> LENGTH: 20
<212> TYPE: DNA
<213> ORGANISM: artificial
<220> FEATURE:
<223> OTHER INFORMATION: PCR primer

<400> SEQUENCE: 1
gacsgatggg cccttggtgg                                              20

<210> SEQ ID NO 2
<211> LENGTH: 20
<212> TYPE: DNA
<213> ORGANISM: artificial
<220> FEATURE:
<223> OTHER INFORMATION: PCR primer

<400> SEQUENCE: 2
gctgtaggtg ctgtctttgc                                              20

<210> SEQ ID NO 3
<211> LENGTH: 39
<212> TYPE: DNA
<213> ORGANISM: artificial
<220> FEATURE:
<223> OTHER INFORMATION: PCR primer

<400> SEQUENCE: 3
tattcccatg gcgcgccsag gtccarctgc arcagyctg                         39

<210> SEQ ID NO 4
<211> LENGTH: 37
<212> TYPE: DNA
<213> ORGANISM: artificial

```
<220> FEATURE:
<223> OTHER INFORMATION: PCR primer

<400> SEQUENCE: 4
tattcccatg gcgcgccgar gtgmagctkg tkgagtc                            37

<210> SEQ ID NO 5
<211> LENGTH: 37
<212> TYPE: DNA
<213> ORGANISM: artificial
<220> FEATURE:
<223> OTHER INFORMATION: PCR primer

<400> SEQUENCE: 5
tattcccatg gcgcgccsag gtgcagctkm aggagtc                            37

<210> SEQ ID NO 6
<211> LENGTH: 37
<212> TYPE: DNA
<213> ORGANISM: artificial
<220> FEATURE:
<223> OTHER INFORMATION: PCR primer

<400> SEQUENCE: 6
tattcccatg gcgcgcccag gttactctga aagagtc                            37

<210> SEQ ID NO 7
<211> LENGTH: 39
<212> TYPE: DNA
<213> ORGANISM: artificial
<220> FEATURE:
<223> OTHER INFORMATION: PCR primer

<400> SEQUENCE: 7
tattcccatg gcgcgcccag atccagttgg tgcagtctg                          39

<210> SEQ ID NO 8
<211> LENGTH: 45
<212> TYPE: DNA
<213> ORGANISM: artificial
<220> FEATURE:
<223> OTHER INFORMATION: PCR primer

<400> SEQUENCE: 8
ggcgcgccat gggaatagct agccgayatc cagatgachc arwct                   45

<210> SEQ ID NO 9
<211> LENGTH: 44
<212> TYPE: DNA
<213> ORGANISM: artificial
<220> FEATURE:
<223> OTHER INFORMATION: PCR primer

<400> SEQUENCE: 9
ggcgcgccat gggaatagct agccracatt gtgmtgachc agtc                    44

<210> SEQ ID NO 10
<211> LENGTH: 46
<212> TYPE: DNA
<213> ORGANISM: artificial
<220> FEATURE:
<223> OTHER INFORMATION: PCR primer

<400> SEQUENCE: 10
ggcgcgccat gggaatagct agccsamatt gtkctsaccc artctc                  46
```

```
<210> SEQ ID NO 11
<211> LENGTH: 45
<212> TYPE: DNA
<213> ORGANISM: artificial
<220> FEATURE:
<223> OTHER INFORMATION: PCR primer

<400> SEQUENCE: 11
ggcgcgccat gggaatagct agccgatrtt gtgatgacbc arrct          45

<210> SEQ ID NO 12
<211> LENGTH: 30
<212> TYPE: DNA
<213> ORGANISM: artificial
<220> FEATURE:
<223> OTHER INFORMATION: PCR primer

<400> SEQUENCE: 12
ggaggcgctc gagacggtga ccgtggtccc                           30

<210> SEQ ID NO 13
<211> LENGTH: 30
<212> TYPE: DNA
<213> ORGANISM: artificial
<220> FEATURE:
<223> OTHER INFORMATION: PCR primer

<400> SEQUENCE: 13
ggaggcgctc gagactgtga gagtggtgcc                           30

<210> SEQ ID NO 14
<211> LENGTH: 30
<212> TYPE: DNA
<213> ORGANISM: artificial
<220> FEATURE:
<223> OTHER INFORMATION: PCR primer

<400> SEQUENCE: 14
ggaggcgctc gagacagtga ccagagtccc                           30

<210> SEQ ID NO 15
<211> LENGTH: 30
<212> TYPE: DNA
<213> ORGANISM: artificial
<220> FEATURE:
<223> OTHER INFORMATION: PCR primer

<400> SEQUENCE: 15
ggaggcgctc gagacggtga ctgaggttcc                           30

<210> SEQ ID NO 16
<211> LENGTH: 24
<212> TYPE: DNA
<213> ORGANISM: artificial
<220> FEATURE:
<223> OTHER INFORMATION: PCR primer

<400> SEQUENCE: 16
ggacagggmt ccakagttcc adkt                                 24

<210> SEQ ID NO 17
<211> LENGTH: 43
<212> TYPE: DNA
<213> ORGANISM: artificial
<220> FEATURE:
<223> OTHER INFORMATION: PCR primer

<400> SEQUENCE: 17
```

-continued gacagatggt gcagccacag ttcgtttgat ttccagcttg gtg         43

<210> SEQ ID NO 18
<211> LENGTH: 43
<212> TYPE: DNA
<213> ORGANISM: artificial
<220> FEATURE:
<223> OTHER INFORMATION: PCR primer

<400> SEQUENCE: 18
gacagatggt gcagccacag ttcgttttat ttccagcttg gtc         43

<210> SEQ ID NO 19
<211> LENGTH: 43
<212> TYPE: DNA
<213> ORGANISM: artificial
<220> FEATURE:
<223> OTHER INFORMATION: PCR primer

<400> SEQUENCE: 19
gacagatggt gcagccacag ttcgttttat ttccaacttt gtc         43

<210> SEQ ID NO 20
<211> LENGTH: 43
<212> TYPE: DNA
<213> ORGANISM: artificial
<220> FEATURE:
<223> OTHER INFORMATION: PCR primer

<400> SEQUENCE: 20
gacagatggt gcagccacag ttcgtttcag ctccagcttg gtc         43

<210> SEQ ID NO 21
<211> LENGTH: 23
<212> TYPE: DNA
<213> ORGANISM: artificial
<220> FEATURE:
<223> OTHER INFORMATION: PCR primer

<400> SEQUENCE: 21
gaactgtggc tgcaccatct gtc                               23

<210> SEQ ID NO 22
<211> LENGTH: 43
<212> TYPE: DNA
<213> ORGANISM: artificial
<220> FEATURE:
<223> OTHER INFORMATION: PCR primer

<400> SEQUENCE: 22
accgcctcca ccggcggccg cttattaaca ctctcccctg ttg         43

<210> SEQ ID NO 23
<211> LENGTH: 51
<212> TYPE: DNA
<213> ORGANISM: artificial
<220> FEATURE:
<223> OTHER INFORMATION: PCR primer

<400> SEQUENCE: 23
accgcctcca ccggcggccg cttattaaca ctctcccctg ttgaagctct t    51

<210> SEQ ID NO 24
<211> LENGTH: 372
<212> TYPE: DNA
<213> ORGANISM: Homo sapiens

<400> SEQUENCE: 24

```
cgcgccgagg tccaactgca gcaacctggg tctgagctgg tgaggcctgg agcttcagtg      60
aagctgtcct gcaaggcttc tggctacaca ttcaccagct actggatgca ctgggtgaag     120
cagaggcctg gacaaggcct tgagtggatt gggaatattt atcctggtag tcgtagtact     180
aactacgatg agaagttcaa gagcaaggcc acactgactg tagacacatc ctccagcaca     240
gcctacatgc agctcagcag cctgacatct gaggactctg cggtctatta ctgtacaaga     300
aatggggatt actacgttag tagcggggat gctatggact actggggtca aggaacctca     360
gtcaccgtct cg                                                         372
```

<210> SEQ ID NO 25
<211> LENGTH: 360
<212> TYPE: DNA
<213> ORGANISM: Homo sapiens

<400> SEQUENCE: 25

```
cgcgcccagg tccaactgca gcagcctggg gctgaactgg tggagcctgg gggttcagtg      60
aagctgtcct gcaaggcttc tggctacacc ttcaccagtc actggatgca ctgggtgaag     120
cagaggcctg gacaaggcct tgagtggata ggtgagatta atcctagcag cggtcgtaat     180
aactacaatg agaagttcaa gagtaaggcc acactgactg tagacaaatc ctccagcaca     240
gcctacatgc aattcagcag cctgacatct gaggactctg cggtctatta ttgtgtaaga     300
tactatggtt acgacgaagc tatggactac tggggtcaag gaacctcagt caccgtctcg     360
```

<210> SEQ ID NO 26
<211> LENGTH: 360
<212> TYPE: DNA
<213> ORGANISM: Homo sapiens

<400> SEQUENCE: 26

```
cgcgccgaag tgcagctggt ggagtctggg ggaggcttag tgaagcctgg agggtccctg      60
aaactctcct gtgcagcctc tggattcact ttcagtagtt atgccctgtc ttgggttcgc     120
cagactccag agaggaggct ggagtgggtc gcatccatta gtggtgttgg tagcacctac     180
tttccagaca gtgtgaaggg ccgtttcacc atgtccagag ataatgccag gaacatcctg     240
tacctccaaa tgagcagtct gaggtctgag gacacggcca tgtattactg tgcaagaggt     300
tctgatggtt acttctatgc tatggactac tggggtcaag gaacctcagt caccgtctcg     360
```

<210> SEQ ID NO 27
<211> LENGTH: 360
<212> TYPE: DNA
<213> ORGANISM: Homo sapiens

<400> SEQUENCE: 27

```
cgcgcccagg tgcagcttca gcagcctggg gctgaactgg tgaagcctgg ggcttcagtg      60
aagctgtcct gtaaggcttc tggctacacc ttcaccagcc actggatgca ctgggtgcag     120
cagaggcctg gacaaggcct tgagtggatt ggagagattc atcctagcaa cggtcgtact     180
aactacaatg agaagttcaa gaacaaggcc acactgactg tagacaaatc tcccagcaca     240
gcctacatgc aactcagcag tttgacatct gaggactctg cggtctatta ctgtgcaaga     300
tactatggtt acgacgatgc tatggactac tggggtcaag gaacctcagt caccgtctcg     360
```

<210> SEQ ID NO 28
<211> LENGTH: 366

```
<212> TYPE: DNA
<213> ORGANISM: Homo sapiens

<400> SEQUENCE: 28
cgcgccgaag tgcagctggt ggagtctggg ggaggcttag tgaagcctgg agggtccctg      60
aaactctcct gtgcagcctc tggattcgct ttcagtagct atgacatgtc ttgggttcgc     120
cagactccgg agaagaggct ggagtgggtc gcatacattg gtagtggtga tgataatacc     180
cactatccag actctgtgaa gggccgattc accatctcca gacacaatgc caaaaacacc     240
ctatacctgc aaatgagcag tctgaagtct gaggacacag ccatgtatta ctgtgcaaga     300
cagaagtatg gtaactacgg ggacactatg gactactggg gtcaaggaac ctcagtcacc     360
gtctcg                                                                366

<210> SEQ ID NO 29
<211> LENGTH: 366
<212> TYPE: DNA
<213> ORGANISM: Homo sapiens

<400> SEQUENCE: 29
cgcgcccagg ttcagctgaa ggagtcagga cctggcctgg tggcgccctc acagagcctg      60
tccatcactt gctctgtctc tggttttttca ttaaccatct atggtgtaca ctgggttcgc     120
cagcctccag gaaagggtct ggagtggctg ggagttatgt gggctggtgg aaatacagat     180
tataattcgg ctctcatgtc cagactgaac atcagcaagg acaattccaa gagccaagtt     240
ttcttaaaag tgaacagtct acaaactgat gacacagcca tgtactattg taccagagat     300
cccgatggtt actacgtggg gtggttcttc gatgtctggg gcgcggggac cacggtcacc     360
gtctcg                                                                366

<210> SEQ ID NO 30
<211> LENGTH: 366
<212> TYPE: DNA
<213> ORGANISM: Homo sapiens

<400> SEQUENCE: 30
cgcgccgaag tgcagctggt ggagtctggg ggaggcttag tgaagcctgg agggtccctg      60
aaactctcct gtgcagcctc tggattcgct tacagtacct atgacatgtc ttgggttcgc     120
cagactccgg agaagaggct ggagtgggtc gcatacatta gtagtggtgg tgatgccgcc     180
tactatcccg acactgtgaa gggccgattc accatctcca gagacaatgc caaaaacacc     240
ctatacctgc aaatgagcag tctgaagtct gaggacacag ccatgtatta ctgtgcgagg     300
tctcgctatg gaaactacgg ggacgctatg gactactggg gtcaaggaac ctcagtcacc     360
gtctcg                                                                366

<210> SEQ ID NO 31
<211> LENGTH: 375
<212> TYPE: DNA
<213> ORGANISM: Homo sapiens

<400> SEQUENCE: 31
cgcgccgagg tccagctgca acagtctgga cctgagctgg tgaaacctgg ggcttcagtg      60
aagataccct gcaagacttc tggatacact ttcactgact acaacatggc ctgggtgaag     120
cagagccatg gaaagagcct tgagtggatt ggagatatta ttcctaacaa tggtggtgct     180
atctacaacc agaaattcaa gggcaaggcc actttgactg tagacaaatc ctccagtaca     240
gcctccatgg agctccgcag cctgacatct gaggacactg cagtctattt ctgtgcaaga     300
```

```
aagaatatct actataggta cgacggggca ggtgctctgg actactgggg tcaaggaacc        360
tcagtcaccg tctcg                                                         375

<210> SEQ ID NO 32
<211> LENGTH: 351
<212> TYPE: DNA
<213> ORGANISM: Homo sapiens

<400> SEQUENCE: 32
cgcgcccagg tgcagctgaa ggagtcagga cctggcctgg tggcgccctc acagagcctg         60
tccatcactt gcactgtctc tgggttttca ttaaccacct atgggtaca ctgggttcgc        120 cagcctccag gaaagggtct ggagtggctg gagtaatat gggctggtgg aagcacaaat        180
tataattcgg ctctcatgtc cagactgagc atcaagaaag acaactccaa gagccaagtt       240
ttcttaaaaa tgaacagtct gcaaactgat gacacagcca tgtactactg tgccagagcc       300
tatggttaca actttgacta ttggggccaa ggcaccactc tcacagtctc g                351

<210> SEQ ID NO 33
<211> LENGTH: 372
<212> TYPE: DNA
<213> ORGANISM: Homo sapiens

<400> SEQUENCE: 33
cgcgccgaag tgcagctggt ggagtctggg ggaggcttag tgaagcctgg agggtccctg         60
aaactctcct gtgcagtctc tggattcact ttcagtagct atgtcatgtc ttgggttcgc       120
cagactccgg agaagaggct ggagtgggtc gcaaccatta ctagtggtgg taggaacatc      180
tactatctag acagtgtgaa ggggcgattc actatctcca gagacaatgc caagaacacc      240
ctgtacctgc aaatgagcag tctgaggtct gaggacacgg ccatgtatta ctgtgcaaga     300
catgaggact ataggtacga cggttactat gctatggact actggggtca aggaaccct      360 gtcaccgtct cg                                                           372

<210> SEQ ID NO 34
<211> LENGTH: 354
<212> TYPE: DNA
<213> ORGANISM: Homo sapiens

<400> SEQUENCE: 34
cgcgccgaag tgcagctggt ggagtctggg ggaggcttag tgaagcctgg agagtccttg         60
aaactctcct gtgcagcctc tggattcgct ttcagttact ctgacatgtc ttgggttcgc       120
cagactccgg agaagaggct ggagtgggtc gcatacatga gtagtgctgg tgatgtcacc      180
ttctattcag acactgtgaa gggccgattc accatctcca gagacaatgc caagaacacc      240
ctgtatctgc aagtgagcag tctgaagtct gaggacacag ccatatatta ctgtgtaaga     300
caccgggacg tggctatgga ctactgggt caaggaacct cagtcaccgt ctcg             354

<210> SEQ ID NO 35
<211> LENGTH: 357
<212> TYPE: DNA
<213> ORGANISM: Homo sapiens

<400> SEQUENCE: 35
cgcgcccagg tccaactgca gcagcctggg gctgaactgg tgaagcctgg ggcttcagtg         60
aagctgtcct gcaaggcttc tggctacacc ttcaccagcg actggatgca ctggatgaaa      120
cagaggcctg gacaaggcct tgagtggatt ggagagatta atcctagtaa cggtcgctct      180
```

```
agctacaatg agaagttcaa gagcaaggcc acactgactg tagacaaatc ctccagcaca    240
gcctacatgc aactcagcag cctgacatct gaggactctg cggtctatta ctgtgcaaga    300
ataggtggta tctacgtgga gacttactgg ggccaaggga ctctggtcac tgtctcg      357

<210> SEQ ID NO 36
<211> LENGTH: 375
<212> TYPE: DNA
<213> ORGANISM: Homo sapiens

<400> SEQUENCE: 36
cgcgccgagg tccagcttca gcagtctgga gctgagctgg tgaggcctgg gtcctcagtg    60
aagatttcct gcaaggcttc tggctatgca ttcagtagct actggatgaa ctgggtgagg    120
cagaggcctg gacagggtct tgagtggatt ggacagattt atcctggaga tggtgatact    180
aactacaatg gaaagttcaa gggtagagcc acactgactg caaacaaatc ctccagcaca    240
gcctacatgc agctcagcag cctaacatct gaggactctg cggtctattt ctgtgcaaga    300
agggcatctt ccctctatga tgtttacccc tactactttg actactgggg ccaaggcacc    360
actctcacag tctcg                                                    375

<210> SEQ ID NO 37
<211> LENGTH: 363
<212> TYPE: DNA
<213> ORGANISM: Homo sapiens

<400> SEQUENCE: 37
cgcgcccagg tccaactgca gcagcctggg gctgaactgg tgaagcctgg ggcttcaatg    60
aagctgtcct gcaaggcttc tggctacacc ttcaccaact actggatgca ctgggtgaag    120
cagaggcctg gacaaggcct tgaatggatt ggagaaatta atcctagcaa cggtcgtact    180
aattacaatg agaagttcaa gagcaaggcc acactgactg tagacaaatc gtccagcaca    240
gcctacatgc aactcagcag cctgacatct gaggactctg gggtctatta ctgtgcaaaa    300 gggggaact actatgatta cgactgggac tactggggcc aaggcaccac tctcacagtc    360
tcg                                                                 363

<210> SEQ ID NO 38
<211> LENGTH: 351
<212> TYPE: DNA
<213> ORGANISM: Homo sapiens

<400> SEQUENCE: 38
cgcgcccagg tgcagctgaa ggagtcagga cctggcctgg tggcgccctc acagagcctg    60
tccatcactt gcactgtctc tgggttttca ttaaccatct atggtgtaca ctgggttcgc    120
cagcctccag gaaagggtct ggagtggctg gagtaatat gggctggtgg aaacacaaat    180
tataattcgg ctctcatgtc cagactgagc atcagcaaag acaactccaa gagtcaagtt    240
ttcttaaaaa tgaacagtct gcaaactgat gacacagcca tgtacttctg tgccagaggc    300
tatggctaca atttagacta ttggggccaa ggcaccactc tcacagtctc g             351

<210> SEQ ID NO 39
<211> LENGTH: 357
<212> TYPE: DNA
<213> ORGANISM: Homo sapiens

<400> SEQUENCE: 39
cgcgcccagg tgcagctgaa ggagtcagga cctggcctgg tggcgccctc acagagcctg    60
```

-continued

| | | | |
|---|---|---|---|
| tccatcacat gcaccgtctc aggattctca ttaaccggcc atggtgtaaa ctgggttcgc | | | 120 |
| cagcctccag gaaagggtct ggagtggctg ggaatgatat ggggtgatgg aagcacggac | | | 180 |
| tataattcaa ctctcaaatc cagactgagt atcagcaagg acaactccaa gagccaagtt | | | 240 |
| ttcttaaaaa tgaacagtct gcagactgat gacaccgcca ggtactactg tgccagaggc | | | 300 |
| tacggctacc tttactactt tgactactgg ggccaaggca ccactctcac agtctcg | | | 357 |

```
<210> SEQ ID NO 40
<211> LENGTH: 124
<212> TYPE: PRT
<213> ORGANISM: Homo sapiens

<400> SEQUENCE: 40
```

Arg Ala Glu Val Gln Leu Gln Gln Pro Gly Ser Glu Leu Val Arg Pro
1               5                   10                  15

Gly Ala Ser Val Lys Leu Ser Cys Lys Ala Ser Gly Tyr Thr Phe Thr
            20                  25                  30

Ser Tyr Trp Met His Trp Val Lys Gln Arg Pro Gly Gln Gly Leu Glu
        35                  40                  45

Trp Ile Gly Asn Ile Tyr Pro Gly Ser Arg Ser Thr Asn Tyr Asp Glu
    50                  55                  60

Lys Phe Lys Ser Lys Ala Thr Leu Thr Val Asp Thr Ser Ser Ser Thr
65                  70                  75                  80

Ala Tyr Met Gln Leu Ser Ser Leu Thr Ser Glu Asp Ser Ala Val Tyr
                85                  90                  95

Tyr Cys Thr Arg Asn Gly Asp Tyr Tyr Val Ser Ser Gly Asp Ala Met
            100                 105                 110

Asp Tyr Trp Gly Gln Gly Thr Ser Val Thr Val Ser
        115                 120

```
<210> SEQ ID NO 41
<211> LENGTH: 120
<212> TYPE: PRT
<213> ORGANISM: Homo sapiens

<400> SEQUENCE: 41
```

Arg Ala Gln Val Gln Leu Gln Gln Pro Gly Ala Glu Leu Val Glu Pro
1               5                   10                  15

Gly Gly Ser Val Lys Leu Ser Cys Lys Ala Ser Gly Tyr Thr Phe Thr
            20                  25                  30

Ser His Trp Met His Trp Val Lys Gln Arg Pro Gly Gln Gly Leu Glu
        35                  40                  45

Trp Ile Gly Glu Ile Asn Pro Ser Ser Gly Arg Asn Asn Tyr Asn Glu
    50                  55                  60

Lys Phe Lys Ser Lys Ala Thr Leu Thr Val Asp Lys Ser Ser Ser Thr
65                  70                  75                  80

Ala Tyr Met Gln Phe Ser Ser Leu Thr Ser Glu Asp Ser Ala Val Tyr
                85                  90                  95

Tyr Cys Val Arg Tyr Tyr Gly Tyr Asp Glu Ala Met Asp Tyr Trp Gly
            100                 105                 110

Gln Gly Thr Ser Val Thr Val Ser
        115                 120

```
<210> SEQ ID NO 42
<211> LENGTH: 120
<212> TYPE: PRT
<213> ORGANISM: Homo sapiens
```

<400> SEQUENCE: 42

Arg Ala Glu Val Gln Leu Val Glu Ser Gly Gly Gly Leu Val Lys Pro
1               5                   10                  15

Gly Gly Ser Leu Lys Leu Ser Cys Ala Ala Ser Gly Phe Thr Phe Ser
            20                  25                  30

Ser Tyr Ala Leu Ser Trp Val Arg Gln Thr Pro Glu Arg Arg Leu Glu
        35                  40                  45

Trp Val Ala Ser Ile Ser Gly Val Gly Ser Thr Tyr Phe Pro Asp Ser
    50                  55                  60

Val Lys Gly Arg Phe Thr Met Ser Arg Asp Asn Ala Arg Asn Ile Leu
65                  70                  75                  80

Tyr Leu Gln Met Ser Ser Leu Arg Ser Glu Asp Thr Ala Met Tyr Tyr
                85                  90                  95

Cys Ala Arg Gly Ser Asp Gly Tyr Phe Tyr Ala Met Asp Tyr Trp Gly
            100                 105                 110

Gln Gly Thr Ser Val Thr Val Ser
        115                 120

<210> SEQ ID NO 43
<211> LENGTH: 120
<212> TYPE: PRT
<213> ORGANISM: Homo sapiens

<400> SEQUENCE: 43

Arg Ala Gln Val Gln Leu Gln Gln Pro Gly Ala Glu Leu Val Lys Pro
1               5                   10                  15

Gly Ala Ser Val Lys Leu Ser Cys Lys Ala Ser Gly Tyr Thr Phe Thr
            20                  25                  30

Ser His Trp Met His Trp Val Gln Gln Arg Pro Gly Gln Gly Leu Glu
        35                  40                  45

Trp Ile Gly Glu Ile His Pro Ser Asn Gly Arg Thr Asn Tyr Asn Glu
    50                  55                  60

Lys Phe Lys Asn Lys Ala Thr Leu Thr Val Asp Lys Ser Pro Ser Thr
65                  70                  75                  80

Ala Tyr Met Gln Leu Ser Ser Leu Thr Ser Glu Asp Ser Ala Val Tyr
                85                  90                  95

Tyr Cys Ala Arg Tyr Tyr Gly Tyr Asp Asp Ala Met Asp Tyr Trp Gly
            100                 105                 110

Gln Gly Thr Ser Val Thr Val Ser
        115                 120

<210> SEQ ID NO 44
<211> LENGTH: 122
<212> TYPE: PRT
<213> ORGANISM: Homo sapiens

<400> SEQUENCE: 44

Arg Ala Glu Val Gln Leu Val Glu Ser Gly Gly Gly Leu Val Lys Pro
1               5                   10                  15

Gly Gly Ser Leu Lys Leu Ser Cys Ala Ala Ser Gly Phe Ala Phe Ser
            20                  25                  30

Ser Tyr Asp Met Ser Trp Val Arg Gln Thr Pro Glu Lys Arg Leu Glu
        35                  40                  45

Trp Val Ala Tyr Ile Gly Ser Gly Asp Asp Asn Thr His Tyr Pro Asp
    50                  55                  60

Ser Val Lys Gly Arg Phe Thr Ile Ser Arg His Asn Ala Lys Asn Thr

```
            65                  70                  75                  80
Leu Tyr Leu Gln Met Ser Ser Leu Lys Ser Glu Asp Thr Ala Met Tyr
                85                  90                  95
Tyr Cys Ala Arg Gln Lys Tyr Gly Asn Tyr Gly Asp Thr Met Asp Tyr
            100                 105                 110
Trp Gly Gln Gly Thr Ser Val Thr Val Ser
        115                 120

<210> SEQ ID NO 45
<211> LENGTH: 122
<212> TYPE: PRT
<213> ORGANISM: Homo sapiens

<400> SEQUENCE: 45

Arg Ala Gln Val Gln Leu Lys Glu Ser Gly Pro Gly Leu Val Ala Pro
1               5                   10                  15
Ser Gln Ser Leu Ser Ile Thr Cys Ser Val Ser Gly Phe Ser Leu Thr
            20                  25                  30
Ile Tyr Gly Val His Trp Val Arg Gln Pro Pro Gly Lys Gly Leu Glu
        35                  40                  45
Trp Leu Gly Val Met Trp Ala Gly Gly Asn Thr Asp Tyr Asn Ser Ala
    50                  55                  60
Leu Met Ser Arg Leu Asn Ile Ser Lys Asp Asn Ser Lys Ser Gln Val
65                  70                  75                  80
Phe Leu Lys Val Asn Ser Leu Gln Thr Asp Asp Thr Ala Met Tyr Tyr
                85                  90                  95
Cys Thr Arg Asp Pro Asp Gly Tyr Tyr Val Gly Trp Phe Phe Asp Val
            100                 105                 110
Trp Gly Ala Gly Thr Thr Val Thr Val Ser
        115                 120

<210> SEQ ID NO 46
<211> LENGTH: 122
<212> TYPE: PRT
<213> ORGANISM: Homo sapiens

<400> SEQUENCE: 46

Arg Ala Glu Val Gln Leu Val Glu Ser Gly Gly Gly Leu Val Lys Pro
1               5                   10                  15
Gly Gly Ser Leu Lys Leu Ser Cys Ala Ala Ser Gly Phe Ala Tyr Ser
            20                  25                  30
Thr Tyr Asp Met Ser Trp Val Arg Gln Thr Pro Glu Lys Arg Leu Glu
        35                  40                  45
Trp Val Ala Tyr Ile Ser Ser Gly Gly Asp Ala Ala Tyr Tyr Pro Asp
    50                  55                  60
Thr Val Lys Gly Arg Phe Thr Ile Ser Arg Asp Asn Ala Lys Asn Thr
65                  70                  75                  80
Leu Tyr Leu Gln Met Ser Ser Leu Lys Ser Glu Asp Thr Ala Met Tyr
                85                  90                  95
Tyr Cys Ala Arg Ser Arg Tyr Gly Asn Tyr Gly Asp Ala Met Asp Tyr
            100                 105                 110
Trp Gly Gln Gly Thr Ser Val Thr Val Ser
        115                 120

<210> SEQ ID NO 47
<211> LENGTH: 125
<212> TYPE: PRT
<213> ORGANISM: Homo sapiens
```

<400> SEQUENCE: 47

Arg Ala Glu Val Gln Leu Gln Gln Ser Gly Pro Glu Leu Val Lys Pro
1               5                   10                  15

Gly Ala Ser Val Lys Ile Pro Cys Lys Thr Ser Gly Tyr Thr Phe Thr
            20                  25                  30

Asp Tyr Asn Met Ala Trp Val Lys Gln Ser His Gly Lys Ser Leu Glu
        35                  40                  45

Trp Ile Gly Asp Ile Ile Pro Asn Asn Gly Gly Ala Ile Tyr Asn Gln
    50                  55                  60

Lys Phe Lys Gly Lys Ala Thr Leu Thr Val Asp Lys Ser Ser Ser Thr
65                  70                  75                  80

Ala Ser Met Glu Leu Arg Ser Leu Thr Ser Glu Asp Thr Ala Val Tyr
                85                  90                  95

Phe Cys Ala Arg Lys Asn Ile Tyr Tyr Arg Tyr Asp Gly Ala Gly Ala
            100                 105                 110

Leu Asp Tyr Trp Gly Gln Gly Thr Ser Val Thr Val Ser
        115                 120                 125

<210> SEQ ID NO 48
<211> LENGTH: 117
<212> TYPE: PRT
<213> ORGANISM: Homo sapiens

<400> SEQUENCE: 48

Arg Ala Gln Val Gln Leu Lys Glu Ser Gly Pro Gly Leu Val Ala Pro
1               5                   10                  15

Ser Gln Ser Leu Ser Ile Thr Cys Thr Val Ser Gly Phe Ser Leu Thr
            20                  25                  30

Thr Tyr Gly Val His Trp Val Arg Gln Pro Pro Gly Lys Gly Leu Glu
        35                  40                  45

Trp Leu Gly Val Ile Trp Ala Gly Gly Ser Thr Asn Tyr Asn Ser Ala
    50                  55                  60

Leu Met Ser Arg Leu Ser Ile Lys Lys Asp Asn Ser Lys Ser Gln Val
65                  70                  75                  80

Phe Leu Lys Met Asn Ser Leu Gln Thr Asp Asp Thr Ala Met Tyr Tyr
                85                  90                  95

Cys Ala Arg Ala Tyr Gly Tyr Asn Phe Asp Tyr Trp Gly Gln Gly Thr
            100                 105                 110

Thr Leu Thr Val Ser
        115

<210> SEQ ID NO 49
<211> LENGTH: 124
<212> TYPE: PRT
<213> ORGANISM: Homo sapiens

<400> SEQUENCE: 49

Arg Ala Glu Val Gln Leu Val Glu Ser Gly Gly Gly Leu Val Lys Pro
1               5                   10                  15

Gly Gly Ser Leu Lys Leu Ser Cys Ala Val Ser Gly Phe Thr Phe Ser
            20                  25                  30

Ser Tyr Val Met Ser Trp Val Arg Gln Thr Pro Glu Lys Arg Leu Glu
        35                  40                  45

Trp Val Ala Thr Ile Thr Ser Gly Gly Arg Asn Ile Tyr Tyr Leu Asp
    50                  55                  60

Ser Val Lys Gly Arg Phe Thr Ile Ser Arg Asp Asn Ala Lys Asn Thr

```
                65                  70                  75                  80
Leu Tyr Leu Gln Met Ser Ser Leu Arg Ser Glu Asp Thr Ala Met Tyr
                    85                  90                  95

Tyr Cys Ala Arg His Glu Asp Tyr Arg Tyr Asp Gly Tyr Tyr Ala Met
                    100                 105                 110

Asp Tyr Trp Gly Gln Gly Thr Ser Val Thr Val Ser
                115                 120

<210> SEQ ID NO 50
<211> LENGTH: 118
<212> TYPE: PRT
<213> ORGANISM: Homo sapiens

<400> SEQUENCE: 50

Arg Ala Glu Val Gln Leu Val Glu Ser Gly Gly Gly Leu Val Lys Pro
1               5                   10                  15

Gly Glu Ser Leu Lys Leu Ser Cys Ala Ala Ser Gly Phe Ala Phe Ser
                20                  25                  30

Tyr Ser Asp Met Ser Trp Val Arg Gln Thr Pro Glu Lys Arg Leu Glu
                35                  40                  45

Trp Val Ala Tyr Met Ser Ser Ala Gly Asp Val Thr Phe Tyr Ser Asp
                50                  55                  60

Thr Val Lys Gly Arg Phe Thr Ile Ser Arg Asp Asn Ala Lys Asn Thr
65                  70                  75                  80

Leu Tyr Leu Gln Val Ser Ser Leu Lys Ser Glu Asp Thr Ala Ile Tyr
                85                  90                  95

Tyr Cys Val Arg His Arg Asp Val Ala Met Asp Tyr Trp Gly Gln Gly
                100                 105                 110

Thr Ser Val Thr Val Ser
                115

<210> SEQ ID NO 51
<211> LENGTH: 119
<212> TYPE: PRT
<213> ORGANISM: Homo sapiens

<400> SEQUENCE: 51

Arg Ala Gln Val Gln Leu Gln Gln Pro Gly Ala Glu Leu Val Lys Pro
1               5                   10                  15

Gly Ala Ser Val Lys Leu Ser Cys Lys Ala Ser Gly Tyr Thr Phe Thr
                20                  25                  30

Ser Asp Trp Met His Trp Met Lys Gln Arg Pro Gly Gln Gly Leu Glu
                35                  40                  45

Trp Ile Gly Glu Ile Asn Pro Ser Asn Gly Arg Ser Tyr Asn Glu
                50                  55                  60

Lys Phe Lys Ser Lys Ala Thr Leu Thr Val Asp Lys Ser Ser Ser Thr
65                  70                  75                  80

Ala Tyr Met Gln Leu Ser Ser Leu Thr Ser Glu Asp Ser Ala Val Tyr
                85                  90                  95

Tyr Cys Ala Arg Ile Gly Gly Ile Tyr Val Glu Thr Tyr Trp Gly Gln
                100                 105                 110

Gly Thr Leu Val Thr Val Ser
                115

<210> SEQ ID NO 52
<211> LENGTH: 125
<212> TYPE: PRT
<213> ORGANISM: Homo sapiens
```

```
<400> SEQUENCE: 52

Arg Ala Glu Val Gln Leu Gln Gln Ser Gly Ala Glu Leu Val Arg Pro
1               5                   10                  15

Gly Ser Ser Val Lys Ile Ser Cys Lys Ala Ser Gly Tyr Ala Phe Ser
            20                  25                  30

Ser Tyr Trp Met Asn Trp Val Arg Gln Arg Pro Gly Gln Gly Leu Glu
        35                  40                  45

Trp Ile Gly Gln Ile Tyr Pro Gly Asp Gly Asp Thr Asn Tyr Asn Gly
    50                  55                  60

Lys Phe Lys Gly Arg Ala Thr Leu Thr Ala Asn Lys Ser Ser Ser Thr
65                  70                  75                  80

Ala Tyr Met Gln Leu Ser Ser Leu Thr Ser Glu Asp Ser Ala Val Tyr
                85                  90                  95

Phe Cys Ala Arg Arg Ala Ser Ser Leu Tyr Asp Val Tyr Pro Tyr Tyr
            100                 105                 110

Phe Asp Tyr Trp Gly Gln Gly Thr Thr Leu Thr Val Ser
            115                 120                 125

<210> SEQ ID NO 53
<211> LENGTH: 121
<212> TYPE: PRT
<213> ORGANISM: Homo sapiens

<400> SEQUENCE: 53

Arg Ala Gln Val Gln Leu Gln Gln Pro Gly Ala Glu Leu Val Lys Pro
1               5                   10                  15

Gly Ala Ser Met Lys Leu Ser Cys Lys Ala Ser Gly Tyr Thr Phe Thr
            20                  25                  30

Asn Tyr Trp Met His Trp Val Lys Gln Arg Pro Gly Gln Gly Leu Glu
        35                  40                  45

Trp Ile Gly Glu Ile Asn Pro Ser Asn Gly Arg Thr Asn Tyr Asn Glu
    50                  55                  60

Lys Phe Lys Ser Lys Ala Thr Leu Thr Val Asp Lys Ser Ser Ser Thr
65                  70                  75                  80

Ala Tyr Met Gln Leu Ser Ser Leu Thr Ser Glu Asp Ser Gly Val Tyr
                85                  90                  95

Tyr Cys Ala Lys Gly Gly Asn Tyr Tyr Asp Tyr Asp Trp Asp Tyr Trp
            100                 105                 110

Gly Gln Gly Thr Thr Leu Thr Val Ser
            115                 120

<210> SEQ ID NO 54
<211> LENGTH: 117
<212> TYPE: PRT
<213> ORGANISM: Homo sapiens

<400> SEQUENCE: 54

Arg Ala Gln Val Gln Leu Lys Glu Ser Gly Pro Gly Leu Val Ala Pro
1               5                   10                  15

Ser Gln Ser Leu Ser Ile Thr Cys Thr Val Ser Gly Phe Ser Leu Thr
            20                  25                  30

Ile Tyr Gly Val His Trp Val Arg Gln Pro Pro Gly Lys Gly Leu Glu
        35                  40                  45

Trp Leu Gly Val Ile Trp Ala Gly Gly Asn Thr Asn Tyr Asn Ser Ala
    50                  55                  60

Leu Met Ser Arg Leu Ser Ile Ser Lys Asp Asn Ser Lys Ser Gln Val
```

```
                65                  70                  75                  80
Phe Leu Lys Met Asn Ser Leu Gln Thr Asp Asp Thr Ala Met Tyr Phe
                    85                  90                  95
Cys Ala Arg Gly Tyr Gly Tyr Asn Leu Asp Tyr Trp Gly Gln Gly Thr
                100                 105                 110
Thr Leu Thr Val Ser
        115

<210> SEQ ID NO 55
<211> LENGTH: 119
<212> TYPE: PRT
<213> ORGANISM: Homo sapiens

<400> SEQUENCE: 55

Arg Ala Gln Val Gln Leu Lys Glu Ser Gly Pro Gly Leu Val Ala Pro
1               5                   10                  15
Ser Gln Ser Leu Ser Ile Thr Cys Thr Val Ser Gly Phe Ser Leu Thr
            20                  25                  30
Gly His Gly Val Asn Trp Val Arg Gln Pro Pro Gly Lys Gly Leu Glu
        35                  40                  45
Trp Leu Gly Met Ile Trp Gly Asp Gly Ser Thr Asp Tyr Asn Ser Thr
    50                  55                  60
Leu Lys Ser Arg Leu Ser Ile Ser Lys Asp Asn Ser Lys Ser Gln Val
65              70                  75                  80
Phe Leu Lys Met Asn Ser Leu Gln Thr Asp Asp Thr Ala Arg Tyr Tyr
                    85                  90                  95
Cys Ala Arg Gly Tyr Gly Tyr Leu Tyr Tyr Phe Asp Tyr Trp Gly Gln
                100                 105                 110
Gly Thr Thr Leu Thr Val Ser
        115

<210> SEQ ID NO 56
<211> LENGTH: 648
<212> TYPE: DNA
<213> ORGANISM: Homo sapiens

<400> SEQUENCE: 56
ctagccgaca ttcagatgac tcagactaca tcctccctgt ctgcctctct gggagacaga     60
gtcaccatca gttgcaggac aagtcaggac attggcaatt atttaaactg gtatcagcag    120
aaaccagatg gaactgttaa actcctgatc tactacacat caagattaca ctcaggagtc    180
ccatcaaggt tcagtggcag tgggtctgga acagattttt ctctcaccat taacaacgtg    240
gagcaagagg atgttgccac ttactttgc caacactata tacggttcc tccgacgttc     300
ggtggaggca ccaagctgga aatcaaacga actgtggctg caccatctgt cttcatcttc    360
ccgccatctg atgagcagtt gaaatctgga actgcctctg ttgtgtgcct gctgaataac    420
ttctatccca gagaggccaa agtacagtgg aaggtggata cgccctcca atcgggtaac     480
tcccaggaga gtgtcacaga gcaggacagc aaggacagca cctacagcct cagcagcacc    540
ctgacgctga gcaaagcaga ctacgagaaa cacaaagtct acgcctgcga agtcacccat    600
cagggcctga gctcgcccgt cacaaagagc ttcaacaggg gagagtgt                 648

<210> SEQ ID NO 57
<211> LENGTH: 663
<212> TYPE: DNA
<213> ORGANISM: Homo sapiens

<400> SEQUENCE: 57
```

```
ctagccgaca tcgtgatgac acaagctgca ttctccaatc cagtcactct tggaacatca      60
gcttccatct cctgcaggtc tagtaagagt ctcctacata gtaatggcat cacttatttg     120
tattggtatc tgcagaagcc aggccagtct cctcagctcc tgatttatca gatgtccaac     180
cttgcctcag gagtcccaga caggttcagt agcagtgggt caggaactga tttcacactg     240
agaatcagca gagtggaggc tgaggatgtg ggtgtttatt actgtgctca aaatctagaa     300
cttccgtaca cgttcggagg ggggaccaag ctggaaataa aacgaactgt ggctgcacca     360
tctgtcttca tcttcccgcc atctgatgag cagttgaaat ctggaactgc ctctgttgtg     420
tgcctgctga ataacttcta tcccagagag gccaaagtac agtggaaggt ggataacgcc     480
ctccaatcgg gtaactccca ggagagtgtc acagagcagg acagcaagga cagcacctac     540
agcctcagca gcaccctgac gctgagcaaa gcagactacg agaaacacaa agtctacgcc     600
tgcgaagtca cccatcaggg cctgagctcg cccgtcacaa agagcttcaa caggggagag     660
tgt                                                                   663

<210> SEQ ID NO 58
<211> LENGTH: 660
<212> TYPE: DNA
<213> ORGANISM: Homo sapiens

<400> SEQUENCE: 58
ctagccgaca ttgtgctgac tcagtctcct gcttccttag ctgtatctct ggggcagagg      60
gccaccattt catgcagggc cagcaaaagt gtcagtacat ctggctatag ttttatgcac     120
tggtaccaac tgaaaccagg acagccaccc aaactcctca tctatcttgc atccaaccta     180
gaatctgggg tccctgccag gttcagtggc agtgggtctg gacagacttc accctcaac     240 atccatcctg tggaagagga ggatgctgca acctattact gtcagcacag tagggagttt     300
ccgttaacgt tcgaggggga ccaagctg aaataaaac gaactgtggc tgcaccatct     360
gtcttcatct ccccgccatc tgatgagcag ttgaaatctg gaactgcctc tgttgtgtgc     420
ctgctgaata acttctatcc cagagaggcc aaagtacagt ggaaggtgga taacgccctc     480
caatcgggta actcccagga gagtgtcaca gagcaggaca gcaaggacag cacctacagc     540
ctcagcagca cctgacgct gagcaaagca gactacgaga acacaaagt ctacgcctgc     600 gaagtcaccc atcagggcct gagctcgccc gtcacaaaga gcttcaacag gggagagtgt     660

<210> SEQ ID NO 59
<211> LENGTH: 657
<212> TYPE: DNA
<213> ORGANISM: Homo sapiens

<400> SEQUENCE: 59
gatattgtga tgactcaggc tgcattctcc aatccagtca ctcttggaac atcagcttcc      60
atctcctgca ggtctagtaa gagtctccta catagtaatg gcatcactta tttgtattgg     120
tatctgcaga agccaggcca gtctcctcag ctcctgattt atcagatgtc caaccttgcc     180
tcaggagtcc cagacaggtt cagtagcagt gggtcaagaa ctgatttcac actgagaatc     240
agcagagtgg aggctgagga tgtgggtgtt tattactgtg ctcaaaatct agaacttccg     300
tacacgttcg gagggggac caagctgaa ataaaacgaa ctgtggctgc accatctgtc     360
ttcatcttcc cgccatctga tgagcagttg aaatctggaa ctgcctctgt tgtgtgcctg     420
ctgaataact tctatcccag agaggccaaa gtacagtgga aggtggataa cgccctccaa     480
tcgggtaact cccaggagag tgtcacagag caggacagca aggacagcac ctacagcctc     540
```

```
agcagcaccc tgacgctgag caaagcagac tacgagaaac acaaagtcta cgcctgcgaa    600
gtcacccatc agggcctgag ctcgcccgtc acaaagagct tcaacagggg agagtgt       657
```

<210> SEQ ID NO 60
<211> LENGTH: 660
<212> TYPE: DNA
<213> ORGANISM: Homo sapiens

<400> SEQUENCE: 60

```
ctagccgatg ttgtgatgac tcagactcca ctctccctgc ctgtcagtct tggagatcaa     60
gcctccatct cttgcagatc tagtcagagc cttgtacaca gtaatggaaa cacctattta    120
cattggtacc tgcagaagcc aggccagtct ccaaaactcc tgatctacaa agtttccaac    180
cgattttctg gggtcccaga caggttcagt ggcagtggat cagggacaga tttcacactc    240
aagatcagca gagtggaggc tgaggatctg ggagtttatt tctgctctca aagtacacat    300
gttcccacgt tcggagggg gaccaagctg gaaatcaaac gaactgtggc tgcaccatct    360
gtcttcatct cccgccatc tgatgagcag ttgaaatctg gaactgcctc tgttgtgtgc    420
ctgctgaata cttctatcc cagagaggcc aaagtacagt ggaaggtgga taacgccctc    480
caatcgggta actcccagga gagtgtcaca gagcaggaca gcaaggacag cacctacagc    540
ctcagcagca ccctgacgct gagcaaagca gactacgaga acacaaagt ctacgcctgc    600 gaagtcaccc atcagggcct gagctcgccc gtcacaaaga gcttcaacag gggagagtgt    660
```

<210> SEQ ID NO 61
<211> LENGTH: 648
<212> TYPE: DNA
<213> ORGANISM: Homo sapiens

<400> SEQUENCE: 61

```
ctagccgaca ttgtgatgac ccagtctcac aaattcatgt ccacatcagt gggagacagg     60
gtcagcatca cctgcaaggc cagtcaggat gtgactaatg ccgtagcctg gtatcaacaa    120
aaaccaggac aatctcctaa actactgatt tactgggcat ccatccgaca cactggagtc    180
cctgatcgct tcacaggcag tagatctggg acagattata ctctcaccat caacagtgtg    240
caggctgaag acctggccct ttattattgt cagcaacatt ataacactcc gctcacgttc    300
ggtgctggga ccaagctgga aataaaacga actgtggctg caccatctgt cttcatcttc    360
ccgccatctg atgagcagtt gaaatctgga actgcctctg ttgtgtgcct gctgaataac    420
ttctatccca gagaggccaa agtacagtgg aaggtggata acgccctcca atcgggtaac    480
tcccaggaga gtgtcacaga gcaggacagc aaggacagca cctacagcct cagcagcacc    540
ctgacgctga gcaaagcaga ctacgagaaa cacaaagtct acgcctgcga agtcacccat    600
cagggcctga gctcgcccgt cacaaagagc ttcaacaggg gagagtgt                 648
```

<210> SEQ ID NO 62
<211> LENGTH: 660
<212> TYPE: DNA
<213> ORGANISM: Homo sapiens

<400> SEQUENCE: 62

```
ctagccgatg ttgtgatgac acagactcca ctctccctgc ctgtcagtct tggagatcaa     60
gcctccatct cttgcagatc tagtcagagc cttgtacaca gtaatggtaa cacctattta    120
cattggtacc tgcagaagcc aggccagtct ccaaagctcc tgctctacaa agtttccaac    180
cgattttctg gggtcccaga caggttcagt ggcagtggat cagggacaga tttcacactc    240
```

-continued

```
aagatcagca gagtggagtc tgaggatctg ggagtttatt tctgctctca aaatacacat    300
gtgtacacgt tcggaggggg gacaaagttg gaaataaaac gaactgtggc tgcaccatct    360
gtcttcatct tcccgccatc tgatgagcag ttgaaatctg gaactgcctc tgttgtgtgc    420
ctgctgaata acttctatcc cagagaggcc aaagtacagt ggaaggtgga taacgccctc    480
caatcgggta actcccagga gagtgtcaca gagcaggaca gcaaggacag cacctacagc    540
ctcagcagca ccctgacgct gagcaaagca gactacgaga aacacaaagt ctacgcctgc    600
gaagtcaccc atcagggcct gagctcgccc gtcacaaaga gcttcaacag gggagagtgt    660
```

<210> SEQ ID NO 63
<211> LENGTH: 645
<212> TYPE: DNA
<213> ORGANISM: Homo sapiens

<400> SEQUENCE: 63

```
ctagcccaaa ttgtgctcac acagtctcca gcaatcatgt ctgcatctcc aggggagaag     60
gtcaccatga cctgcagtgc cagctcaagt gtaagttaca tttactggta ccagcagaag    120
ccaggatcct cccccagact cctgatttat gacgcatcca acctggcttc tggagtccct    180
gttcgcttca gtggcagtgg gtctgggacc tcttactctc tcacaatcag ccgaatggag    240
gctgaagatg ctgccactta ttactgccag cagtggagca gttacccaat cacgttcggc    300
tcggggacaa agttggaaat aaaacgaact gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca aagcagacta cgagaaacac aaagtctacg cctgcgaagt cacccatcag    600
ggcctgagct cgcccgtcac aaagagcttc aacaggggag agtgt                    645
```

<210> SEQ ID NO 64
<211> LENGTH: 648
<212> TYPE: DNA
<213> ORGANISM: Homo sapiens

<400> SEQUENCE: 64

```
ctagccgata tccagatgac tcagactaca tcctcccctgt ctgcctctct gggagacaga    60
gtcaccatca gttgcagtgc aagtcagggc attaccaatt atttaaactg gtatcagcag    120
aaaccagatg gaactgttaa actcctgatc tattactcat caagtttaca ctcaggagtc    180
ccatcaaggt tcagtggcag tgggtctggg acagattatt ctctcaccat cagcaacctg    240
gaacctgaag atattgccac ttactattgt cagcagtata gtgagattcc gtacacgttc    300
ggagggggga ccaagctgga gctgaaacga actgtggctg caccatctgt cttcatcttc    360
ccgccatctg atgagcagtt gaaatctgga actgcctctg ttgtgtgcct gctgaataac    420
ttctatccca gagaggccaa agtacagtgg aaggtggata cgccctcca atcgggtaac    480 tcccaggaga gtgtcacaga gcaggacagc aaggacagca cctacagcct cagcagcacc    540
ctgacgctga gcaaagcaga ctacgagaaa cacaaagtct acgcctgcga agtcacccat    600
cagggcctga gctcgcccgt cacaaagagc ttcaacaggg gagagtgt                  648
```

<210> SEQ ID NO 65
<211> LENGTH: 645
<212> TYPE: DNA
<213> ORGANISM: Homo sapiens

<400> SEQUENCE: 65

```
ctagcccaaa ttgtgctgac ccagtctcca gcaatcatgt ctgcatctcc aggggagaag    60
gtcaccataa cctgcagtgc cagctcaagt gtaagttaca tgcactggtt ccagcagaag   120
ccaggcactt ctcccaaact ctggatttat agtacatcca acctggcttc tggagtccct   180
gctcgcttca gtggcagtgg atctgggacc tcttactctc tcacaatcag ccgaatggag   240
gctgaagatg ctgccactta ttactgccag caaaggagta gttacccata cacgttcgga   300
ggggggacca agctggagct gaaacgaact gtggctgcac catctgtctt catcttcccg   360
ccatctgatg agcagttgaa atctggaact gcctctgttg tgtgcctgct gaataacttc   420
tatcccagag aggccaaagt acagtggaag gtggataacg ccctccaatc gggtaactcc   480
caggagagtg tcacagagca ggacagcaag gacagcacct acagcctcag cagcaccctg   540
acgctgagca agcagactac gagaaacac aaagtctacg cctgcgaagt cacccatcag   600
ggcctgagct cgcccgtcac aaagagcttc aacagggag agtgt            645
```

<210> SEQ ID NO 66
<211> LENGTH: 660
<212> TYPE: DNA
<213> ORGANISM: Homo sapiens

<400> SEQUENCE: 66

```
ctagccgatg ttgtgatgac ccagactcca ctctccctgc ctgtcagtct tggagatcaa    60
gcctccatct cttgcagatc tagtcagagc cttgtacaca gtaatggaaa cacctattta   120
cattggtacc tgcagaagcc aggccagtct ccaaagctcc tgatctacaa agtttccaac   180
cgattttctg gggtcccaga caggttcagt ggcagtggat cagggacaga tttcacactc   240
aagatcagca gagtggaggc tgaggatctg ggagtttatt tctgctctca agtacacat   300
gttccgacgt tcggtggagg caccaagctg gaaatcaaac gaactgtggc tgcaccatct   360
gtcttcatct tcccgccatc tgatgagcag ttgaaatctg gaactgcctc tgttgtgtgc   420
ctgctgaata acttctatcc cagagaggcc aaagtacagt ggaaggtgga taacgccctc   480
caatcgggta actcccagga gagtgtcaca gagcaggaca gcaaggacag cacctacagc   540
ctcagcagca cctgacgct gagcaaagca gactacgaga acacaaagt ctacgcctgc   600
gaagtcaccc atcagggcct gagctcgccc gtcacaaaga gcttcaacag gggagagtgt   660
```

<210> SEQ ID NO 67
<211> LENGTH: 660
<212> TYPE: DNA
<213> ORGANISM: Homo sapiens

<400> SEQUENCE: 67

```
ctagccgaca ttgtgctaac acagtctcct gcttccttag ctgtatctct ggggcagagg    60
gccaccatct catgcagggc cagccaaagt gtcagtacat ctacctatag ttatatgcac   120
tggtatcaac agaaatcagg acagccaccc aaactcctca tcaagtatgc atccaaccta   180
gagtctgggg tccctgccag gttcagtggc agtgggtctg gacagactt caccctcaac   240
atccatcctg tggaggagga ggatactgca acatattact gtcagcacag ttgggagatt   300
ccgtggacgt tcggtggagg caccaagctg gaaatcaaac gaactgtggc tgcaccatct   360
gtcttcatct tcccgccatc tgatgagcag ttgaaatctg gaactgcctc tgttgtgtgc   420
ctgctgaata acttctatcc cagagaggcc aaagtacagt ggaaggtgga taacgccctc   480
caatcgggta actcccagga gagtgtcaca gagcaggaca gcaaggacag cacctacagc   540
```

```
ctcagcagca ccctgacgct gagcaaagca gactacgaga acacaaagt ctacgcctgc    600
gaagtcaccc atcagggcct gagctcgccc gtcacaaaga gcttcaacag gggagagtgt   660
```

<210> SEQ ID NO 68
<211> LENGTH: 648
<212> TYPE: DNA
<213> ORGANISM: Homo sapiens

<400> SEQUENCE: 68

```
ctagccgaca tccagatgac acaaactaca tcctccctgt ctgcctctct gggagacaga    60
gtcaccatca gttgcagggc aagtcaggac attagcaatt atttaaactg gtatcagcag   120
aaaccagatg gaactgttaa agtcctgatc tactacacat caagattaca ctcaggagtc   180
ccatcaaggt tcagtggcag tgggtctgga acagattatt ctctcaccat tagcaacctg   240
gagcaagaag atattgccac ttacttttgc aacagggta atacgcttcc gtacacgttc    300
ggaggggga ccaagctgga aataaaacga actgtggctg caccatctgt cttcatcttc   360
ccgccatctg atgagcagtt gaaatctgga actgcctctg ttgtgtgcct gctgaataac   420
ttctatccca gagaggccaa agtacagtgg aaggtggata acgcccttcca atcgggtaac   480
tcccaggaga gtgtcacaga gcaggacagc aaggacagca cctacagcct cagcagcacc   540
ctgacgctga gcaaagcaga ctacgagaaa cacaaagtct acgcctgcga agtcacccat   600
cagggcctga gctcgcccgt cacaaagagc ttcaacaggg gagagtgt              648
```

<210> SEQ ID NO 69
<211> LENGTH: 648
<212> TYPE: DNA
<213> ORGANISM: Homo sapiens

<400> SEQUENCE: 69

```
ctagccgaca ttcagatgac ccagactaca tcctccctgt ctgcctctct gggagacaga    60
gtcaccatca gttgcagtgc aagtcaggac attagcaatt atttaaactg gtatcagcag   120
aaaccagatg gaactgttaa actcctgatc tatcacacat caactttaca ctcaggagtc   180
ccatcaaggt tcagtggcag tgggtctggg acagattatt ctctcaccat cagcaacctg   240
gaacctgaag atattgccac ttactattgt cagcaatata gtaagcttcc gtggacgttc    300
ggtggaggca ccaagctgga aatcaaacga actgtggctg caccatctgt cttcatcttc   360
ccgccatctg atgagcagtt gaaatctgga actgcctctg ttgtgtgcct gctgaataac   420
ttctatccca gagaggccaa agtacagtgg aaggtggata acgcccttcca atcgggtaac   480
tcccaggaga gtgtcacaga gcaggacagc aaggacagca cctacagcct cagcagcacc   540
ctgacgctga gcaaagcaga ctacgagaaa cacaaagtct acgcctgcga agtcacccat   600
cagggcctga gctcgcccgt cacaaagagc ttcaacaggg gagagtgt              648
```

<210> SEQ ID NO 70
<211> LENGTH: 648
<212> TYPE: DNA
<213> ORGANISM: Homo sapiens

<400> SEQUENCE: 70

```
ctagccgaca ttcagatgac acagactact tcctccctgt ctgcctctct gggagacaga    60
gtcaccatta gttgcagtgc aagtcagggc attagtaatt atttaaactg gtatcagcag   120
aaaccagatg gaactgttaa actcctgatc tattacacat caagtttaca ctcaggagtc   180
ccatcaaggt tcagtggcag tgggtctggg acagattatt ctctcaccat cagcaacctg   240
```

```
gaacctgaag atattgccac ttactattgt cagcagtata gtaagcttcc gtacacgttc    300
ggagggggga ccaagctgga aatcaaacga actgtggctg caccatctgt cttcatcttc    360
ccgccatctg atgagcagtt gaaatctgga actgcctctg ttgtgtgcct gctgaataac    420
ttctatccca gagaggccaa agtacagtgg aaggtggata acgcccctcca atcgggtaac   480 tcccaggaga gtgtcacaga gcaggacagc aaggacagca cctacagcct cagcagcacc    540
ctgacgctga gcaaagcaga ctacgagaaa cacaaagtct acgcctgcga agtcacccat    600
cagggcctga gctcgcccgt cacaaagagc ttcaacaggg gagagtgt                 648
```

<210> SEQ ID NO 71
<211> LENGTH: 651
<212> TYPE: DNA
<213> ORGANISM: Homo sapiens

<400> SEQUENCE: 71

```
ctagccgaaa atgtgctgac tcagtctcca gcaatcatgt ctgcatctcc aggggaaaag     60
gtcaccatga cctgcagggc cagctcaagt gtaagttcca gttacttgca ctggtaccag    120
caaaagtcag gtgcctcccc caaactctgg atttatagca catccaactt ggcttctgga    180
gtccctgctc gcttcagtgg cagtgggtct gggacctctt actctctcac agtcaacagt    240
gtggagactg aagatgctgc cacttattac tgccaccagt acagtggttt cccattcacg    300
ttcggctcgg ggaccaagct ggagctgaaa cgaactgtgg ctgcaccatc tgtcttcatc    360
ttcccgccat ctgatgagca gttgaaatct ggaactgcct ctgttgtgtg cctgctgaat    420
aacttctatc ccagagaggc caaagtacag tggaaggtgg ataacgcccct ccaatcgggt   480 aactcccagg agagtgtcac agagcaggac agcaaggaca gcacctacag cctcagcagc    540
accctgacgc tgagcaaagc agactacgag aaacacaaag tctacgcctg cgaagtcacc    600
catcagggcc tgagctcgcc cgtcacaaag agcttcaaca ggggagagtg t             651
```

<210> SEQ ID NO 72
<211> LENGTH: 216
<212> TYPE: PRT
<213> ORGANISM: Homo sapiens

<400> SEQUENCE: 72

```
Leu Ala Asp Ile Gln Met Thr Gln Thr Thr Ser Ser Leu Ser Ala Ser
1               5                   10                  15

Leu Gly Asp Arg Val Thr Ile Ser Cys Arg Thr Ser Gln Asp Ile Gly
            20                  25                  30

Asn Tyr Leu Asn Trp Tyr Gln Gln Lys Pro Asp Gly Thr Val Lys Leu
        35                  40                  45

Leu Ile Tyr Tyr Thr Ser Arg Leu His Ser Gly Val Pro Ser Arg Phe
    50                  55                  60

Ser Gly Ser Gly Ser Gly Thr Asp Phe Ser Leu Thr Ile Asn Asn Val
65                  70                  75                  80

Glu Gln Glu Asp Val Ala Thr Tyr Phe Cys Gln His Tyr Asn Thr Val
                85                  90                  95

Pro Pro Thr Phe Gly Gly Gly Thr Lys Leu Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140
```

```
Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215
```

<210> SEQ ID NO 73
<211> LENGTH: 221
<212> TYPE: PRT
<213> ORGANISM: Homo sapiens

<400> SEQUENCE: 73

```
Leu Ala Asp Ile Val Met Thr Gln Ala Ala Phe Ser Asn Pro Val Thr
1               5                   10                  15

Leu Gly Thr Ser Ala Ser Ile Ser Cys Arg Ser Ser Lys Ser Leu Leu
            20                  25                  30

His Ser Asn Gly Ile Thr Tyr Leu Tyr Trp Tyr Leu Gln Lys Pro Gly
        35                  40                  45

Gln Ser Pro Gln Leu Leu Ile Tyr Gln Met Ser Asn Leu Ala Ser Gly
    50                  55                  60

Val Pro Asp Arg Phe Ser Ser Ser Gly Ser Gly Thr Asp Phe Thr Leu
65                  70                  75                  80

Arg Ile Ser Arg Val Glu Ala Glu Asp Val Gly Val Tyr Tyr Cys Ala
                85                  90                  95

Gln Asn Leu Glu Leu Pro Tyr Thr Phe Gly Gly Gly Thr Lys Leu Glu
            100                 105                 110

Ile Lys Arg Thr Val Ala Ala Pro Ser Val Phe Ile Phe Pro Pro Ser
        115                 120                 125

Asp Glu Gln Leu Lys Ser Gly Thr Ala Ser Val Val Cys Leu Leu Asn
    130                 135                 140

Asn Phe Tyr Pro Arg Glu Ala Lys Val Gln Trp Lys Val Asp Asn Ala
145                 150                 155                 160

Leu Gln Ser Gly Asn Ser Gln Glu Ser Val Thr Glu Gln Asp Ser Lys
                165                 170                 175

Asp Ser Thr Tyr Ser Leu Ser Ser Thr Leu Thr Leu Ser Lys Ala Asp
            180                 185                 190

Tyr Glu Lys His Lys Val Tyr Ala Cys Glu Val Thr His Gln Gly Leu
        195                 200                 205

Ser Ser Pro Val Thr Lys Ser Phe Asn Arg Gly Glu Cys
    210                 215                 220
```

<210> SEQ ID NO 74
<211> LENGTH: 220
<212> TYPE: PRT
<213> ORGANISM: Homo sapiens

<400> SEQUENCE: 74

```
Leu Ala Asp Ile Val Leu Thr Gln Ser Pro Ala Ser Leu Ala Val Ser
1               5                   10                  15

Leu Gly Gln Arg Ala Thr Ile Ser Cys Arg Ala Ser Lys Ser Val Ser
            20                  25                  30

Thr Ser Gly Tyr Ser Phe Met His Trp Tyr Gln Leu Lys Pro Gly Gln
```

```
              35                  40                  45
Pro Pro Lys Leu Leu Ile Tyr Leu Ala Ser Asn Leu Glu Ser Gly Val
 50                  55                  60

Pro Ala Arg Phe Ser Gly Ser Gly Ser Gly Thr Asp Phe Thr Leu Asn
 65                  70                  75                  80

Ile His Pro Val Glu Glu Asp Ala Ala Thr Tyr Tyr Cys Gln His
                     85                  90                  95

Ser Arg Glu Phe Pro Leu Thr Phe Gly Gly Gly Thr Lys Leu Glu Ile
                100                 105                 110

Lys Arg Thr Val Ala Ala Pro Ser Val Phe Ile Phe Pro Pro Ser Asp
                115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
                180                 185                 190

Glu Lys His Lys Val Tyr Ala Cys Glu Val Thr His Gln Gly Leu Ser
                195                 200                 205

Ser Pro Val Thr Lys Ser Phe Asn Arg Gly Glu Cys
                210                 215                 220

<210> SEQ ID NO 75
<211> LENGTH: 219
<212> TYPE: PRT
<213> ORGANISM: Homo sapiens

<400> SEQUENCE: 75

Asp Ile Val Met Thr Gln Ala Ala Phe Ser Asn Pro Val Thr Leu Gly
  1               5                  10                  15

Thr Ser Ala Ser Ile Ser Cys Arg Ser Lys Ser Leu Leu His Ser
                 20                  25                  30

Asn Gly Ile Thr Tyr Leu Tyr Trp Tyr Leu Gln Lys Pro Gly Gln Ser
                 35                  40                  45

Pro Gln Leu Leu Ile Tyr Gln Met Ser Asn Leu Ala Ser Gly Val Pro
 50                  55                  60

Asp Arg Phe Ser Ser Ser Gly Ser Arg Thr Asp Phe Thr Leu Arg Ile
 65                  70                  75                  80

Ser Arg Val Glu Ala Glu Asp Val Gly Val Tyr Tyr Cys Ala Gln Asn
                 85                  90                  95

Leu Glu Leu Pro Tyr Thr Phe Gly Gly Gly Thr Lys Leu Glu Ile Lys
                100                 105                 110

Arg Thr Val Ala Ala Pro Ser Val Phe Ile Phe Pro Pro Ser Asp Glu
                115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
```

```
            195                 200                 205
Pro Val Thr Lys Ser Phe Asn Arg Gly Glu Cys
    210                 215
```

<210> SEQ ID NO 76
<211> LENGTH: 220
<212> TYPE: PRT
<213> ORGANISM: Homo sapiens

<400> SEQUENCE: 76

```
Leu Ala Asp Val Val Met Thr Gln Thr Pro Leu Ser Leu Pro Val Ser
1               5                   10                  15

Leu Gly Asp Gln Ala Ser Ile Ser Cys Arg Ser Ser Gln Ser Leu Val
            20                  25                  30

His Ser Asn Gly Asn Thr Tyr Leu His Trp Tyr Leu Gln Lys Pro Gly
        35                  40                  45

Gln Ser Pro Lys Leu Leu Ile Tyr Lys Val Ser Asn Arg Phe Ser Gly
    50                  55                  60

Val Pro Asp Arg Phe Ser Gly Ser Gly Ser Gly Thr Asp Phe Thr Leu
65                  70                  75                  80

Lys Ile Ser Arg Val Glu Ala Glu Asp Leu Gly Val Tyr Phe Cys Ser
                85                  90                  95

Gln Ser Thr His Val Pro Thr Phe Gly Gly Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 77
<211> LENGTH: 216
<212> TYPE: PRT
<213> ORGANISM: Homo sapiens

<400> SEQUENCE: 77

```
Leu Ala Asp Ile Val Met Thr Gln Ser His Lys Phe Met Ser Thr Ser
1               5                   10                  15

Val Gly Asp Arg Val Ser Ile Thr Cys Lys Ala Ser Gln Asp Val Thr
            20                  25                  30

Asn Ala Val Ala Trp Tyr Gln Gln Lys Pro Gly Gln Ser Pro Lys Leu
        35                  40                  45

Leu Ile Tyr Trp Ala Ser Ile Arg His Thr Gly Val Pro Asp Arg Phe
    50                  55                  60

Thr Gly Ser Arg Ser Gly Thr Asp Tyr Thr Leu Thr Ile Asn Ser Val
65                  70                  75                  80

Gln Ala Glu Asp Leu Ala Leu Tyr Tyr Cys Gln Gln His Tyr Asn Thr
                85                  90                  95
```

```
Pro Leu Thr Phe Gly Ala Gly Thr Lys Leu Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 78
<211> LENGTH: 220
<212> TYPE: PRT
<213> ORGANISM: Homo sapiens

<400> SEQUENCE: 78

Leu Ala Asp Val Val Met Thr Gln Thr Pro Leu Ser Leu Pro Val Ser
1               5                   10                  15

Leu Gly Asp Gln Ala Ser Ile Ser Cys Arg Ser Ser Gln Ser Leu Val
            20                  25                  30

His Ser Asn Gly Asn Thr Tyr Leu His Trp Tyr Leu Gln Lys Pro Gly
        35                  40                  45

Gln Ser Pro Lys Leu Leu Leu Tyr Lys Val Ser Asn Arg Phe Ser Gly
    50                  55                  60

Val Pro Asp Arg Phe Ser Gly Ser Gly Ser Gly Thr Asp Phe Thr Leu
65                  70                  75                  80

Lys Ile Ser Arg Val Glu Ser Glu Asp Leu Gly Val Tyr Phe Cys Ser
                85                  90                  95

Gln Asn Thr His Val Tyr Thr Phe Gly Gly Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 79
<211> LENGTH: 215
<212> TYPE: PRT
<213> ORGANISM: Homo sapiens
```

<400> SEQUENCE: 79

```
Leu Ala Gln Ile Val Leu Thr Gln Ser Pro Ala Ile Met Ser Ala Ser
1               5                   10                  15

Pro Gly Glu Lys Val Thr Met Thr Cys Ser Ala Ser Ser Ser Val Ser
            20                  25                  30

Tyr Ile Tyr Trp Tyr Gln Gln Lys Pro Gly Ser Ser Pro Arg Leu Leu
        35                  40                  45

Ile Tyr Asp Ala Ser Asn Leu Ala Ser Gly Val Pro Val Arg Phe Ser
    50                  55                  60

Gly Ser Gly Ser Gly Thr Ser Tyr Ser Leu Thr Ile Ser Arg Met Glu
65                  70                  75                  80

Ala Glu Asp Ala Ala Thr Tyr Tyr Cys Gln Gln Trp Ser Ser Tyr Pro
                85                  90                  95

Ile Thr Phe Gly Ser Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 80
<211> LENGTH: 216
<212> TYPE: PRT
<213> ORGANISM: Homo sapiens

<400> SEQUENCE: 80

```
Leu Ala Asp Ile Gln Met Thr Gln Thr Thr Ser Ser Leu Ser Ala Ser
1               5                   10                  15

Leu Gly Asp Arg Val Thr Ile Ser Cys Ser Ala Ser Gln Gly Ile Thr
            20                  25                  30

Asn Tyr Leu Asn Trp Tyr Gln Gln Lys Pro Asp Gly Thr Val Lys Leu
        35                  40                  45

Leu Ile Tyr Tyr Ser Ser Ser Leu His Ser Gly Val Pro Ser Arg Phe
    50                  55                  60

Ser Gly Ser Gly Ser Gly Thr Asp Tyr Ser Leu Thr Ile Ser Asn Leu
65                  70                  75                  80

Glu Pro Glu Asp Ile Ala Thr Tyr Tyr Cys Gln Gln Tyr Ser Glu Ile
                85                  90                  95

Pro Tyr Thr Phe Gly Gly Gly Thr Lys Leu Glu Leu Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
130                 135                 140
```

```
Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215
```

<210> SEQ ID NO 81
<211> LENGTH: 215
<212> TYPE: PRT
<213> ORGANISM: Homo sapiens

<400> SEQUENCE: 81

```
Leu Ala Gln Ile Val Leu Thr Gln Ser Pro Ala Ile Met Ser Ala Ser
1               5                   10                  15

Pro Gly Glu Lys Val Thr Ile Thr Cys Ser Ala Ser Ser Ser Val Ser
            20                  25                  30

Tyr Met His Trp Phe Gln Gln Lys Pro Gly Thr Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Arg Met Glu
65                  70                  75                  80

Ala Glu Asp Ala Ala Thr Tyr Tyr Cys Gln Gln Arg Ser Ser Tyr Pro
                85                  90                  95

Tyr Thr Phe Gly Gly Gly Thr Lys Leu Glu Leu Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 82
<211> LENGTH: 220
<212> TYPE: PRT
<213> ORGANISM: Homo sapiens

<400> SEQUENCE: 82

```
Leu Ala Asp Val Val Met Thr Gln Thr Pro Leu Ser Leu Pro Val Ser
1               5                   10                  15

Leu Gly Asp Gln Ala Ser Ile Ser Cys Arg Ser Ser Gln Ser Leu Val
            20                  25                  30

His Ser Asn Gly Asn Thr Tyr Leu His Trp Tyr Leu Gln Lys Pro Gly
```

```
                35                  40                  45
Gln Ser Pro Lys Leu Leu Ile Tyr Lys Val Ser Asn Arg Phe Ser Gly
 50                  55                  60
Val Pro Asp Arg Phe Ser Gly Ser Gly Ser Gly Thr Asp Phe Thr Leu
 65                  70                  75                  80
Lys Ile Ser Arg Val Glu Ala Glu Asp Leu Gly Val Tyr Phe Cys Ser
                 85                  90                  95
Gln Ser Thr His Val Pro Thr Phe Gly Gly Gly Thr Lys Leu Glu Ile
             100                 105                 110
Lys Arg Thr Val Ala Ala Pro Ser Val Phe Ile Phe Pro Pro Ser Asp
         115                 120                 125
Glu Gln Leu Lys Ser Gly Thr Ala Ser Val Val Cys Leu Leu Asn Asn
     130                 135                 140
Phe Tyr Pro Arg Glu Ala Lys Val Gln Trp Lys Val Asp Asn Ala Leu
145                 150                 155                 160
Gln Ser Gly Asn Ser Gln Glu Ser Val Thr Glu Gln Asp Ser Lys Asp
                165                 170                 175
Ser Thr Tyr Ser Leu Ser Ser Thr Leu Thr Leu Ser Lys Ala Asp Tyr
            180                 185                 190
Glu Lys His Lys Val Tyr Ala Cys Glu Val Thr His Gln Gly Leu Ser
        195                 200                 205
Ser Pro Val Thr Lys Ser Phe Asn Arg Gly Glu Cys
    210                 215                 220

<210> SEQ ID NO 83
<211> LENGTH: 220
<212> TYPE: PRT
<213> ORGANISM: Homo sapiens

<400> SEQUENCE: 83

Leu Ala Asp Ile Val Leu Thr Gln Ser Pro Ala Ser Leu Ala Val Ser
  1               5                  10                  15
Leu Gly Gln Arg Ala Thr Ile Ser Cys Arg Ala Ser Gln Ser Val Ser
                 20                  25                  30
Thr Ser Thr Tyr Ser Tyr Met His Trp Tyr Gln Gln Lys Ser Gly Gln
             35                  40                  45
Pro Pro Lys Leu Leu Ile Lys Tyr Ala Ser Asn Leu Glu Ser Gly Val
 50                  55                  60
Pro Ala Arg Phe Ser Gly Ser Gly Ser Gly Thr Asp Phe Thr Leu Asn
 65                  70                  75                  80
Ile His Pro Val Glu Glu Asp Thr Ala Thr Tyr Tyr Cys Gln His
                 85                  90                  95
Ser Trp Glu Ile Pro Trp Thr Phe Gly Gly Gly Thr Lys Leu Glu Ile
             100                 105                 110
Lys Arg Thr Val Ala Ala Pro Ser Val Phe Ile Phe Pro Pro Ser Asp
         115                 120                 125
Glu Gln Leu Lys Ser Gly Thr Ala Ser Val Val Cys Leu Leu Asn Asn
     130                 135                 140
Phe Tyr Pro Arg Glu Ala Lys Val Gln Trp Lys Val Asp Asn Ala Leu
145                 150                 155                 160
Gln Ser Gly Asn Ser Gln Glu Ser Val Thr Glu Gln Asp Ser Lys Asp
                165                 170                 175
Ser Thr Tyr Ser Leu Ser Ser Thr Leu Thr Leu Ser Lys Ala Asp Tyr
            180                 185                 190
Glu Lys His Lys Val Tyr Ala Cys Glu Val Thr His Gln Gly Leu Ser
```

Ser Pro Val Thr Lys Ser Phe Asn Arg Gly Glu Cys
    210                 215                 220

<210> SEQ ID NO 84
<211> LENGTH: 216
<212> TYPE: PRT
<213> ORGANISM: Homo sapiens

<400> SEQUENCE: 84

Leu Ala Asp Ile Gln Met Thr Gln Thr Thr Ser Ser Leu Ser Ala Ser
1               5                   10                  15

Leu Gly Asp Arg Val Thr Ile Ser Cys Arg Ala Ser Gln Asp Ile Ser
            20                  25                  30

Asn Tyr Leu Asn Trp Tyr Gln Gln Lys Pro Asp Gly Thr Val Lys Val
        35                  40                  45

Leu Ile Tyr Tyr Thr Ser Arg Leu His Ser Gly Val Pro Ser Arg Phe
    50                  55                  60

Ser Gly Ser Gly Ser Gly Thr Asp Tyr Ser Leu Thr Ile Ser Asn Leu
65                  70                  75                  80

Glu Gln Glu Asp Ile Ala Thr Tyr Phe Cys Gln Gln Gly Asn Thr Leu
                85                  90                  95

Pro Tyr Thr Phe Gly Gly Gly Thr Lys Leu Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 85
<211> LENGTH: 216
<212> TYPE: PRT
<213> ORGANISM: Homo sapiens

<400> SEQUENCE: 85

Leu Ala Asp Ile Gln Met Thr Gln Thr Thr Ser Ser Leu Ser Ala Ser
1               5                   10                  15

Leu Gly Asp Arg Val Thr Ile Ser Cys Ser Ala Ser Gln Asp Ile Ser
            20                  25                  30

Asn Tyr Leu Asn Trp Tyr Gln Gln Lys Pro Asp Gly Thr Val Lys Leu
        35                  40                  45

Leu Ile Tyr His Thr Ser Thr Leu His Ser Gly Val Pro Ser Arg Phe
    50                  55                  60

Ser Gly Ser Gly Ser Gly Thr Asp Tyr Ser Leu Thr Ile Ser Asn Leu
65                  70                  75                  80

Glu Pro Glu Asp Ile Ala Thr Tyr Tyr Cys Gln Gln Tyr Ser Lys Leu
                85                  90                  95

Pro Trp Thr Phe Gly Gly Gly Thr Lys Leu Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 86
<211> LENGTH: 216
<212> TYPE: PRT
<213> ORGANISM: Homo sapiens

<400> SEQUENCE: 86

Leu Ala Asp Ile Gln Met Thr Gln Thr Thr Ser Ser Leu Ser Ala Ser
1               5                   10                  15

Leu Gly Asp Arg Val Thr Ile Ser Cys Ser Ala Ser Gln Gly Ile Ser
            20                  25                  30

Asn Tyr Leu Asn Trp Tyr Gln Gln Lys Pro Asp Gly Thr Val Lys Leu
        35                  40                  45

Leu Ile Tyr Tyr Thr Ser Ser Leu His Ser Gly Val Pro Ser Arg Phe
    50                  55                  60

Ser Gly Ser Gly Ser Gly Thr Asp Tyr Ser Leu Thr Ile Ser Asn Leu
65                  70                  75                  80

Glu Pro Glu Asp Ile Ala Thr Tyr Tyr Cys Gln Gln Tyr Ser Lys Leu
                85                  90                  95

Pro Tyr Thr Phe Gly Gly Gly Thr Lys Leu Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 87
<211> LENGTH: 217
<212> TYPE: PRT
<213> ORGANISM: Homo sapiens

<400> SEQUENCE: 87

Leu Ala Glu Asn Val Leu Thr Gln Ser Pro Ala Ile Met Ser Ala Ser
1               5                   10                  15

Pro Gly Glu Lys Val Thr Met Thr Cys Arg Ala Ser Ser Ser Val Ser
            20                  25                  30

Ser Ser Tyr Leu His Trp Tyr Gln Gln Lys Ser Gly Ala Ser Pro Lys
        35                  40                  45

Leu Trp Ile Tyr Ser Thr Ser Asn Leu Ala Ser Gly Val Pro Ala Arg
    50                  55                  60

Phe Ser Gly Ser Gly Ser Gly Thr Ser Tyr Ser Leu Thr Val Asn Ser
65                  70                  75                  80

Val Glu Thr Glu Asp Ala Ala Thr Tyr Tyr Cys His Gln Tyr Ser Gly
                85                  90                  95

Phe Pro Phe Thr Phe Gly Ser Gly Thr Lys Leu Glu Leu Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 88
<211> LENGTH: 324
<212> TYPE: DNA
<213> ORGANISM: Homo sapiens

<400> SEQUENCE: 88
ttcatcttcc cgccatctga tgagcagttg aaatctggaa ctgcctctgt tgtgtgcctg      60
ctgaataact tctatcccag agaggccaaa gtacagtgga aggtggataa cgccctccaa     120
tcgggtaact cccaggagag tgtcacagag caggacagca aggacagcac ctacagcctc     180
agcagcaccc tgacgctgag caaagcagac tacgagaaac acaaagtcta cgcctgcgaa     240
gtcacccatc agggcctgag ctcgcccgtc acaaagagct tcaacagggg agagtgttaa     300
taagcggccg ccggtggagg cggt                                           324

<210> SEQ ID NO 89
<211> LENGTH: 106
<212> TYPE: PRT
<213> ORGANISM: Homo sapiens

<400> SEQUENCE: 89

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser

```
                                    35                  40                  45
Gly Asn Ser Gln Glu Ser Val Thr Glu Gln Asp Ser Lys Asp Ser Thr
 50                  55                  60
Tyr Ser Leu Ser Ser Thr Leu Thr Leu Ser Lys Ala Asp Tyr Glu Lys
 65                  70                  75                  80
His Lys Val Tyr Ala Cys Glu Val Thr His Gln Gly Leu Ser Ser Pro
                 85                  90                  95
Val Thr Lys Ser Phe Asn Arg Gly Glu Cys
            100                 105

<210> SEQ ID NO 90
<211> LENGTH: 1602
<212> TYPE: DNA
<213> ORGANISM: Homo sapiens
<220> FEATURE:
<221> NAME/KEY: exon
<222> LOCATION: (1)..(297)
<220> FEATURE:
<221> NAME/KEY: Intron
<222> LOCATION: (298)..(688)
<220> FEATURE:
<221> NAME/KEY: exon
<222> LOCATION: (689)..(733)
<220> FEATURE:
<221> NAME/KEY: Intron
<222> LOCATION: (734)..(851)
<220> FEATURE:
<221> NAME/KEY: exon
<222> LOCATION: (852)..(1181)
<220> FEATURE:
<221> NAME/KEY: Intron
<222> LOCATION: (1182)..(1278)
<220> FEATURE:
<221> NAME/KEY: exon
<222> LOCATION: (1279)..(1602)

<400> SEQUENCE: 90 agt gcc tcc acc aag ggc cca tcg gtc ttc ccc ctg gca ccc tcc tcc      48
Ser Ala Ser Thr Lys Gly Pro Ser Val Phe Pro Leu Ala Pro Ser Ser
  1               5                  10                  15 aag agc acc tct ggg ggc aca gcg gcc ctg ggc tgc ctg gtc aag gac      96
Lys Ser Thr Ser Gly Gly Thr Ala Ala Leu Gly Cys Leu Val Lys Asp
             20                  25                  30 tac ttc ccc gaa ccg gtg acg gtg tcg tgg aac tca ggc gcc ctg acc     144
Tyr Phe Pro Glu Pro Val Thr Val Ser Trp Asn Ser Gly Ala Leu Thr
         35                  40                  45 agc ggc gtg cac acc ttc ccg gct gtc cta cag tcc tca gga ctc tac     192
Ser Gly Val His Thr Phe Pro Ala Val Leu Gln Ser Ser Gly Leu Tyr
     50                  55                  60 tcc ctc agc agc gtg gtg acc gtg ccc tcc agc agc ttg ggc acc cag     240
Ser Leu Ser Ser Val Val Thr Val Pro Ser Ser Ser Leu Gly Thr Gln
 65                  70                  75                  80 acc tac atc tgc aac gtg aat cac aag ccc agc aac acc aag gtg gac     288
Thr Tyr Ile Cys Asn Val Asn His Lys Pro Ser Asn Thr Lys Val Asp
                 85                  90                  95 aag aga gtt ggtgagaggc cagcacaggg agggagggtg tctgctggaa              337
Lys Arg Val gccaggctca gcgctcctgc ctggacgcat cccggctatg cagtcccagt ccagggcagc    397
aaggcaggcc ccgtctgcct cttcacccgg aggcctctgc ccgccccact catgctcagg    457
gagagggtct tctggctttt tccccaggct ctgggcaggc acaggctagg tgcccctaac    517
ccaggccctg cacacaaagg ggcaggtgct gggctcagac ctgccaagag ccatatccgg    577
gaggaccctg cccctgacct aagcccaccc caaaggccaa actctccact ccctcagctc    637
```

```
ggacaccttc tctcctccca gattccagta actcccaatc ttctctctgc a gag ccc      694
                                                        Glu Pro
                                                            100 aaa tct tgt gac aaa act cac aca tgc cca ccg tgc cca ggtaagccag        743
Lys Ser Cys Asp Lys Thr His Thr Cys Pro Pro Cys Pro
            105                 110 cccaggcctc gccctccagc tcaaggcggg acaggtgccc tagagtagcc tgcatccagg     803
gacaggcccc agccgggtgc tgacacgtcc acctccatct cttcctca gca cct gaa     860
                                                     Ala Pro Glu
                                                             115 ctc ctg ggg gga ccg tca gtc ttc ctc ttc ccc cca aaa ccc aag gac      908
Leu Leu Gly Gly Pro Ser Val Phe Leu Phe Pro Pro Lys Pro Lys Asp
            120                 125                 130 acc ctc atg atc tcc cgg acc cct gag gtc aca tgc gtg gtg gtg gac      956
Thr Leu Met Ile Ser Arg Thr Pro Glu Val Thr Cys Val Val Val Asp
        135                 140                 145 gtg agc cac gaa gac cct gag gtc aag ttc aac tgg tac gtg gac ggc      1004
Val Ser His Glu Asp Pro Glu Val Lys Phe Asn Trp Tyr Val Asp Gly
150                 155                 160                 165 gtg gag gtg cat aat gcc aag aca aag ccg cgg gag gag cag tac aac      1052
Val Glu Val His Asn Ala Lys Thr Lys Pro Arg Glu Glu Gln Tyr Asn
                170                 175                 180 agc acg tac cgt gtg gtc agc gtc ctc acc gtc ctg cac cag gac tgg      1100
Ser Thr Tyr Arg Val Val Ser Val Leu Thr Val Leu His Gln Asp Trp
            185                 190                 195 ctg aat ggc aag gag tac aag tgc aag gtc tcc aac aaa gcc ctc cca      1148
Leu Asn Gly Lys Glu Tyr Lys Cys Lys Val Ser Asn Lys Ala Leu Pro
        200                 205                 210 gcc ccc atc gag aaa acc atc tcc aaa gcc aaa ggtgggaccc gtggggtgcg   1201
Ala Pro Ile Glu Lys Thr Ile Ser Lys Ala Lys
    215                 220 agggccacat ggacagaggc cggctcggcc caccctctgc cctgagagtg accgctgtac   1261
caacctctgt ccctaca ggg cag ccc cga gaa cca cag gtg tac acc ctg       1311
                   Gly Gln Pro Arg Glu Pro Gln Val Tyr Thr Leu
                       225                 230                 235 ccc cca tcc cgg gag gag atg acc aag aac cag gtc agc ctg acc tgc     1359
Pro Pro Ser Arg Glu Glu Met Thr Lys Asn Gln Val Ser Leu Thr Cys
            240                 245                 250 ctg gtc aaa ggc ttc tat ccc agc gac atc gcc gtg gag tgg gag agc     1407
Leu Val Lys Gly Phe Tyr Pro Ser Asp Ile Ala Val Glu Trp Glu Ser
        255                 260                 265 aat ggg cag ccg gag aac aac tac aag acc acg cct ccc gtg ctg gac     1455
Asn Gly Gln Pro Glu Asn Asn Tyr Lys Thr Thr Pro Pro Val Leu Asp
    270                 275                 280 tcc gac ggc tcc ttc ttc ctc tat agc aag ctc acc gtg gac aag agc     1503
Ser Asp Gly Ser Phe Phe Leu Tyr Ser Lys Leu Thr Val Asp Lys Ser
285                 290                 295 agg tgg cag cag ggg aac gtc ttc tca tgc tcc gtg atg cat gag gct     1551
Arg Trp Gln Gln Gly Asn Val Phe Ser Cys Ser Val Met His Glu Ala
300                 305                 310                 315 ctg cac aac cac tac acg cag aag agc ctc tcc ctg tcc ccg ggt aaa     1599
Leu His Asn His Tyr Thr Gln Lys Ser Leu Ser Leu Ser Pro Gly Lys
                320                 325                 330 tga                                                                  1602

<210> SEQ ID NO 91
<211> LENGTH: 331
<212> TYPE: PRT
<213> ORGANISM: Homo sapiens
```

<400> SEQUENCE: 91

Ser Ala Ser Thr Lys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp
            20                  25                  30

Tyr Phe Pro Glu Pro Val Thr Val Ser Trp Asn Ser Gly Ala Leu Thr
        35                  40                  45

Ser Gly Val His Thr Phe Pro Ala Val Leu Gln Ser Ser Gly Leu Tyr
    50                  55                  60

Ser Leu Ser Ser Val Val Thr Val Pro Ser Ser Ser Leu Gly Thr Gln
65                  70                  75                  80

Thr Tyr Ile Cys Asn Val Asn His Lys Pro Ser Asn Thr Lys Val Asp
                85                  90                  95

Lys Arg Val Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
        115                 120                 125

Pro Lys Pro Lys Asp Thr Leu Met Ile Ser Arg Thr Pro Glu Val Thr
    130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
        195                 200                 205

Asn Lys Ala Leu Pro Ala Pro Ile Glu Lys Thr Ile Ser Lys Ala Lys
210                 215                 220

Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
            260                 265                 270

Asn Asn Tyr Lys Thr Thr Pro Pro Val Leu Asp Ser Asp Gly Ser Phe
        275                 280                 285

Phe Leu Tyr Ser Lys Leu Thr Val Asp Lys Ser Arg Trp Gln Gln Gly
    290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330

<210> SEQ ID NO 92
<211> LENGTH: 751
<212> TYPE: DNA
<213> ORGANISM: artificial
<220> FEATURE:
<223> OTHER INFORMATION: Synthetic construct

<400> SEQUENCE: 92
ggcgcgccga ggtccaactg cagcaacctg gtctgagctg gtgaggcct ggagcttcag      60 tgaagctgtc ctgcaaggct tctggctaca cattcaccag ctactggatg cactgggtga     120
agcagaggcc tggacaaggc cttgagtgga ttgggaatat ttatcctggt agtcgtagta     180

```
ctaactacga tgagaagttc aagagcaagg ccacactgac tgtagacaca tcctccagca    240
cagcctacat gcagctcagc agcctgacat ctgaggactc tgcggtctat tactgtacaa    300
gaaatgggga ttactacgtt agtagcgggg atgctatgga ctactggggt caaggaacct    360
cagtcaccgt ctcgtcagcc agcaccaagg ccccaggt ccaactgcag cagcctgggg      420
ctgaactggt ggagcctggg ggttcagtga agctgtcctg caaggcttct ggctacacct    480
tcaccagtca ctggatgcac tgggtgaagc agaggcctgg acaaggcctt gagtggatag    540
gtgagattaa tcctagcagc ggtcgtaata actacaatga aagttcaag agtaaggcca    600 cactgactgt agacaaatcc tccagcacag cctacatgca attcagcagc ctgacatctg    660
aggactctgc ggtctattat tgtgtaagat actatggtta cgacgaagct atggactact    720
ggggtcaagg aacctcagtc accgtctcga g                                   751
```

<210> SEQ ID NO 93
<211> LENGTH: 1017
<212> TYPE: DNA
<213> ORGANISM: artificial
<220> FEATURE:
<223> OTHER INFORMATION: Synthetic construct

<400> SEQUENCE: 93

```
gctagccgac attcagatga ctcagactac atcctccctg tctgcctctc tgggagacag     60
agtcaccatc agttgcagga caagtcagga cattggcaat tatttaaact ggtatcagca    120
gaaaccagat ggaactgtta aactcctgat ctactacaca tcaagattac actcaggagt    180
cccatcaagg ttcagtggca gtgggtctgg aacagatttt tctctcacca ttaacaacgt    240
ggagcaagag gatgttgcca cttactttg ccaacactat aatacggttc ctccgacgtt    300
cggtggaggc accaagctgg aaatcaaacg aactgtggct gcaccagaca tcgtgatgac    360
acaagctgca ttctccaatc cagtcactct tggaacatca gcttccatct cctgcaggtc    420
tagtaagagt ctcctacata gtaatggcat cacttatttg tattggtatc tgcagaagcc    480
aggccagtct cctcagctcc tgatttatca gatgtccaac cttgcctcag agtcccaga    540 caggttcagt agcagtgggt caggaactga tttcacactg agaatcagca gagtggaggc    600
tgaggatgtg ggtgttatt actgtgctca aatctagaa cttccgtaca cgttcggagg    660
ggggaccaag ctggaaataa aacgaactgt ggctgcacca tctgtcttca tcttcccgcc    720
atctgatgag cagttgaaat ctggaactgc ctctgttgtg tgcctgctga ataacttcta    780
tcccagagag gccaaagtac agtggaaggt ggataacgcc ctccaatcgg gtaactccca    840
ggagagtgtc acagagcagg acagcaagga cagcacctac agcctcagca gcaccctgac    900
gctgagcaaa gcagactacg agaaacacaa agtctacgcc tgcgaagtca cccatcaggg    960
cctgagctcg cccgtcacaa agagcttcaa caggggagag tgttaataag cggccgc     1017
```

<210> SEQ ID NO 94
<211> LENGTH: 751
<212> TYPE: DNA
<213> ORGANISM: artificial
<220> FEATURE:
<223> OTHER INFORMATION: Synthetic construct

<400> SEQUENCE: 94

```
ggcgcgccca ggtccaactg cagcagcctg ggctgaact ggtggagcct gggggttcag      60
tgaagctgtc ctgcaaggct tctggctaca ccttcaccag tcactggatg cactgggtga    120
agcagaggcc tggacaaggc cttgagtgga taggtgagat taatcctagc agcggtcgta    180
```

```
ataactacaa tgagaagttc aagagtaagg ccacactgac tgtagacaaa tcctccagca    240
cagcctacat gcaattcagc agcctgacat ctgaggactc tgcggtctat tattgtgtaa    300
gatactatgg ttacgacgaa gctatggact actggggtca aggaacctca gtcaccgtct    360
cgtcagccag caccaagggc cccgaggtcc aactgcagca acctgggtct gagctggtga    420
ggcctggagc ttcagtgaag ctgtcctgca aggcttctgg ctacacattc accagctact    480
ggatgcactg ggtgaagcag aggcctggac aaggccttga gtggattggg aatatttatc    540
ctggtagtcg tagtactaac tacgatgaga agttcaagag caaggccaca ctgactgtag    600
acacatcctc cagcacagcc tacatgcagc tcagcagcct gacatctgag gactctgcgg    660
tctattactg tacaagaaat ggggattact acgttagtag cggggatgct atggactact    720
ggggtcaagg aacctcagtc accgtctcga g                                  751
```

<210> SEQ ID NO 95
<211> LENGTH: 1017
<212> TYPE: DNA
<213> ORGANISM: artificial
<220> FEATURE:
<223> OTHER INFORMATION: Synthetic construct

<400> SEQUENCE: 95

```
gctagccgac atcgtgatga cacaagctgc attctccaat ccagtcactc ttggaacatc     60
agcttccatc tcctgcaggt ctagtaagag tctcctacat agtaatggca tcacttattt    120
gtattggtat ctgcagaagc caggccagtc tcctcagctc ctgatttatc agatgtccaa    180
ccttgcctca ggagtcccag acaggttcag tagcagtggg tcaggaactg atttcacact    240
gagaatcagc agagtggagg ctgaggatgt gggtgtttat tactgtgctc aaaatctaga    300
acttccgtac acgttcggag gggggaccaa gctggaaata aaacgaactg tggctgcacc    360
agacattcag atgactcaga ctacatcctc cctgtctgcc tctctgggag acagagtcac    420
catcagttgc aggacaagtc aggacattgg caattatttg aactggtatc agcagaaacc    480
agatggaact gttaaactcc tgatctacta cacatcaaga ttacactcag gagtcccatc    540
aaggttcagt ggcagtgggt ctggaacaga ttttctctc accattaaca cgtggagca    600 agaggatgtt gccacttact tttgccaaca ctataatacg gttcctccga cgttcggtgg    660
aggcaccaag ctggaaatca aacgaactgt ggctgcacca tctgtcttca tcttcccgcc    720
atctgatgag cagttgaaat ctggaactgc ctctgttgtg tgcctgctga ataacttcta    780
tcccagagag gccaaagtac agtggaaggt ggataacgcc ctccaatcgg gtaactccca    840
ggagagtgtc acagagcagg acagcaagga cagcacctac agcctcagca gcaccctgac    900
gctgagcaaa gcagactacg agaaacacaa agtctacgcc tgcgaagtca cccatcaggg    960
cctgagctcg cccgtcacaa agagcttcaa caggggagag tgttaataag cggccgc      1017
```

<210> SEQ ID NO 96
<211> LENGTH: 249
<212> TYPE: PRT
<213> ORGANISM: artificial
<220> FEATURE:
<223> OTHER INFORMATION: Synthetic construct

<400> SEQUENCE: 96

```
Arg Ala Glu Val Gln Leu Gln Gln Pro Gly Ser Glu Leu Val Arg Pro
1               5                  10                  15

Gly Ala Ser Val Lys Leu Ser Cys Lys Ala Ser Gly Tyr Thr Phe Thr
            20                  25                  30
```

```
Ser Tyr Trp Met His Trp Val Lys Gln Arg Pro Gly Gln Gly Leu Glu
        35                  40                  45

Trp Ile Gly Asn Ile Tyr Pro Gly Ser Arg Ser Thr Asn Tyr Asp Glu
 50                  55                  60

Lys Phe Lys Ser Lys Ala Thr Leu Thr Val Asp Thr Ser Ser Ser Thr
 65                  70                  75                  80

Ala Tyr Met Gln Leu Ser Ser Leu Thr Ser Glu Asp Ser Ala Val Tyr
                 85                  90                  95

Tyr Cys Thr Arg Asn Gly Asp Tyr Tyr Val Ser Ser Gly Asp Ala Met
            100                 105                 110

Asp Tyr Trp Gly Gln Gly Thr Ser Val Thr Val Ser Ser Ala Ser Thr
            115                 120                 125

Lys Gly Pro Gln Val Gln Leu Gln Gln Pro Gly Ala Glu Leu Val Glu
130                 135                 140

Pro Gly Gly Ser Val Lys Leu Ser Cys Lys Ala Ser Gly Tyr Thr Phe
145                 150                 155                 160

Thr Ser His Trp Met His Trp Val Lys Gln Arg Pro Gly Gln Gly Leu
                165                 170                 175

Glu Trp Ile Gly Glu Ile Asn Pro Ser Gly Arg Asn Asn Tyr Asn
            180                 185                 190

Glu Lys Phe Lys Ser Lys Ala Thr Leu Thr Val Asp Lys Ser Ser Ser
                195                 200                 205

Thr Ala Tyr Met Gln Phe Ser Ser Leu Thr Ser Glu Asp Ser Ala Val
210                 215                 220

Tyr Tyr Cys Val Arg Tyr Tyr Gly Tyr Asp Glu Ala Met Asp Tyr Trp
225                 230                 235                 240

Gly Gln Gly Thr Ser Val Thr Val Ser
                245

<210> SEQ ID NO 97
<211> LENGTH: 334
<212> TYPE: PRT
<213> ORGANISM: artificial
<220> FEATURE:
<223> OTHER INFORMATION: Synthetic construct

<400> SEQUENCE: 97

Leu Ala Asp Ile Gln Met Thr Gln Thr Thr Ser Ser Leu Ser Ala Ser
 1               5                  10                  15

Leu Gly Asp Arg Val Thr Ile Ser Cys Arg Thr Ser Gln Asp Ile Gly
             20                  25                  30

Asn Tyr Leu Asn Trp Tyr Gln Gln Lys Pro Asp Gly Thr Val Lys Leu
         35                  40                  45

Leu Ile Tyr Tyr Thr Ser Arg Leu His Ser Gly Val Pro Ser Arg Phe
 50                  55                  60

Ser Gly Ser Gly Ser Gly Thr Asp Phe Ser Leu Thr Ile Asn Asn Val
 65                  70                  75                  80

Glu Gln Glu Asp Val Ala Thr Tyr Phe Cys Gln His Tyr Asn Thr Val
                 85                  90                  95

Pro Pro Thr Phe Gly Gly Gly Thr Lys Leu Glu Ile Lys Arg Thr Val
            100                 105                 110

Ala Ala Pro Asp Ile Val Met Thr Gln Ala Ala Phe Ser Asn Pro Val
            115                 120                 125

Thr Leu Gly Thr Ser Ala Ser Ile Ser Cys Arg Ser Ser Lys Ser Leu
130                 135                 140
```

-continued

```
Leu His Ser Asn Gly Ile Thr Tyr Leu Tyr Trp Tyr Leu Gln Lys Pro
145                 150                 155                 160

Gly Gln Ser Pro Gln Leu Leu Ile Tyr Gln Met Ser Asn Leu Ala Ser
            165                 170                 175

Gly Val Pro Asp Arg Phe Ser Ser Gly Ser Gly Thr Asp Phe Thr
        180                 185                 190

Leu Arg Ile Ser Arg Val Glu Ala Glu Asp Val Gly Val Tyr Tyr Cys
            195                 200                 205

Ala Gln Asn Leu Glu Leu Pro Tyr Thr Phe Gly Gly Gly Thr Lys Leu
        210                 215                 220

Glu Ile Lys Arg Thr Val Ala Ala Pro Ser Val Phe Ile Phe Pro Pro
225                 230                 235                 240

Ser Asp Glu Gln Leu Lys Ser Gly Thr Ala Ser Val Val Cys Leu Leu
                245                 250                 255

Asn Asn Phe Tyr Pro Arg Glu Ala Lys Val Gln Trp Lys Val Asp Asn
            260                 265                 270

Ala Leu Gln Ser Gly Asn Ser Gln Glu Ser Val Thr Glu Gln Asp Ser
        275                 280                 285

Lys Asp Ser Thr Tyr Ser Leu Ser Ser Thr Leu Thr Leu Ser Lys Ala
290                 295                 300

Asp Tyr Glu Lys His Lys Val Tyr Ala Cys Glu Val Thr His Gln Gly
305                 310                 315                 320

Leu Ser Ser Pro Val Thr Lys Ser Phe Asn Arg Gly Glu Cys
                325                 330

<210> SEQ ID NO 98
<211> LENGTH: 249
<212> TYPE: PRT
<213> ORGANISM: artificial
<220> FEATURE:
<223> OTHER INFORMATION: Synthetic construct

<400> SEQUENCE: 98

Arg Ala Gln Val Gln Leu Gln Gln Pro Gly Ala Glu Leu Val Glu Pro
1               5                   10                  15

Gly Gly Ser Val Lys Leu Ser Cys Lys Ala Ser Gly Tyr Thr Phe Thr
                20                  25                  30

Ser His Trp Met His Trp Val Lys Gln Arg Pro Gly Gln Gly Leu Glu
            35                  40                  45

Trp Ile Gly Glu Ile Asn Pro Ser Ser Gly Arg Asn Asn Tyr Asn Glu
        50                  55                  60

Lys Phe Lys Ser Lys Ala Thr Leu Thr Val Asp Lys Ser Ser Ser Thr
65                  70                  75                  80

Ala Tyr Met Gln Phe Ser Ser Leu Thr Ser Glu Asp Ser Ala Val Tyr
                85                  90                  95

Tyr Cys Val Arg Tyr Tyr Gly Tyr Asp Glu Ala Met Asp Tyr Trp Gly
            100                 105                 110

Gln Gly Thr Ser Val Thr Val Ser Ser Ala Ser Thr Lys Gly Pro Glu
        115                 120                 125

Val Gln Leu Gln Gln Pro Gly Ser Glu Leu Val Arg Pro Gly Ala Ser
    130                 135                 140

Val Lys Leu Ser Cys Lys Ala Ser Gly Tyr Thr Phe Thr Ser Tyr Trp
145                 150                 155                 160

Met His Trp Val Lys Gln Arg Pro Gly Gln Gly Leu Glu Trp Ile Gly
                165                 170                 175

Asn Ile Tyr Pro Gly Ser Arg Ser Thr Asn Tyr Asp Glu Lys Phe Lys
```

```
                   180                 185                 190
Ser Lys Ala Thr Leu Thr Val Asp Thr Ser Ser Ser Thr Ala Tyr Met
            195                 200                 205

Gln Leu Ser Ser Leu Thr Ser Glu Asp Ser Ala Val Tyr Tyr Cys Thr
            210                 215                 220

Arg Asn Gly Asp Tyr Tyr Val Ser Ser Gly Asp Ala Met Asp Tyr Trp
225                 230                 235                 240

Gly Gln Gly Thr Ser Val Thr Val Ser
                245

<210> SEQ ID NO 99
<211> LENGTH: 334
<212> TYPE: PRT
<213> ORGANISM: artificial
<220> FEATURE:
<223> OTHER INFORMATION: Synthetic construct

<400> SEQUENCE: 99

Leu Ala Asp Ile Val Met Thr Gln Ala Ala Phe Ser Asn Pro Val Thr
1               5                   10                  15

Leu Gly Thr Ser Ala Ser Ile Ser Cys Arg Ser Ser Lys Ser Leu Leu
            20                  25                  30

His Ser Asn Gly Ile Thr Tyr Leu Tyr Trp Tyr Leu Gln Lys Pro Gly
        35                  40                  45

Gln Ser Pro Gln Leu Leu Ile Tyr Gln Met Ser Asn Leu Ala Ser Gly
    50                  55                  60

Val Pro Asp Arg Phe Ser Ser Gly Ser Gly Thr Asp Phe Thr Leu
65                  70                  75                  80

Arg Ile Ser Arg Val Glu Ala Glu Asp Val Gly Val Tyr Tyr Cys Ala
                85                  90                  95

Gln Asn Leu Glu Leu Pro Tyr Thr Phe Gly Gly Gly Thr Lys Leu Glu
            100                 105                 110

Ile Lys Arg Thr Val Ala Ala Pro Asp Ile Gln Met Thr Gln Thr Thr
        115                 120                 125

Ser Ser Leu Ser Ala Ser Leu Gly Asp Arg Val Thr Ile Ser Cys Arg
    130                 135                 140

Thr Ser Gln Asp Ile Gly Asn Tyr Leu Asn Trp Tyr Gln Gln Lys Pro
145                 150                 155                 160

Asp Gly Thr Val Lys Leu Leu Ile Tyr Tyr Thr Ser Arg Leu His Ser
                165                 170                 175

Gly Val Pro Ser Arg Phe Ser Gly Ser Gly Ser Gly Thr Asp Phe Ser
            180                 185                 190

Leu Thr Ile Asn Asn Val Glu Gln Glu Asp Val Ala Thr Tyr Phe Cys
        195                 200                 205

Gln His Tyr Asn Thr Val Pro Pro Thr Phe Gly Gly Gly Thr Lys Leu
    210                 215                 220

Glu Ile Lys Arg Thr Val Ala Ala Pro Ser Val Phe Ile Phe Pro Pro
225                 230                 235                 240

Ser Asp Glu Gln Leu Lys Ser Gly Thr Ala Ser Val Val Cys Leu Leu
                245                 250                 255

Asn Asn Phe Tyr Pro Arg Glu Ala Lys Val Gln Trp Lys Val Asp Asn
            260                 265                 270

Ala Leu Gln Ser Gly Asn Ser Gln Glu Ser Val Thr Glu Gln Asp Ser
        275                 280                 285

Lys Asp Ser Thr Tyr Ser Leu Ser Ser Thr Leu Thr Leu Ser Lys Ala
    290                 295                 300
```

Asp Tyr Glu Lys His Lys Val Tyr Ala Cys Glu Val Thr His Gln Gly
305                 310                 315                 320

Leu Ser Ser Pro Val Thr Lys Ser Phe Asn Arg Gly Glu Cys
                325                 330

<210> SEQ ID NO 100
<211> LENGTH: 1863
<212> TYPE: DNA
<213> ORGANISM: Macaca fascicularis

<400> SEQUENCE: 100

```
ctggaggaaa agaaagtttg ccaaggcacg agtaacaaac tcacgcagtt gggcactttt        60
gaagatcatt ttctcagcct ccagaggatg ttcaataact gtgaggtggt ccttgggaat       120
ttggaaatta cctacgtgca gaggaattat gatctttcct tcttaaagac catccaggag       180
gtggctggtt atgtcctcat cgccctcaac acagtggagc ggattccttt ggaaaacctg       240
cagatcatca gaggaaacat gtactatgaa aattcctatg ccttagcagt cttatctaac       300
tatgatgcaa ataaaaccgg actgaaggag ctgcccatga aaacttaca ggaaatcctg       360
catggcgccg tgcggttcag caacaaccct gccctgtgca cgtggagag catccagtgg       420
cgggacatag tcagcagcga gtttctcagc aacatgtcga tggacttcca gaaccacctg       480
ggcagctgcc aaaagtgtga tccaagctgt cccaatggga gctgctgggg tgcaggagag       540
gagaactgcc agaaactgac caaaatcatc tgtgcccagc agtgctccgg cgctgccgc       600
ggcaagtccc ccagtgactg ctgccacaac cagtgtgccg cgggctgcac gggccccgg        660
gagagcgact gcctggtctg ccgcaaattc cgagacgaag ccacgtgcaa ggacacctgc       720
cccccactca tgctctacaa ccccaccaca taccagatgg atgtgaaccc cgagggcaaa       780
tacagctttg gtgccacctg cgtgaagaag tgtccccgta attatgtggt gacagatcac       840
ggctcgtgcg tccgagcctg cggggccgac agctatgaga tggaggaaga cggcgtccgc       900
aagtgtaaga agtgcgaagg ccttgccgc aaagtgtgta atggaatagg tattggtgaa        960
tttaaagaca cactctccat aaatgctaca atattaaac acttcaaaaa ctgcaccctcc      1020
atcagtggcg atctccacat cctgccggtg gcatttaggg gtgactcctt cacacacact      1080
ccgcctctgg atccacagga actggatatt ctgaaaaccg taaggaaat cacagggttt       1140
ttgctgattc aggcttggcc tgaaaacagg acggacctcc atgcttttga gaacctagaa      1200
atcatacgtg gcaggaccaa gcaacacggt cagttttctc ttgcggtcgt cagcctgaac      1260
ataacatcct tgggattacg ctccctcaag gagataagcg atggagatgt gataatttca       1320
ggaaacaaaa atttgtgcta tgcaaataca ataaactgga aaaaactgtt tgggacctcc      1380
agtcagaaaa ccaaaattat aagcaacaga ggtgaaaaca gctgcaaggc cacgggccag      1440
gtctgccatg ccttgtgctc ccccgagggc tgctggggcc cggagcccag ggactgcgtc      1500
tcctgccaga atgtcagccg aggcagagaa tgcgtggaca gtgcaacat cctggagggc       1560
gagccaaggg agtttgtgga aactctgag tgcatacagt gccacccaga atgcctgccc        1620
caggtcatga acatcacctg cacaggacgg ggaccagaca actgtatcca gtgtgcccac      1680
tacattgacg gcccccactg cgtcaagacc tgcccagcag gagtcatggg agaaaacaac      1740
accctggtct ggaagtacgc agacgccggc cacgtgtgcc acctgtgcca tccaaactgc      1800
acctacggat gcactgggcc aggtcttgaa ggctgtgcaa ggaacgggcc taagatccca      1860
tcc                                                                     1863
```

<210> SEQ ID NO 101
<211> LENGTH: 621
<212> TYPE: PRT
<213> ORGANISM: Macaca fascicularis

<400> SEQUENCE: 101

```
Leu Glu Glu Lys Lys Val Cys Gln Gly Thr Ser Asn Lys Leu Thr Gln
1               5                   10                  15

Leu Gly Thr Phe Glu Asp His Phe Leu Ser Leu Gln Arg Met Phe Asn
            20                  25                  30

Asn Cys Glu Val Val Leu Gly Asn Leu Glu Ile Thr Tyr Val Gln Arg
        35                  40                  45

Asn Tyr Asp Leu Ser Phe Leu Lys Thr Ile Gln Glu Val Ala Gly Tyr
    50                  55                  60

Val Leu Ile Ala Leu Asn Thr Val Glu Arg Ile Pro Leu Glu Asn Leu
65                  70                  75                  80

Gln Ile Ile Arg Gly Asn Met Tyr Tyr Glu Asn Ser Tyr Ala Leu Ala
                85                  90                  95

Val Leu Ser Asn Tyr Asp Ala Asn Lys Thr Gly Leu Lys Glu Leu Pro
            100                 105                 110

Met Arg Asn Leu Gln Glu Ile Leu His Gly Ala Val Arg Phe Ser Asn
        115                 120                 125

Asn Pro Ala Leu Cys Asn Val Glu Ser Ile Gln Trp Arg Asp Ile Val
    130                 135                 140

Ser Ser Glu Phe Leu Ser Asn Met Ser Met Asp Phe Gln Asn His Leu
145                 150                 155                 160

Gly Ser Cys Gln Lys Cys Asp Pro Ser Cys Pro Asn Gly Ser Cys Trp
                165                 170                 175

Gly Ala Gly Glu Glu Asn Cys Gln Lys Leu Thr Lys Ile Ile Cys Ala
            180                 185                 190

Gln Gln Cys Ser Gly Arg Cys Arg Gly Lys Ser Pro Ser Asp Cys Cys
        195                 200                 205

His Asn Gln Cys Ala Ala Gly Cys Thr Gly Pro Arg Glu Ser Asp Cys
    210                 215                 220

Leu Val Cys Arg Lys Phe Arg Asp Glu Ala Thr Cys Lys Asp Thr Cys
225                 230                 235                 240

Pro Pro Leu Met Leu Tyr Asn Pro Thr Thr Tyr Gln Met Asp Val Asn
                245                 250                 255

Pro Glu Gly Lys Tyr Ser Phe Gly Ala Thr Cys Val Lys Lys Cys Pro
            260                 265                 270

Arg Asn Tyr Val Val Thr Asp His Gly Ser Cys Val Arg Ala Cys Gly
        275                 280                 285

Ala Asp Ser Tyr Glu Met Glu Glu Asp Gly Val Arg Lys Cys Lys Lys
    290                 295                 300

Cys Glu Gly Pro Cys Arg Lys Val Cys Asn Gly Ile Gly Ile Gly Glu
305                 310                 315                 320

Phe Lys Asp Thr Leu Ser Ile Asn Ala Thr Asn Ile Lys His Phe Lys
                325                 330                 335

Asn Cys Thr Ser Ile Ser Gly Asp Leu His Ile Leu Pro Val Ala Phe
            340                 345                 350

Arg Gly Asp Ser Phe Thr His Thr Pro Pro Leu Asp Pro Gln Glu Leu
        355                 360                 365

Asp Ile Leu Lys Thr Val Lys Glu Ile Thr Gly Phe Leu Leu Ile Gln
    370                 375                 380

Ala Trp Pro Glu Asn Arg Thr Asp Leu His Ala Phe Glu Asn Leu Glu
```

```
                385                 390                 395                 400
Ile Ile Arg Gly Arg Thr Lys Gln His Gly Gln Phe Ser Leu Ala Val
            405                 410                 415
Val Ser Leu Asn Ile Thr Ser Leu Gly Leu Arg Ser Leu Lys Glu Ile
            420                 425                 430
Ser Asp Gly Asp Val Ile Ile Ser Gly Asn Lys Asn Leu Cys Tyr Ala
            435                 440                 445
Asn Thr Ile Asn Trp Lys Lys Leu Phe Gly Thr Ser Gln Lys Thr
        450                 455                 460
Lys Ile Ile Ser Asn Arg Gly Glu Asn Ser Cys Lys Ala Thr Gly Gln
465                 470                 475                 480
Val Cys His Ala Leu Cys Ser Pro Glu Gly Cys Trp Gly Pro Glu Pro
                485                 490                 495
Arg Asp Cys Val Ser Cys Gln Asn Val Ser Arg Gly Arg Glu Cys Val
            500                 505                 510
Asp Lys Cys Asn Ile Leu Glu Gly Glu Pro Arg Glu Phe Val Glu Asn
            515                 520                 525
Ser Glu Cys Ile Gln Cys His Pro Glu Cys Leu Pro Gln Val Met Asn
        530                 535                 540
Ile Thr Cys Thr Gly Arg Gly Pro Asp Asn Cys Ile Gln Cys Ala His
545                 550                 555                 560
Tyr Ile Asp Gly Pro His Cys Val Lys Thr Cys Pro Ala Gly Val Met
                565                 570                 575
Gly Glu Asn Asn Thr Leu Val Trp Lys Tyr Ala Asp Ala Gly His Val
            580                 585                 590
Cys His Leu Cys His Pro Asn Cys Thr Tyr Gly Cys Thr Gly Pro Gly
                595                 600                 605
Leu Glu Gly Cys Ala Arg Asn Gly Pro Lys Ile Pro Ser
        610                 615                 620

<210> SEQ ID NO 102
<211> LENGTH: 3633
<212> TYPE: DNA
<213> ORGANISM: Macaca fascicularis

<400> SEQUENCE: 102
atgcgaccct ccgggacggc cggggccgcg ctcctggcgc tgctggctgc gctttgcccc      60
gcgagtcggg ctctggagga aaagaaagtt tgccaaggca cgagtaacaa actcacgcag     120
ttgggcactt ttgaagatca ttttctcagc ctccagagga tgttcaataa ctgtgaggtg     180
gtccttggga atttggaaat tacctacgtg cagaggaatt atgatctttc cttcttaaag     240
accatccagg aggtggctgg ttatgtcctc atcgccctca cacagtggaa gcggattcct     300
ttggaaaacc tgcagatcat cagaggaaac atgtactatg aaaattccta tgccttagca     360
gtcttatcta actatgatgc aaataaaacc ggactgaagg agctgcccat gagaaactta     420
caggaaatcc tgcatggcgc cgtgcggttc agcaacaacc ctgccctgtg caacgtggag     480
agcatccagt ggcgggacat agtcagcagc gagtttctca gcaacatgtc gatggacttc     540
cagaaccacc tgggcagctg ccaaaagtgt gatccaagct gtcccaatgg agctgctgg     600 ggtgcaggag aggagaactg ccagaaactg accaaaatca tctgtgccca gcagtgctcc     660
gggcgctgcc gcggcaagtc ccccagtgac tgctgccaca ccagtgtgc gcgggctgc     720 acgggccccc gggagagcga ctgcctggtc tgccgcaaat tccgagacga agccacgtgc     780
aaggacacct gccccccact catgctctac aaccccacca cataccagat ggatgtgaac     840
```

```
cccgagggca atacagctt tggtgccacc tgcgtgaaga agtgtccccg taattatgtg    900
gtgacagatc acggctcgtg cgtccgagcc tgcgggccg acagctatga gatggaggaa    960
gacggcgtcc gcaagtgtaa gaagtgcgaa gggccttgcc gcaaagtgtg taatggaata   1020
ggtattggtg aatttaaaga cacactctcc ataaatgcta caaatattaa acacttcaaa   1080
aactgcacct ccatcagtgg cgatctccac atcctgccgg tggcatttag gggtgactcc   1140
ttcacacaca ctccgcctct ggatccacag gaactgata ttctgaaaac cgtaaaggaa    1200
atcacagggt ttttgctgat tcaggcttgg cctgaaaaca ggacggacct ccatgctttt   1260
gagaacctag aaatcatacg tggcaggacc aagcaacacg gtcagttttc tcttgcggtc   1320
gtcagcctga acataacatc cttgggatta cgctccctca aggagataag cgatggagat   1380
gtgataattt caggaaacaa aaatttgtgc tatgcaaata caataaactg gaaaaaactg   1440
tttgggacct ccagtcagaa aaccaaaatt ataagcaaca gaggtgaaaa cagctgcaag   1500
gccacgggcc aggtctgcca tgccttgtgc tcccccgagg gctgctgggg cccggagccc   1560
agggactgcg tctcctgtca gaatgtcagc cgaggcagag aatgcgtgga caagtgcaac   1620
atcctggagg gcgagccaag ggagtttgtg gagaactctg agtgcataca gtgtcaccca   1680
gaatgcctgc cccaggtcat gaacatcacc tgcacaggac ggggaccaga caactgtatc   1740
cagtgtgccc actacattga cggcccccac tgcgtcaaga cctgcccagc aggagtcatg   1800
ggagaaaaca cacccctggt ctggaagtac gcagacgccg gccacgtgtg ccacctgtgc   1860
catccaaact gcacctacgg atgcactggg ccaggtcttg aaggctgtgc aaggaacggg   1920
cctaagatcc catccatcgc cactgggatg gtgggggccc tcctcttgct gctggtggtg   1980
gccctgggga tcggcctctt catgcgaagg cgccacatcg ttcggaagcg cacactgcgg   2040
aggctgctgc aggagaggga gcttgtggag cctcttacgc ccagtggaga agctcccaac   2100
caagctctct tgaggatctt gaaggaaact gaattcaaga agatcaaagt gctgggctcc   2160
ggtgcgttcg gaactgtgta aagggactc tggatcccag aaggtgagaa agttaaaatt    2220
cccgtcgcta tcaaggaatt aagagaagca acatctccga aagccaacaa ggaaatcctc   2280
gatgaagcct acgtgatggc cagcgtggac aaccccatg tgtgccgcct gctgggcatc    2340
tgcctcacct ccaccgtgca gctcattacg cagctcatgc ccttcggctg cctcctggac   2400
tacgtccggg aacacaagga caatatcggc tcccagtacc tgctcaactg gtgtgtgcag   2460
attgcaaagg gcatgaacta cttggaggac cggcgcttgg tgcaccgcga cctggcagcc   2520
aggaacgtac tggtgaaaac gccacagcat gtcaagatca cagattttgg gctggccaaa   2580
ctgctgggtg cagaagagaa agaataccat gcagaaggag gcaaagtgcc tatcaagtgg   2640
atggcgttgg aatcaatttt acaccgaatt tatacccacc agagtgatgt ctggagctac   2700
ggggtgaccg tttgggagtt gatgaccttt ggatccaagc catatgacgg aatccctgcc   2760
agcgagatct cctccatcct ggagaaagga gaacgcctcc cccagccacc catatgtacc   2820
atcgatgtct acatgatcat ggtcaagtgc tggatgatag acgcagatag tcgcccaaag   2880
ttccgtgagt tgatcattga attctccaaa atgccccgag accccagcg ctaccttgtt    2940
attcaggggg atgaaagaat gcatttgcca agccctacag actccaactt ctaccgtgcc   3000
ctgatggatg aagaagacat ggacgacgtg gtggatgccg acgagtacct catcccacag   3060
caaggcttct tcagcagccc ctccacgtca cggactcccc tcctgagctc tctgagtgca   3120
actagcaaca attccactgt ggcttgcatt gatagaaatg ggctgcaaag ctgttccatc   3180
aaggaagaca gcttcttaca gcgatacagc tcagacccca caggcgcctt gactgaggac   3240
```

```
agcatagacg acaccttcct cccagtgcct gaatacataa accagtctgt tcccaaaagg    3300
cccgctggct ctgtgcagaa tcctgtctat cacaatcagc ctctgaaccc tgcgcccagc    3360
agagacccac actaccagga cccccacagc accgcagtgg gcaaccccga gtatctcaac    3420
actgtccagc ccacctgtgt caacagcaca ttcgacagcc tgctcattg  ggcccagaaa    3480 ggcagccacc aaattagcct ggacaaccct gactaccagc aggacttctt tcccaaggaa    3540
gccaagccaa atggcatctt taagggctcc acagctgaaa atgcagaata cctaagggtc    3600
gcaccacaaa gcagtgaatt tattggagca tga                                3633
```

<210> SEQ ID NO 103
<211> LENGTH: 1210
<212> TYPE: PRT
<213> ORGANISM: Macaca fascicularis

<400> SEQUENCE: 103

```
Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Glu Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
```

```
            305                 310                 315                 320
Asp Gly Val Arg Lys Cys Lys Cys Glu Gly Pro Cys Arg Lys Val
                    325                 330                 335

Cys Asn Gly Ile Gly Ile Gly Glu Phe Lys Asp Thr Leu Ser Ile Asn
                340                 345                 350

Ala Thr Asn Ile Lys His Phe Lys Asn Cys Thr Ser Ile Ser Gly Asp
                355                 360                 365

Leu His Ile Leu Pro Val Ala Phe Arg Gly Asp Ser Phe Thr His Thr
            370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
                420                 425                 430

His Gly Gln Phe Ser Leu Ala Val Val Ser Leu Asn Ile Thr Ser Leu
            435                 440                 445

Gly Leu Arg Ser Leu Lys Glu Ile Ser Asp Gly Asp Val Ile Ile Ser
    450                 455                 460

Gly Asn Lys Asn Leu Cys Tyr Ala Asn Thr Ile Asn Trp Lys Lys Leu
465                 470                 475                 480

Phe Gly Thr Ser Ser Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Gln Asn
            515                 520                 525

Val Ser Arg Gly Arg Glu Cys Val Asp Lys Cys Asn Ile Leu Glu Gly
    530                 535                 540

Glu Pro Arg Glu Phe Val Glu Asn Ser Glu Cys Ile Gln Cys His Pro
545                 550                 555                 560

Glu Cys Leu Pro Gln Val Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
            595                 600                 605

Lys Tyr Ala Asp Ala Gly His Val Cys His Leu Cys His Pro Asn Cys
            610                 615                 620

Thr Tyr Gly Cys Thr Gly Pro Gly Leu Glu Gly Cys Ala Arg Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg Arg His
                660                 665                 670

Ile Val Arg Lys Arg Thr Leu Arg Arg Leu Leu Gln Glu Arg Glu Leu
                675                 680                 685

Val Glu Pro Leu Thr Pro Ser Gly Glu Ala Pro Asn Gln Ala Leu Leu
            690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
                725                 730                 735
```

-continued

Lys Val Lys Ile Pro Val Ala Ile Lys Glu Leu Arg Glu Ala Thr Ser
            740                 745                 750

Pro Lys Ala Asn Lys Glu Ile Leu Asp Glu Ala Tyr Val Met Ala Ser
            755                 760                 765

Val Asp Asn Pro His Val Cys Arg Leu Leu Gly Ile Cys Leu Thr Ser
770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
                805                 810                 815

Trp Cys Val Gln Ile Ala Lys Gly Met Asn Tyr Leu Glu Asp Arg Arg
                820                 825                 830

Leu Val His Arg Asp Leu Ala Ala Arg Asn Val Leu Val Lys Thr Pro
                835                 840                 845

Gln His Val Lys Ile Thr Asp Phe Gly Leu Ala Lys Leu Leu Gly Ala
    850                 855                 860

Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                885                 890                 895

Val Trp Ser Tyr Gly Val Thr Val Trp Glu Leu Met Thr Phe Gly Ser
            900                 905                 910

Lys Pro Tyr Asp Gly Ile Pro Ala Ser Glu Ile Ser Ser Ile Leu Glu
            915                 920                 925

Lys Gly Glu Arg Leu Pro Gln Pro Pro Ile Cys Thr Ile Asp Val Tyr
930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                965                 970                 975

Arg Tyr Leu Val Ile Gln Gly Asp Glu Arg Met His Leu Pro Ser Pro
            980                 985                 990

Thr Asp Ser Asn Phe Tyr Arg Ala Leu Met Asp Glu Glu Asp Met Asp
            995                 1000                1005

Asp Val Val Asp Ala Asp Glu Tyr Leu Ile Pro Gln Gln Gly Phe
    1010                1015                1020

Phe Ser Ser Pro Ser Thr Ser Arg Thr Pro Leu Leu Ser Ser Leu
    1025                1030                1035

Ser Ala Thr Ser Asn Asn Ser Thr Val Ala Cys Ile Asp Arg Asn
    1040                1045                1050

Gly Leu Gln Ser Cys Ser Ile Lys Glu Asp Ser Phe Leu Gln Arg
    1055                1060                1065

Tyr Ser Ser Asp Pro Thr Gly Ala Leu Thr Glu Asp Ser Ile Asp
    1070                1075                1080

Asp Thr Phe Leu Pro Val Pro Glu Tyr Ile Asn Gln Ser Val Pro
    1085                1090                1095

Lys Arg Pro Ala Gly Ser Val Gln Asn Pro Val Tyr His Asn Gln
    1100                1105                1110

Pro Leu Asn Pro Ala Pro Ser Arg Asp Pro His Tyr Gln Asp Pro
    1115                1120                1125

His Ser Thr Ala Val Gly Asn Pro Glu Tyr Leu Asn Thr Val Gln
    1130                1135                1140

Pro Thr Cys Val Asn Ser Thr Phe Asp Ser Pro Ala His Trp Ala
    1145                1150                1155

Gln Lys Gly Ser His Gln Ile Ser Leu Asp Asn Pro Asp Tyr Gln
    1160                1165                1170

Gln Asp Phe Phe Pro Lys Glu Ala Lys Pro Asn Gly Ile Phe Lys
    1175                1180                1185

Gly Ser Thr Ala Glu Asn Ala Glu Tyr Leu Arg Val Ala Pro Gln
    1190                1195                1200

Ser Ser Glu Phe Ile Gly Ala
    1205            1210

<210> SEQ ID NO 104
<211> LENGTH: 122
<212> TYPE: PRT
<213> ORGANISM: artificial
<220> FEATURE:
<223> OTHER INFORMATION: Synthetic construct

<400> SEQUENCE: 104

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Ile Ile Tyr Pro Gly Ser Arg Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Asn Gly Asp Tyr Tyr Val Ser Ser Gly Asp Ala Met Asp Tyr
            100                 105                 110

Trp Gly Gln Gly Thr Leu Val Thr Val Ser
        115                 120

<210> SEQ ID NO 105
<211> LENGTH: 107
<212> TYPE: PRT
<213> ORGANISM: artificial
<220> FEATURE:
<223> OTHER INFORMATION: Synthetic construct

<400> SEQUENCE: 105

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Asn Tyr
            20                  25                  30

Leu Ala Trp Tyr Gln Gln Lys Pro Gly Lys Val Pro Lys Leu Leu Ile
        35                  40                  45

Tyr Tyr Thr Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln His Tyr Asn Thr Val Pro Pro
                85                  90                  95

Thr Phe Gly Gly Gly Thr Lys Val Glu Ile Lys
            100                 105

<210> SEQ ID NO 106

<211> LENGTH: 118
<212> TYPE: PRT
<213> ORGANISM: artificial
<220> FEATURE:
<223> OTHER INFORMATION: Synthetic construct

<400> SEQUENCE: 106

Gln Val Gln Leu Val Gln Ser Gly Ala Glu Val Lys Pro Gly Ala
1               5                   10                  15

Ser Val Lys Val Ser Cys Lys Ala Ser Gly Tyr Thr Phe Thr Ser His
            20                  25                  30

Trp Met His Trp Val Arg Gln Ala Pro Gly Gln Gly Leu Glu Trp Met
        35                  40                  45

Gly Trp Ile Asn Pro Ser Ser Gly Arg Asn Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Thr Ser Asp Asp Thr Ala Val Tyr Tyr Cys
                85                  90                  95

Ala Arg Tyr Tyr Gly Tyr Asp Glu Ala Met Asp Tyr Trp Gly Gln Gly
            100                 105                 110

Thr Ser Val Thr Val Ser
        115

<210> SEQ ID NO 107
<211> LENGTH: 112
<212> TYPE: PRT
<213> ORGANISM: artificial
<220> FEATURE:
<223> OTHER INFORMATION: Synthetic construct

<400> SEQUENCE: 107

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Asp Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Ser Ser Gly Ser Gly Thr Asp Phe Thr Leu Arg Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gly Gly Thr Lys Leu Glu Ile Lys
            100                 105                 110

<210> SEQ ID NO 108
<211> LENGTH: 621
<212> TYPE: PRT
<213> ORGANISM: Homo sapiens

<400> SEQUENCE: 108

Leu Glu Glu Lys Lys Val Cys Gln Gly Thr Ser Asn Lys Leu Thr Gln
1               5                   10                  15

Leu Gly Thr Phe Glu Asp His Phe Leu Ser Leu Gln Arg Met Phe Asn
            20                  25                  30

Asn Cys Glu Val Val Leu Gly Asn Leu Glu Ile Thr Tyr Val Gln Arg
        35                  40                  45

```
Asn Tyr Asp Leu Ser Phe Leu Lys Thr Ile Gln Glu Val Ala Gly Tyr
 50                  55                  60

Val Leu Ile Ala Leu Asn Thr Val Glu Arg Ile Pro Leu Glu Asn Leu
 65                  70                  75                  80

Gln Ile Ile Arg Gly Asn Met Tyr Tyr Glu Asn Ser Tyr Ala Leu Ala
                 85                  90                  95

Val Leu Ser Asn Tyr Asp Ala Asn Lys Thr Gly Leu Lys Glu Leu Pro
                100                 105                 110

Met Arg Asn Leu Gln Glu Ile Leu His Gly Ala Val Arg Phe Ser Asn
                115                 120                 125

Asn Pro Ala Leu Cys Asn Val Glu Ser Ile Gln Trp Arg Asp Ile Val
130                 135                 140

Ser Ser Asp Phe Leu Ser Asn Met Ser Met Asp Phe Gln Asn His Leu
145                 150                 155                 160

Gly Ser Cys Gln Lys Cys Asp Pro Ser Cys Pro Asn Gly Ser Cys Trp
                165                 170                 175

Gly Ala Gly Glu Glu Asn Cys Gln Lys Leu Thr Lys Ile Ile Cys Ala
                180                 185                 190

Gln Gln Cys Ser Gly Arg Cys Arg Gly Lys Ser Pro Ser Asp Cys Cys
                195                 200                 205

His Asn Gln Cys Ala Ala Gly Cys Thr Gly Pro Arg Glu Ser Asp Cys
210                 215                 220

Leu Val Cys Arg Lys Phe Arg Asp Glu Ala Thr Cys Lys Asp Thr Cys
225                 230                 235                 240

Pro Pro Leu Met Leu Tyr Asn Pro Thr Thr Tyr Gln Met Asp Val Asn
                245                 250                 255

Pro Glu Gly Lys Tyr Ser Phe Gly Ala Thr Cys Val Lys Lys Cys Pro
                260                 265                 270

Arg Asn Tyr Val Val Thr Asp His Gly Ser Cys Val Arg Ala Cys Gly
                275                 280                 285

Ala Asp Ser Tyr Glu Met Glu Glu Asp Gly Val Arg Lys Cys Lys Lys
                290                 295                 300

Cys Glu Gly Pro Cys Arg Lys Val Cys Asn Gly Ile Gly Ile Gly Glu
305                 310                 315                 320

Phe Lys Asp Ser Leu Ser Ile Asn Ala Thr Asn Ile Lys His Phe Lys
                325                 330                 335

Asn Cys Thr Ser Ile Ser Gly Asp Leu His Ile Leu Pro Val Ala Phe
                340                 345                 350

Arg Gly Asp Ser Phe Thr His Thr Pro Pro Leu Asp Pro Gln Glu Leu
                355                 360                 365

Asp Ile Leu Lys Thr Val Lys Glu Ile Thr Gly Phe Leu Leu Ile Gln
370                 375                 380

Ala Trp Pro Glu Asn Arg Thr Asp Leu His Ala Phe Glu Asn Leu Glu
385                 390                 395                 400

Ile Ile Arg Gly Arg Thr Lys Gln His Gly Gln Phe Ser Leu Ala Val
                405                 410                 415

Val Ser Leu Asn Ile Thr Ser Leu Gly Leu Arg Ser Leu Lys Glu Ile
                420                 425                 430

Ser Asp Gly Asp Val Ile Ile Ser Gly Asn Lys Asn Leu Cys Tyr Ala
                435                 440                 445

Asn Thr Ile Asn Trp Lys Lys Leu Phe Gly Thr Ser Gly Gln Lys Thr
                450                 455                 460

Lys Ile Ile Ser Asn Arg Gly Glu Asn Ser Cys Lys Ala Thr Gly Gln
465                 470                 475                 480
```

```
Val Cys His Ala Leu Cys Ser Pro Glu Gly Cys Trp Gly Pro Glu Pro
            485                 490                 495

Lys Asp Cys Val Ser Cys Arg Asn Val Ser Arg Gly Arg Glu Cys Val
            500                 505                 510

Asp Lys Cys Asn Leu Leu Glu Gly Glu Pro Arg Glu Phe Val Glu Asn
            515                 520                 525

Ser Glu Cys Ile Gln Cys His Pro Glu Cys Leu Pro Gln Ala Met Asn
            530                 535                 540

Ile Thr Cys Thr Gly Arg Gly Pro Asp Asn Cys Ile Gln Cys Ala His
545                 550                 555                 560

Tyr Ile Asp Gly Pro His Cys Val Lys Thr Cys Pro Ala Gly Val Met
                    565                 570                 575

Gly Glu Asn Asn Thr Leu Val Trp Lys Tyr Ala Asp Ala Gly His Val
                580                 585                 590

Cys His Leu Cys His Pro Asn Cys Thr Tyr Gly Cys Thr Gly Pro Gly
                    595                 600                 605

Leu Glu Gly Cys Pro Thr Asn Gly Pro Lys Ile Pro Ser
610                 615                 620

<210> SEQ ID NO 109
<211> LENGTH: 616
<212> TYPE: PRT
<213> ORGANISM: artificial
<220> FEATURE:
<223> OTHER INFORMATION: Consensus sequence

<400> SEQUENCE: 109

Leu Glu Glu Lys Lys Val Cys Gln Gly Thr Ser Asn Lys Leu Thr Gln
1               5                   10                  15

Leu Gly Thr Phe Glu Asp His Phe Leu Ser Leu Gln Arg Met Phe Asn
                20                  25                  30

Asn Cys Glu Val Val Leu Gly Asn Leu Glu Ile Thr Tyr Val Gln Arg
            35                  40                  45

Asn Tyr Asp Leu Ser Phe Leu Lys Thr Ile Gln Glu Val Ala Gly Tyr
        50                  55                  60

Val Leu Ile Ala Leu Asn Thr Val Glu Arg Ile Pro Leu Glu Asn Leu
65                  70                  75                  80

Gln Ile Ile Arg Gly Asn Met Tyr Tyr Glu Asn Ser Tyr Ala Leu Ala
                85                  90                  95

Val Leu Ser Asn Tyr Asp Ala Asn Lys Thr Gly Leu Lys Glu Leu Pro
            100                 105                 110

Met Arg Asn Leu Gln Glu Ile Leu His Gly Ala Val Arg Phe Ser Asn
        115                 120                 125

Asn Pro Ala Leu Cys Asn Val Glu Ser Ile Gln Trp Arg Asp Ile Val
    130                 135                 140

Ser Ser Asp Phe Leu Ser Asn Met Ser Met Asp Phe Gln Asn His Leu
145                 150                 155                 160

Gly Ser Cys Gln Lys Cys Asp Pro Ser Cys Pro Asn Gly Ser Cys Trp
                165                 170                 175

Gly Ala Gly Glu Glu Asn Cys Gln Lys Leu Thr Lys Ile Ile Cys Ala
            180                 185                 190

Gln Gln Cys Ser Gly Arg Cys Arg Gly Lys Ser Pro Ser Asp Cys Cys
        195                 200                 205

His Asn Gln Cys Ala Ala Gly Cys Thr Gly Pro Arg Glu Ser Asp Cys
    210                 215                 220
```

```
Leu Val Cys Arg Lys Phe Arg Asp Glu Ala Thr Cys Lys Asp Thr Cys
225                 230                 235                 240

Pro Pro Leu Met Leu Tyr Asn Pro Thr Thr Tyr Gln Met Asp Val Asn
                245                 250                 255

Pro Glu Gly Lys Tyr Ser Phe Gly Ala Thr Cys Val Lys Lys Cys Pro
            260                 265                 270

Arg Asn Tyr Val Val Thr Asp His Gly Ser Cys Val Arg Ala Cys Gly
        275                 280                 285

Ala Asp Ser Tyr Glu Met Glu Glu Asp Gly Val Arg Lys Cys Lys Lys
    290                 295                 300

Cys Glu Gly Pro Cys Arg Lys Val Cys Asn Gly Ile Gly Ile Gly Glu
305                 310                 315                 320

Phe Lys Asp Ser Leu Ser Ile Asn Ala Thr Asn Ile Lys His Phe Lys
                325                 330                 335

Asn Cys Thr Ser Ile Ser Gly Asp Leu His Ile Leu Pro Val Ala Phe
                340                 345                 350

Arg Gly Asp Ser Phe Thr His Thr Pro Pro Leu Asp Pro Gln Glu Leu
            355                 360                 365

Asp Ile Leu Lys Thr Val Lys Glu Ile Thr Gly Phe Leu Leu Ile Gln
370                 375                 380

Ala Trp Pro Glu Asn Arg Thr Asp Leu His Ala Phe Glu Asn Leu Glu
385                 390                 395                 400

Ile Ile Arg Gly Arg Thr Lys Gln His Gly Gln Phe Ser Leu Ala Val
                405                 410                 415

Val Ser Leu Asn Ile Thr Ser Leu Gly Leu Arg Ser Leu Lys Glu Ile
            420                 425                 430

Ser Asp Gly Asp Val Ile Ile Ser Gly Asn Lys Asn Leu Cys Tyr Ala
            435                 440                 445

Asn Thr Ile Asn Trp Lys Lys Leu Phe Gly Thr Ser Gln Lys Thr Lys
        450                 455                 460

Ile Ile Ser Asn Arg Gly Glu Asn Ser Cys Lys Ala Thr Gly Gln Val
465                 470                 475                 480

Cys His Ala Leu Cys Ser Pro Glu Gly Cys Trp Gly Pro Glu Pro Lys
                485                 490                 495

Asp Cys Val Ser Cys Asn Val Ser Arg Gly Arg Glu Cys Val Asp Lys
            500                 505                 510

Cys Asn Ile Leu Glu Gly Glu Pro Arg Glu Phe Val Glu Asn Ser Glu
        515                 520                 525

Cys Ile Gln Cys His Pro Glu Cys Leu Pro Gln Met Asn Ile Thr Cys
    530                 535                 540

Thr Gly Arg Gly Pro Asp Asn Cys Ile Gln Cys Ala His Tyr Ile Asp
545                 550                 555                 560

Gly Pro His Cys Val Lys Thr Cys Pro Ala Gly Val Met Gly Glu Asn
                565                 570                 575

Asn Thr Leu Val Trp Lys Tyr Ala Asp Ala Gly His Val Cys His Leu
            580                 585                 590

Cys His Pro Asn Cys Thr Tyr Gly Cys Thr Gly Pro Gly Leu Glu Gly
        595                 600                 605

Cys Asn Gly Pro Lys Ile Pro Ser
    610                 615

<210> SEQ ID NO 110
<211> LENGTH: 18
<212> TYPE: PRT
<213> ORGANISM: Mus musculus
```

```
<400> SEQUENCE: 110

Cys Thr Arg Asn Gly Asp Tyr Tyr Ile Ser Ser Gly Asp Ala Met Asp
1               5                   10                  15

Tyr Trp

<210> SEQ ID NO 111
<211> LENGTH: 18
<212> TYPE: PRT
<213> ORGANISM: Mus musculus

<400> SEQUENCE: 111

Cys Thr Arg Asn Gly Asp Tyr Tyr Val Ser Ser Gly Asp Ala Met Asp
1               5                   10                  15

Tyr Trp

<210> SEQ ID NO 112
<211> LENGTH: 15
<212> TYPE: PRT
<213> ORGANISM: Mus musculus

<400> SEQUENCE: 112

Cys Ala Arg Gly Ser Asp Gly Tyr Phe Tyr Ala Met Asp Tyr Trp
1               5                   10                  15

<210> SEQ ID NO 113
<211> LENGTH: 14
<212> TYPE: PRT
<213> ORGANISM: Mus musculus

<400> SEQUENCE: 113

Cys Ala Arg Tyr Tyr Gly Tyr Asp Asp Ala Met Asp Tyr Trp
1               5                   10

<210> SEQ ID NO 114
<211> LENGTH: 14
<212> TYPE: PRT
<213> ORGANISM: Mus musculus

<400> SEQUENCE: 114

Cys Val Arg Tyr Tyr Gly Tyr Asp Glu Ala Met Asp Tyr Trp
1               5                   10

<210> SEQ ID NO 115
<211> LENGTH: 14
<212> TYPE: PRT
<213> ORGANISM: Mus musculus

<400> SEQUENCE: 115

Cys Val Arg Tyr Tyr Gly Tyr Asp Glu Val Met Asp Tyr Trp
1               5                   10

<210> SEQ ID NO 116
<211> LENGTH: 11
<212> TYPE: PRT
<213> ORGANISM: Mus musculus

<400> SEQUENCE: 116

Cys Gln His Tyr Asn Thr Val Pro Pro Thr Phe
1               5                   10

<210> SEQ ID NO 117
<211> LENGTH: 11
<212> TYPE: PRT
```

```
<213> ORGANISM: Mus musculus

<400> SEQUENCE: 117

Cys Gln Gln Phe Thr Thr Ser Pro Phe Thr Phe
1               5                   10

<210> SEQ ID NO 118
<211> LENGTH: 11
<212> TYPE: PRT
<213> ORGANISM: Mus musculus

<400> SEQUENCE: 118

Cys Gln His Tyr Asn Thr Val Pro Pro Thr Phe
1               5                   10

<210> SEQ ID NO 119
<211> LENGTH: 11
<212> TYPE: PRT
<213> ORGANISM: Mus musculus

<400> SEQUENCE: 119

Cys Gln His Ser Arg Glu Phe Pro Leu Thr Phe
1               5                   10

<210> SEQ ID NO 120
<211> LENGTH: 11
<212> TYPE: PRT
<213> ORGANISM: Mus musculus

<400> SEQUENCE: 120

Cys Ala Gln Asn Leu Glu Leu Pro Tyr Thr Phe
1               5                   10

<210> SEQ ID NO 121
<211> LENGTH: 35
<212> TYPE: DNA
<213> ORGANISM: artificial
<220> FEATURE:
<223> OTHER INFORMATION: PCR primer

<400> SEQUENCE: 121
ggaggcgctc gagacggtga ctgaggttcc ttgac                          35

<210> SEQ ID NO 122
<211> LENGTH: 52
<212> TYPE: DNA
<213> ORGANISM: artificial
<220> FEATURE:
<223> OTHER INFORMATION: PCR primer

<400> SEQUENCE: 122
ccagccgggg cgcgccgagg tccaactgca gcaacctggg tctgagctgg tg        52

<210> SEQ ID NO 123
<211> LENGTH: 49
<212> TYPE: DNA
<213> ORGANISM: artificial
<220> FEATURE:
<223> OTHER INFORMATION: PCR primer

<400> SEQUENCE: 123
ccagccgggg cgcgcccagg tccaactgca gcagcctggg gctgaactg            49

<210> SEQ ID NO 124
<211> LENGTH: 50
<212> TYPE: DNA
```

```
<213> ORGANISM: artificial
<220> FEATURE:
<223> OTHER INFORMATION: PCR primer

<400> SEQUENCE: 124
catgggaata gctagccgac attcagatga ctcagactac atcctccctg          50

<210> SEQ ID NO 125
<211> LENGTH: 51
<212> TYPE: DNA
<213> ORGANISM: artificial
<220> FEATURE:
<223> OTHER INFORMATION: PCR primer

<400> SEQUENCE: 125
catgggaata gctagccgac atcgtgatga cacaagctgc attctccaat c        51

<210> SEQ ID NO 126
<211> LENGTH: 43
<212> TYPE: DNA
<213> ORGANISM: artificial
<220> FEATURE:
<223> OTHER INFORMATION: PCR primer

<400> SEQUENCE: 126
accgcctcca ccggcggccg cttattaaca ctctcccctg ttg                 43

<210> SEQ ID NO 127
<211> LENGTH: 44
<212> TYPE: DNA
<213> ORGANISM: artificial
<220> FEATURE:
<223> OTHER INFORMATION: PCR primer

<400> SEQUENCE: 127
ctgggggccc ttggtgctgg ctgacgagac ggtgactgag gttc                44

<210> SEQ ID NO 128
<211> LENGTH: 37
<212> TYPE: DNA
<213> ORGANISM: artificial
<220> FEATURE:
<223> OTHER INFORMATION: PCR primer

<400> SEQUENCE: 128
gccagcacca agggccccca ggtccaactg cagcagc                        37

<210> SEQ ID NO 129
<211> LENGTH: 38
<212> TYPE: DNA
<213> ORGANISM: artificial
<220> FEATURE:
<223> OTHER INFORMATION: PCR primer

<400> SEQUENCE: 129
cggggccctt ggtgctggct gacgagacgg tgactgag                       38

<210> SEQ ID NO 130
<211> LENGTH: 37
<212> TYPE: DNA
<213> ORGANISM: PCR primer

<400> SEQUENCE: 130
gccagcacca agggcccga ggtccaactg cagcaac                         37

<210> SEQ ID NO 131
```

```
<211> LENGTH: 40
<212> TYPE: DNA
<213> ORGANISM: artificial
<220> FEATURE:
<223> OTHER INFORMATION: PCR primer

<400> SEQUENCE: 131
gtctggtgca gccacagttc gtttgatttc cagcttggtg                                40

<210> SEQ ID NO 132
<211> LENGTH: 38
<212> TYPE: DNA
<213> ORGANISM: artificial
<220> FEATURE:
<223> OTHER INFORMATION: PCR primer

<400> SEQUENCE: 132
cgaactgtgg ctgcaccaga catcgtgatg acacaagc                                 38

<210> SEQ ID NO 133
<211> LENGTH: 41
<212> TYPE: DNA
<213> ORGANISM: artificial
<220> FEATURE:
<223> OTHER INFORMATION: PCR primer

<400> SEQUENCE: 133
gtctggtgca gccacagttc gttttatttc cagcttggtc c                             41

<210> SEQ ID NO 134
<211> LENGTH: 41
<212> TYPE: DNA
<213> ORGANISM: artificial
<220> FEATURE:
<223> OTHER INFORMATION: PCR primer

<400> SEQUENCE: 134
cgaactgtgg ctgcaccaga cattcagatg actcagacta c                             41

<210> SEQ ID NO 135
<211> LENGTH: 20
<212> TYPE: DNA
<213> ORGANISM: Artificial
<220> FEATURE:
<223> OTHER INFORMATION: PCR primer

<400> SEQUENCE: 135
tcttcgggaa gcagctatgc                                                     20

<210> SEQ ID NO 136
<211> LENGTH: 20
<212> TYPE: DNA
<213> ORGANISM: artificial
<220> FEATURE:
<223> OTHER INFORMATION: PCR primer

<400> SEQUENCE: 136
ttctccactg ggcgtaagag                                                     20

<210> SEQ ID NO 137
<211> LENGTH: 41
<212> TYPE: DNA
<213> ORGANISM: artificial
<220> FEATURE:
<223> OTHER INFORMATION: PCR primer

<400> SEQUENCE: 137
```

-continued

```
atctgcattc tagactggag gaaaagaaag tttgccaagg c         41

<210> SEQ ID NO 138
<211> LENGTH: 41
<212> TYPE: DNA
<213> ORGANISM: artificial
<220> FEATURE:
<223> OTHER INFORMATION: PCR primer

<400> SEQUENCE: 138
tactcgatga cgcgtttagg atgggatctt aggcccgttc c         41

<210> SEQ ID NO 139
<211> LENGTH: 22
<212> TYPE: DNA
<213> ORGANISM: artificial
<220> FEATURE:
<223> OTHER INFORMATION: PCR primer

<400> SEQUENCE: 139
tcatgctcca ataaattcac tg                              22

<210> SEQ ID NO 140
<211> LENGTH: 37
<212> TYPE: DNA
<213> ORGANISM: artificial
<220> FEATURE:
<223> OTHER INFORMATION: PCR primer

<400> SEQUENCE: 140
ggagtcggcg gccgcaccat gcgaccctcc gggacgg              37

<210> SEQ ID NO 141
<211> LENGTH: 37
<212> TYPE: DNA
<213> ORGANISM: artificial
<220> FEATURE:
<223> OTHER INFORMATION: PCR primer

<400> SEQUENCE: 141
gcatgtgact cgagtcatgc tccaataaat tcactgc              37
```